US 11,236,097 B2
Feb. 1, 2022

(12) United States Patent
Mulcahy et al.

(54) 11,13-MODIFIED SAXITOXINS FOR THE TREATMENT OF PAIN

(71) Applicants: SITEONE THERAPEUTICS, INC., Bozeman, MT (US); THE BOARD OF TRUSTEES OF THE LELAND STANFORD JUNIOR UNIVERSITY, Stanford, CA (US)

(72) Inventors: John Mulcahy, Redwood City, CA (US); Hassan Pajouhesh, Mountain View, CA (US); George Miljanich, Redwood City, CA (US); Anton Delwig, Albany, CA (US); Jacob Beckley, Bozeman, MT (US); Grant Masaaki Shibuya, South San Francisco, CA (US); Justin Du Bois, Menlo Park, CA (US)

(73) Assignees: SITEONE THERAPEUTICS, INC., Bozeman, MT (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/499,205

(22) PCT Filed: Mar. 29, 2018

(86) PCT No.: PCT/US2018/025301
§ 371 (c)(1),
(2) Date: Sep. 27, 2019

(87) PCT Pub. No.: WO2018/183781
PCT Pub. Date: Oct. 4, 2018

(65) Prior Publication Data
US 2020/0102318 A1    Apr. 2, 2020

Related U.S. Application Data

(60) Provisional application No. 62/478,523, filed on Mar. 29, 2017.

(51) Int. Cl.
*C07D 487/14* (2006.01)
(52) U.S. Cl.
CPC .................. *C07D 487/14* (2013.01)
(58) Field of Classification Search
CPC .................................................. C07D 487/14
See application file for complete search history.

(56) References Cited

U.S. PATENT DOCUMENTS

| | | | |
|---|---|---|---|
| 3,957,996 A | 5/1976 | Adams et al. | |
| 6,030,974 A | 2/2000 | Schwartz et al. | |
| 6,326,020 B1 | 12/2001 | Kohane | |
| 7,576,202 B2 | 8/2009 | Myasoedov | |
| 9,174,999 B2 | 11/2015 | Du Bois et al. | |
| 10,513,525 B2 | 12/2019 | Du Bois et al. | |
| 2002/0161013 A1 | 10/2002 | Liu et al. | |
| 2005/0137177 A1 | 6/2005 | Shafer | |
| 2005/0202093 A1 | 9/2005 | Kohane et al. | |
| 2006/0057647 A1 | 3/2006 | Robillot | |
| 2007/0280970 A1 | 12/2007 | Wilson | |
| 2008/0021051 A1 | 1/2008 | Wilson | |
| 2008/0045553 A1 | 2/2008 | Wilson | |
| 2010/0284913 A1 | 11/2010 | Bois et al. | |
| 2016/0115173 A1 | 4/2016 | Du Bois et al. | |

(Continued)

FOREIGN PATENT DOCUMENTS

| | | |
|---|---|---|
| CN | 1192903 A | 9/1998 |
| CN | 1363275 A | 8/2002 |

(Continued)

OTHER PUBLICATIONS

Parkinson's disease [online]. Retrieved from the interneton Jan. 14, 2021 URL is https://www.mayoclinic.org/diseases-conditions/parkinsons-disease/symptoms-causes/syc-.*

Akimoto et al. "Synthesis of Saxitoxin Derivatives Bearing Guanidine and Urea Groups at C13 and Evaluation of their Inhibitory Activity on Voltage-Gated Sodium Channels," *Org. Biomol. Chem.*, 2013, 11(38), 6642-6649.

Anderson, et al., "Voltage-Gated Sodium Channel Blockers as Cytostatic Inhibitors of the Androgen-Independent Prostate Cancer Cell Line PC-3", *Mol. Cancer Ther.*, Nov. 14, 2003, vol. 2, pp. 1149-1154.

Arakawa et al., "Occurrence of carbamoyl-N-hydroxy derivatives of saxitoxin and neosaxitoxin in a xanthid crab *Zosimus aeneus*", *Toxicon*, 1994, vol. 32, pp. 175-183.

(Continued)

*Primary Examiner* — Shawquia Jackson
(74) *Attorney, Agent, or Firm* — Squire Patton Boggs (US) LLP

(57) ABSTRACT

Provided herein are compounds, pharmaceutical compositions comprising the compounds, methods of preparing the compounds, and methods of using the compounds and compositions in treating conditions associated with voltage-gated sodium channel function where the compounds are 11,13-modified saxitoxins according to Formula (I): where $R^4$, $R^{4a}$, $R^7$, $R^{7a}$, and $X^2$ are as described herein.

29 Claims, No Drawings

(56) References Cited

U.S. PATENT DOCUMENTS

| | | | |
|---|---|---|---|
| 2017/0029431 A1 | 2/2017 | Pajouhesh et al. | |
| 2017/0233398 A1 | 8/2017 | Mulcahy et al. | |
| 2020/0102317 A1 | 4/2020 | Mulcahy et al. | |

FOREIGN PATENT DOCUMENTS

| | | |
|---|---|---|
| CN | 101513408 A | 8/2009 |
| EP | 0857972 A1 | 8/1998 |
| WO | WO 2003/006507 A1 | 1/2003 |
| WO | WO 2010/027641 A2 | 3/2010 |
| WO | WO 2010/129864 | 11/2010 |
| WO | WO 2011/098539 A1 | 8/2011 |
| WO | WO 2012/116440 A1 | 9/2012 |
| WO | WO 2015/157559 | 10/2015 |
| WO | WO 2017/059385 A1 * | 4/2017 |
| WO | WO 2018/183782 A1 | 10/2018 |

OTHER PUBLICATIONS

Arakawa et al., "A New Saxitoxin Analogue from a Xanthid Crab *Atergatis Floridus*", *Toxicon*, 1995, vol. 33, pp. 1577-1584.
Bennett et al., "Contribution of Sialic Acid to the Voltage Dependence of Sodium Channel Gating", *J. Gen. Physiol.*, Mar. 1997, vol. 109, No. 3, pp. 327-343.
Biotinylation web site (http://www.piercenet.com/browse.cfm?fldID=84EBE112-F871-4CA5-807F-47327153CFCB retrieved Apr. 5, 2012).
Biswal et al. "Molecular Imaging: Integration of Molecular Imaging into the Musculoskeletal Imaging Practice", Radiology 244(3):651-671 (2007).
Bundgaard, Design of Prodrugs, 1985, Elsevier, Chapter 1, p. 1-4.
Cox et al., "An SCN9A channelopathy causes congenital inability to experience pain," *Nature*, vol. 444, Dec. 14, 2006, pp. 894-898.
Dell'Aversano et al., "Isolation and Structure Elucidation of New and Unusual Saxitoxin Analogues from Mussels," *Journal of Natural Products*, 2008, vol. 71, pp. 1518-1523.
Dib-Hajj et al. "From genes to pain: Na v 1.7 and human pain disorders", Trends Neurosci. 30(11):555-563.
Dorr et al. "Intriguing differences in the gas-phase dissociation behavior of protonated and deprotonated gonyautoxin epimers", J. American Society Mass. Spec. 22:2011-2020.
Fleming et al. "(+)-Saxitoxin: A First and Second Generation Stereoselective Synthesis", *J. Am. Chemical Society*, 2007, vol. 129, pp. 9964-9975.
Fleming et al. "A synthesis of (+)-saxitoxin", J. Am. Chem. Soc. 128:3926-3927 (2006).
Goldberg et al. "Loss-of-function mutations in the Nav1.7 gene underlie congenital indifference to pain in multiple human populations", Clinical Genetics 71(4):311-319 (2007).
Hall et al., "Dinoflagellate Neurotoxins Related To Saxitoxin: structures of toxins C3 and C4, and confirmation of the structure of neosaxitoxin", *Tet Lett*, 1984; vol. 25, pp. 3537-3538.
Han, Targeted Prodrug Design to Optimize Drug Deliver, 2000, AAPS Pharmsci, vol. 2(1), p. 1-11.
Harada et al., "Natural Occurrence Of Decarbamoylsaxitoxin in Tropical Dinoflagellate and Bivalves", *Agric Biol Chem*, 1983; vol. 47, pp. 191-193.
International Search Report and Written Opinion for PCT/US2018/025301 dated Jul. 2, 2018, 8 pages.
Iwamoto et al., "Total synthesis of (−)- and (+)-decarbamoyloxysaxitoxin and (+)-saxitoxin", *Chem Asian J*, 2009, vol. 4, pp. 277-285.
Jacobi et al., "Total Synthesis of +/− Saxitoxin", *J Am Chem Soc*, 1984, vol. 106, pp. 5594-5598.
Klugbauer et al., "Structure and Functional Expression of a New Member of the Tetrodotoxin-Sensitive Voltageactivated Sodium Channel Family From Human Neuroendocrine Cells", *The EMBO Journal*, 1995, vol. 14 No. 6, pp. 1084-1090.
Koehn Fe et al., "Dinoflagellate Neurotoxins Related To Saxitoxin: Structure and Latent Activity of Toxins B1 and B2", *Tetrahedron Letters*, 1982; vol. 23, pp. 2247-2248.
Llewellyn Le, "Saxitoxin, a Toxic Marine Natural Product that Targets a Multitude of Receptors", *Nat Prod Rep*, 2006, vol. 23, pp. 200-222.
Mao et al., "Novel modulator of NaV1.1 and NaV1.2 Na+ channels in rat neuronal cells", *Med Chem Lett*, 2010, vol. 1, pp. 135-138.
Momin et al., "Sensory Neuron Voltage-Gated Sodium Channels as Analgesic Drug Targets", *Current Opinion in Neurobiology*, 2008, vol. 18, pp. 383-388.
Mulcahy et al., "A Stereoselective Synthesis of (+)-Gonyautoxin 3", *J Am Chem Soc.*, Sep. 24, 2008; vol. 130, No. 38, pp. 12630-12631.
Mulcahy et al. "Synthesis of the Paralytic Shellfish Poisons (+)-Gonyautoxin 2, (+)-Gonyautoxin 3, and (+)-11,11-Dihydroxysaxitoxin," *J. Am. Chem. Soc.* 2016, 138(18), 5994-6001.
Mulcahy et al. "Challenges and Opportunities for Therapeutics Targeting the Voltage-Gated Sodium Channel Isoform Nav1.7," *J. Med. Chem.* 2019, 62(19), 8695-8710.
Negri et al., "Three Novel Hydroxybenzoate Saxitoxin Analogues Isolated From The Dinoflagellate Gymnodinium Catenatum", *Chem Res Toxicol*, 2003, vol. 16, pp. 1029-1033.
Nishikawa et al., "Synthesis of an Advanced Model of Zetekitoxin AB Focusing on the N-Acylisoxazolidine Amide Structure Corresponding to C13-C17", *Asian Journal of Organic Chemistry*, Oct. 23, 2014, vol. 3, No. 12, pp. 1308-1311.
Ogata et al., "Molecular Diversity of Structure and Function of the Voltage-Gated $Na^+$ Channels", *Jpn. J. Pharmacol.*, 2002, vol. 88, pp. 365-377.
Onodera et al., "New Saxitoxin Analogues from the Freshwater Filamentous Cyanobacterium *Lyngbya wollei*", *Natural Toxins*, 1997, vol. 5, pp. 146-151.
Robillot et al., "Synthesis of Bifunctional Saxitoxin Analogues by Biotinylation", *Toxicon*, 2009; vol. 53, pp. 460-465.
Rush et al. "Multiple Sodium Channels and their Roles in electrogenesis within Dorsal Root Ganglion Neurons", *J. Physiol*, 2007, 579 (Pt 1), pp. 1-14.
Sato et al., "Identification of Thioether Intermediates in the Reductive Transformation of Gonyautoxins Into Saxitoxins by Thiols", *Bioorganic & Medicinal Chemistry Letters*, vol. 10, No. 6, Aug. 21, 2000, pp. 1787-1789.
Schlager et al., "Micromole scale biotinylation of saxitoxin (STX) for use as a screening moiety for peptide binding libraries", *Medical Defense Bioscience Proceedings*, May 16, 1996, vol. 12, No. 3, pp. 1590-1597.
Shimizu et al., "Isolation of Side-Chain Sulfated Saxitoxin Analogs", *Tetrahedron*, 1984; vol. 40, pp. 539-544.
Shimizu et al., Structure of Saxitoxin in Solutions and Stereochemistry of Dihydrosaxitoxins. *J Am Chem Soc*, 1981, vol. 103, pp. 605-609.
Shimuzu et al., "Toxigenesis and Biosynthesis of Saxitoxin Analogues," *Pure and Applied Chemistry*, 1986, vol. 58, No. 2, pp. 257-262.
Strichartz GR et al., "The Potencies of Synthetic Analogues of Saxitoxin and the Absolute Stereoselectivity of Decarbamoyl Saxitoxin", *Toxicon*, 1995, vol. 33, pp. 723-737.
Tanino et al., "A Stereospecific Total Synthesis of d,l-Saxitoxin", *J Am Chem Soc*, 1977, vol. 99, pp. 2818-2819.
Vale P., "Metabolites of Saxitoxin Analogues in Bivalves Contaminated by Gymnodinium Catenatum", *Toxicon*, 2010; vol. 55, pp. 162-165.
Vale P., "New Saxitoxin Analogues in the Marine Environment: Developments in Toxin Chemistry, Detection and Biotransformation During the 2000s", *Phytochem Rev*, 2010, vol. 9, pp. 525-535.
Walls, et al., "Synthesis And Biological Evaluation of a Fluorescent Analog of Phenytoin as a Potential Inhibitor of Neuropathic Pain and Imaging Agent", *Bioorg. Med. Chem.*, Jul. 3, 2012, vol. 20, pp. 5269-5276.
Watanabe et al., "Development of Saxitoxin-Conjugated Affinity Gels" Bioconjugate Chem., 17:459-465 (2006).
Waxman, Stephen G., "A Channel Sets the Gain on Pain" Nature, 444:831-832.
West, Anthony R., Solid State Chemistry and it's Applications, Wiley, New York, 1988, p. 358 and p. 365.
Yotsu-Yamashita et al., "The Structure of Zetekitoxin Ab, A Saxitoxin Analog From the Panamian Golden Frog *Atelopus zeteki*: A Potent Sodium-Channel Blocker", *PNAS*, 2004; vol. 101, pp. 4346-4351.

(56) References Cited

OTHER PUBLICATIONS

Zaman et al., "Occurrence of a Methyl Derivative of Saxitoxin In Bangladeshi Freshwater Puffers", *Toxicon*, 1998, vol. 36, pp. 627-630.

De Lera Ruiz et al. "Voltage-Gated Sodium Channels: Structure, Function, Pharmacology, and Clinical Indications," Journal of Medicinal Chemistry, J. Med. Chem. 2015, 58, 7093-7118,; DOI: 10.1021/jm501981g.

Devigili et al., "Paroxysmal itch caused by gain-of-function Nav1.7 mutation," Pain 2014, 155(9), pp. 1702-1707.

Goldberg et al., "Loss-of-function mutations in the Nav1.7 gene underlie congenital indifference to pain in multiple human populations," Clinical Genetics 2007: 71: 311-319, doi: 10.1111/j.1399-0004.2007.00790.x.

Momin et al., "Sensory neuron voltage-gated sodium channels as analgesic drug Targets," Curr Opin Neurobiol. 18(4): 383-8, 2008; DOI 10.1016/j.conb.2008.08.017.

Muroi et al. "Selective silencing of NaV1.7 decreases excitability and conduction in vagal sensory neurons," J. Physiol. 589.23 pp. 5663-5676, 2011, 14 pages.

Pergolizzi Jr. et al., "Treating Acute Pain in Light of thre Chronifiction of Pain," Pain Management Nursing, (2014), vol. 15, No. 1 pp. 380-390, http://dx.doi.org/10.1016/j.pmn.2012.07.004.

Rush et al., "Multiple sodium channels and their roles in electrogenesis within dorsal root ganglion neurons," J. Physiol. 579(Pt 1): 1-14, 2007; DOI: 10.1113/jphysiol.2006.121483.

Voscopoulos et al. "When does acute pain become chronic?" British Journal of Anaesthesia 105 (S1): i69-i85 (2010); doi:10.1093/bja/aeq323.

\* cited by examiner

11,13-MODIFIED SAXITOXINS FOR THE TREATMENT OF PAIN

This application is a 371 of International Application No. PCT/US2018/025301 filed Mar. 29, 2018, and which claims priority benefit of U.S. Provisional Patent Application No. 62/478,523 filed Mar. 29, 2017. The contents of which applications are hereby incorporated by reference herein in their entireties.

STATEMENT OF GOVERNMENT RIGHTS

The invention was made with Government support under contract NS081887 awarded by the National Institutes of Health. The U.S. Government has certain rights in this invention.

FIELD

Provided herein are compounds, pharmaceutical compositions comprising the compounds, and methods of using the compounds and compositions in treating conditions associated with voltage-gated sodium channel function, for example pain and conditions associated with pain. The compounds are 11,13-modified saxitoxins. Also provided herein are methods of treating pain in a mammal comprising administering a therapeutically or prophylactically effective amount of a 11,13-modified saxitoxin or composition to a mammal. In some or any embodiments, the mammal is a human.

BACKGROUND

Voltage-gated sodium channels are large integral membrane protein complexes present in neurons and excitable tissues where they contribute to processes such as membrane excitability and muscle contraction (Ogata et al., *Jpn. J. Pharmacol.* (2002) 88 (4) 365-77). They have been identified as a primary target for the treatment of pain. Genes encoding for nine distinct mammalian isoforms of $Na_V$ channels ($Na_V$ isoforms 1.1-1.9) have been sequenced. Variation in the gating properties of different $Na_V$ isoforms, cellular distributions, and expression levels influence the physiology of nerve cell conduction. A mounting body of evidence suggests that individual $Na_V$ isoforms $Na_V$ 1.3, 1.7, and 1.8 are disproportionately involved in pain signaling and nociception, and that an isoform-specific inhibitor of $Na_V$ could provide pain relief without the accompanying undesirable effects of a non-specific $Na_V$ antagonist or an opioid drug (Momin et al., *Curr Opin Neurobiol.* 18(4): 383-8, 2008; Rush et al., *J. Physiol.* 579 (Pt 1): 1-14, 2007).

A human genetic disorder resulting in a loss of function mutation in $Na_V$ 1.7 has been correlated with congenital insensitivity to pain (Cox et al., Nature. (2006) 444 (7121) 894-898). The design of a drug which selectively inhibits $Na_V$ 1.7 over the other $Na_V$ channels is therefore desirable. Such a drug design is challenging given the high structural homology (75-96%) of the mammalian $Na_V$ isoforms. There exists a need for compounds which treat pain and conditions associated with voltage-gated sodium channel function, particularly which selectively inhibit $Na_V$ 1.7 over other $Na_V$ isoforms.

SUMMARY

Provided herein are compounds, pharmaceutical compositions comprising the compounds, and methods of using the compounds and compositions for the treatment of conditions modulated by voltage-gated sodium channels, in some or any embodiments, in the treatment of pain. The compounds are 11,13-modified saxitoxins. Also provided herein are methods of treating pain and/or conditions modulated by voltage-gated sodium channels in a mammal comprising administering a therapeutically or prophylactically effective amount of a 11,13-modified saxitoxin or composition to a mammal. In some or any embodiments, the mammal is a human.

In one aspect, provided is a Compound of Formula (I):

(I)

wherein
$X^2$ is —C($R^4$)($R^{4a}$)— or —N($R^8$)—;
each $R^4$ and $R^{4a}$ is independently hydrogen or $C_{1-6}$alkyl;
$R^7$ is hydrogen or $C_{1-6}$alkyl;
$R^{7a}$ is aryl optionally substituted with 1, 2, 3, or 4 $R^{7b}$; heterocyclic optionally substituted with 1, 2, 3, or 4 $R^{7b}$; or biphenyl optionally substituted with 1, 2, 3, or 4 $R^{7b}$;
each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and
$R^8$ is hydrogen; $C_{1-6}$alkyl; carboxy-$C_{1-6}$alkyl; halo-$C_{1-6}$alkyl; hydroxy-$C_{1-6}$alkyl; $C_3$-$C_8$-cycloalkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or
a pharmaceutically acceptable salt, hydrate, solvate, stereoisomer, tautomer, or mixture thereof;
provided that the compound is not selected from Group A:

Group A

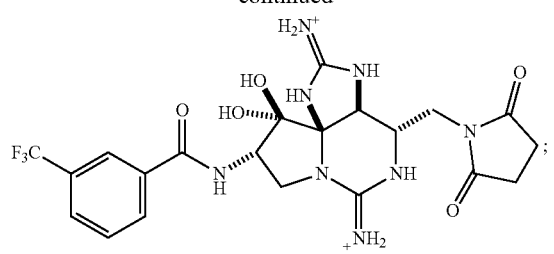
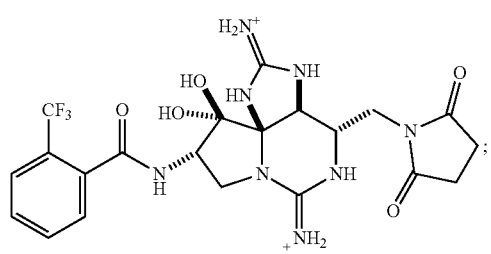
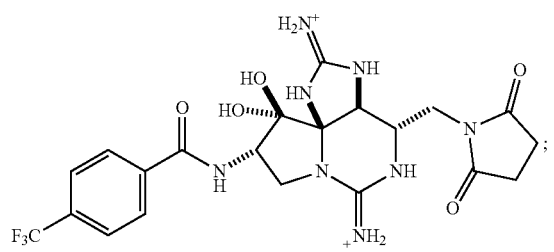
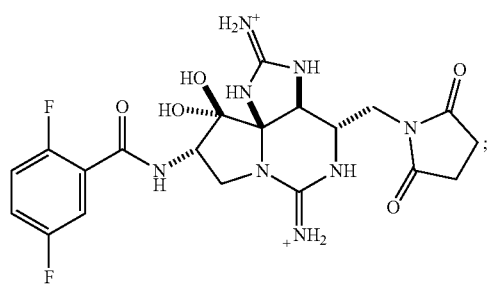
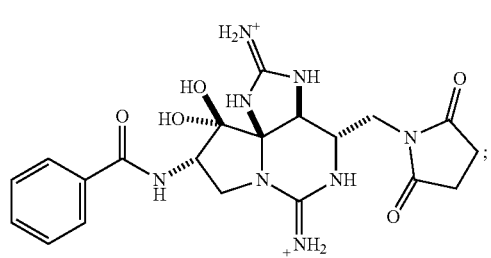
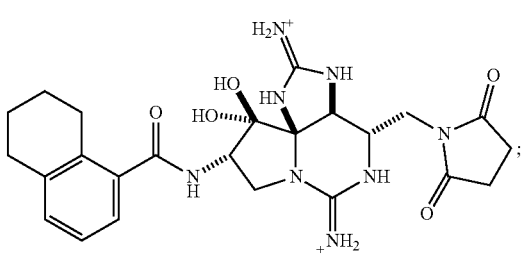
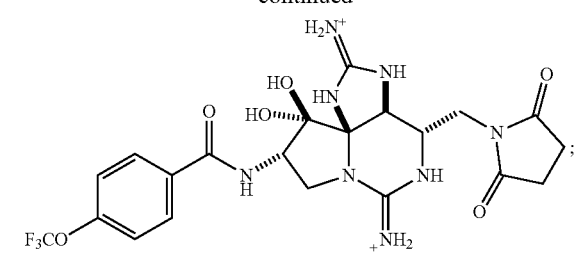
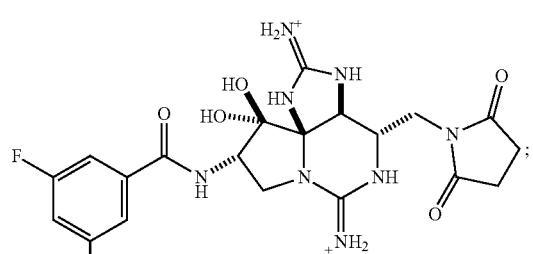
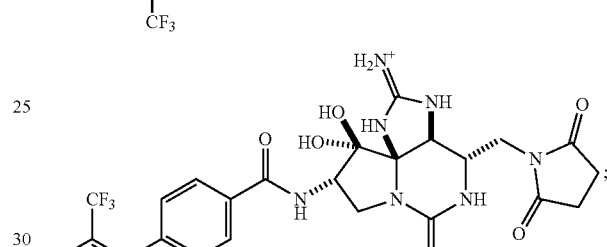
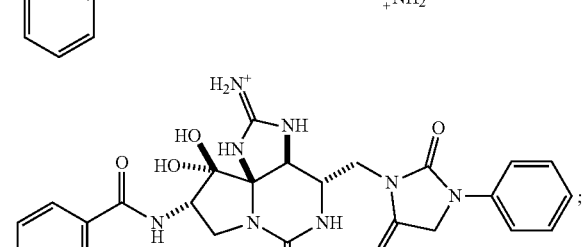
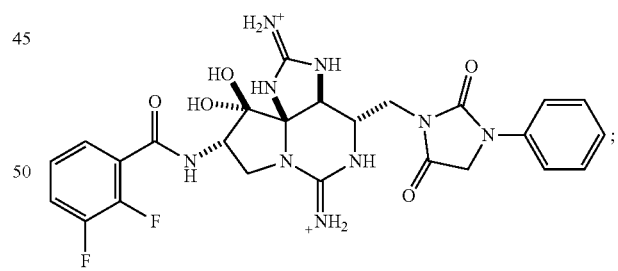
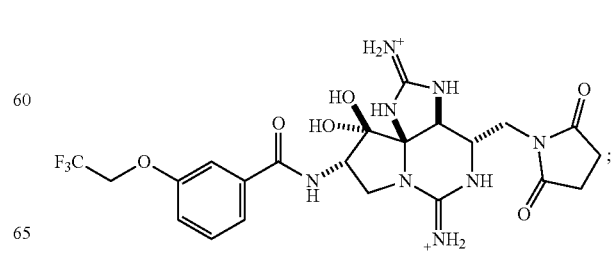

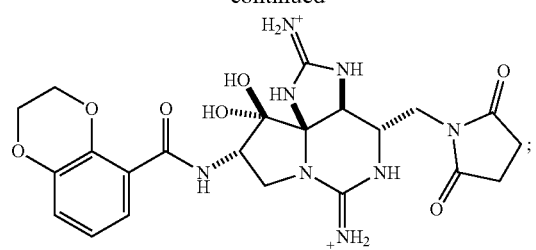
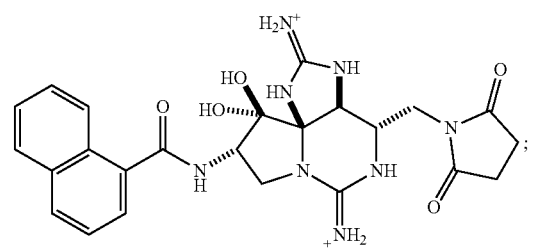
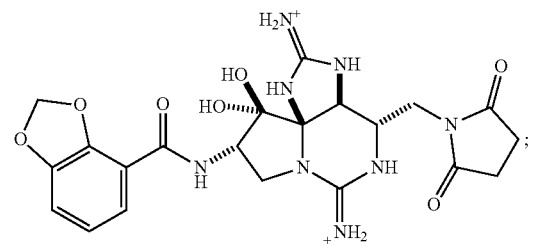
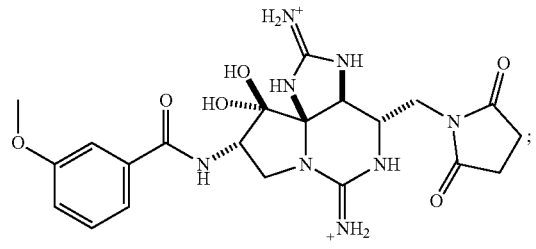
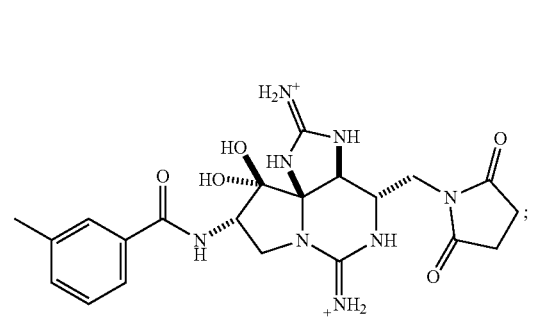
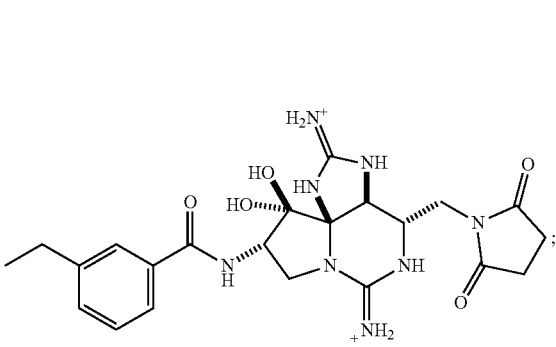
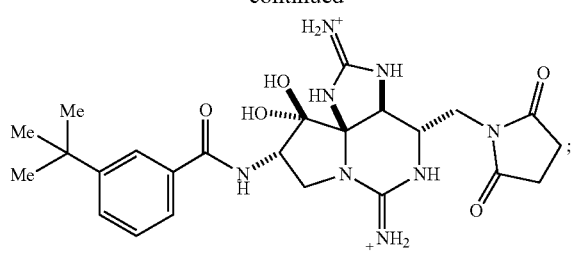
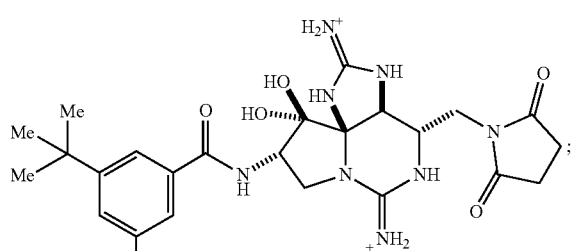
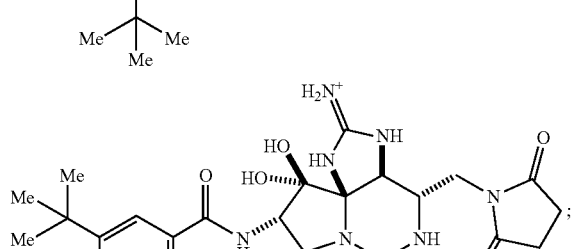
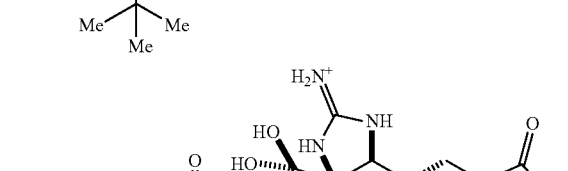
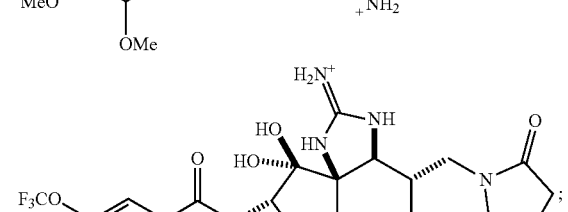
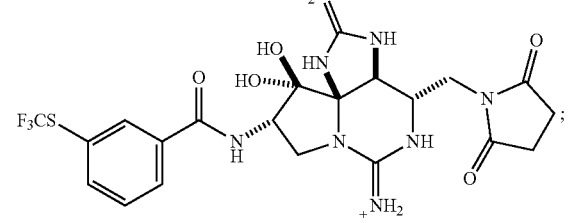

-continued
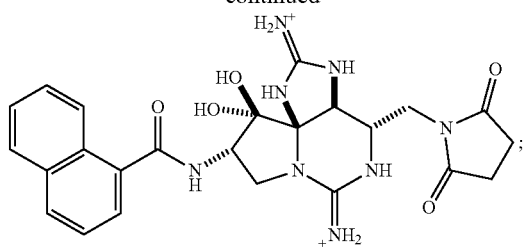
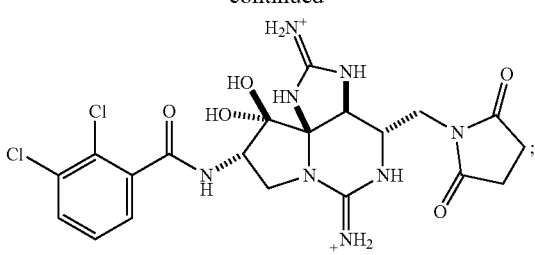
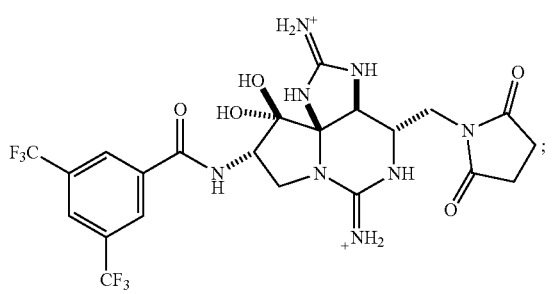
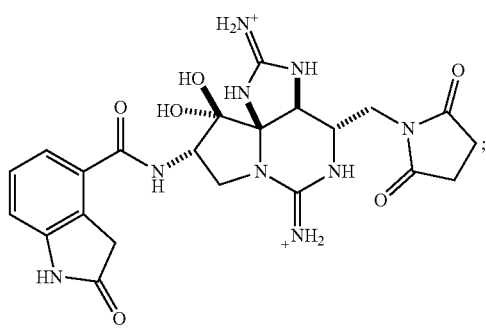
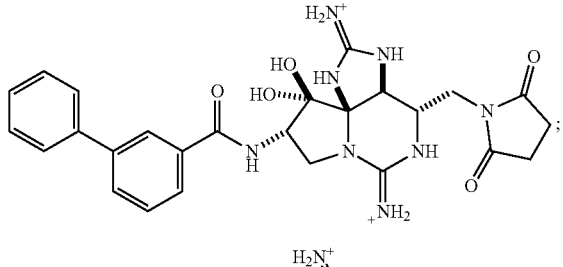
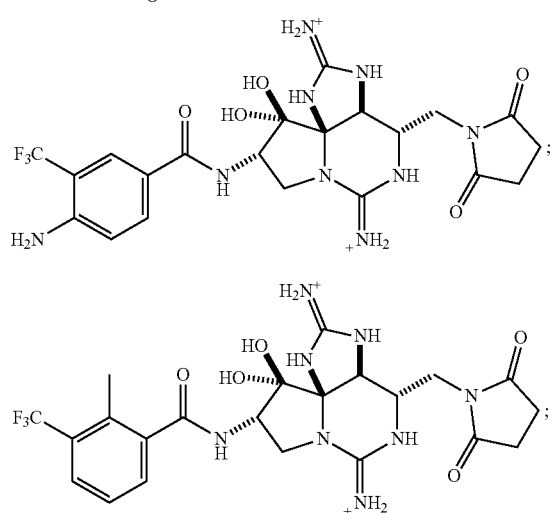
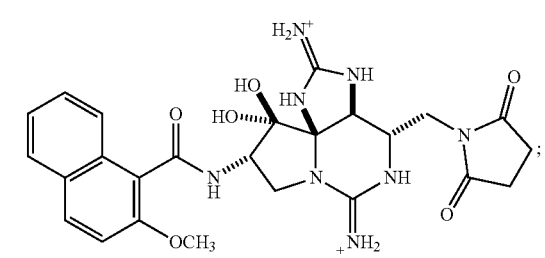
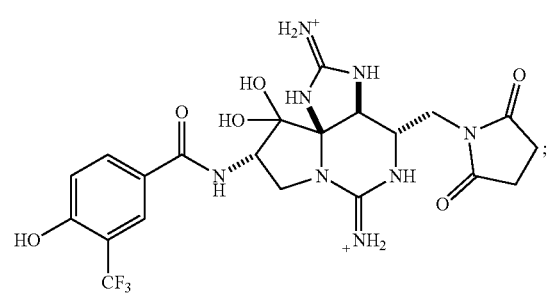
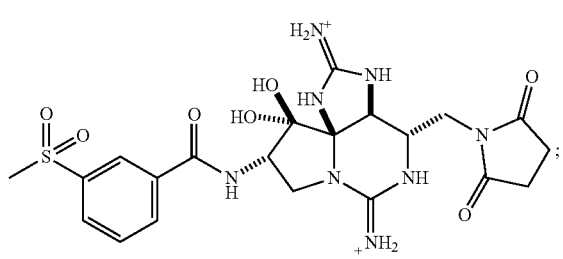
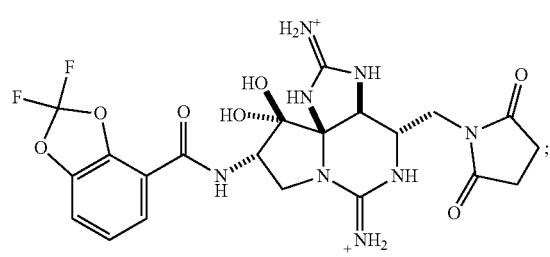

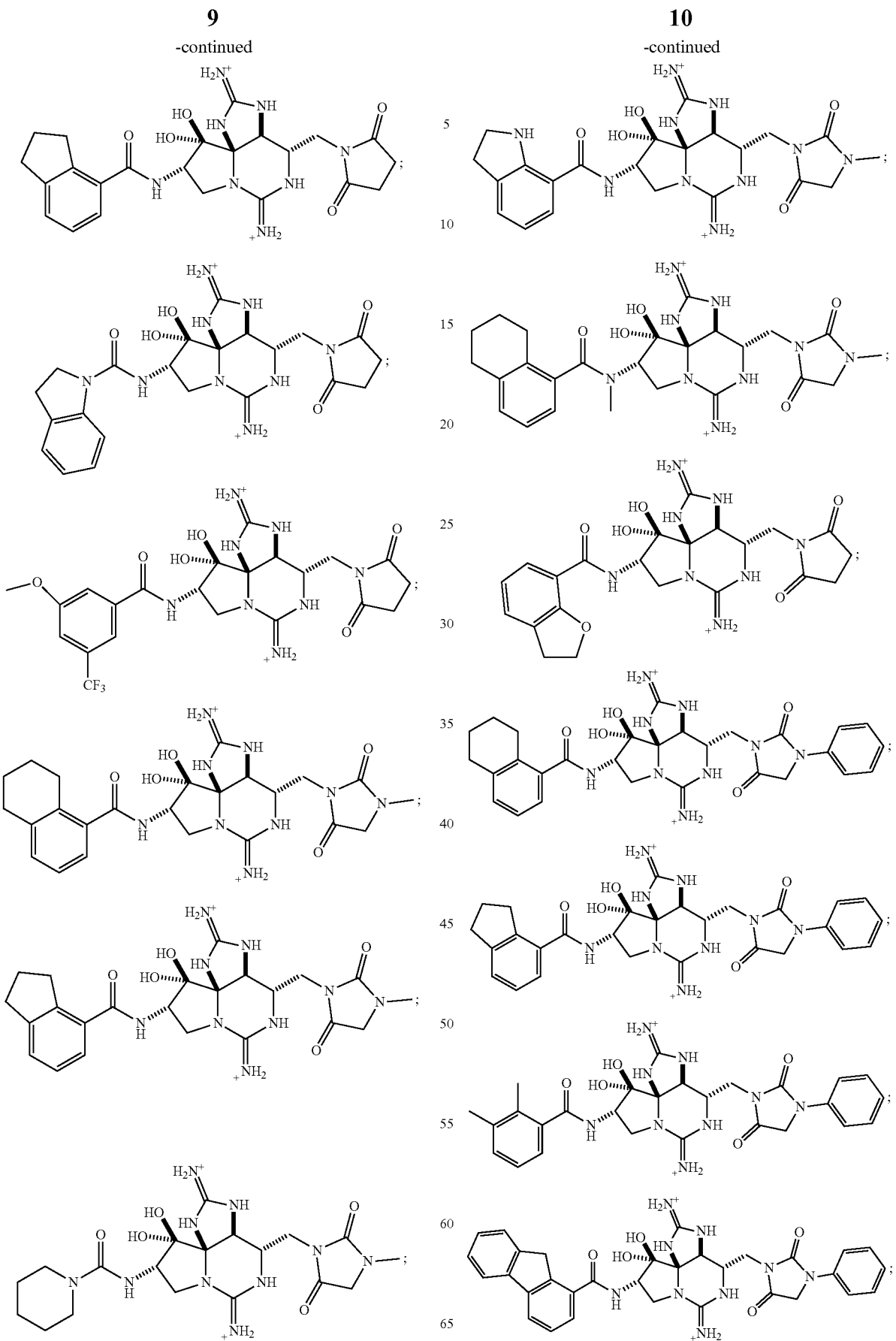

-continued

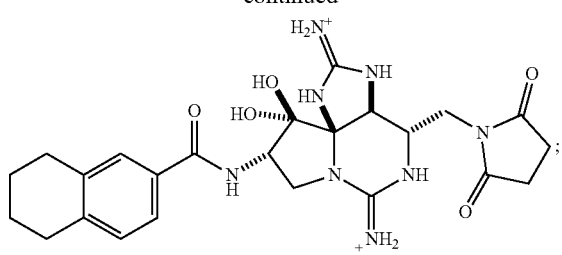

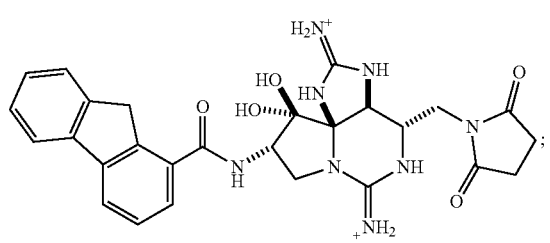

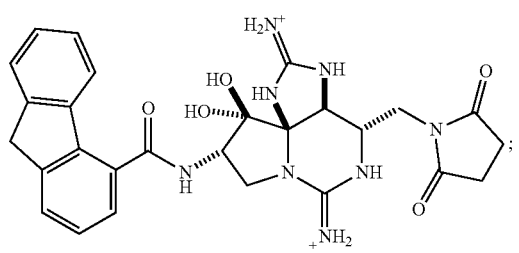

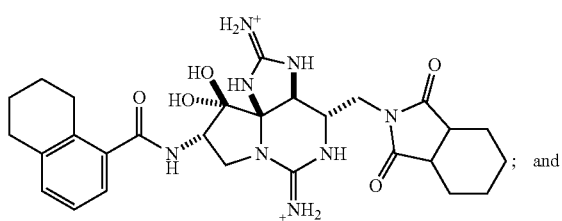

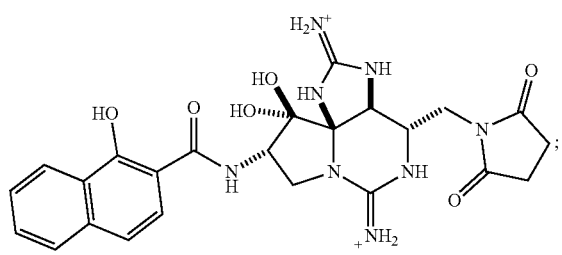

or a pharmaceutically acceptable salt, hydrate, solvate, stereoisomer, tautomer, or mixture thereof.

In another aspect, provided is a Compound of Formula (I-P):

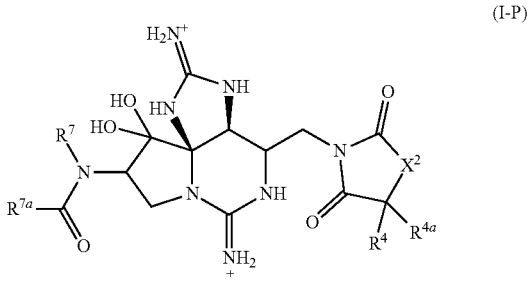

(I-P)

wherein $X^2$ is —C($R^4$)($R^{4a}$)— or —N($R^8$)—;

each $R^4$ and $R^{4a}$ is independently hydrogen or $C_{1-6}$alkyl;

$R^7$ is hydrogen or $C_{1-6}$alkyl;

$R^{7a}$ is aryl optionally substituted with 1, 2, 3, or 4 $R^{7b}$; heterocyclic optionally substituted with 1, 2, 3, or 4 $R^{7b}$; or biphenyl optionally substituted with 1, 2, 3, or 4 $R^{7b}$;

each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and $R^8$ is hydrogen; $C_{1-6}$alkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or a pharmaceutically acceptable salt, hydrate, solvate, stereoisomer, tautomer, or mixture thereof;

provided that the compound is not selected from Group A:

Group A

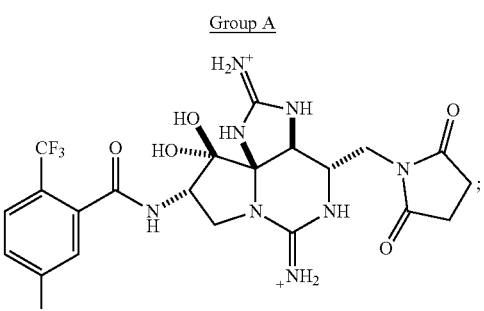

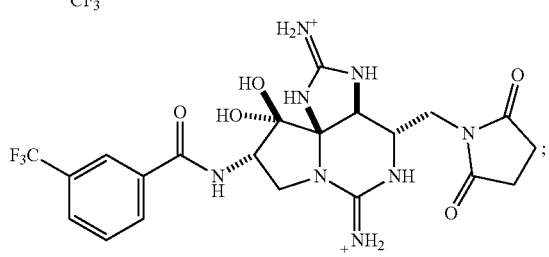

-continued
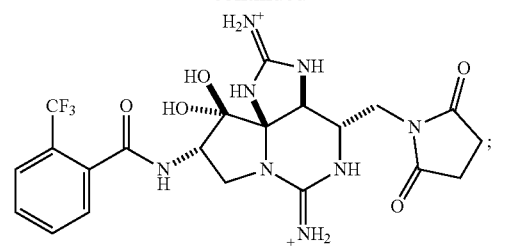
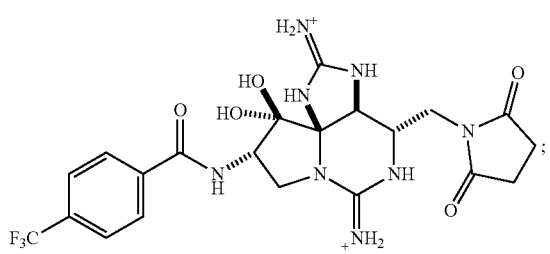
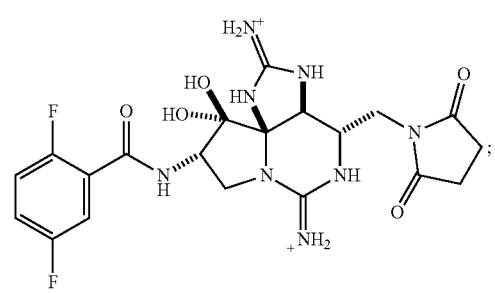
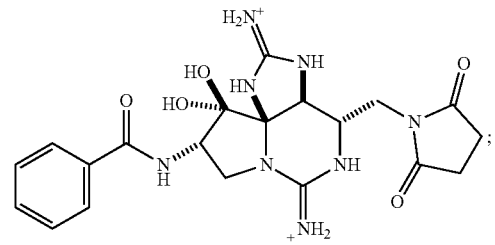
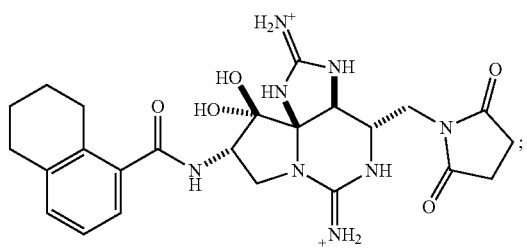
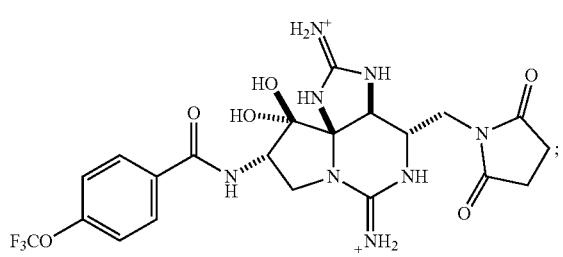
-continued
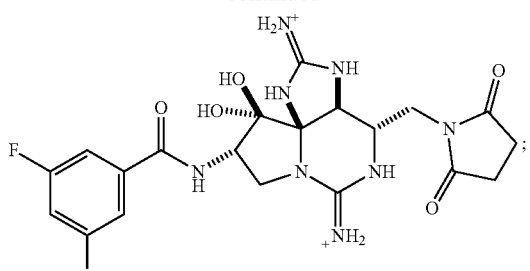
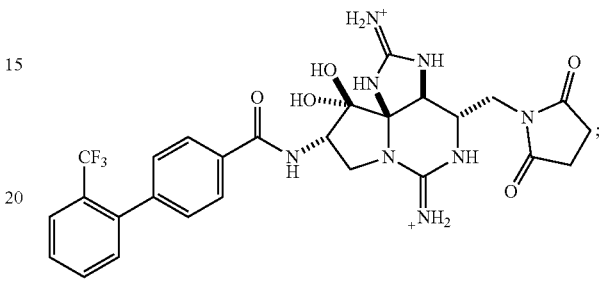
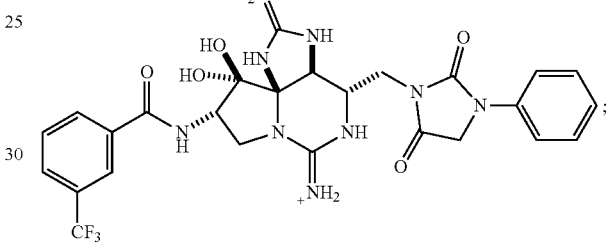
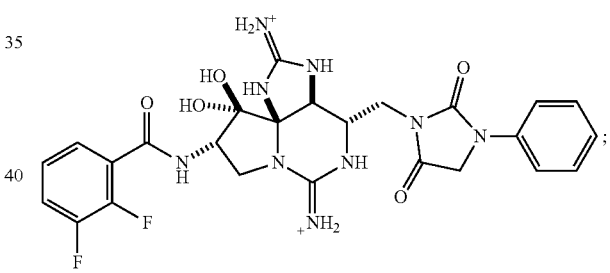
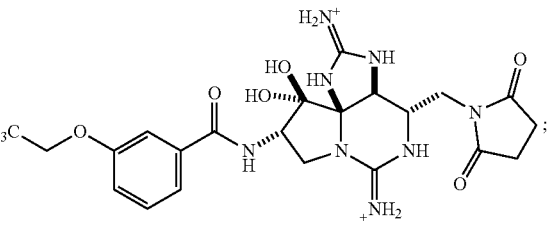
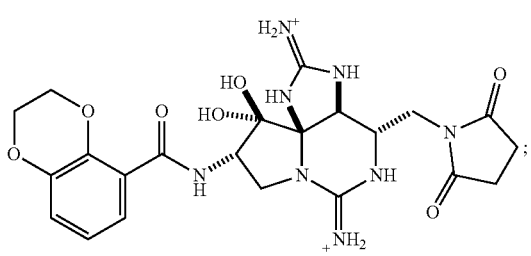

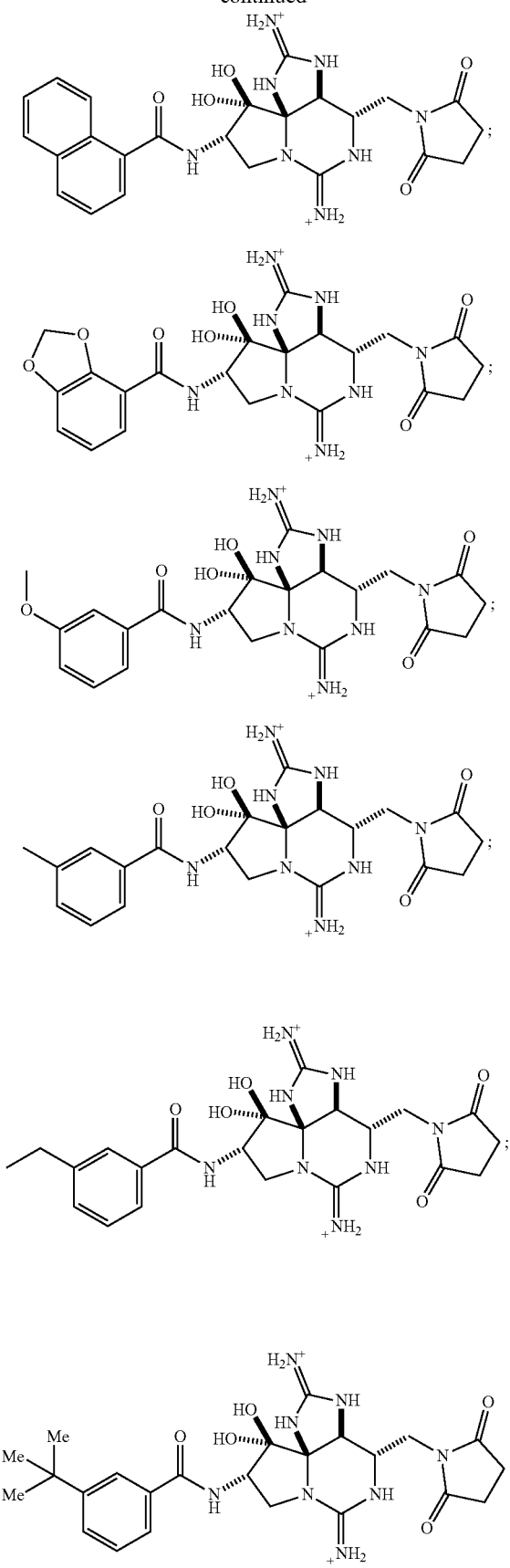
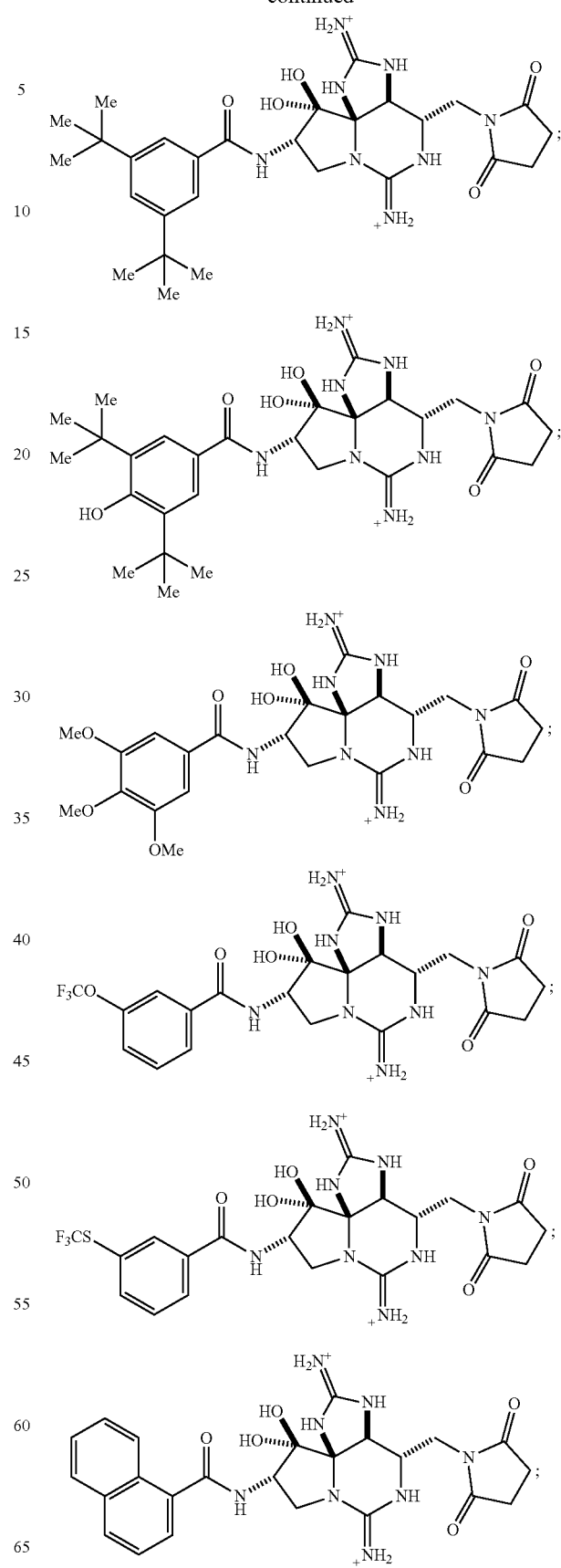

17
-continued
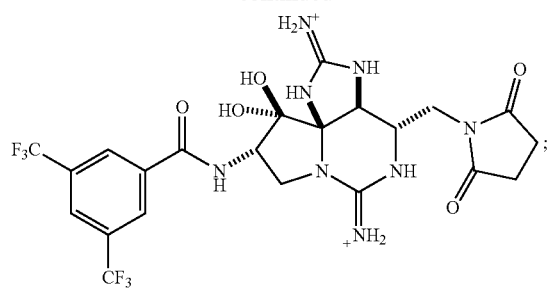
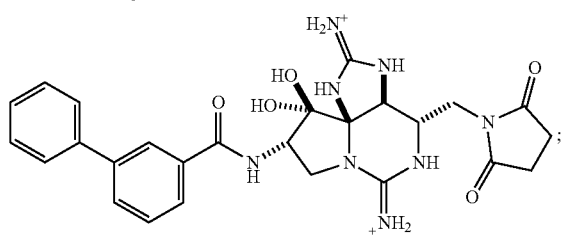
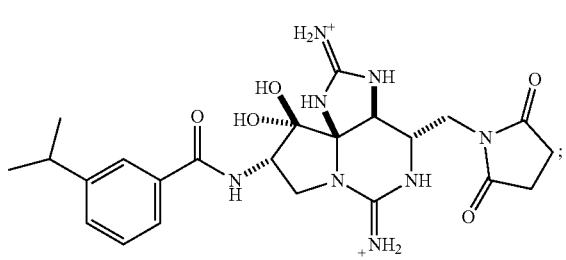
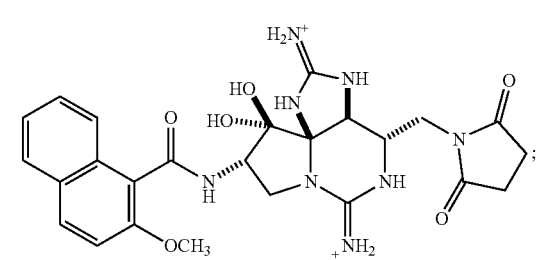
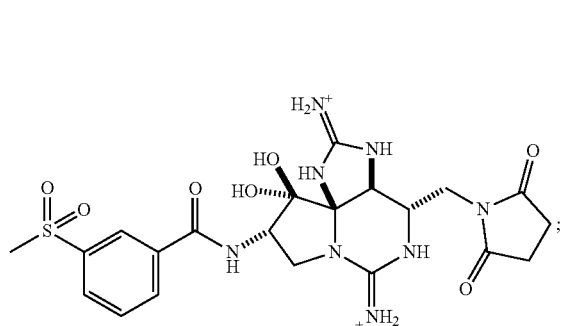
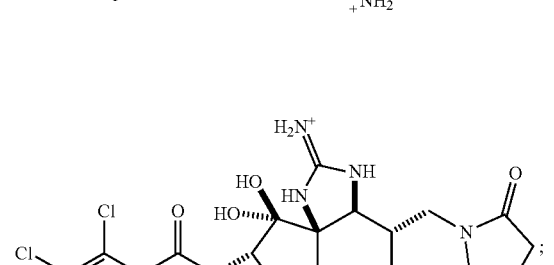
18
-continued
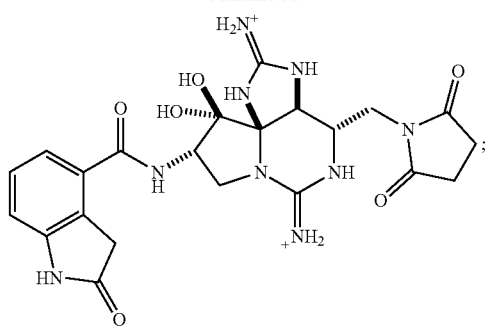
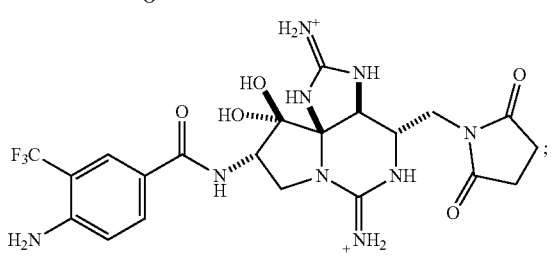
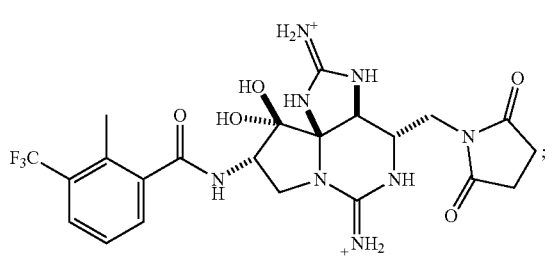
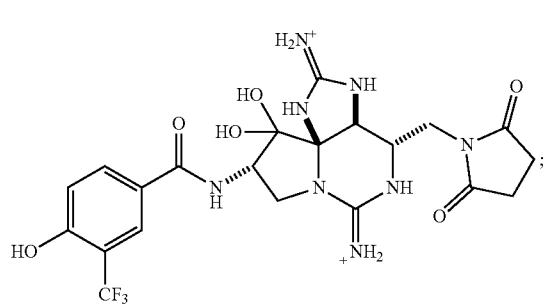
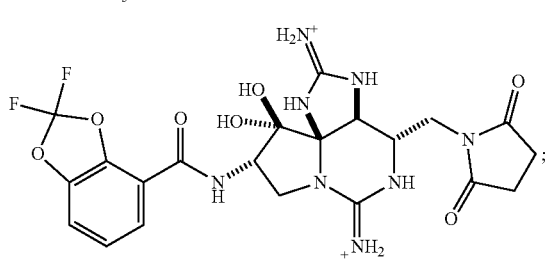
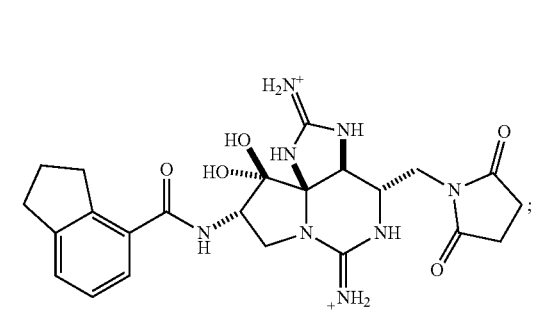

-continued
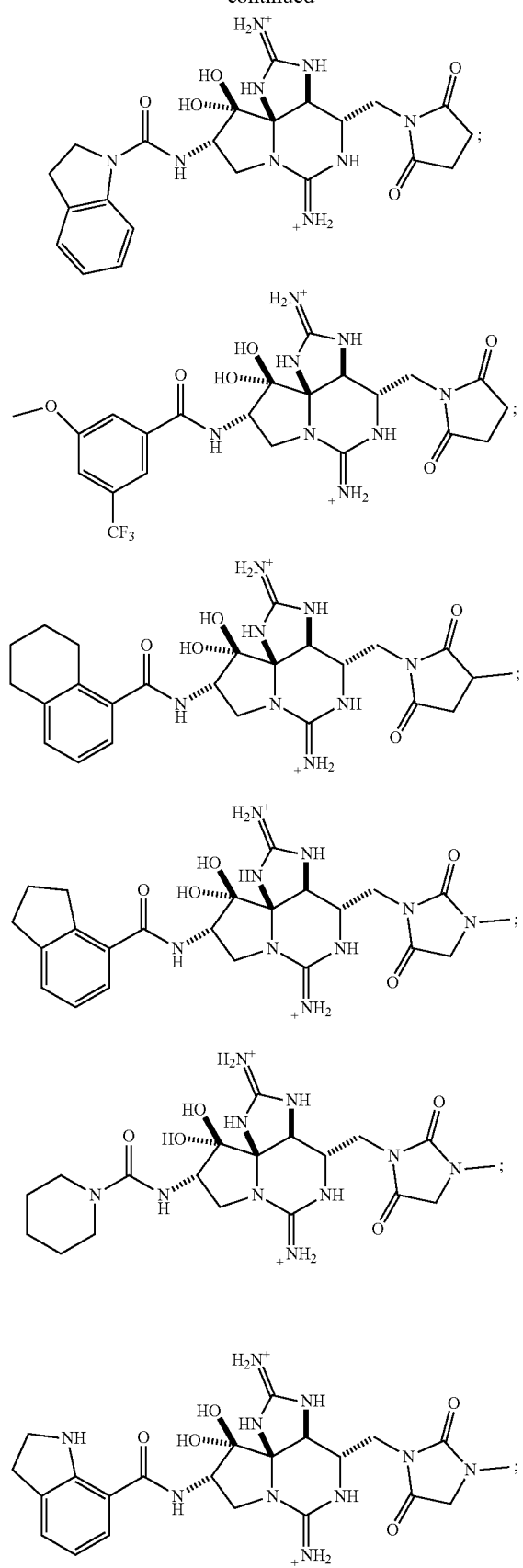
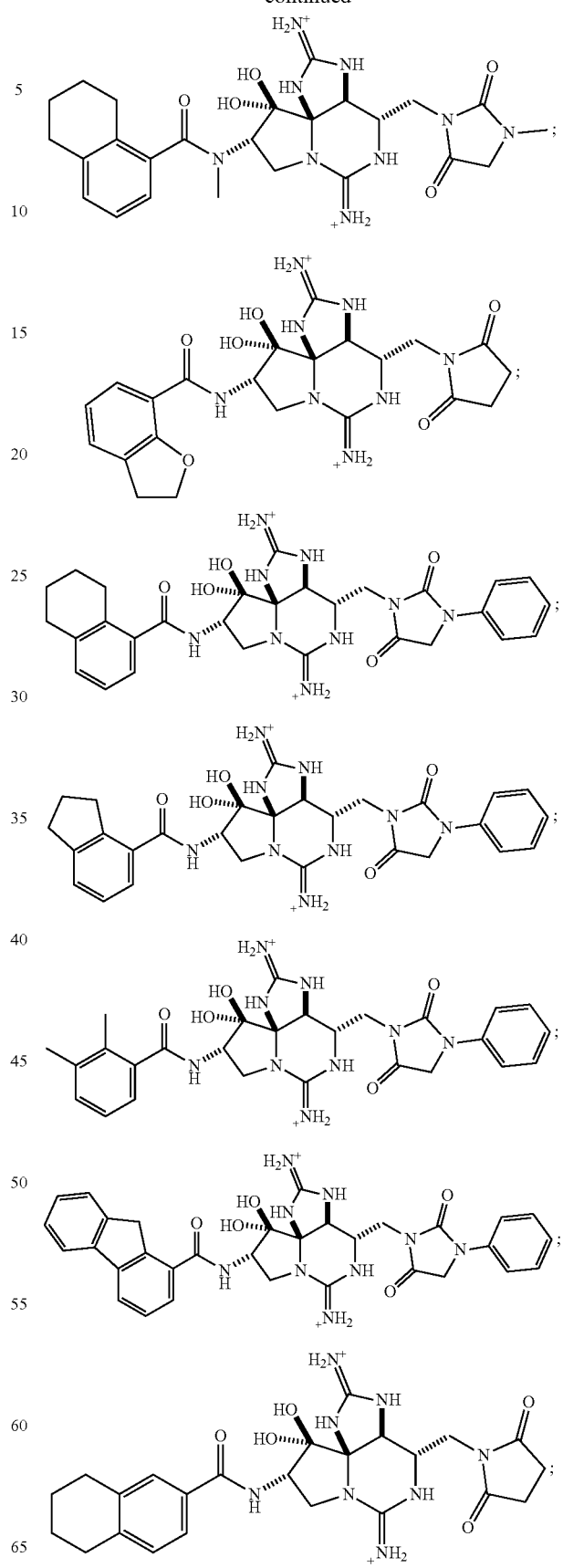

-continued

[chemical structures]

or a pharmaceutically acceptable salt, hydrate, solvate, stereoisomer, tautomer, or mixture thereof.

In another aspect, provided herein are pharmaceutical compositions, single unit dosage forms, and kits suitable for use in treating pain and/or conditions modulated by voltage-gated sodium channels which comprise a therapeutically or prophylactically effective amount of a compound provided herein, e.g., of some or any of the embodiments, of Formula (I)-(Id) and (I-P) and compounds 1-95.

In an aspect, a method of treatment of pain and/or conditions modulated by voltage-gated sodium channels is provided comprising administering to an individual in need thereof a therapeutically or prophylactically effective amount of a 11,13-modified saxitoxin described herein, e.g., of some or any of the embodiments, of Formula (I)-(Id) and (I-P) and compounds 1-95.

In another aspect, provided herein is a compound of Formula Xe

Xe

[chemical structure]

or a salt thereof, where
PG$^1$ is a nitrogen-protecting group;
PG$^2$ is a nitrogen-protecting group;
X$^2$ is —C(R$^4$)(R$^4$)— or —N(R$^8$)—;
each R$^4$ and R$^{4a}$ is independently hydrogen or C$_{1-6}$alkyl;
R$^7$ is hydrogen or C$_{1-6}$alkyl;
R$^{7a}$ is aryl optionally substituted with 1, 2, 3, or 4 R$^{7b}$; heterocyclic optionally substituted with 1, 2, 3, or 4 R$^{7b}$; or biphenyl optionally substituted with 1, 2, 3, or 4 R$^{7b}$;
each R$^{7b}$, when present, is independently halo, C$_{1-6}$alkyl, halo-C$_{1-6}$alkyl, aryl-C$_{1-6}$alkyl, hydroxy, C$_{1-6}$alkoxy, halo-C$_{1-6}$alkoxy, aryloxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, —C(O)(heterocycloalkyl), or cyano; where the aryl in aryloxy and aryl-C$_{1-6}$alkyl are optionally substituted with 1, 2, or 3 groups independently selected from C$_{1-6}$alkyl, halo, and halo-C$_{1-6}$alkyl; and
R$^8$ is hydrogen; C$_{1-6}$alkyl; carboxy-C$_{1-6}$alkyl; halo-C$_{1-6}$alkyl; hydroxy-C$_{1-6}$alkyl; C$_3$-C$_8$-cycloalkyl; or phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano;
provided that the compound is not selected from Group B:

Group B.

[chemical structures]

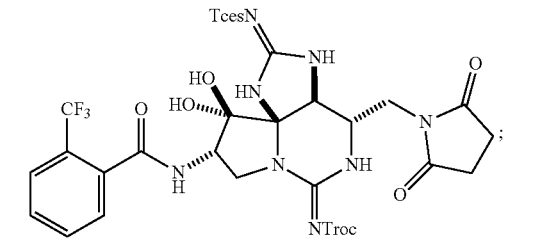
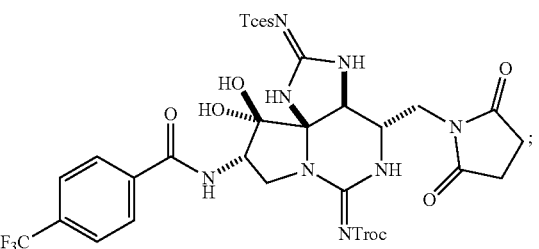
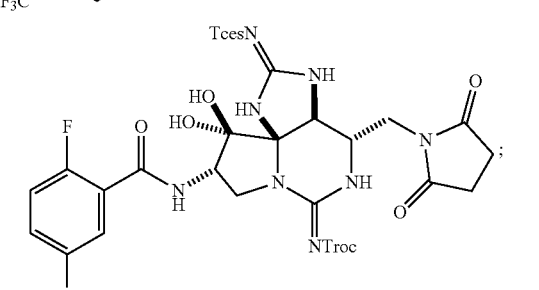
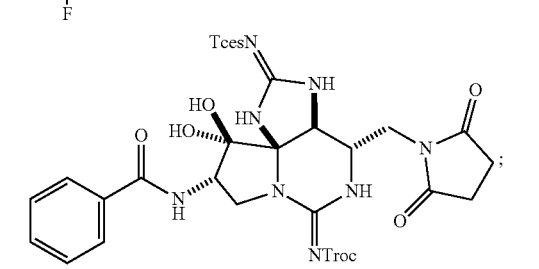
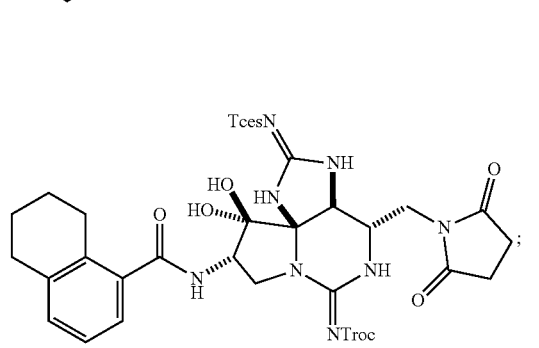
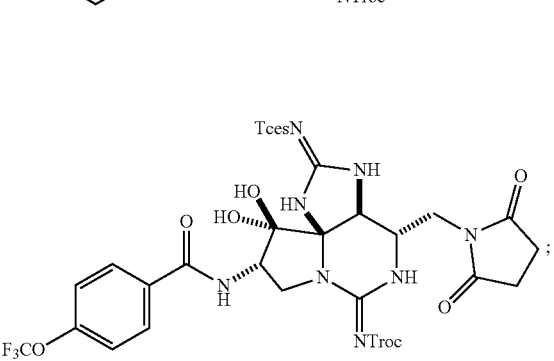
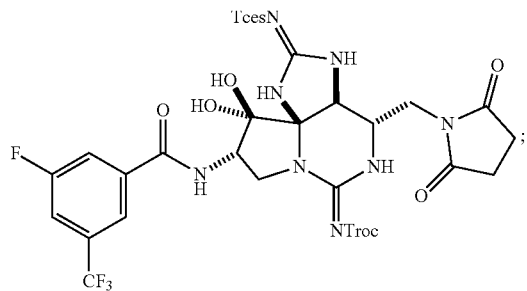
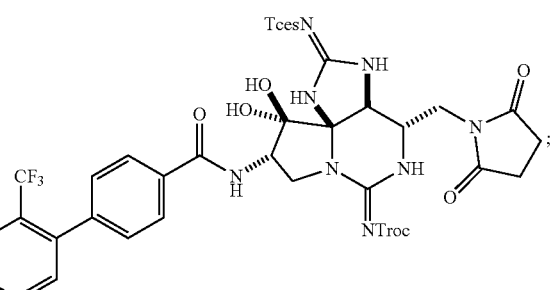
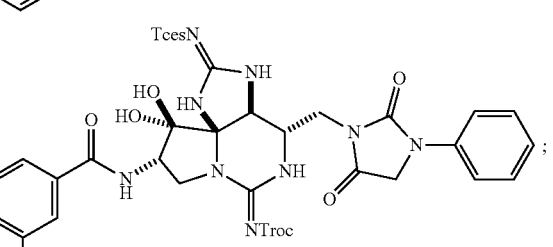
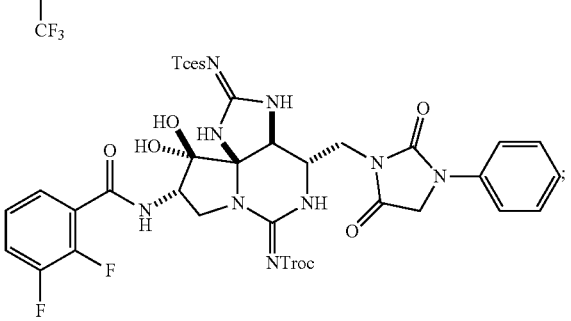
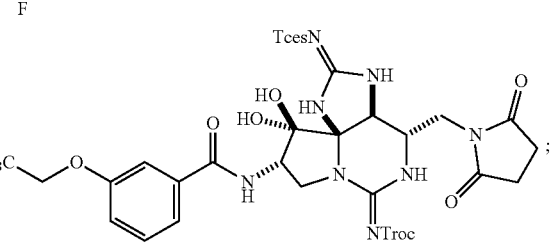
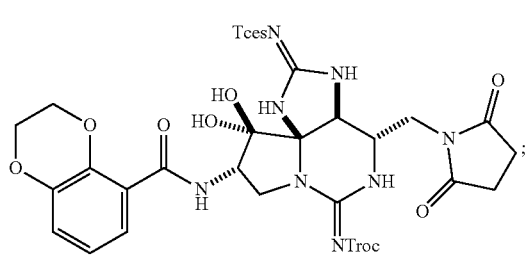

25
-continued
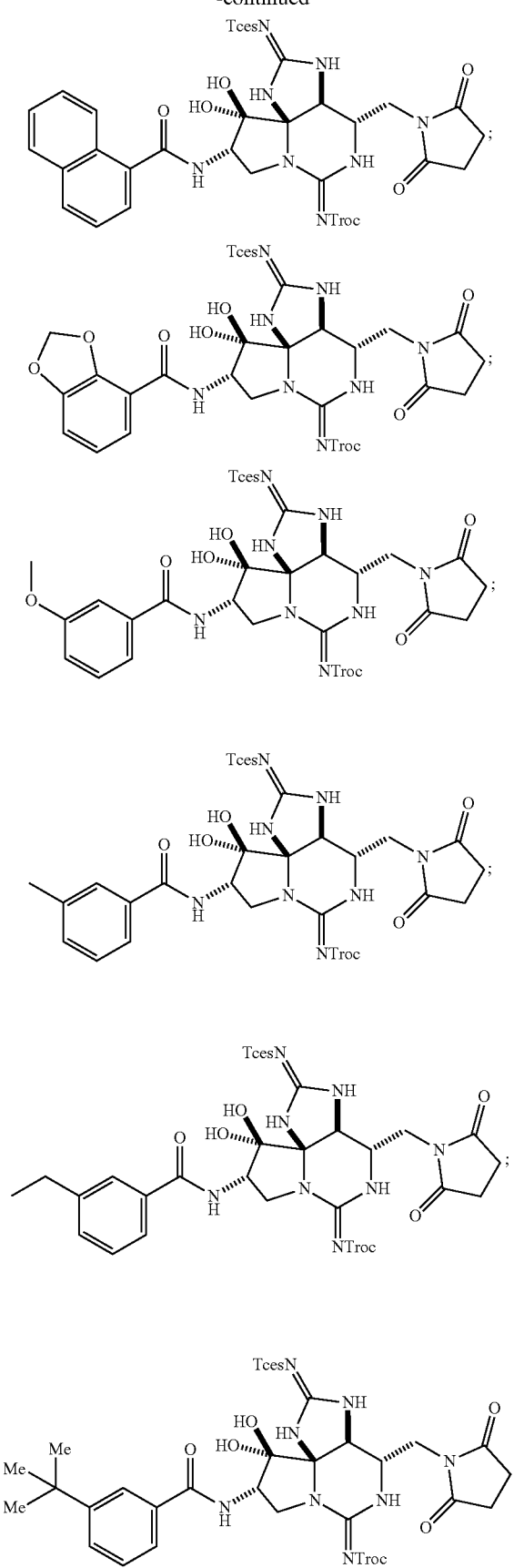
26
-continued
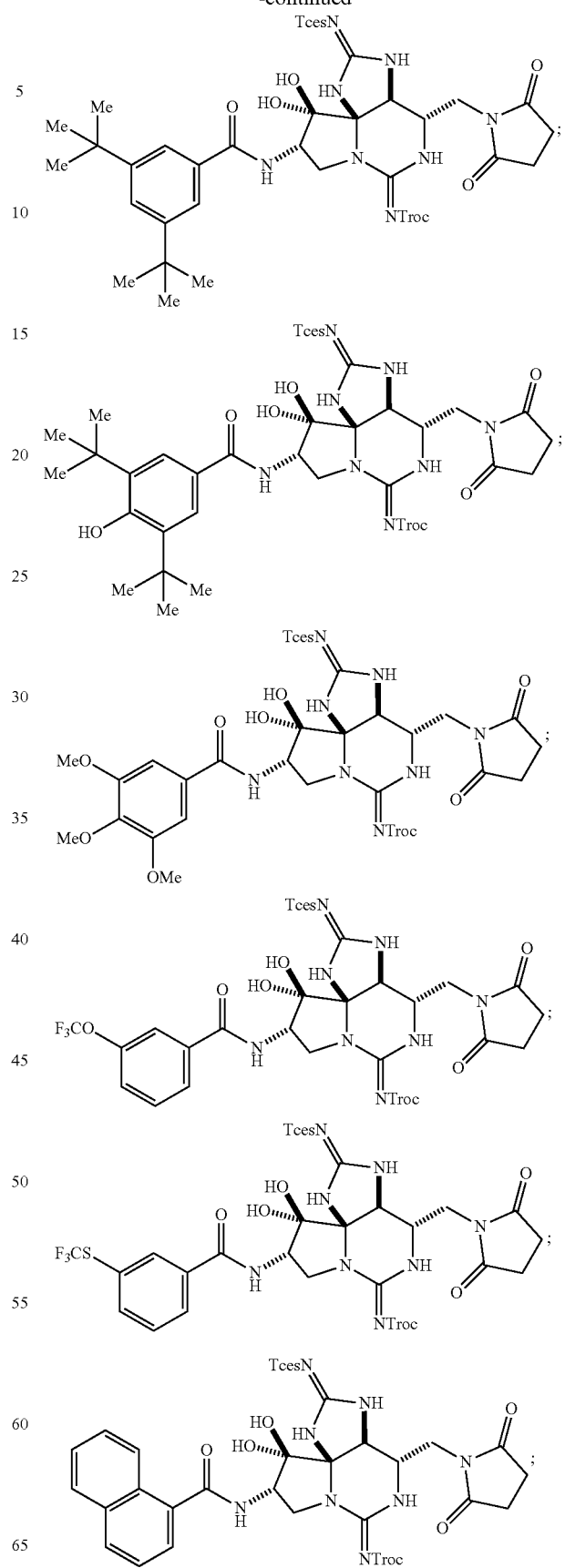

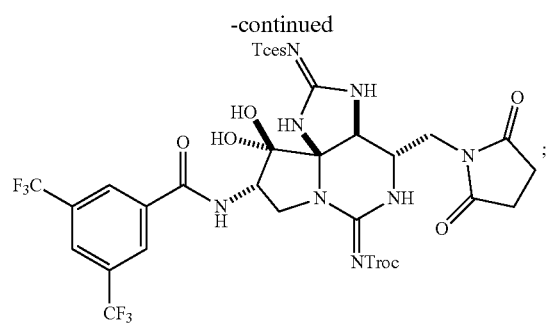
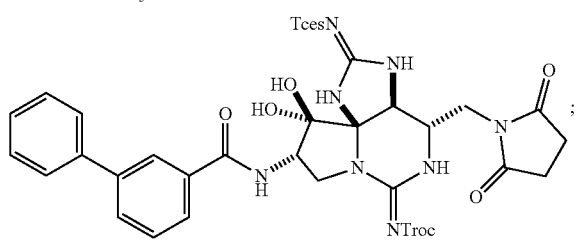
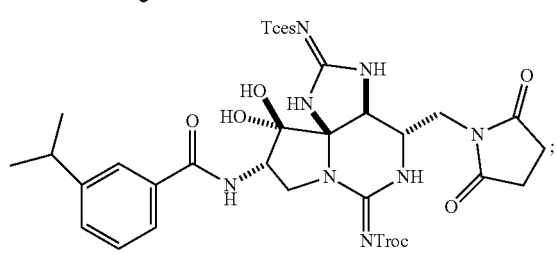
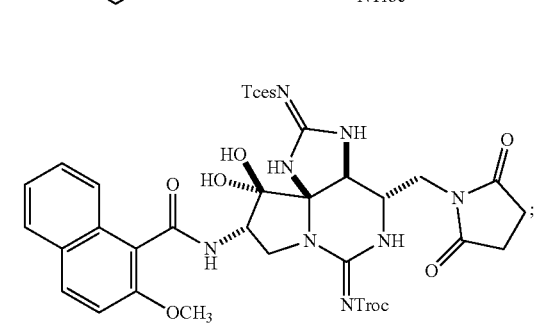
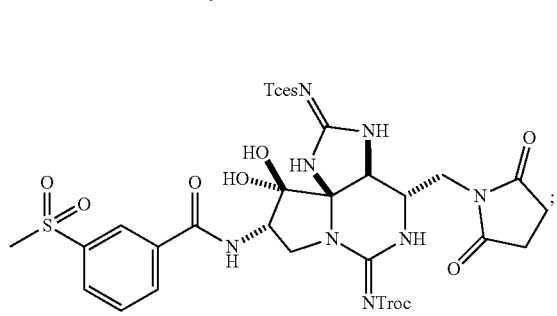
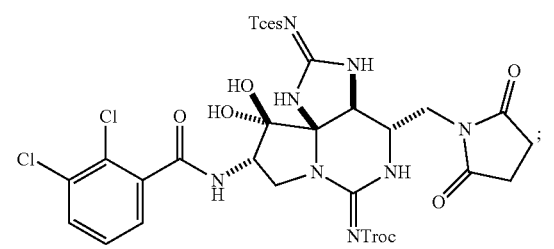
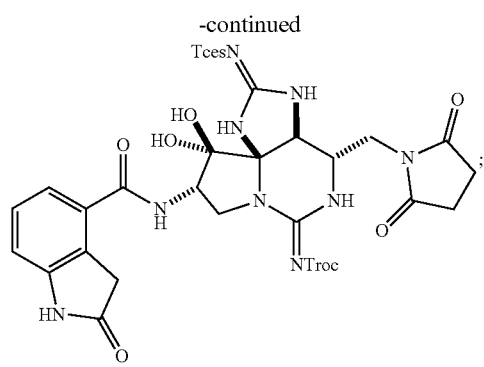
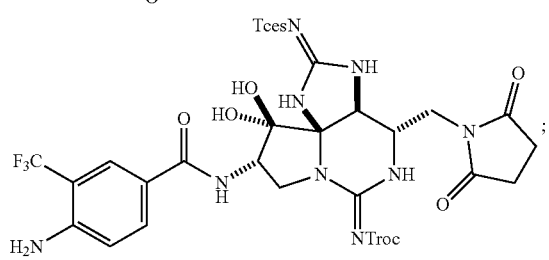
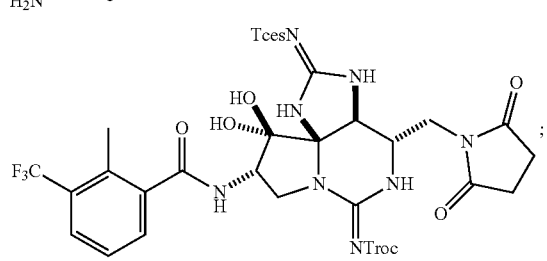
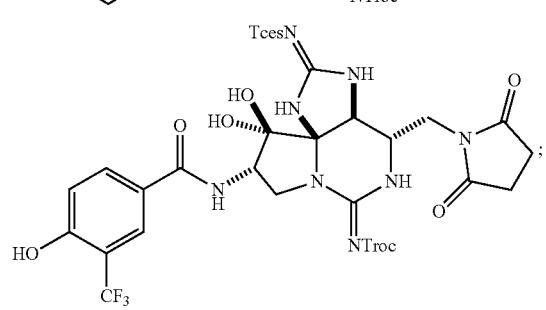
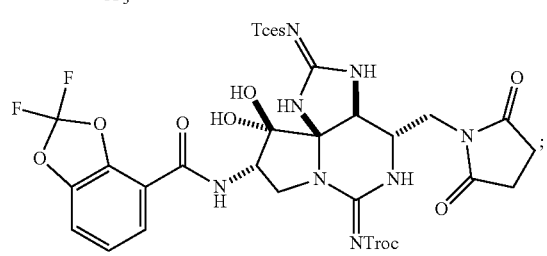
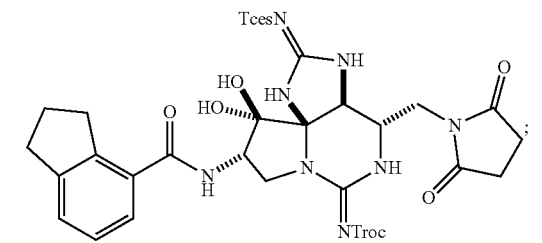

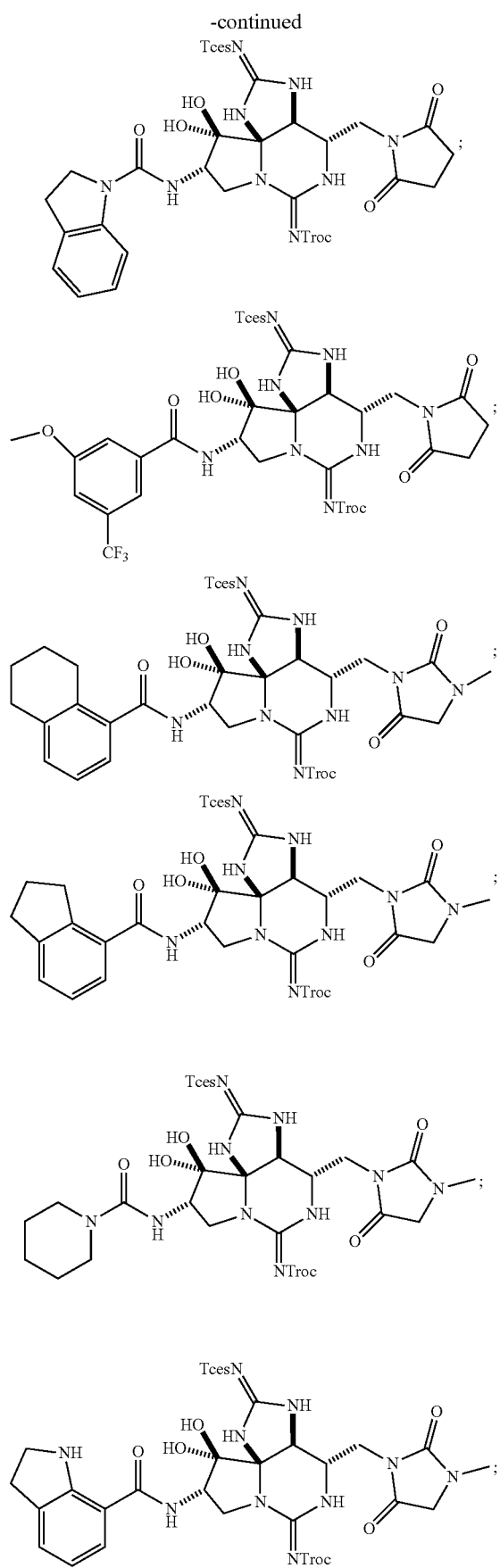
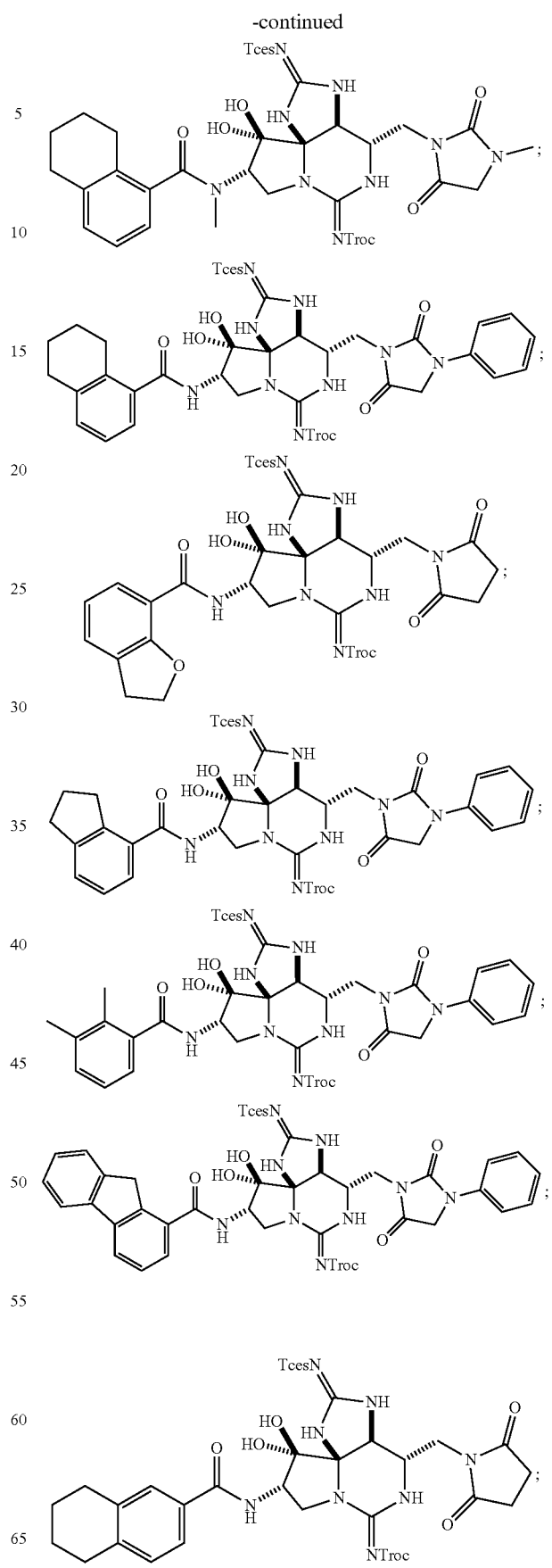

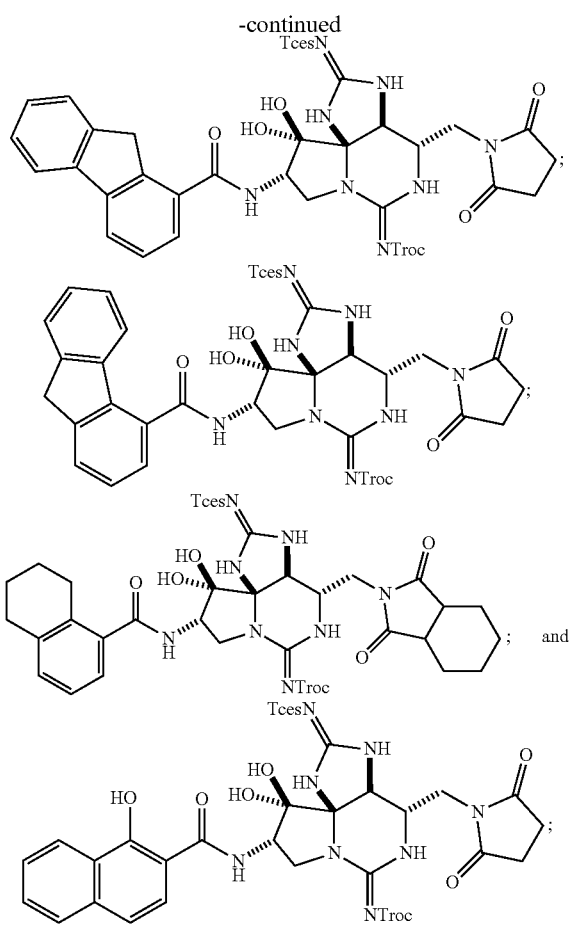

or a salt thereof.

In another aspect, provided herein is a compound of Formula Xe-P

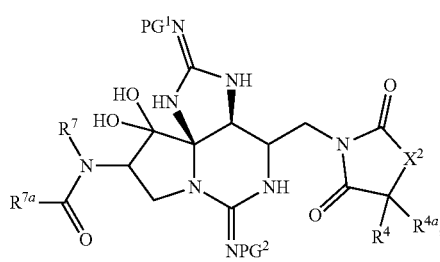

Xe-P or a salt thereof, where
PG$^1$ is a nitrogen-protecting group;
PG$^2$ is a nitrogen-protecting group;
X$^2$ is —C(R$^4$)(R$^{4a}$)— or —N(R$^8$)—;
each R$^4$ and R$^{4a}$ is independently hydrogen or C$_{1-6}$alkyl;
R$^7$ is hydrogen or C$_{1-6}$alkyl;
R$^{7a}$ is aryl optionally substituted with 1, 2, 3, or 4 R$^{7b}$;
heterocyclic optionally substituted with 1, 2, 3, or 4 R$^{7b}$;
or biphenyl optionally substituted with 1, 2, 3, or 4 R$^{7b}$;
each R$^{7b}$, when present, is independently halo, C$_{1-6}$alkyl, halo-C$_{1-6}$alkyl, aryl-C$_{1-6}$alkyl, hydroxy, C$_{1-6}$alkoxy, halo-C$_{1-6}$alkoxy, aryloxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, —C(O)(heterocycloalkyl), or cyano; where the aryl in aryloxy and aryl-C$_{1-6}$alkyl are optionally substituted with 1, 2, or 3 groups independently selected from C$_{1-6}$alkyl, halo, and halo-C$_{1-6}$alkyl; and R$^8$ is hydrogen; C$_{1-6}$alkyl; or phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano;

provided that the compound is not selected from Group B:

Group B.

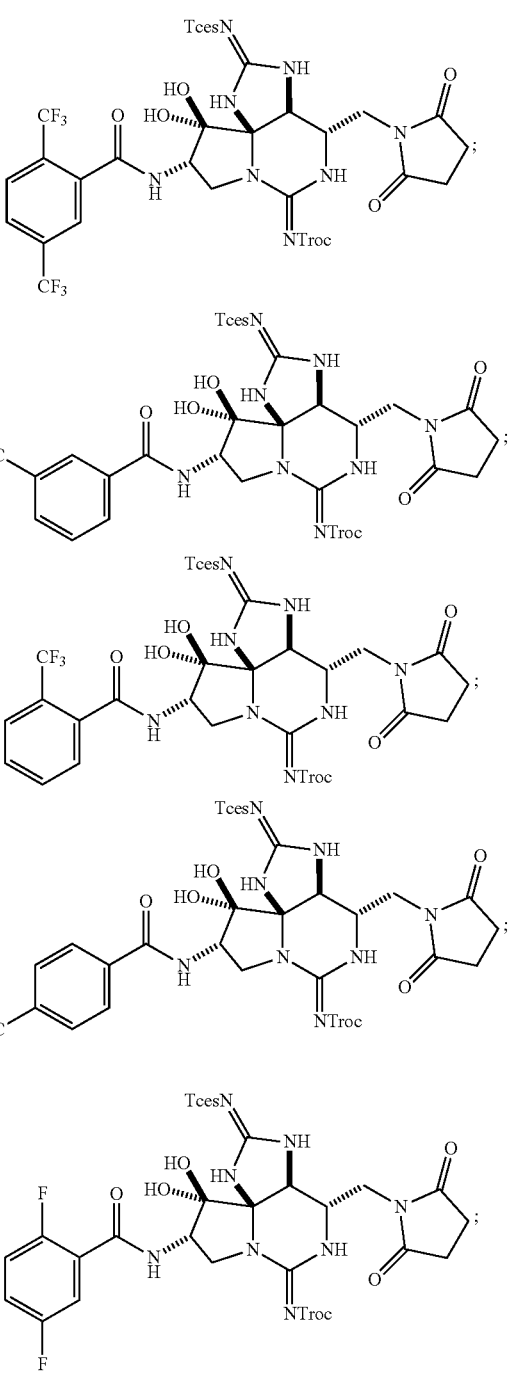

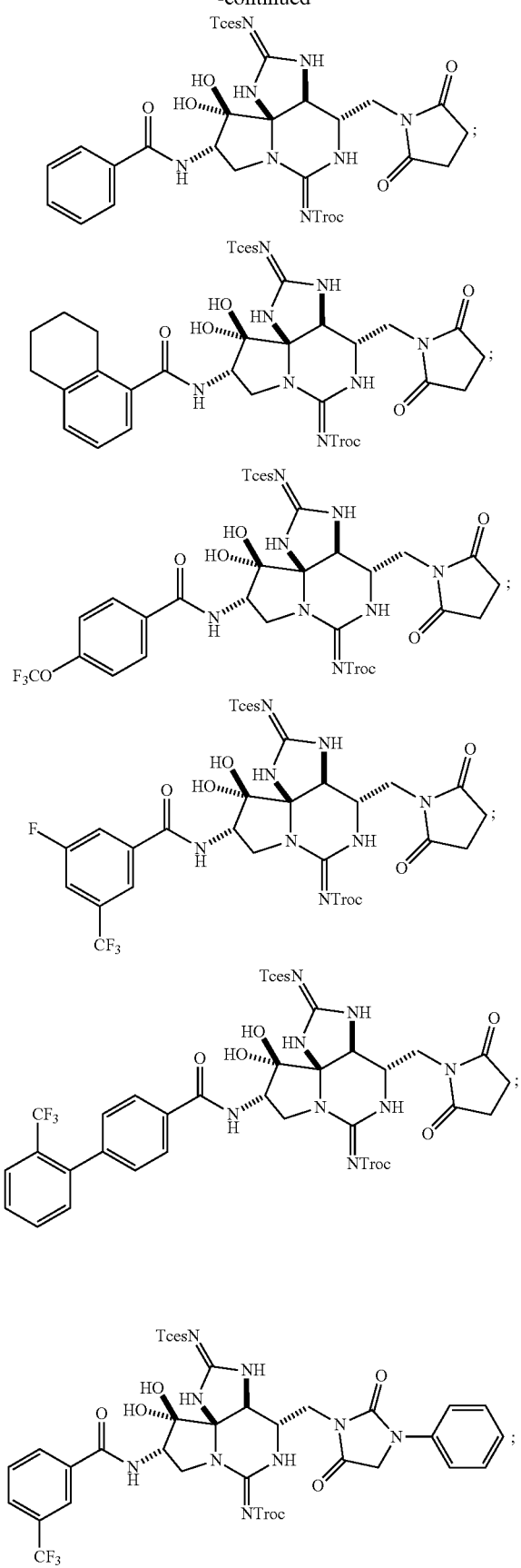
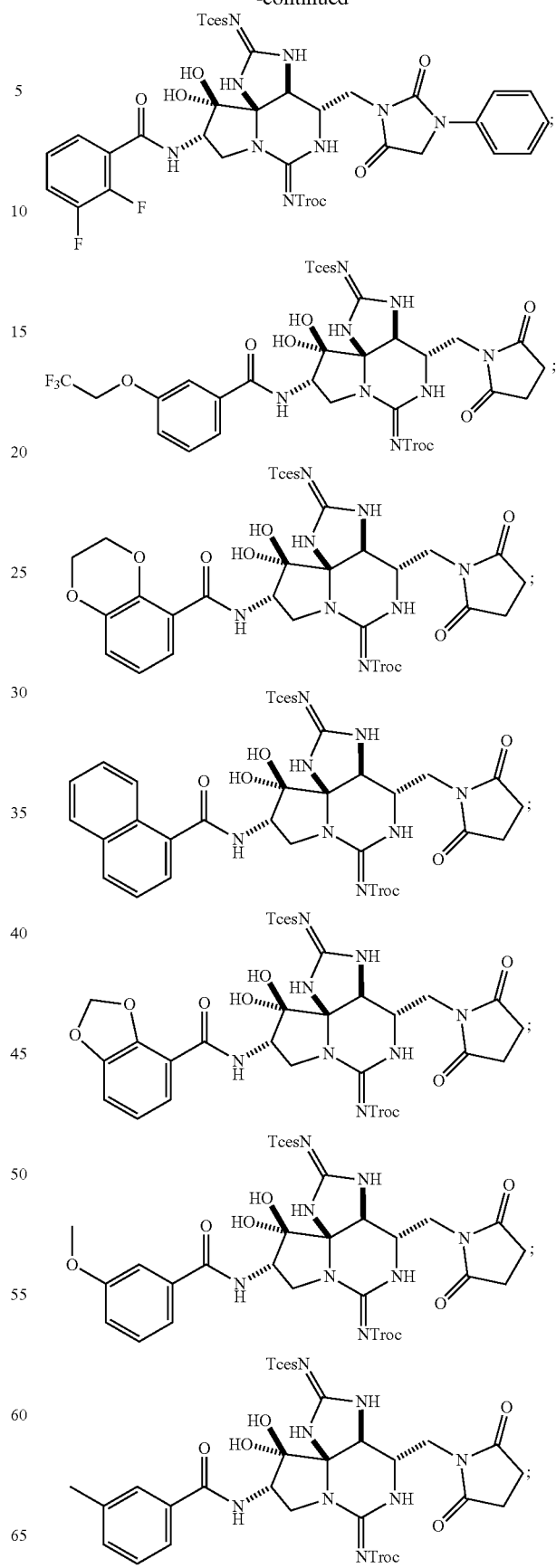

35
-continued
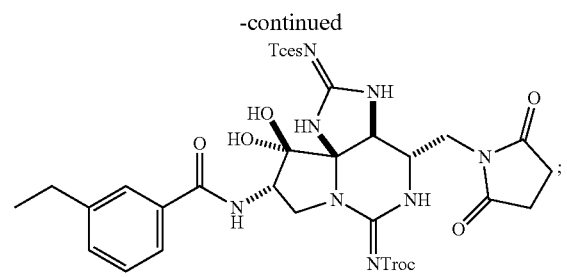
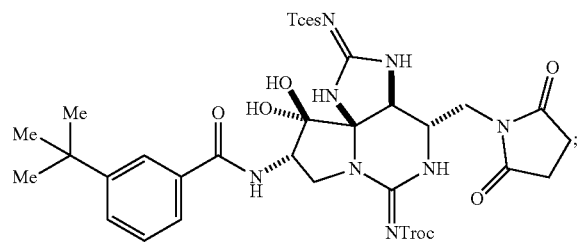
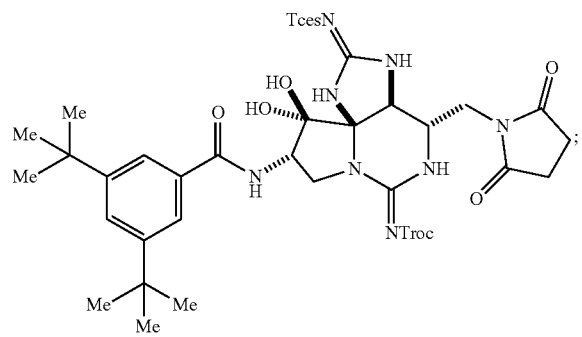
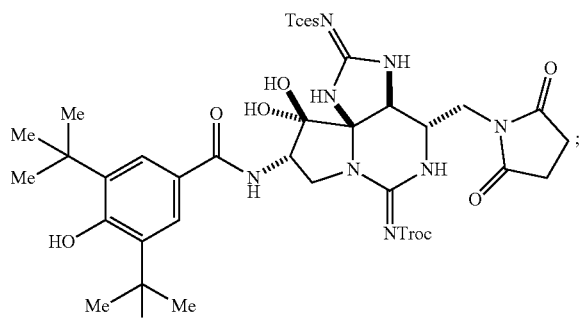
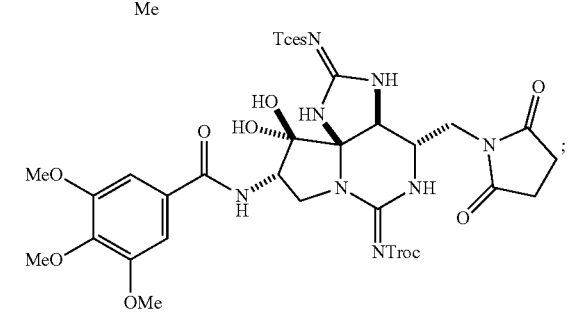
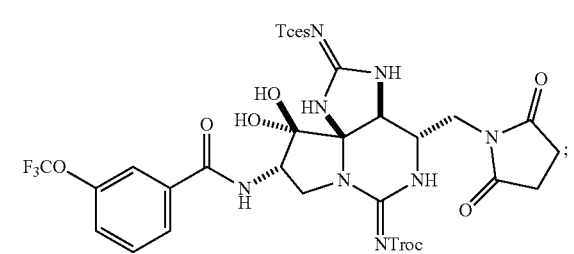
36
-continued
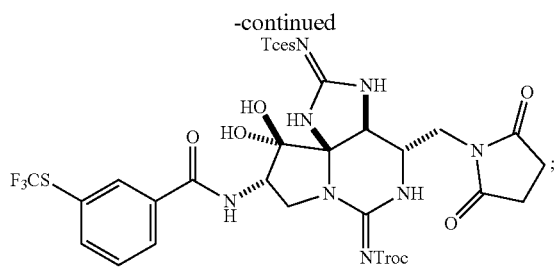
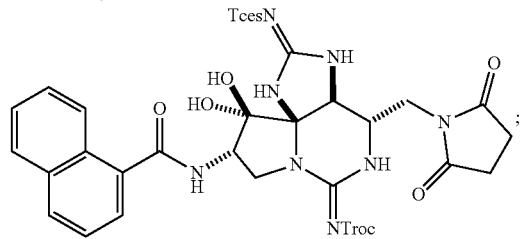
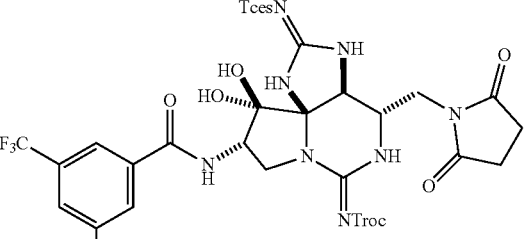
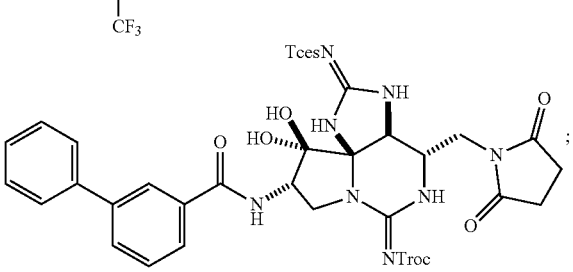
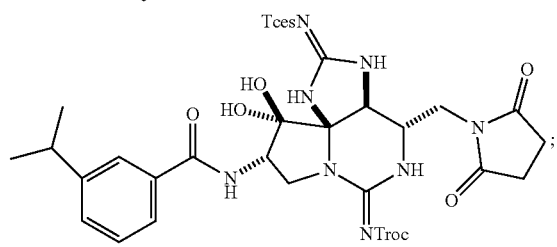
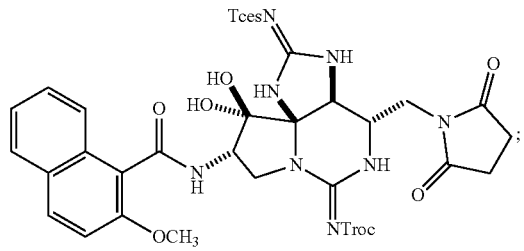
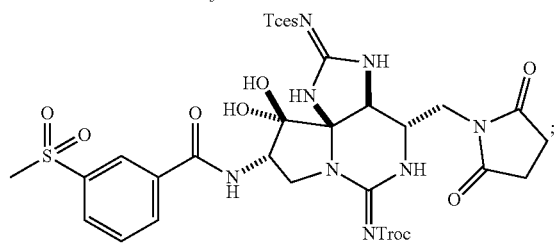

-continued
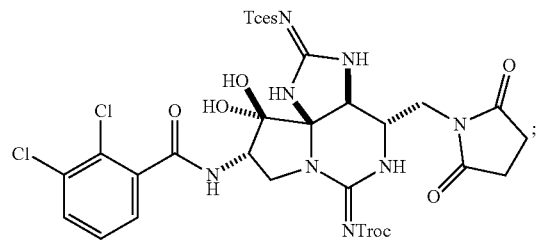
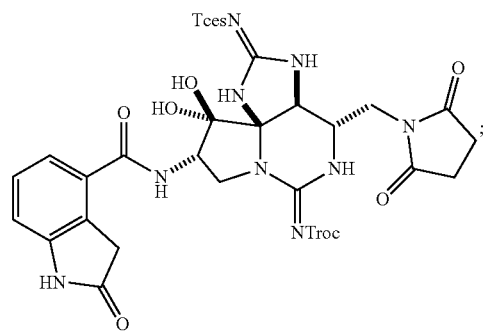
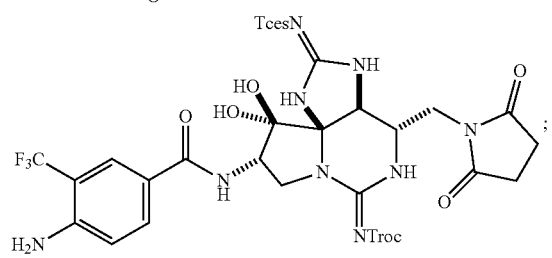
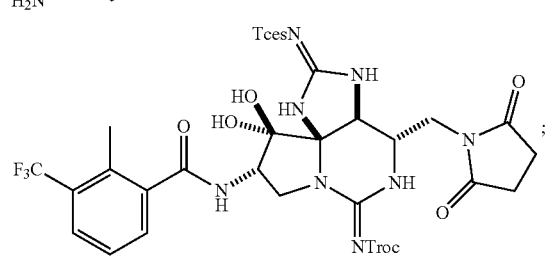
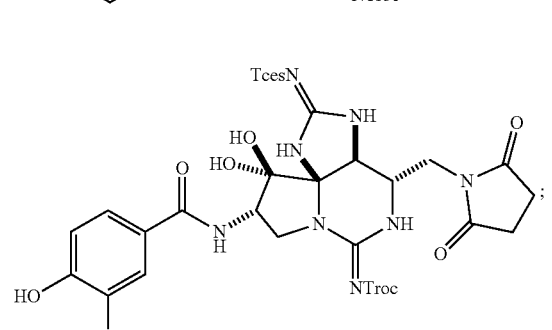
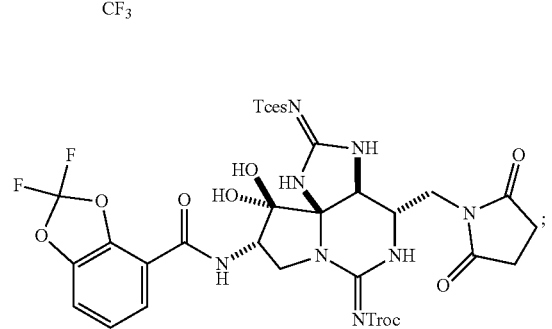
-continued
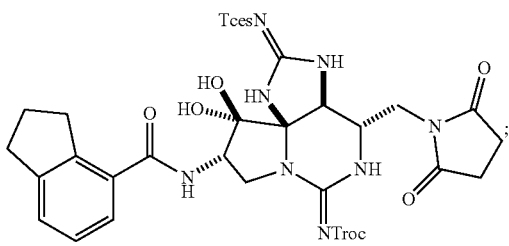
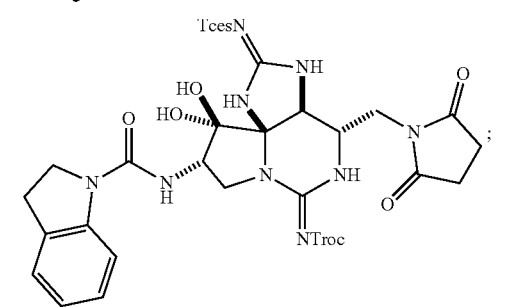
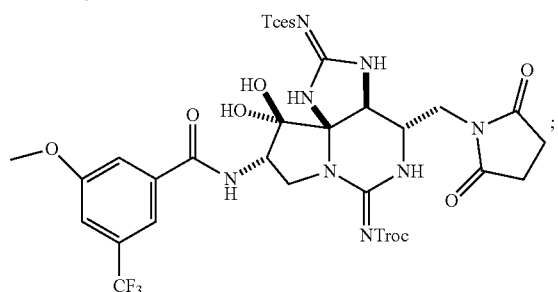
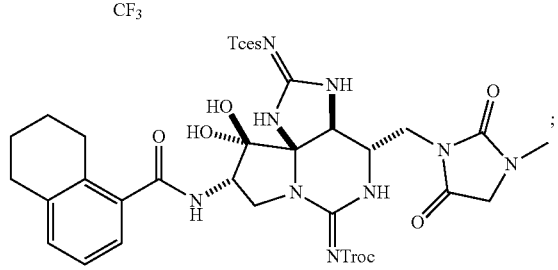
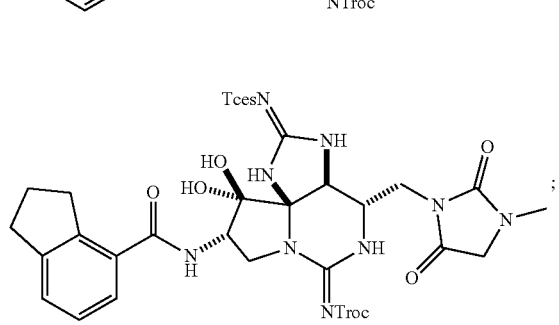
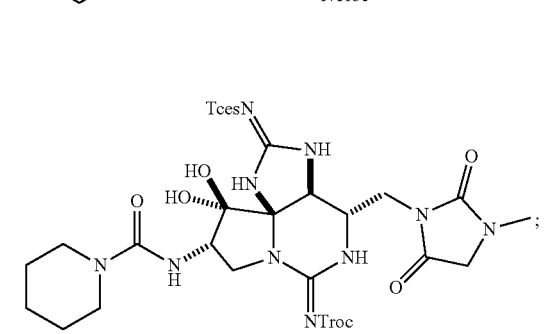

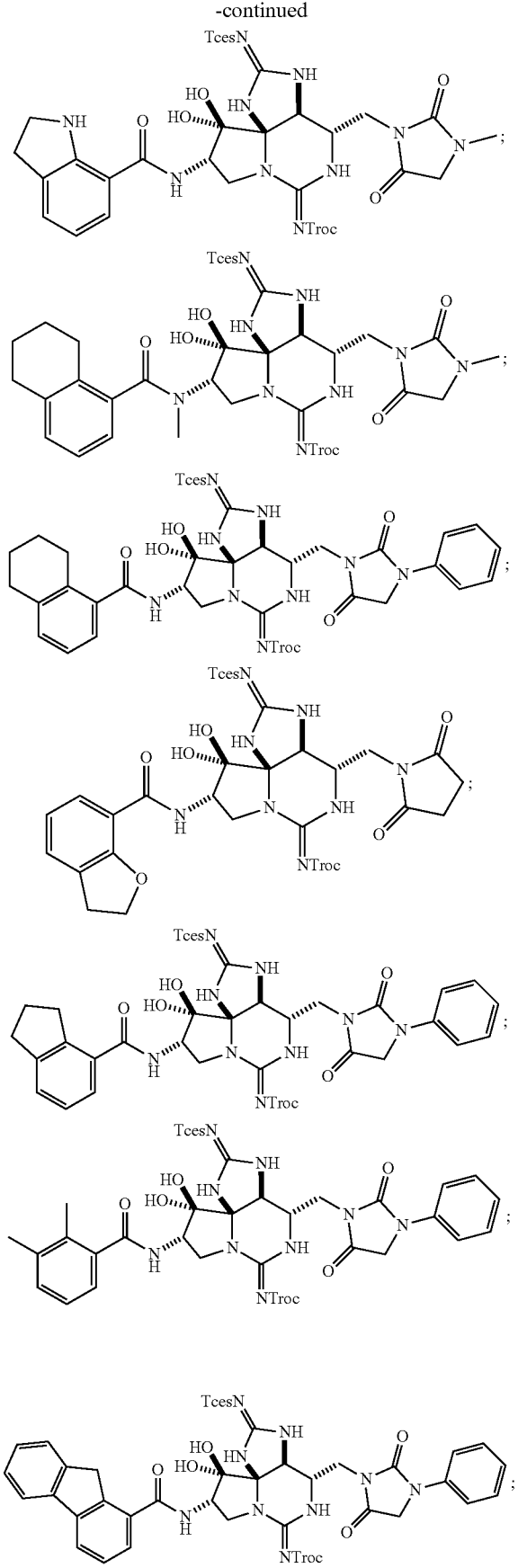
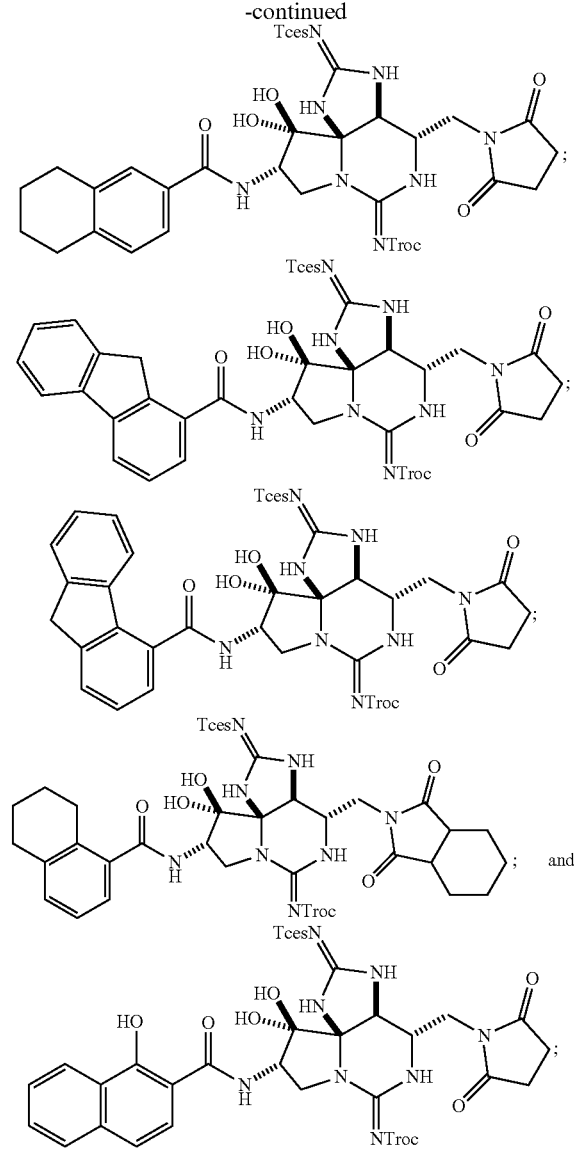
or a salt thereof.
In another aspect, provided is a method of preparing a compound of Formula (I) comprising
a) deprotecting a compound of Formula Xe
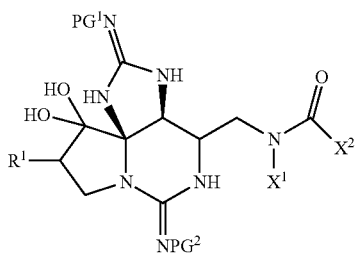
or a salt thereof, where
PG$^1$ is a nitrogen-protecting group;
PG$^2$ is a nitrogen-protecting group;
X$^2$ is —C(R$^4$)(R$^{4a}$)— or —N(R$^8$)—;

each $R^4$ and $R^{4a}$ is independently hydrogen or $C_{1-6}$alkyl;
$R^7$ is hydrogen or $C_{1-6}$alkyl;
$R^{7a}$ is aryl optionally substituted with 1, 2, 3, or 4 $R^{7b}$; heterocyclic optionally substituted with 1, 2, 3, or 4 $R^{7b}$; or biphenyl optionally substituted with 1, 2, 3, or 4 $R^{7b}$;
each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and
$R^8$ is hydrogen; $C_{1-6}$alkyl; carboxy-$C_{1-6}$-alkyl; halo-$C_{1-6}$-alkyl; hydroxy-$C_{1-6}$-alkyl; $C_3$-$C_8$-cycloalkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano;
provided that the compound is not selected from Group B, or a salt thereof, as described herein, to yield a compound of Formula I; and
b) optionally isolating the compound of Formula I.

In another aspect, provided is a method of preparing a compound of Formula (I) or (I-P) comprising
a) deprotecting a compound of Formula Xe or a salt thereof, where
$PG^1$ is a nitrogen-protecting group;
$PG^2$ is a nitrogen-protecting group;
$X^2$ is —C($R^4$)($R^{4a}$)— or —N($R^8$)—;
each $R^4$ and $R^{4a}$ is independently hydrogen or $C_{1-6}$alkyl;
$R^7$ is hydrogen or $C_{1-6}$alkyl;
$R^{7a}$ is aryl optionally substituted with 1, 2, 3, or 4 $R^{7b}$; heterocyclic optionally substituted with 1, 2, 3, or 4 $R^{7b}$; or biphenyl optionally substituted with 1, 2, 3, or 4 $R^{7b}$;
each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and
$R^8$ is hydrogen; $C_{1-6}$alkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano;
provided that the compound is not selected from Group B, or a salt thereof, as described herein, to yield a compound of Formula I; and
b) optionally isolating the compound of Formula I.

DESCRIPTION OF EXEMPLARY EMBODIMENTS

Provided herein are compounds, pharmaceutical compositions comprising the compounds, and methods of using the compounds and compositions in the treatment of pain and/or conditions modulated by voltage-gated sodium channels. The compounds are 11,13-modified saxitoxins. Also provided herein are methods of treating pain in a mammal comprising administering a therapeutically or prophylactically effective amount of a 11,13-modified saxitoxin or composition to a mammal. In an embodiment, the mammal is a human.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being substituted, the groups in the list of substituents are themselves unsubstituted. For example, a substituted alkyl group can be substituted, for example, with a cycloalkyl group, and the cycloalkyl group is not further substituted unless specified otherwise.

Reference to "about" a value or parameter herein includes (and describes) variations that are directed to that value or parameter per se. For example, description referring to "about X" includes description of "X". As used herein, and unless otherwise specified, the terms "about" and "approximately," when used in connection with temperatures, doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

The terms "a" or "an," as used in herein means one or more, unless context clearly dictates otherwise.

The term "alkyl," as used herein, unless otherwise specified, refers to a saturated straight or branched hydrocarbon. In some or any embodiments, the alkyl group is a primary, secondary, or tertiary hydrocarbon. In some or any embodiments, the alkyl group includes one to ten carbon atoms, i.e., $C_1$ to $C_{10}$ alkyl. In some or any embodiments, the alkyl is a $C_{1-6}$alkyl. In some or any embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "alkoxy" as used herein, and unless otherwise specified, refers to the group —OR' where R' is alkyl. Alkoxy groups include, in some or any embodiments, methoxy, ethoxy, n-propoxy, isopropoxy, n-butoxy, tertbutoxy, sec-butoxy, n-pentoxy, n-hexyloxy, 1,2-dimethylbutoxy, and the like.

The term "alkylthio" as used herein, and unless otherwise specified, refers to the group —SR' where R' is $C_{1-10}$alkyl. In some or any embodiments, alkylthio is $C_{1-6}$alkylthio. In some or any embodiments, alkylthio is methylthio.

The term "alkylsulfinyl" as used herein, and unless otherwise specified, refers to the group —S(O)R' where R' is $C_{1-10}$alkyl. In some or any embodiments, the alkylsulfinyl is $C_{1-6}$alkylsulfinyl.

The term "alkylsulfonyl" as used herein, and unless otherwise specified, refers to the group —S(O)$_2$R' where R' is $C_{1-10}$alkyl. In some or any embodiments, the alkylsulfonyl is $C_{1-6}$alkylsulfonyl.

The term "amino" means -NH$_2$.

The term "alkylamino," as used herein, and unless otherwise specified, refers to the group —NHR' where R' is $C_{1-10}$alkyl, as defined herein. In some or any embodiments, the alkylamino is $C_{1-6}$alkylamino.

The term "dialkylamino," as used herein, and unless otherwise specified, refers to the group —NR'R' where each R' is independently $C_{1-10}$alkyl, as defined herein. In some or any embodiments, the dialkylamino is di-$C_{1-6}$alkylamino.

The term "aryl," as used herein, and unless otherwise specified, refers to a monovalent $C_6$-$C_{15}$ carbocyclic ring system which comprises at least one aromatic ring wherein the aryl ring system is mono, di, or tricyclic. The aryl may be attached to the main structure through any of its rings, i.e. any aromatic or nonaromatic ring. In some or any embodiments, the aryl group may be a bridged (where chemically feasible) or non-bridged, spirocyclic (where chemically feasible) or not spirocyclic, and/or fused or not fused multicyclic group. In some or any embodiments, aryl is phenyl, naphthyl, bicyclo[4.2.0]octa-1,3,5-trienyl, indanyl, fluorenyl, 6,7,8,9-tetrahydro-5H-benzo[7]annulenyl,

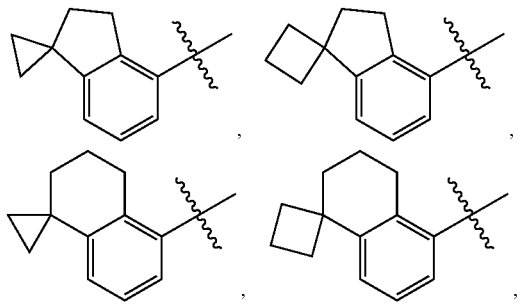

or tetrahydronaphthyl. When aryl is substituted, it can be substituted on any ring, i.e. on any aromatic or nonaromatic ring comprised by aryl. In some or any embodiments, aryl is phenyl, naphthyl, tetrahydronaphthyl, fluorenyl, 6,7,8,9-tetrahydro-5H-benzo[7]annulenyl, or indanyl; each of which is optionally substituted with 1, 2, 3, or 4 groups as defined throughout the specification, including in some or any embodiments with group(s) independently selected from amino, hydroxy, halo, halo-$C_{1-6}$alkoxy, $C_{1-6}$alkoxy, $C_{1-6}$alkyl, halo-$C_{1-6}$alkyl, $C_{1-6}$alkylthio, $C_{1-6}$alkylsulfonyl, and phenyl.

The term "biphenyl," as used herein, unless otherwise specified, refers to a phenyl group substituted with a second phenyl group. When the biphenyl is "optionally substituted," the optional substituent(s) can be substituted on either of the phenyl rings.

The term "aryloxy," as used herein, and unless otherwise specified, refers to an —OR group where R is aryl, as defined herein.

The term "arylalkyl," as used herein, and unless otherwise specified refers to an alkyl group substituted with one or two aryl groups as defined herein, where the alkyl group is the point of attachment to the remainder of the molecule. In some embodiments, aralkyl is phenylmethyl, phenyleth-1-yl, phenyleth-2-yl, diphenylmethyl, 2,2-diphenylethyl, 3,3-diphenylpropyl, or 3-phenylpropyl; each of which is optionally substituted on the ring with 1, 2, 3, or 4 groups as defined throughout the specification.

The term "carboxy-$C_{1-6}$alkyl," as used herein, refers to a $C_{1-6}$alkyl group, as defined herein, substituted with one or two —C(O)OH groups. In some embodiments, carboxy-$C_{1-6}$alkyl is —CH$_2$C(O)OH, —CH$_2$CH$_2$C(O)OH, or —CH$_2$CH$_2$CH$_2$C(O)OH. In some embodiments, carboxy-$C_{1-6}$alkyl is —CH$_2$C(O)OH.

The term "$C_3$-$C_8$-cycloalkyl," as used herein, refers to a monovalent, saturated, monocyclic hydrocarbon. In some or any embodiments, the cycloalkyl group includes three to six carbon atoms, i.e., $C_3$ to $C_6$ cycloalkyl. In some or any embodiments, the cycloalkyl has 3, 4, or 5 ($C_{3-5}$); 3 or 4 ($C_{3-4}$); 3 ($C_3$); 4 ($C_4$); or 5 ($C_5$) carbon atoms. In some or any embodiments, the cycloalkyl group is cyclopropyl, cyclobutyl, cyclopentyl, or cyclohexyl. In some or any embodiments, the cycloalkyl group is cyclopropyl, cyclobutyl, or cyclopentyl. In some or any embodiments, the cycloalkyl group is cyclopropyl. In some or any embodiments, the cycloalkyl group is cyclobutyl. In some or any embodiments, the cycloalkyl group is cyclopentyl.

The term "cycloalkylene," as used herein, and unless otherwise specified, refers to a divalent, saturated, monocyclic hydrocarbon. In some or any embodiments, the cycloalkylene group includes three to six carbon atoms, i.e., $C_3$ to $C_6$ cycloalkylene. In some or any embodiments, the cycloalkylene has 3, 4, or 5 ($C_{3-5}$); 3 or 4 ($C_{3-4}$); 3 ($C_3$); 4 ($C_4$); or 5 ($C_5$) carbon atoms. In some or any embodiments, the cycloalkylene group is cycloprop-diyl, cyclobut-diyl, cyclopent-diyl, or cyclohex-diyl. In some or any embodiments, the cycloalkylene group is cycloprop-diyl, cyclobut-diyl, or cyclopent-diyl. In some or any embodiments, the cycloalkylene group is cycloprop-diyl. In some or any embodiments, the cycloalkylene group is cyclobut-diyl. In some or any embodiments, the cycloalkylene group is cyclopent-diyl.

The term "haloalkyl," as used herein, and unless otherwise specified, refers to an alkyl group substituted with 1, 2, 3, 4, or 5 halo groups. In some or any embodiments, the haloalkyl is a halo-$C_{1-6}$alkyl. In some or any embodiments, the haloalkyl is —CF$_3$, —CH$_2$F, —CHF$_2$, or —CH$_2$CF$_3$.

The term "haloalkylthio," as used herein, and unless otherwise specified, refers to an —SR group where R is halo-$C_{1-10}$alkyl as defined herein. In some or any embodiments, the haloalkylthio is a halo-$C_{1-6}$alkylthio.

The term "haloalkoxy," as used herein, and unless otherwise specified, refers to an —OR group where R is halo-$C_{1-10}$alkyl as defined herein. In some or any embodiments, the haloalkoxy is a halo-$C_{1-6}$alkoxy.

The term "haloalkylsulfinyl," as used herein, and unless otherwise specified, refers to an —S(O)R group where R is halo-$C_{1-10}$alkyl as defined herein. In some or any embodiments, the haloalkylsulfinyl is a halo-$C_{1-6}$alkylsulfinyl.

The term "haloalkylsulfonyl," as used herein, and unless otherwise specified, refers to an —S(O)$_2$R group where R is halo-$C_{1-10}$alkyl as defined herein. In some or any embodiments, the haloalkylsulfonyl is a halo-$C_{1-6}$alkylsulfonyl.

The terms "halogen" and "halo," as used herein, and unless otherwise specified, are synonymous and refer to chloro, bromo, fluoro or iodo.

The term "heterocyclic," as used herein, and unless otherwise specified, refers to a monovalent monocyclic non-aromatic ring system and/or a multicyclic ring system that contains at least one non-aromatic ring; wherein one or more (in some or any embodiments, 1, 2, 3, or 4) of the non-aromatic monocyclic ring atoms is a heteroatom independently selected from O, S(O)$_{0-2}$, and N, and the remaining ring atoms are carbon atoms; and wherein one or more (in some or any embodiments, 1, 2, 3, or 4) of any of the ring atoms in the multicyclic ring system is a heteroatom(s) independently selected from O, S(O)$_{0-2}$, and N, and the remaining ring atoms are carbon. The term "heterocyclic" does not include fully aromatic ring(s), i.e. does not include imidazole, pyrimidine, pyridine, and the like. In some or any embodiments, the heterocyclic ring comprises one or two heteroatom(s) which are independently selected from nitrogen and oxygen. In some or any embodiments, the heterocyclic ring comprises one or two heteroatom(s) which are oxygen. In some or any embodiments, the heterocyclic ring comprises one or two heteroatom(s) which are nitrogen (where the nitrogen is substituted as described in any aspect or embodiment described herein). In some or any embodiments, heterocyclic is multicyclic and comprises one heteroatom in a non-aromatic ring, or comprises one heteroatom in an aromatic ring, or comprises two heteroatoms in an aromatic ring, or comprises two heteroatoms where one is in an aromatic ring and the other is in a non-aromatic ring. In some or any embodiments, the heterocyclic group has from 3 to 20, 3 to 15, 3 to 10, 3 to 8, 4 to 7, or 5 to 6 ring atoms. In some or any embodiments, the heterocyclic is a monocyclic, bicyclic, tricyclic, or tetracyclic ring system. In some or any embodiments, the heterocyclic group may be a bridged or non-bridged, spirocyclic or not spirocyclic, and/or fused or not fused multicyclic group. One or more of the nitrogen and sulfur atoms may be optionally oxidized, one or more of the nitrogen atoms may be optionally quaternized, one or more of the carbon atoms may be optionally replaced with

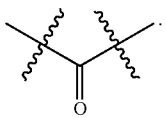 [SMILES: *C(*)=O]

Some rings may be partially or fully saturated, or aromatic provided that heterocyclic is not fully aromatic. The monocyclic and multicyclic heterocyclic rings may be attached to the main structure at any heteroatom or carbon atom which results in a stable compound. The multicyclic heterocyclic may be attached to the main structure through any of its rings, including any aromatic or nonaromatic ring, regardless of whether the ring contains a heteroatom. In some or any embodiments, heterocyclic is "heterocycloalkyl" which is 1) a saturated or partially unsaturated (but not aromatic) monovalent monocyclic group which contains at least one ring heteroatom, as described herein, or 2) a saturated or partially unsaturated (but not aromatic) monovalent bi- or tri-cyclic group in which at least one ring contains at least one heteroatom as described herein. When heterocyclic and heterocycloalkyl are substituted, they can be substituted on any ring, i.e. on any aromatic or nonaromatic ring comprised by heterocyclic and heterocycloalkyl. In some or any embodiments, such heterocyclic includes, but are not limited to, azepinyl, benzodioxanyl, benzodioxolyl, 3,4-dihydro-2H-benzo[b][1,4]oxazinyl, 3,4-dihydro-2H-benzo[b][1,4] dioxepinyl, 1,3-dihydroisobenzofuranyl, benzofuranonyl, benzopyranonyl, benzopyranyl, dihydrobenzofuranyl,

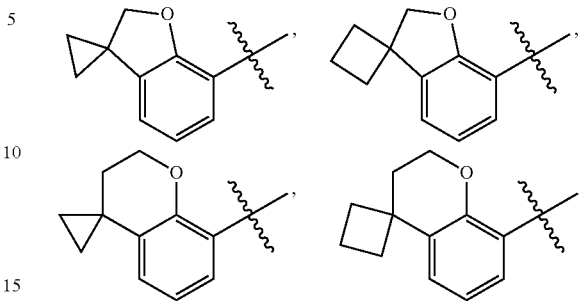

benzotetrahydrothienyl, 2,2-dioxo-1,3-dihydrobenzo[c]thienyl, benzothiopyranyl, benzoxazinyl, (3-carbolinyl, chromanyl, chromonyl, cinnolinyl, coumarinyl, decahydroquinolinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isochromanyl, isocoumarinyl, isoindolinyl, 1-oxo-isoindolinyl, 1,3-dioxo-isoindolinyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidonyl, pyrazolidinyl, pyrazolinyl, pyrrolidinyl, pyrrolinyl, 2-oxopyrrolidinyl, 2,5-dioxopyrrolidinyl, quinuclidinyl, tetrahydrofuryl, tetrahydroisoquinolinyl, tetrahydropyranyl, tetrahydrothienyl, thiamorpholinyl, thiomorpholinyl, 3,5-dioxo-thiomorpholinyl, thiazolidinyl, 2,4-dioxo-thiazolidinyl, tetrahydroquinolinyl, phenothiazinyl, phenoxazinyl, xanthenyl, and 1,3,5-trithianyl. In some or any embodiments, heterocyclic is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, 3, or 4 groups as defined throughout the specification, including in some or any embodiments with group(s) independently selected from halo, alkyl, and phenyl.

The term "hydroxy-C$_{1-6}$alkyl," as used herein refers to an alkyl group, as defined herein substituted with one or two hydroxy groups. In some embodiments, the "hydroxy-C$_{1-6}$alkyl" is —CH$_2$CH$_2$OH, —CH$_2$CH$_2$CH$_2$OH, or —CH$_2$CH(OH)CH$_2$OH.

The term "protecting group," as used herein, and unless otherwise specified, refers to a group that is added to an oxygen, nitrogen or phosphorus atom to prevent its further reaction or for other purposes. A wide variety of oxygen and nitrogen protecting groups are known to those skilled in the art of organic synthesis. (See for example those described in Greene, et al., Protective Groups in Organic Synthesis, John Wiley and Sons, Fourth Edition, 2006, hereby incorporated by reference.) In some or any embodiments, a nitrogen-protecting group (e.g. for PG$^1$ and PG$^2$) is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl). In some or any embodiments, an oxygen-protecting group (e.g. for $X^1$) is methoxymethyl (MOM), ethoxyethyl, methoxyethoxymethyl, tetrahydrofuranyl, tetrahydropyranyl, methyl, tert-butyl, allyl, benzyl, trimethylsilyl, triethylsilyl, triisopropylsilyl, tert-butyldimethylsilyl, tert-butyldiphenylsilyl, acetyl, pivalyl, benzoyl, dimethoxytrityl, trityl, methoxytrityl, p-methoxybenzyl, or methylthiomethyl.

The term "pharmaceutically acceptable salt," as used herein, and unless otherwise specified, refers to any salt of a compound provided herein which retains its biological properties and which is not toxic or otherwise desirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; and (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, omithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, in some or any embodiments, and without limitation, sodium, potassium, calcium, magnesium, ammonium, tetraalkylammonium salts and the like. When the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" stereoisomers with respect to a composition refers to a composition that includes at least 85 or 90% by weight, in some or any embodiments 95%, 98%, 99% or 100% by weight, of a designated stereoisomer of a compound in the composition. In some or any embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In some or any embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, the term "local anesthetic" means a drug which provides local numbness or pain relief. In some or any embodiments, local anesthetic includes aminoacylanilide compounds (in some or any embodiments, lidocaine, prilocaine, bupivacaine, ropivacaine, and mepivacaine) and related local anesthetic compounds having various substituents on the ring system or amine nitrogen; aminoalkyl benzoate compounds (in some or any embodiments, procaine, chloroprocaine, propoxycaine, hexylcaine, tetracaine, cyclomethycaine, benoxinate, butacaine, and proparacaine) and related local anesthetic compounds; cocaine; amino carbonate compounds (in some or any embodiments, diperodon); N-phenylamidine compounds (in some or any embodiments, phenacaine); N-aminoalkyl amide compounds (in some or any embodiments, dibucaine); aminoketone compounds (in some or any embodiments, falicaine and dyclonine); and amino ether compounds (in some or any embodiments, pramoxine and dimethisoquien).

As used herein, "alkyl," "cycloalkyl," "aryl," "alkoxy," "heterocycloalkyl," and "heterocyclic" groups optionally comprise deuterium at one or more positions where hydrogen atoms are present, and wherein the deuterium composition of the atom or atoms is other than the natural isotopic composition.

Also as used herein, "alkyl," "cycloalkyl," "aryl," "alkoxy," "heterocycloalkyl," "heterocyclic" groups optionally comprise carbon-13 at an amount other than the natural isotopic composition.

As used herein, and unless otherwise specified, the term "$IC_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and in some or any embodiments, a human. In some or any embodiments, the subject is a farm animal (e.g., a horse, a cow, a pig, etc.) or a pet (e.g., a dog or a cat). In some or any embodiments, the subject is a human.

As used herein, the terms "therapeutic agent" and "therapeutic agents" refer to any agent(s) which can be used in the treatment or prevention of a disorder or one or more symptoms thereof. In some or any embodiments, the term "therapeutic agent" includes a compound provided herein. In some or any embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a condition, is sufficient to effect such treatment for the condition. A "therapeutically effective amount" can vary depending on, inter alia, the compound, the condition and its severity, and the age, weight, etc., of the subject to be treated.

"Treating" or "treatment" of any condition or disorder refers, in some or any embodiments, to ameliorating a condition or disorder that exists in a subject, including prophylactically. In another embodiment, "treating" or "treatment" includes ameliorating at least one physical parameter, which may be indiscernible by the subject. In yet another embodiment, "treating" or "treatment" includes modulating the condition or disorder, either physically (e.g., stabilization of a discernible symptom) or physiologically (e.g., stabilization of a physical parameter) or both. In yet another embodiment, "treating" or "treatment" includes delaying the onset of the condition or disorder. In yet another embodiment, "treating" or "treatment" includes the reduction or elimination of either the condition (e.g. pain) or one or more symptoms (e.g. pain) of the condition (e.g. sciatica), or to retard the progression of the condition (e.g. pain) or of one or more symptoms (e.g. pain) of the condition (e.g. sciatica), or to reduce the severity of the condition (e.g. pain) or of one or more symptoms (e.g. pain) of the condition (e.g. sciatica). In yet another embodiment, "treating" or "treatment" includes administering a compound described herein prophylactically.

As used herein, the terms "prophylactic agent" and "prophylactic agents" refer to any agent(s) which can be used in the prevention of a condition or one or more symptoms thereof and/or which prevents or impedes the onset, development, progression and/or severity of a condition. In some or any embodiments, the term "prophylactic agent" includes a compound provided herein. In some or any other embodiments, the term "prophylactic agent" does not refer a compound provided herein.

As used herein, the phrase "prophylactically effective amount" refers to the amount of a therapy (e.g., prophylactic agent) which is sufficient to result in the prevention or reduction of the development, recurrence or onset of one or more symptoms associated with a condition, or to enhance or improve the prophylactic effect(s) of another therapy (e.g., another prophylactic agent).

Compounds

Provided herein are compounds that can modulate the activity of voltage-gated ion channels (e.g., voltage-gated sodium channels). The 11,13-modified saxitoxins can be formed as described herein and used for the treatment of conditions associated with voltage-gated sodium channel function. In some or any embodiments, the condition associated with voltage-gated sodium channel function is pain or is a condition associated with pain. In some or any embodiments, the condition associated with voltage-gated sodium channel function is a condition associated with pain. In some or any embodiments, the condition associated with voltage-gated sodium channel function is pain, itch, cough, epilepsy, Parkinson's disease, a mood disorder, psychosis, amyotrophic lateral sclerosis, glaucoma, ischemia, spasticity disorders and obsessive compulsive disorder. In some or any embodiments, the condition associated with voltage-gated sodium channel function is pain (in some embodiments, subacute or chronic pain). In some embodiments, the pain associated with voltage-gated sodium channel function includes pain and/or discomfort associated with dry eye syndrome, pain associated with (acute) corneal injuries or abrasions, acute ocular pain, chronic ocular pain, pain associated with corneal infections, and pain associated with surgery (in some embodiments, ocular surgery). Saxitoxin has the chemical structure provided below with selected atom numbering used herein:

(Saxitoxin)

The embodiments described herein include the recited compounds as well as a pharmaceutically acceptable salt, hydrate, solvate, stereoisomer, tautomer, or mixture thereof.

Certain multicyclic structures provided herein are drawn with one or more floating substituents. Unless provided otherwise or otherwise clear from the context, the substituent(s) may be present on any atom of the multicyclic ring, where chemically feasible and valency rules permitting. For example, in the structure:

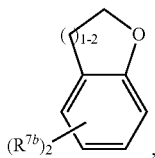

the $R^{7b}$ substituents can be on the benzo portion of the bicyclic ring or the dihydrofuranyl portion of the bicyclic ring.

The specific compounds in PCT/US2016/055050 are excluded from any of the formula or embodiments described herein.

The compounds in Group A—or a pharmaceutically acceptable salt, hydrate, solvate, stereoisomer, tautomer, or mixture thereof—are excluded from the scope of the Compound of Formula (I), (I-P), (Ia), (Ib), (Ic), and (Id) and any of the embodiments described herein.

The compounds in Group B—or a salt, pharmaceutically acceptable salt, hydrate, solvate, stereoisomer, tautomer, or mixture thereof—are excluded from the scope of the compound of formulas Xe and Xe-P and any of the embodiments described herein.

In some or any embodiments, provided is a Compound of Formula (I), where $X^2$ is —C($R^4$)($R^{4a}$)— or —N($R^8$)—;
each $R^4$ and $R^{4a}$ is independently hydrogen or $C_{1-6}$alkyl;
$R^7$ is hydrogen or $C_{1-6}$alkyl;
$R^{7a}$ is aryl optionally substituted with 1, 2, 3, or 4 $R^{7b}$; or heterocyclic optionally substituted with 1, 2, 3, or 4 $R^{7b}$;
each $R^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and
$R^8$ is hydrogen; $C_{1-6}$alkyl; carboxy-$C_{1-6}$alkyl; halo-$C_{1-6}$alkyl; hydroxy-$C_{1-6}$alkyl; $C_3$-$C_8$-cycloalkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or
a pharmaceutically acceptable salt, hydrate, solvate, stereoisomer, tautomer, or mixture thereof;
provided that the compound is not selected from Group A, or a pharmaceutically acceptable salt, hydrate, solvate, stereoisomer, tautomer, or mixture thereof.

In some or any embodiments, provided is a Compound of Formula (I) or (I-P), where $X^2$ is —C($R^4$)($R^{4a}$)— or —N($R^8$)—;
each $R^4$ and $R^{4a}$ is independently hydrogen or $C_{1-6}$alkyl;
$R^7$ is hydrogen or $C_{1-6}$alkyl;
$R^{7a}$ is aryl optionally substituted with 1, 2, 3, or 4 $R^{7b}$; or heterocyclic optionally substituted with 1, 2, 3, or 4 $R^{7b}$;
each $R^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and
$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or
a pharmaceutically acceptable salt, hydrate, solvate, stereoisomer, tautomer, or mixture thereof;
provided that the compound is not selected from Group A, or a pharmaceutically acceptable salt, hydrate, solvate, stereoisomer, tautomer, or mixture thereof.

In some or any embodiments, provided is a Compound of Formula (I), (I-P), (Ia), or (Ib) where
$X^2$ is —C($R^4$)($R^{4a}$)— or —N($R^8$)—;
each $R^4$ and $R^{4a}$ is hydrogen;
$R^7$ is hydrogen;
$R^{7a}$ is aryl optionally substituted with 1, 2, or 3 $R^{7b}$; heterocyclic optionally substituted with 1, 2, or 3 $R^{7b}$; or biphenyl optionally substituted with 1, 2, or 3 $R^{7b}$;
each $R^{7b}$, when present, is independently halo or $C_{1-6}$alkyl; and
$R^8$ is hydrogen, $C_{1-6}$alkyl, halo-$C_{1-6}$alkyl, hydroxy-$C_{1-6}$alkyl, $C_3$-$C_8$-cycloalkyl, or unsubstituted phenyl; or
a pharmaceutically acceptable salt, hydrate, solvate, stereoisomer, tautomer, or mixture thereof.

In some or any embodiments, provided is a Compound of Formula (I), (I-P), (Ia), or (Ib) where
$X^2$ is —C($R^4$)($R^{4a}$)— or —N($R^8$)—;
each $R^4$ and $R^{4a}$ is hydrogen;
$R^7$ is hydrogen;
$R^{7a}$ is aryl optionally substituted with 1, 2, or 3 $R^{7b}$; or heterocyclic optionally substituted with 1, 2, or 3 $R^{7b}$;
each $R^{7b}$, when present, is independently halo or $C_{1-6}$alkyl; and
$R^8$ is phenyl; or
a pharmaceutically acceptable salt, hydrate, solvate, stereoisomer, tautomer, or mixture thereof.

In some or any embodiments, the compound of Formula (I) or (I-P) is according to Formula (Ia):

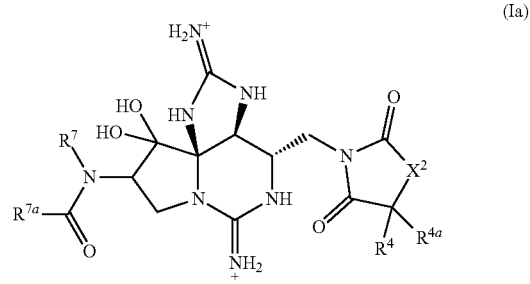

where $R^4$, $R^{4a}$, $R^7$, $R^{7a}$, and $X^2$ are as defined in Formula (I) or (I-P) in the Summary of the Invention or as defined in some or any embodiments described herein.

In some or any embodiments, the compound of Formula (I), (I-P), or (Ia) is according to Formula (Ib):

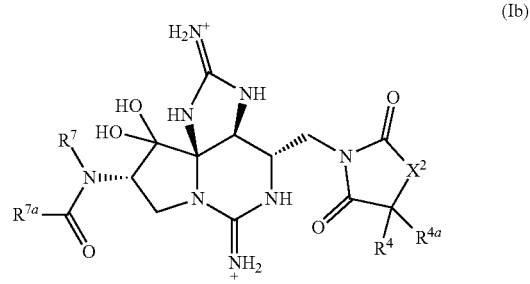

where $R^4$, $R^{4a}$, $R^7$, $R^{7a}$, and $X^2$ are as defined in Formula (I) or (I-P) in the Summary of the Invention or as defined in some or any embodiments described herein.

In some or any embodiments, the compound is according to Formula (I), (I-P), (Ia), (Ib), (Ic), or (Id) where each $R^4$ and $R^{4a}$ is hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where each $R^4$ and $R^{4a}$ is $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where each $R^4$ and $R^{4a}$ is methyl; and all other groups are as defined in Formula (I) or (I-P) in the Summary of the Invention or as defined in some or any embodiments described herein.

In some or any embodiments, the compound is according to Formula (I), (I-P), (Ia), (Ib), (Ic), or (Id) where $X^2$ is —$C(R^4)(R^{4a})$—; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— where $R^4$ and $R^{4a}$ in $X^2$ are both hydrogen or are both $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— where $R^4$ and $R^{4a}$ in $X^2$ are both hydrogen or are both methyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— where $R^4$ and $R^{4a}$ in $X^2$ are both hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— where both of the $R^4$ and $R^{4a}$ in one pair of $R^4$ and $R^{4a}$, which are attached to the same carbon, are $C_{1-6}$alkyl and $R^4$ and $R^{4a}$ in the other pair of $R^4$ and $R^{4a}$, which are attached to the same carbon, are hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— where both of the $R^4$ and $R^{4a}$ in one pair of $R^4$ and $R^{4a}$, which are attached to the same carbon, are methyl and $R^4$ and $R^{4a}$ in the other pair of $R^4$ and $R^{4a}$, which are attached to the same carbon, are hydrogen; and all other groups are as defined in Formula (I) or (I-P) in the Summary of the Invention or as defined in some or any embodiments described herein.

In some or any embodiments, the compound is according to Formula (I), (I-P), (Ia), (Ib), (Ic), or (Id) where $X^2$ is —$C(R^4)(R^{4a})$— and both $R^4$ and both $R^{4a}$ in

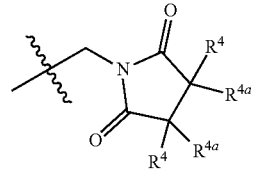

are hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— and both $R^4$ and both $R^{4a}$ in

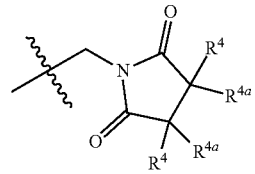

are $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —$C(R^4)(R^{4a})$— and both $R^4$ and both $R^{4a}$ in

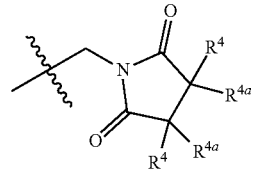

are methyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where

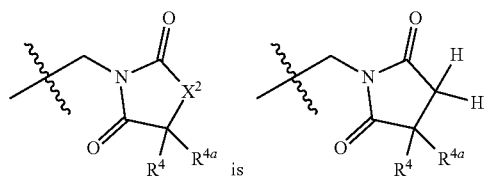

and $R^4$ and $R^{4a}$ are both $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where

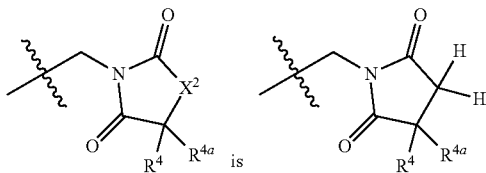

and $R^4$ and $R^{4a}$ are both methyl; and all other groups are as defined in Formula (I) or (I-P) in the Summary of the Invention or as defined in some or any embodiments described herein.

In some or any embodiments, the compound is according to Formula (I), (I-P), (Ia), (Ib), (Ic), or (Id) where $X^2$ is —N($R^8$)—; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is hydrogen; $C_{1-6}$alkyl; or phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is methyl; and all other groups are as defined in Formula (I) (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is unsubstituted phenyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^8$ is hydrogen, methyl, or unsubstituted phenyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is carboxy-$C_{1-6}$alkyl (in some embodiments, —$CH_2C(O)OH$), halo-$C_{1-6}$alkyl (in some embodiments, —$CH_2CF_3$), hydroxy-$C_{1-6}$alkyl (in some embodiments, —$CH_2CH_2OH$), or $C_3$-$C_8$-cycloalkyl (in some embodiments, $C_3$-$C_6$ cycloalkyl; in some embodiments, cyclopropyl, cyclobutyl, or cyclopentyl); and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is halo-$C_{1-6}$alkyl (in some embodiments, —$CH_2CF_3$), hydroxy-$C_{1-6}$alkyl (in some embodiments, —$CH_2CH_2OH$), or $C_3$-$C_8$-cycloalkyl (in some embodiments, $C_3$-$C_6$ cycloalkyl; in some embodiments, cyclopropyl, cyclobutyl, or cyclopentyl); and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is carboxy-$C_{1-6}$alkyl (in some embodiments, —$CH_2C(O)OH$); and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is halo-$C_{1-6}$alkyl (in some embodiments, —$CH_2CF_3$); and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is hydroxy-$C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— where $R^8$ is $C_3$-$C_5$-cycloalkyl (in some embodiments, $C_3$-$C_6$cycloalkyl; in some embodiments, cyclopropyl, cyclobutyl, or cyclopentyl); and all other groups are as defined in Formula (I) or (I-P) in the Summary of the Invention or as defined in some or any embodiments described herein.

In some or any embodiments, the compound is according to Formula (I), (I-P), (Ia), (Ib), (Ic), or (Id) where $X^2$ is —N($R^8$)— and $R^4$ and $R^{4a}$ in

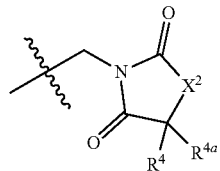

are both hydrogen or are both $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^4$ and $R^{4a}$ in

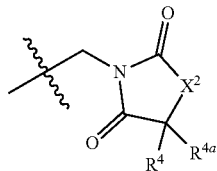

are both hydrogen or are both methyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^4$ and $R^{4a}$ in

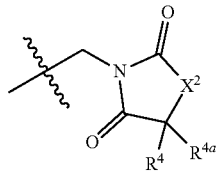

are both hydrogen; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^4$ and $R^{4a}$ in

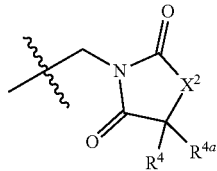

are both $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), (Ib), (Ic), or (Id) where $X^2$ is —N($R^8$)— and $R^4$ and $R^{4a}$ in

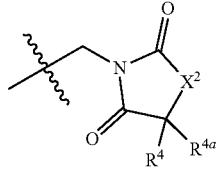

are both methyl; and all other groups are as defined in Formula (I) or (I-P) in the Summary of the Invention or as defined in some or any embodiments described herein.

In some or any embodiments, the compound is according to Formula (I), (I-P), (Ia), or (Ib), where $R^7$ is hydrogen; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^7$ is $C_{1-6}$alkyl; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^7$ is methyl; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^7$ is hydrogen or methyl; and all other groups are as defined in Formula (I) or (I-P) in the Summary of the Invention or as defined in some or any embodiments described herein.

In some or any embodiments, the compound is according to Formula (I), (I-P), (Ia), or (Ib), where $R^{7a}$ is

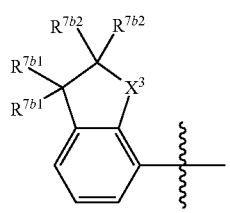

and $X^3$ is —O—, —O—C($R^{7b3}$)($R^{7b3}$)—, —C($R^{7b3}$)($R^{7b3}$)—O—, —C($R^{7b3}$)($R^{7b3}$)—, —C($R^{7b3}$)($R^{7b3}$)—C($R^{7b4}$)($R^{7b4}$)—, or —C($R^{7b3}$)($R^{7b3}$)—C($R^{7b4}$)($R^{7b4}$)—C($R^{7b5}$)($R^{7b5}$)—; each $R^{7b1}$, $R^{7b2}$, $R^{7b3}$, $R^{7b4}$, and $R^{7b5}$ is independently hydrogen, halo, or $C_{1-3}$-alkyl; or the two $R^{7b}$, the two $R^{7b2}$, the two $R^{7b3}$, the two $R^{7b4}$, or the two $R^{7b5}$ together with the carbon to which they are attached form a $C_{3-5}$cycloalkylene ring, and the remaining of $R^{7b1}$, $R^{7b2}$, $R^{7b3}$, $R^{7b4}$, and $R^{7b5}$ are independently hydrogen, halo, or $C_{1-3}$-alkyl; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

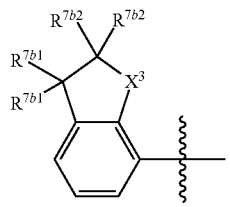

where $X^3$ is —O—; each $R^{7b1}$ and $R^{7b2}$ is independently hydrogen, halo, or $C_{1-3}$-alkyl; or the two $R^{7b1}$ or the two $R^{7b2}$ together with the carbon to which the two $R^{7b1}$ or the two $R^{7b2}$ are attached form a $C_{3-5}$cycloalkylene ring and the remaining of $R^{7b}$ and $R^{7b2}$ are hydrogen; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

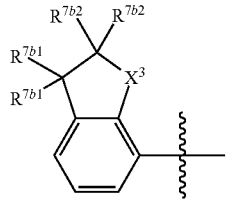

and $X^3$ is —O—C($R^{7b3}$)($R^{7b3}$)—; each $R^{7b1}$, $R^{7b2}$, and $R^{7b3}$ is independently hydrogen, halo, or $C_{1-3}$-alkyl; or the two $R^{7b1}$, the two $R^{7b2}$, or the two $R^{7b3}$, together with the carbon to which they are attached form a $C_{3-5}$cycloalkylene ring, and the remaining of $R^{7b1}$, $R^{7b2}$, and $R^{7b3}$ are independently hydrogen, halo, or $C_{1-3}$-alkyl; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

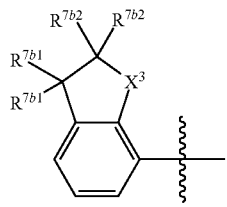

and $X^3$ is —C($R^{7b3}$)($R^{7b3}$)—O—; each $R^{7b1}$, $R^{7b2}$, and $R^{7b3}$ is independently hydrogen, halo, or $C_{1-3}$-alkyl; or the two $R^{7b1}$, the two $R^{7b2}$, or the two $R^{7b3}$, together with the carbon to which they are attached form a $C_{3-5}$cycloalkylene ring, and the remaining of $R^{7b1}$, $R^{7b2}$, and $R^{7b3}$ are independently hydrogen, halo, or $C_{1-3}$-alkyl; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

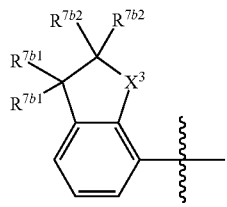

where $X^3$ is —C($R^{7b3}$)($R^{7b3}$)—; each $R^{7b1}$, $R^{7b2}$, and $R^{7b3}$ is independently hydrogen, halo, or $C_{1-3}$-alkyl; or the two $R^{7b1}$, the two $R^{7b2}$, or the two $R^{7b3}$ together with the carbon to which they are attached form a $C_{3-5}$-cycloalkylene ring, and the remaining of $R^{7b1}$, $R^{7b2}$, and $R^{7b3}$ are hydrogen; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

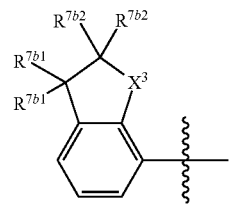

where $X^3$ is —C($R^{7b3}$)($R^{7b3}$)—C($R^{7b4}$)($R^{7b4}$)— and each $R^{7b1}$, $R^{7b2}$, $R^{7b3}$, and $R^{7b4}$ is independently hydrogen, halo, or $C_{1-3}$-alkyl; the two $R^{7b1}$, the two $R^{7b2}$, the two $R^{7b3}$, or the two $R^{7b4}$ together with the carbon to which they are attached form a $C_{3-5}$cycloalkylene ring, and the remaining of $R^{7b1}$, $R^{7b2}$, $R^{7b3}$, and $R^{7b4}$ are hydrogen; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

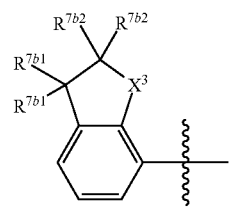

where $X^3$ is —C($R^{7b3}$)($R^{7b3}$)—C($R^{7b4}$)($R^{7b4}$)—C($R^{7b5}$)($R^{7b5}$)—; each $R^{7b1}$, $R^{7b2}$, $R^{7b3}$, $R^{7b4}$, and $R^{7b5}$ is independently hydrogen, halo, or $C_{1-3}$-alkyl; or the two $R^{7b1}$, the two $R^{7b2}$, the two $R^{7b3}$, the two $R^{7b4}$, or the two $R^{7b5}$ together with the carbon to which they are attached form a $C_{3-5}$cycloalkylene ring, and the remaining of $R^{7b1}$, $R^{7b2}$, $R^{7b3}$, $R^{7b4}$, and $R^{7b5}$ are hydrogen; and all other groups are as defined in Formula (I) or (I-P) in the Summary of the Invention or as defined in some or any embodiments described herein. In some or any embodiments, the $R^{7b1}$ groups are the same, the $R^{7b2}$ groups are the same, the $R^{7b3}$ groups are the same, $R^{7b4}$ groups are the same, and $R^{7b5}$ groups are the same; and all other groups are as defined in Formula (I) in the Summary of the Invention or as defined in some or any embodiments described herein. In some or any embodiments, each $R^{7b1}$, $R^{7b2}$, $R^{7b3}$, $R^{7b4}$, and $R^{7b5}$ is hydrogen; and all other groups are as defined in Formula (I) or (I-P) in the Summary of the Invention or as defined in some or any embodiments described herein. In some or any embodiments, the $R^{7b1}$ groups are the same and are selected from halo (in another embodiment fluoro) and $C_{1-3}$-alkyl (in another embodiment methyl); and each $R^{7b2}$, $R^{7b3}$, $R^{7b4}$, and $R^{7b5}$ is hydrogen; and all other groups are as defined in Formula (I) or (I-P) in the Summary of the Invention or as defined in some or any embodiments described herein. In some or any embodiments, the $R^{7b2}$ groups are the same and are selected from halo (in another embodiment fluoro) and $C_{1-3}$-alkyl (in another embodiment methyl); and each $R^{7b1}$, $R^{7b3}$, $R^{7b4}$, and $R^{7b5}$ is hydrogen; and all other groups are as defined in Formula (I) or (I-P) in the Summary of the Invention or as defined in some or any embodiments described herein. In some or any embodiments, the $R^{7b3}$ groups are the same and are selected from halo (in another embodiment fluoro) and $C_{1-3}$-alkyl (in another embodiment methyl); and each $R^{7b1}$, $R^{7b2}$, $R^{7b4}$, and $R^{7b5}$ is hydrogen; and all other groups are as defined in Formula (I) or (I-P) in the Summary of the Invention or as defined in some or any embodiments described herein. In some or any embodiments, the $R^{7b4}$ groups are the same and are selected from halo (in another embodiment fluoro) and $C_{1-3}$-alkyl (in another embodiment methyl); and each $R^{7b1}$, $R^{7b2}$, $R^{7b3}$, and $R^{7b5}$ is hydrogen; and all other groups are as defined in Formula (I) or (I-P) in the Summary of the Invention or as defined in some or any embodiments described herein. In some or any embodiments, the $R^{7b5}$ groups are the same and are selected from halo (in another embodiment fluoro) and $C_{1-3}$-alkyl (in another embodiment methyl); and each $R^{7b}$, $R^{7b2}$, $R^{7b3}$, and $R^{7b4}$ is hydrogen; and all other groups are as defined in Formula (I) or (I-P) in the Summary of the Invention or as defined in some or any embodiments described herein. In some or any embodiments, the $C_{3-5}$cycloalkylene ring is a $C_3$cycloalkylene; and all other groups are as defined in Formula (I) or (I-P) in the Summary of the Invention or as defined in some or any embodiments described herein. In some or any embodiments, the $C_{3-5}$-cycloalkylene ring is a $C_4$cycloalkylene; and all other groups are as defined in Formula (I) or (I-P) in the Summary of the Invention or as defined in some or any embodiments described herein. In some or any embodiments, the $C_{3-5}$cycloalkylene ring is a $C_5$cycloalkylene; and all other groups are as defined in Formula (I) or (I-P) in the Summary of the Invention or as defined in some or any embodiments described herein. In some or any embodiments, the two $R^{7b1}$ together with the carbon to which they are attached form a $C_{3-5}$cycloalkylene ring; and all other groups are as defined in Formula (I) or (I-P) in the Summary of the Invention or as defined in some or any embodiments described herein. In some or any embodiments, the two $R^{7b1}$ together with the carbon to which they are attached form a $C_{3-5}$cycloalkylene ring; when $R^{7b}$, $R^{7b2}$, $R^{7b3}$, $R^{7b4}$, and $R^{7b5}$ are present, each $R^{7b1}$, $R^{7b2}$, $R^{7b3}$, $R^{7b4}$, and $R^{7b5}$ is hydrogen; and all other groups are as defined in Formula (I) or (I-P) in the Summary of the Invention or as defined in some or any embodiments described herein. In some or any embodiments, a) one $R^{7b1}$ is $C_{1-3}$alkyl (in some embodiments methyl or ethyl) and the other $R^{7b1}$ is hydrogen, b) the two $R^{7b}$ are both hydrogen or c) the two $R^{7b1}$ are both $C_{1-3}$alkyl (in some embodiments, methyl), or d) the two $R^{7b}$ together with the carbon to which they are attached form a cyclopropylene ring; and when $R^{7b2}$, $R^{7b3}$, $R^{7b4}$, and $R^{7b5}$ are present, each $R^{7b2}$, $R^{7b3}$, $R^{7b4}$, and $R^{7b5}$ is hydrogen; and all other groups are as defined in Formula (I) or (I-P) in the Summary of the Invention or as defined in some or any embodiments described herein.

In some or any embodiments, the compound is according to Formula (I), (I-P), (Ia), or (Ib), where $R^{7a}$ is

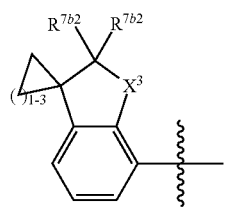

and $X^3$ is —O—, —C($R^{7b3}$)($R^{7b3}$)—, —O—C($R^{7b3}$)($R^{7b3}$)—, or —C($R^{7b3}$)($R^{7b3}$)—O—; $R^{7a}$ is

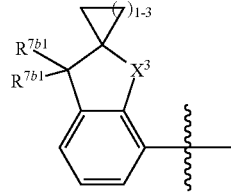

and $X^3$ is —O—, —C($R^{7b3}$)($R^{7b3}$)—, —O—C($R^{7b3}$)($R^{7b3}$)—, or —C($R^{7b3}$)($R^{7b3}$)—O—; or $R^{7a}$ is

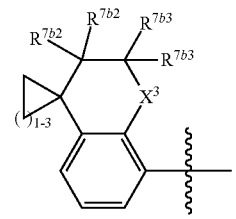

and $X^3$ is —O—, —C($R^{7b4}$)($R^{7b4}$)—, —O—C($R^{7b3}$)($R^{7b3}$)—, or —C($R^{7b3}$)($R^{7b3}$)—O—; and all other groups are as defined in Formula (I) or (I-P) in the Summary of the Invention or as defined in some or any embodiments described herein. In some or any embodiments, when $R^{7b1}$, $R^{7b2}$, $R^{7b3}$, and $R^{7b4}$ are present, each $R^{7b1}$, $R^{7b2}$, $R^{7b3}$, and $R^{7b4}$ is hydrogen. In some or any embodiments, the spirocyclic ring is cycloprop-di-yl or cyclobut-di-yl. In some or any embodiments, when $R^{7b1}$, $R^{7b2}$, $R^{7b3}$, and $R^{7b4}$ are present, each $R^{7b1}$, $R^{7b2}$, $R^{7b3}$, and $R^{7b4}$ is hydrogen; and the spirocyclic ring is cycloprop-di-yl or cyclobut-di-yl.

In some or any embodiments, provided is a Compound of Formula (I), (I-P), (Ia), or (Ib), where $R^{7a}$ is biphenyl optionally substituted with 1, 2, 3, or 4 $R^{7b}$; and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is biphenyl optionally substituted with 1 or 2 $R^{7b}$; and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is biphenyl optionally substituted with 1 or 2 $C_{1-6}$alkyl; and all other groups are as defined in Formula (I) or (I-P) in the Summary of the Invention or as defined in some or any embodiments described herein.

In some or any embodiments, provided is a Compound of Formula (I), (I-P), (Ia), or (Ib), where $R^{7a}$ is

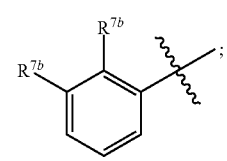

and all other groups are as defined in Formula (I) or (I-P) in the Summary of the Invention or as defined in some or any embodiments described herein. In some or any embodiments, $R^{7a}$ is

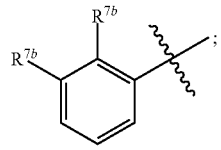

each $R^{7b}$ is independently $C_{1-6}$alkyl, aryl-$C_{1-6}$alkyl, aryloxy, or —C(O)(heterocycloalkyl); and all other groups are as defined in Formula (I) or (I-P) in the Summary of the Invention or as defined in some or any embodiments described herein. In some or any embodiments, $R^{7a}$ is

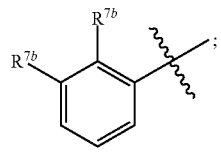

each $R^{7b}$ is independently aryl-$C_{1-6}$alkyl, aryloxy, or —C(O)(heterocycloalkyl); and all other groups are as defined in Formula (I) or (I-P) in the Summary of the Invention or as defined in some or any embodiments described herein.

In some or any embodiments, provided is a Compound of Formula (I), (I-P), (Ia), or (Ib), where $R^{7a}$ is aryl optionally substituted with 1, 2, 3, or 4 $R^{7b}$; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the $R^{7a}$ aryl is phenyl, naphthyl, tetrahydronaphthyl, fluorenyl, 6,7,8,9-tetrahydro-5H-benzo[7]annulenyl,

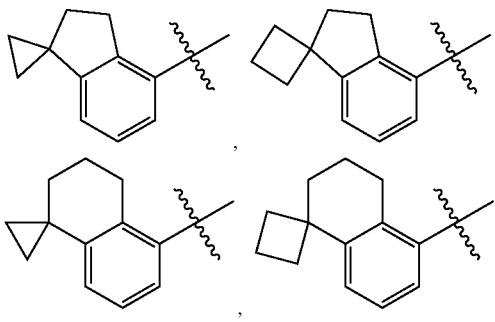

or indanyl; each of which is optionally substituted with 1, 2, 3, or 4 groups independently selected from halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, $C_{1-6}$alkylthio, $C_{1-6}$alkylsulfonyl, —C(O)(heterocycloalkyl), and amino; and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is aryl optionally substituted with 1, 2, 3, or 4 $R^{7b}$; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the $R^{7a}$ aryl is phenyl, naphthyl, tetrahydronaphthyl, fluorenyl, 6,7,8,9-tetrahydro-5H-benzo[7]annulenyl,

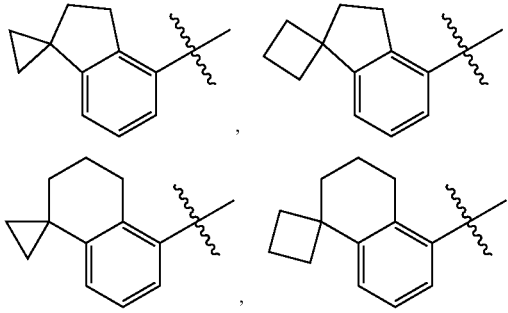

or indanyl; each of which is optionally substituted with 1, 2, 3, or 4 groups independently selected from halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, phenyloxy, $C_{1-6}$alkylthio, $C_{1-6}$alkylsulfonyl, —C(O)(azetidinyl), and amino; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the $R^{7a}$ aryl is tetrahydronaphthyl, 6,7,8,9-tetrahydro-5H-benzo[7]annulenyl, or indanyl, each of which is optionally substituted with one gem-dialkyl or one gem-dihalo. In some or any embodiments, the Compound is according to Formula (I), (I-P), (Ia), or (Ib), where the aryl in $R^{7a}$ is tetrahydronaphthyl, 6,7,8,9-tetrahydro-5H-benzo[7]annulenyl, or indanyl, each of which is optionally substituted with one gem-dimethyl or one gem-difluoro; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the $R^{7a}$ aryl comprises a spirocyclic ring; and all other groups are as defined in Formula (I) or (I-P) in the Summary of the Invention or as defined in some or any embodiments described herein.

In some or any embodiments, provided is a Compound of Formula (I), (I-P), (Ia), or (Ib), where $R^{7a}$ is

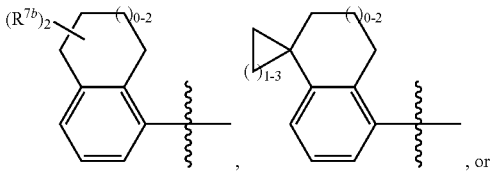, or

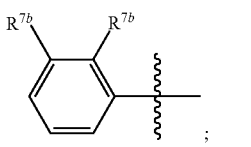;

and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is

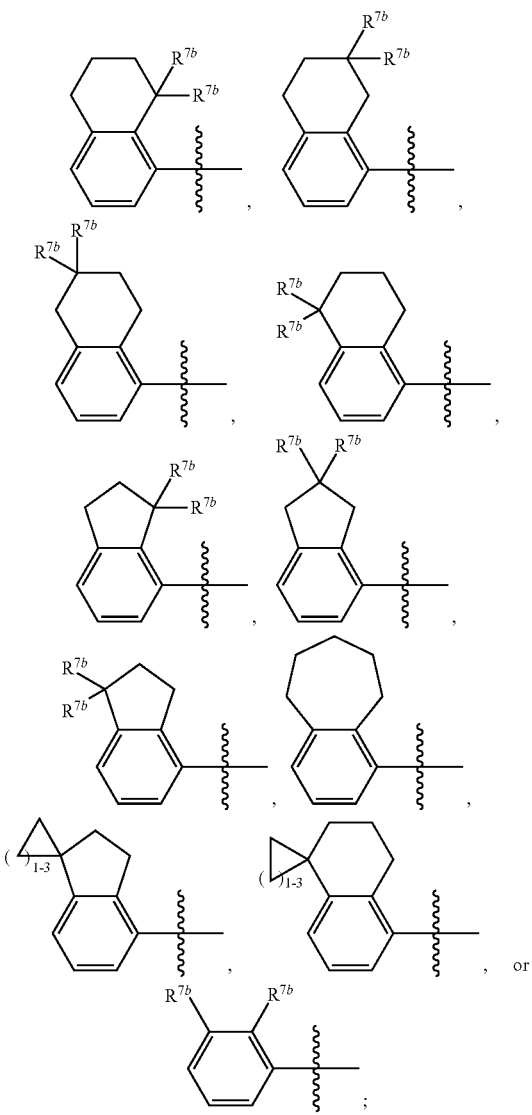

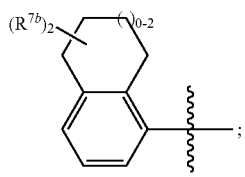

and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is and all other groups are as defined in Formula (I) or (I-P) in the Summary of the Invention or as defined in some or any embodiments described herein. In some or any embodiments, provided is a Compound of Formula (I), (I-P), (Ia), or (Ib), where $R^{7a}$ is

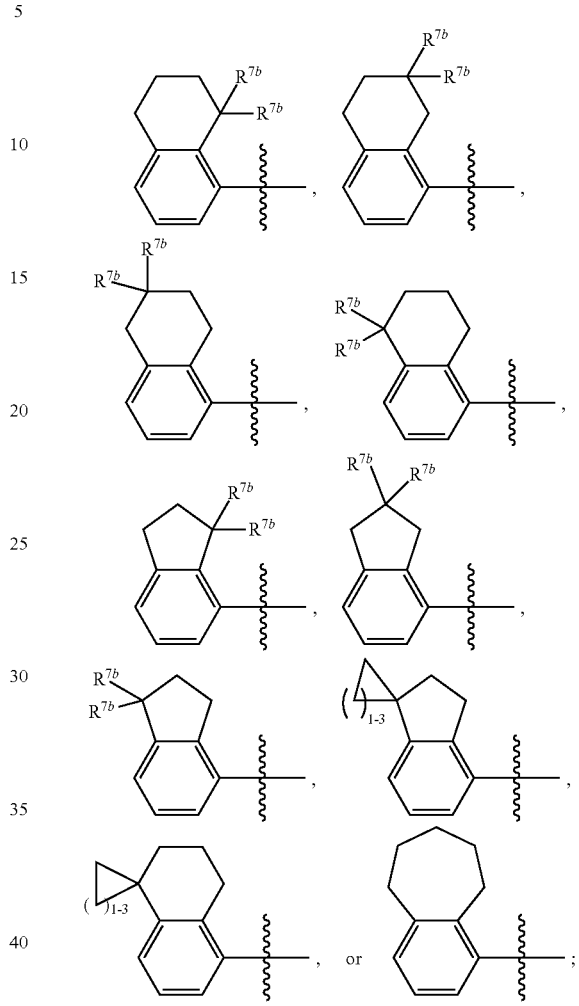

and all other groups are as defined in the Summary of the Invention or as defined in some or any embodiments described herein. In some or any embodiments, both $R^{7b}$ are hydrogen, both $R^{7b}$ are $C_{1-6}$alkyl, or both $R^{7b}$ are halo; and all other groups are as defined in Formula (I) or (I-P) in the Summary of the Invention or as defined in some or any embodiments described herein. In some or any embodiments, both $R^{7b}$ are hydrogen, both $R^{7b}$ are $C_{1-3}$alkyl, or both $R^{7b}$ are halo; and all other groups are as defined in Formula (I) or (I-P) in the Summary of the Invention or as defined in some or any embodiments described herein. In some or any embodiments, both $R^{7b}$ are hydrogen, both $R^{7b}$ are methyl, or both $R^{7b}$ are fluoro; and all other groups are as defined in Formula (I) or (I-P) in the Summary of the Invention or as defined in some or any embodiments described herein. In some or any embodiments, both $R^{7b}$ are hydrogen; and all other groups are as defined in Formula (I) or (I-P) in the Summary of the Invention or as defined in some or any embodiments described herein. In some or any embodiments, both $R^{7b}$ are methyl; and all other groups are as defined in Formula (I) or (I-P) in the Summary of the Invention or as defined in some or any embodiments described herein. In some or any embodiments, both $R^{7b}$ are fluoro; and all other groups are as defined in Formula (I) or (I-P) in the Summary of the Invention or as defined in some or any embodiments described herein.

In some or any embodiments, the compound of Formula I is according to Formula (Ic):

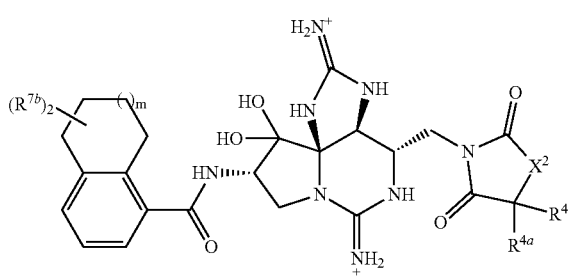

(Ic)

where m is 0, 1, or 2 and $R^4$, $R^{4a}$, $X^2$, and each $R^{7b}$ (independently of each other), are as defined in Formula (I) or (I-P) in the Summary of the Invention or as defined in some or any embodiments described herein. In some or any embodiments, the compound is according to Formula (Ic), where $X^2$ is —C($R^4$)($R^{4a}$)—; and all other groups are as defined in Formula (I) or (I-P) in the Summary of the Invention or as defined in some or any embodiments described herein. In some or any embodiments, the compound is according to Formula (Ic) where $X^2$ is —N($R^8$)—; and all other groups are as defined in Formula (I) or (I-P) in the Summary of the Invention or as defined in some or any embodiments described herein. In some or any embodiments, including any in this paragraph,

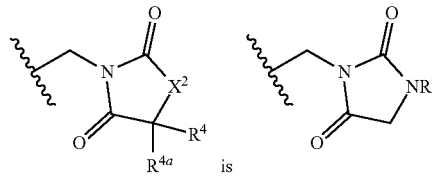 is 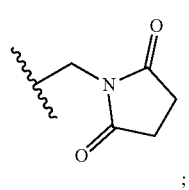 or

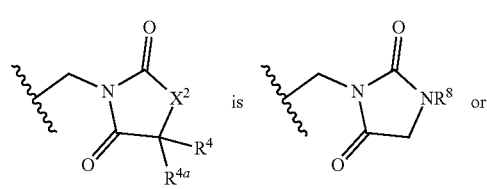

;

where $R^8$ is as defined in the Summary of the Invention or as defined in some or any embodiments described herein. In some or any embodiments, including any in this paragraph,

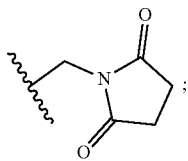

;

where $R^8$ is hydrogen, $C_{1-4}$alkyl, halo-$C_{1-4}$alkyl, hydroxy-$C_{1-4}$alkyl, $C_3$-$C_5$-cycloalkyl, or unsubstituted phenyl. In some or any embodiments, including any in this paragraph,

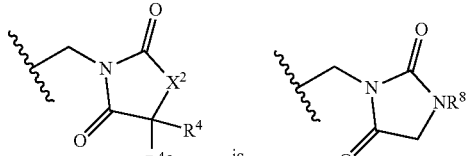

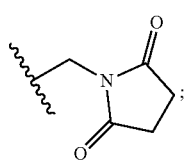

;

where $R^8$ is hydrogen, $C_{1-4}$alkyl, or unsubstituted phenyl. In some or any embodiments, including any in this paragraph,

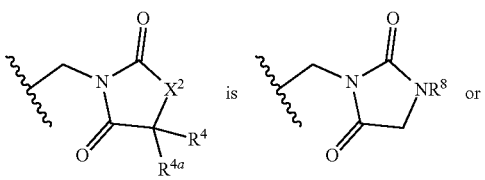

where $R^8$ is halo-$C_{1-4}$alkyl, hydroxy-$C_{1-4}$alkyl, $C_3$-$C_5$-cycloalkyl. In some or any embodiments, including any in this paragraph,

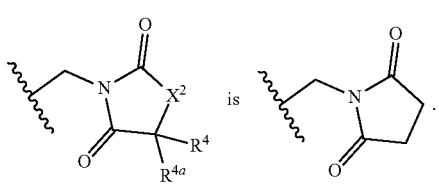

In some or any embodiments, including any in this paragraph,

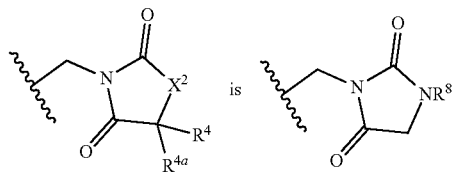 is 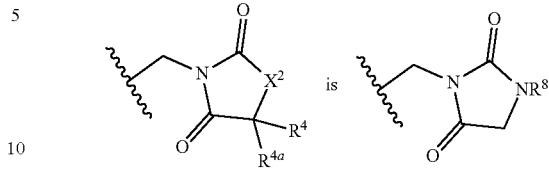

where $R^8$ is as defined in the Summary of the Invention or as defined in some or any embodiments described herein. In some or any embodiments, including any in this paragraph,

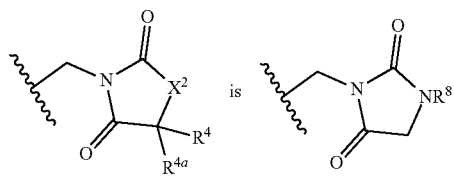

where $R^8$ is hydrogen, $C_{1-4}$alkyl, halo-$C_{1-4}$alkyl, hydroxy-$C_{1-4}$alkyl, $C_3$-$C_5$-cycloalkyl, or unsubstituted phenyl. In some or any embodiments, including any in this paragraph,

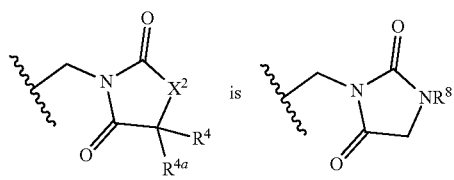

where $R^8$ is hydrogen, $C_{1-4}$alkyl, or unsubstituted phenyl. In some or any embodiments, including any in this paragraph,

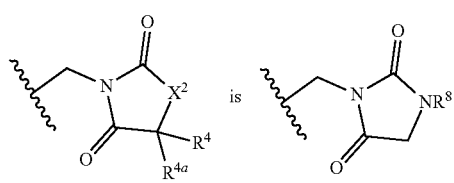

where $R^8$ is halo-$C_{1-4}$alkyl, hydroxy-$C_{1-4}$alkyl, or $C_3$-$C_5$-cycloalkyl. In some or any embodiments, including any in this paragraph,

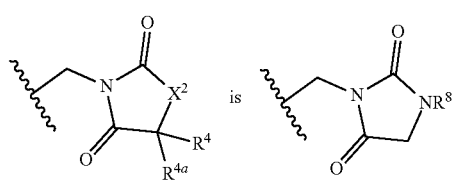

where $R^8$ is halo-$C_{1-4}$alkyl. In some or any embodiments, including any in this paragraph,

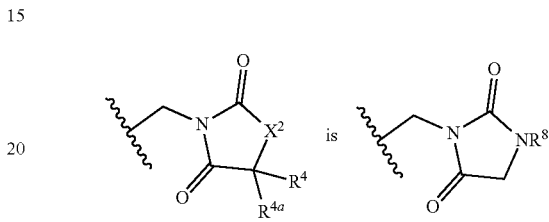

where $R^8$ is hydroxy-$C_{1-4}$alkyl. In some or any embodiments, including any in this paragraph, where $R^8$ is $C_3$-$C_5$-cycloalkyl. In some or any embodiments, the $C_{1-4}$alkyl, alone or as part of another group, is $C_{1-3}$alkyl. In some or any embodiments, the $C_{1-4}$alkyl, alone or as part of another group, is $C_{1-2}$alkyl. In some or any embodiments, the $C_{1-4}$alkyl, alone or as part of another group, is $C_1$alkyl. In some or any embodiments, the compound is according to Formula (Ic) where $X^2$ is —N($R^8$)— where $R^8$ is hydrogen, $C_{1-3}$-alkyl, or unsubstituted phenyl; and all other groups are as defined in Formula (I) or (I-P) in the Summary of the Invention or as defined in some or any embodiments described herein. In some or any embodiments, provided is a Compound of Formula (Ic) where each $R^4$ and $R^{4a}$ are independently hydrogen or methyl; and all other groups are as defined in Formula (I) or (I-P) in the Summary of the Invention or in some or any embodiments described herein. In some or any embodiments, provided is a Compound of Formula (Ic) where each $R^4$ and $R^{4a}$ are hydrogen; and all other groups are as defined in Formula (I) or (I-P) in the Summary of the Invention or in some or any embodiments described herein. In some or any embodiments, provided is a Compound of Formula (Ic) where the two $R^{7b}$ are the same and are substituted on the same carbon atom; and all other groups are as defined in Formula (I) or (I-P) in the Summary of the Invention or in some or any embodiments described herein. In some or any embodiments, provided is a Compound of Formula (Ic) where the two $R^{7b}$ are each hydrogen; and all other groups are as defined in Formula (I) or (I-P) in the Summary of the Invention or in some or any embodiments described herein. In some or any embodiments, provided is a Compound of Formula (Ic) where the two $R^{7b}$ are both $C_{1-3}$-alkyl (in some embodiments, methyl) and are substituted on the same carbon atom; and all other groups are as defined in Formula (I) or (I-P) in the Summary of the Invention or in some or any embodiments described herein. In some or any embodiments, provided is a Compound of Formula (Ic) where the two $R^{7b}$ are both halo (in some embodiments, fluoro) and are substituted on the same carbon atom; and all other groups are as defined in Formula (I) or (I-P) in the Summary of the Invention or in some or any embodiments described herein. In some or any embodiments, provided is a Compound of Formula (Ic) where the two $R^{7b}$ are located on the benzo ring. In some or any embodiments, provided is a Compound of Formula (Ic)

where the two $R^{7b}$ are located on the cyclopentenyl or cyclohexenyl ring. In some or any embodiments, provided is a Compound of Formula (Ic) where the two $R^{7b}$ are located on the same carbon of the cyclopentenyl or cyclohexenyl ring. In some or any embodiments, the compound is according to Formula (Ic), where n is 1; and all other groups are as defined in Formula (I) or (I-P) in the Summary of the Invention or as defined in some or any embodiments described herein. In some or any embodiments, the compound is according to Formula (Ic), where m is 0; and all other groups are as defined in Formula (I) or (I-P) in the Summary of the Invention or as defined in some or any embodiments described herein. In some or any embodiments, the compound is according to Formula (Ic), where m is 1; and all other groups are as defined in Formula (I) or (I-P) in the Summary of the Invention or as defined in some or any embodiments described herein. In some or any embodiments, the compound is according to Formula (Ic), where m is 2; and all other groups are as defined in Formula (I) or (I-P) in the Summary of the Invention or as defined in some or any embodiments described herein.

In some or any embodiments, provided is a Compound of Formula (I), (I-P), (Ia), or (Ib), where $R^{7a}$ is heterocyclic optionally substituted with 1, 2, 3, or 4 $R^{7b}$; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the heterocyclic in $R^{7a}$ is benzo-1,4-dioxanyl, benzodioxolyl, indolinyl, 2-oxo-indolinyl, pyrrolidinyl, piperidinyl, chromanyl, 2,3-dihydrobenzofuranyl,

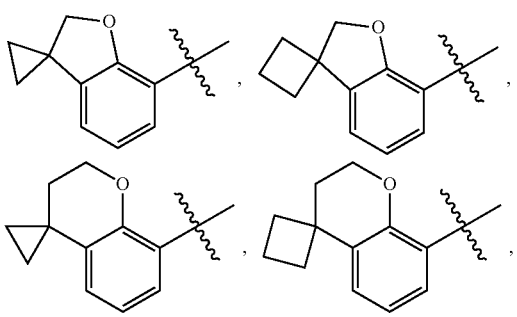

2,2-dioxo-1,3-dihydrobenzo[c]thienyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the heterocyclic in $R^{7a}$ is benzo-1,4-dioxanyl, benzodioxolyl, chromanyl, 2,3-dihydrobenzofuranyl,

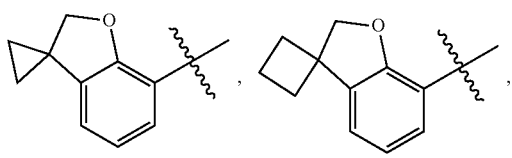

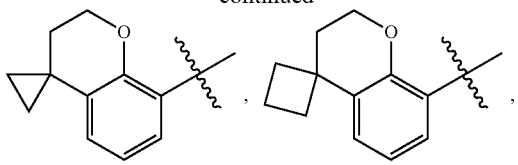

or 2,2-dioxo-1,3-dihydrobenzo[c]thienyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the heterocyclic in $R^{7a}$ comprises one heteroatom which is oxygen; and all other groups are as defined in Formula (I) or (I-P) in the Summary of the Invention or as defined in some or any embodiments described herein. In some or any embodiments, provided is a Compound of Formula (I), (I-P), (Ia), or (Ib), where the $R^{7a}$ heterocyclic is benzo-1,4-dioxanyl, benzodioxolyl, chromanyl, or 2,3-dihydrobenzofuranyl, each of which is optionally substituted with one gem-dialkyl or one gem-dihalo. In some or any embodiments, the Compound is according to Formula (I), (I-P), (Ia), or (Ib), where the aryl in $R^{7a}$ is benzo-1,4-dioxanyl, benzodioxolyl, chromanyl, or 2,3-dihydrobenzofuranyl, each of which is optionally substituted with one gem-dimethyl or one gem-difluoro; and all other groups are as defined in Formula (I) or (I-P) in the Summary of the Invention or as defined in some or any embodiments described herein.

In some or any embodiments, provided is a Compound of Formula (I), (I-P), (Ia), or (Ib), where the heterocyclic in $R^{7a}$ is unsubstituted 2,2-dioxo-1,3-dihydrobenzo[c]thienyl, unsubstituted benzodioxolyl, unsubstituted

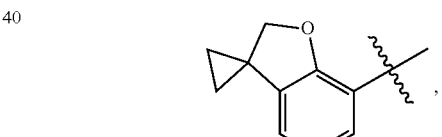

unsubstituted

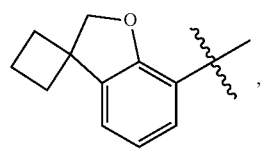 [SMILES: *c1cccc2c1OCC21CCC1]

unsubstituted

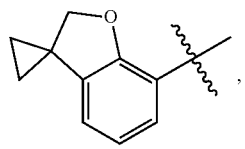 [SMILES: *c1cccc2c1OCC21CC1]

or unsubstituted

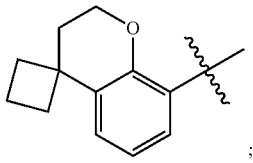 [SMILES: *c1cccc2c1OCCC21CCC1]
;

or $R^{7a}$ is chromanyl, 2,3-dihydrobenzofuranyl, where the chromanyl and 2,3-dihydrobenzofuranyl are optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) or (I-P) in the Summary of the Invention or as defined in some or any embodiments described herein.

In some or any embodiments, the compound of Formula I is according to Formula (Id):

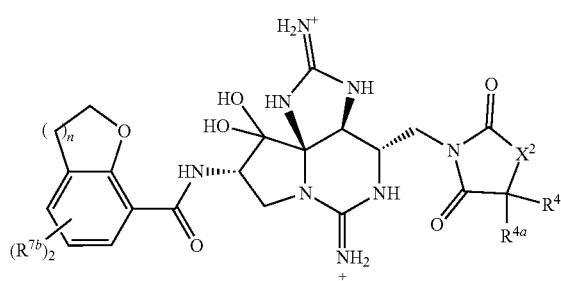
(Id)

where n is 1 or 2 and $R^4$, $R^{4a}$, $X^2$, and each $R^{7b}$ (independently of each other), are as defined in Formula (I) or (I-P) in the Summary of the Invention or as defined in some or any embodiments described herein. In some or any embodiments, including any in this paragraph,

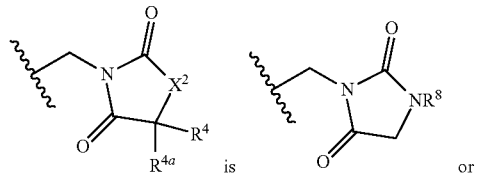

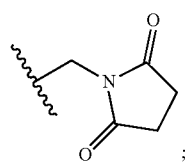
;

where $R^8$ is as defined in the Summary of the Invention or as defined in some or any embodiments described herein. In some or any embodiments, including any in this paragraph,

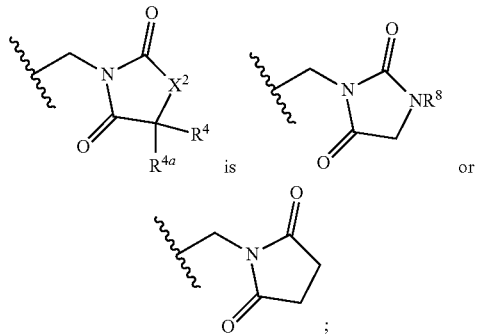

where $R^8$ is hydrogen, $C_{1-4}$alkyl, halo-$C_{1-4}$alkyl, hydroxy-$C_{1-4}$alkyl, $C_3$-$C_5$-cycloalkyl, or unsubstituted phenyl. In some or any embodiments, including any in this paragraph,

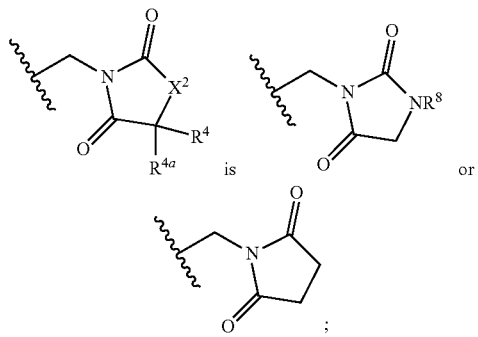
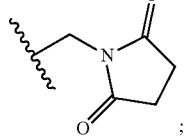

where $R^8$ is hydrogen, $C_{1-4}$alkyl, or unsubstituted phenyl. In some or any embodiments, including any in this paragraph,

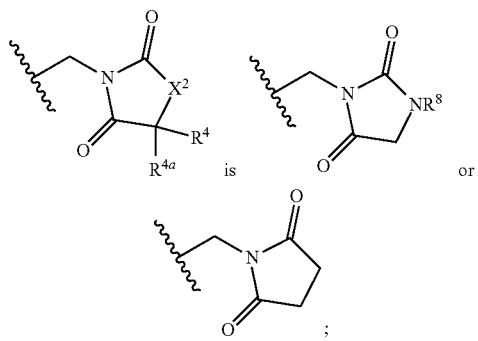
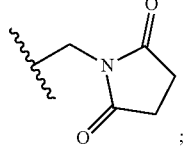

where $R^8$ is halo-$C_{1-4}$alkyl, hydroxy-$C_{1-4}$ alkyl, $C_3$-$C_8$-cycloalkyl. In some or any embodiments, including any in this paragraph, In some or any embodiments, including any in this paragraph,

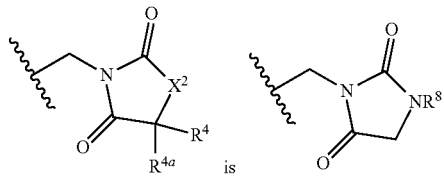 is where $R^8$ is as defined in the Summary of the Invention or as defined in some or any embodiments described herein. In some or any embodiments, including any in this paragraph,

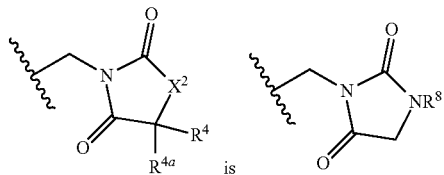 is where $R^8$ is hydrogen, $C_{1-4}$alkyl, halo-$C_{1-4}$alkyl, hydroxy-$C_{1-4}$alkyl, $C_3$-$C_8$-cycloalkyl, or unsubstituted phenyl. In some or any embodiments, including any in this paragraph,

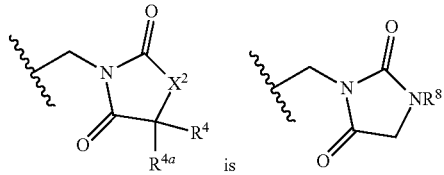 is where $R^8$ is hydrogen, $C_{1-4}$alkyl, or unsubstituted phenyl. In some or any embodiments, including any in this paragraph,

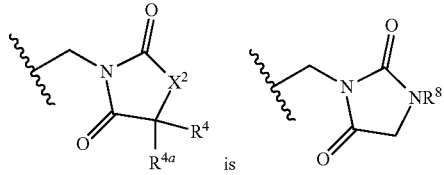 is where $R^8$ is halo-$C_{1-4}$alkyl, hydroxy-$C_{1-4}$alkyl, or $C_3$-$C_5$-cycloalkyl. In some or any embodiments, including any in this paragraph,

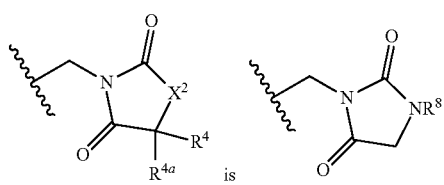 is where $R^8$ is halo-$C_{1-4}$alkyl. In some or any embodiments, including any in this paragraph,

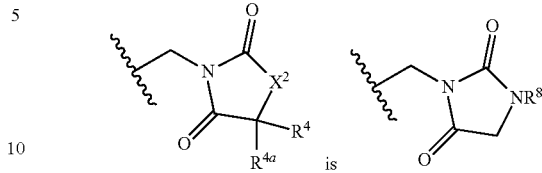 is where $R^8$ is hydroxy-$C_{1-4}$alkyl. In some or any embodiments, including any in this paragraph,

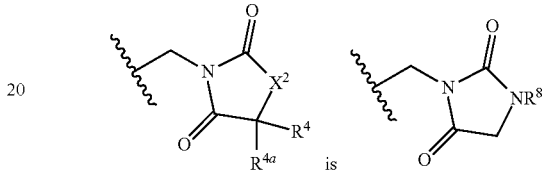 is where $R^8$ is $C_3$-$C_5$-cycloalkyl. In some or any embodiments, the $C_{1-4}$alkyl, alone or as part of another group, is $C_{1-3}$alkyl. In some or any embodiments, the $C_{1-4}$alkyl, alone or as part of another group, is $C_{1-2}$alkyl. In some or any embodiments, the $C_{1-4}$alkyl, alone or as part of another group, is $C_1$alkyl. In some or any embodiments, the compound is according to Formula (Id), where $X^2$ is —C($R^4$)($R^{4a}$)—; and all other groups are as defined in Formula (I) or (I-P) in the Summary of the Invention or as defined in some or any embodiments described herein. In some or any embodiments, the compound is according to Formula (Id) where $X^2$ is —N($R^8$)—; and all other groups are as defined in Formula (I) or (I-P) in the Summary of the Invention or as defined in some or any embodiments described herein. In some or any embodiments, the compound is according to Formula (Id) where $X^2$ is —N($R^8$)— where $R^8$ is hydrogen, $C_{1-3}$-alkyl, or unsubstituted phenyl; and all other groups are as defined in Formula (I) or (I-P) in the Summary of the Invention or as defined in some or any embodiments described herein. In some or any embodiments, provided is a Compound of Formula (Id) where each $R^4$ and $R^{4a}$ are independently hydrogen or methyl; and all other groups are as defined in Formula (I) or (I-P) in the Summary of the Invention or in some or any embodiments described herein. In some or any embodiments, provided is a Compound of Formula (Id) where each $R^4$ and $R^{4a}$ are hydrogen; and all other groups are as defined in Formula (I) or (I-P) in the Summary of the Invention or in some or any embodiments described herein. In some or any embodiments, provided is a Compound of Formula (Id) where the two $R^{7b}$ are the same and are substituted on the same carbon atom; and all other groups are as defined in Formula (I) or (I-P) in the Summary of the Invention or in some or any embodiments described herein. In some or any embodiments, provided is a Compound of Formula (Id) where the two $R^{7b}$ are each hydrogen; and all other groups are as defined in Formula (I) or (I-P) in the Summary of the Invention or in some or any embodiments described herein. In some or any embodiments, provided is a Compound of Formula (Id) where the two $R^{7b}$ are both $C_{1-3}$-alkyl (in some embodiments, methyl) and are substituted on the same carbon atom; and all other groups are as defined in Formula (I) or (I-P) in the Summary of the Invention or in some or any embodiments described herein. In some or any embodiments, provided is a Compound of Formula (Id) where the two $R^{7b}$ are both halo (in some embodiments, fluoro) and are substituted on the same carbon atom; and all other groups are as defined in Formula (I) or (I-P) in the Summary of the Invention or in some or any embodiments described herein. In some or any embodiments, provided is a Compound of Formula (Id) where the two $R^{7b}$ are located on the benzo ring. In some or any embodiments, provided is a Compound of Formula (Id) where the two $R^{7b}$ are located on the dihydrofuranyl or dihydropyranyl ring. In some or any embodiments, provided is a Compound of Formula (Id) where the two $R^{7b}$ are located on the same carbon of the dihydrofuranyl or dihydropyranyl ring. In some or any embodiments, the compound is according to Formula (Id), where n is 1; and all other groups are as defined in Formula (I) or (I-P) in the Summary of the Invention or as defined in some or any embodiments described herein. In some or any embodiments, the compound is according to Formula (Id), where n is 2; and all other groups are as defined in Formula (I) or (I-P) in the Summary of the Invention or as defined in some or any embodiments described herein.

In some or any embodiments, the compound is according to Formula (I), (I-P), (Ia), or (Ib), where $R^{7a}$ is

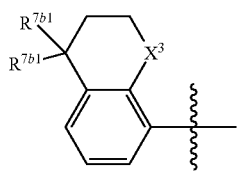

where $X^3$ is $CH_2$ or O; one $R^{7b1}$ is hydrogen and the other is alkyl (in some embodiments, methyl or ethyl), both $R^{7b1}$ are hydrogen, both $R^{7b1}$ are $C_1$-$C_3$alkyl (in some embodiments, methyl), or the two $R^{7b1}$ together with the carbon to which they are attached form cyclopropylene; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

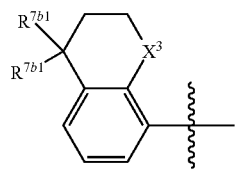

where $X^3$ is $CH_2$; one $R^{7b1}$ is hydrogen and the other is alkyl (in some embodiments, methyl or ethyl), both $R^{7b1}$ are hydrogen, both $R^{7b1}$ are $C_1$-$C_3$alkyl (in some embodiments, methyl), or the two $R^{7b1}$ together with the carbon to which they are attached form cyclopropylene; and all other groups are as defined in Formula (I) or (I-P) in the Summary of the Invention or as defined in some or any embodiments described herein. In some or any embodiments, the compound is according to Formula (I), (I-P), (Ia), or (Ib), where $R^{7a}$ is

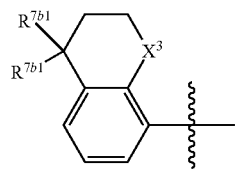

where $X^3$ is O; one $R^{7b1}$ is hydrogen and the other is alkyl (in some embodiments, methyl or ethyl), both $R^{7b1}$ are hydrogen, both $R^{7b1}$ are $C_1$-$C_3$alkyl (in some embodiments, methyl), or the two $R^{7b1}$ together with the carbon to which they are attached form cyclopropylene; and all other groups are as defined in Formula (I) or (I-P) in the Summary of the Invention or as defined in some or any embodiments described herein. In some or any embodiments, including any in this paragraph,

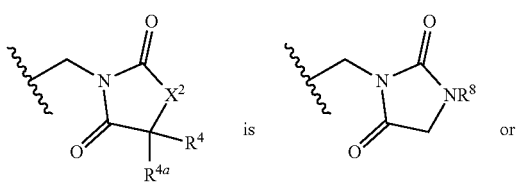

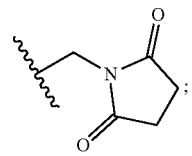

where $R^8$ is as defined in the Summary of the Invention or as defined in some or any embodiments described herein. In some or any embodiments, including any in this paragraph,

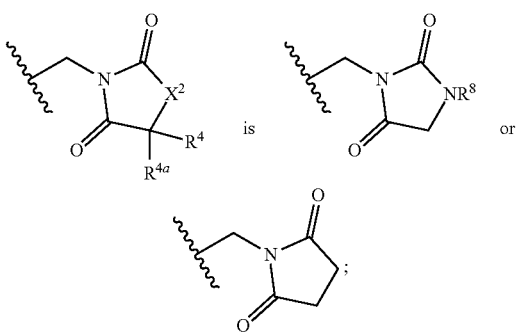

where $R^8$ is hydrogen, $C_{1-6}$alkyl, halo-$C_{1-6}$alkyl, hydroxy-$C_{1-6}$alkyl, $C_3$-$C_5$-cycloalkyl, or unsubstituted phenyl. In some or any embodiments, including any in this paragraph,

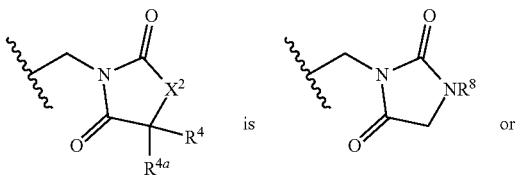

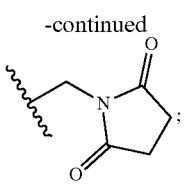

where $R^8$ is hydrogen, $C_{1-6}$alkyl, or unsubstituted phenyl. In some or any embodiments, including any in this paragraph,

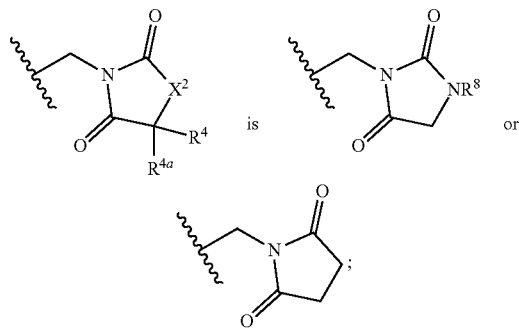

where $R^8$ is halo-$C_{1-6}$alkyl, hydroxy-$C_{1-6}$alkyl, $C_3$-$C_5$-cycloalkyl. In some or any embodiments, including any in this paragraph,

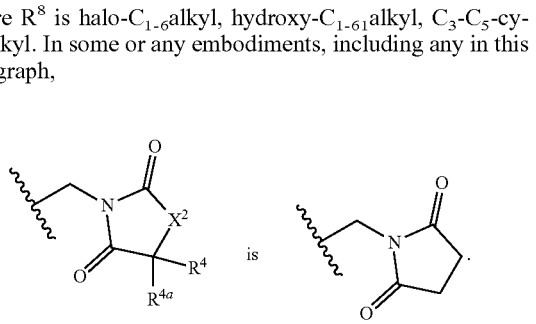

In some or any embodiments, including any in this paragraph,

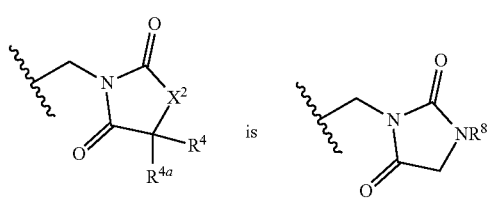

where $R^8$ is as defined in the Summary of the Invention or as defined in some or any embodiments described herein. In some or any embodiments, including any in this paragraph,

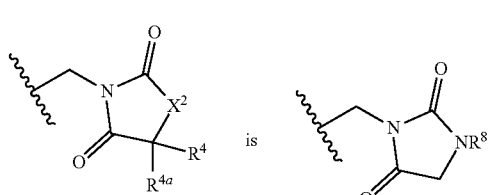

where $R^8$ is hydrogen, $C_{1-6}$alkyl, halo-$C_{1-6}$alkyl, hydroxy-$C_{1-6}$alkyl, $C_3$-$C_5$-cycloalkyl, or unsubstituted phenyl. In some or any embodiments, including any in this paragraph,

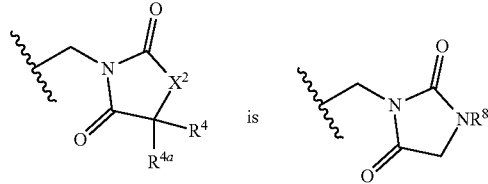

where $R^8$ is hydrogen, $C_{1-6}$alkyl, or unsubstituted phenyl. In some or any embodiments, including any in this paragraph,

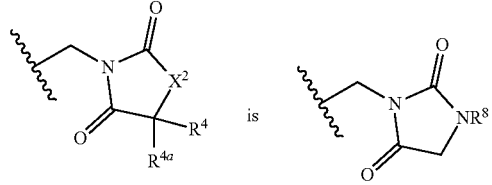

where $R^8$ is halo-$C_{1-6}$alkyl, hydroxy-$C_{1-6}$alkyl, or $C_3$-$C_5$-cycloalkyl. In some or any embodiments, including any in this paragraph,

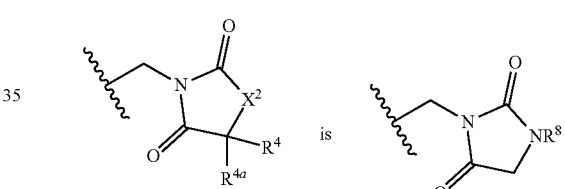

where $R^8$ is halo-$C_{1-6}$alkyl. In some or any embodiments, including any in this paragraph,

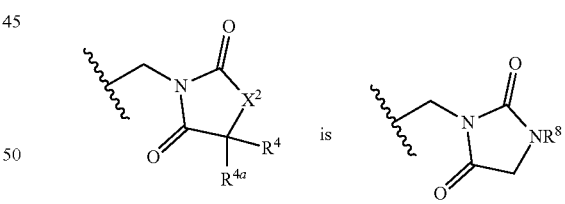

where $R^8$ is hydroxy-$C_{1-6}$alkyl. In some or any embodiments, including any in this paragraph,

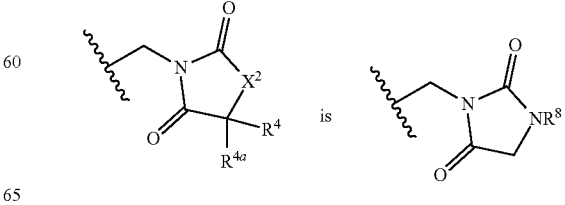

where $R^8$ is $C_3$-$C_5$-cycloalkyl.

In some or any embodiments, provided is a Compound of Formula (I), (I-P), (Ia), or (Ib) where $R^{7a}$ is phenyl, naphthyl, tetrahydronaphthyl, biphenyl, 6,7,8,9-tetrahydro-5H-benzo[7]annulenyl, or indanyl; each of which is optionally substituted with 1, 2, or 3 $R^{7b}$ groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; or $R^{7a}$ is tetrahydronaphthyl, 6,7,8,9-tetrahydro-5H-benzo[7]annulenyl, or indanyl; each of which is optionally substituted with one gem-di-$C_{1-3}$alkyl or one gem-di-halo; or $R^{7a}$ is benzo-1,4-dioxanyl, benzodioxolyl, 3,4-dihydro-2H-benzo[b][1,4]dioxepinyl, 2,3-dihydrobenzofuranyl, 1,3-dihydroisobenzofuranyl, or chromanyl; each of which is optionally substituted with 1, 2, or 3 $R^{7b}$ groups independently selected from halo, $C_{1-6}$alkyl, halo-$C_{1-6}$alkyl, hydroxy, $C_{1-6}$alkoxy, and halo-$C_{1-6}$alkoxy; or $R^{7a}$ is

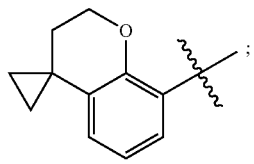 [SMILES: *c1cccc2c1OCCC21CC1]

or $R^{7a}$ is dihydrobenzofuranyl, 1,3-dihydroisobenzofuranyl, or chromanyl; each of which is optionally substituted with one gem-di-$C_{1-3}$alkyl or one gem-di-halo;

and all other groups are as defined in the Summary of the Invention for a Compound of Formula I or I-P or in any embodiments described herein, In some or any embodiments, including any in this paragraph, each $R^{7b}$ and $R^{7b1}$ is independently hydrogen, $C_1$-$C_3$alkyl (in some embodiments, methyl), or halo (in some embodiments, fluoro).

In some or any embodiments, provided is a Compound of Formula (I), (I-P), (Ia), or (Ib) where $R^{7a}$ is

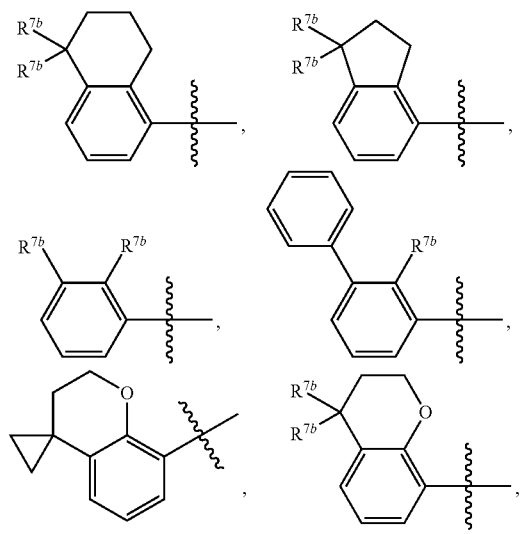

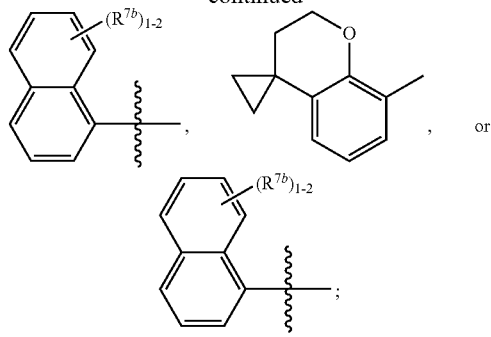

and all other groups are as defined in the Summary of the Invention for a Compound of Formula I or I-P or in any embodiments described herein. In some or any embodiments, a) one $R^{7b}$ is $C_{1-3}$alkyl (in some embodiments methyl or ethyl) and the other $R^{7b}$ is hydrogen, b) the two $R^{7b}$ are both hydrogen, or c) the two $R^{7b}$ are both $C_{1-3}$alkyl (in some embodiments, methyl or ethyl); and all other groups are as defined in Formula (I) or (I-P) in the Summary of the Invention or as defined in some or any embodiments described herein.

In some or any embodiments, provided is a Compound of Formula (I), (I-P), (Ia), or (Ib) where $R^{7a}$ is a heterocyclic ring which comprises one or two oxygen(s) and where the heterocyclic is optionally substituted with 1, 2, or 3 $R^{7b}$ groups independently selected from halo, $C_{1-6}$alkyl, halo-$C_{1-6}$alkyl, hydroxy, $C_{1-6}$alkoxy, or halo-$C_{1-6}$alkoxy; $R^{7a}$ is a heterocyclic ring which comprises one oxygen and where the heterocyclic is optionally substituted with one gem-di-$C_{1-3}$alkyl or one gem-dihalo; and all other groups are as defined in the Summary of the Invention for a Compound of Formula I or I-P or in any embodiments described herein. In some or any embodiments, provided is a Compound of Formula (I), (I-P), (Ia), or (Ib) where $X^2$ is $NR^8$, $R^7$ is hydrogen, $R^{7a}$ is a bicyclic heterocyclic ring which comprises one oxygen and is optionally substituted with 1 or 2 $R^{7b}$ groups or with 1 or 2 $R^{7b1}$ groups, and all other groups are as defined in the Summary of the Invention for a Compound of Formula I or I-P or in any embodiments described herein. In some or any embodiments, including any in this paragraph, each $R^{7b}$ and $R^{7b1}$ is independently hydrogen, $C_1$-$C_3$alkyl (in some embodiments, methyl), or halo (in some embodiments, fluoro).

In some or any embodiments, provided herein is a compound selected from any of Formulas 1-95; or a pharmaceutically acceptable salt, hydrate, solvate, stereoisomer, tautomer, or mixture thereof:

(1)

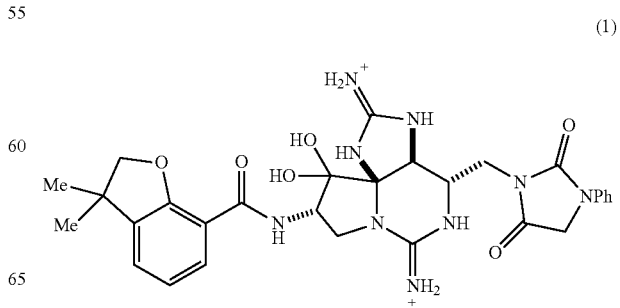

(12)
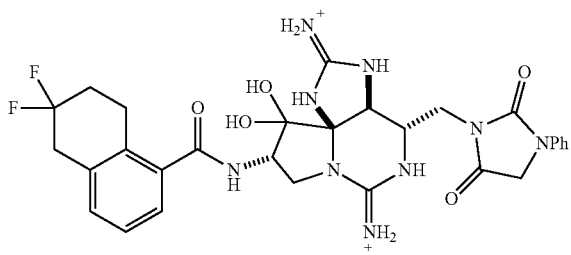
(13)
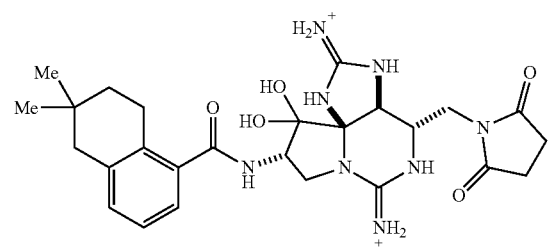
(14)
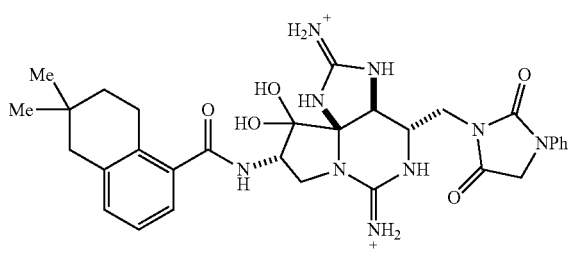
(15)
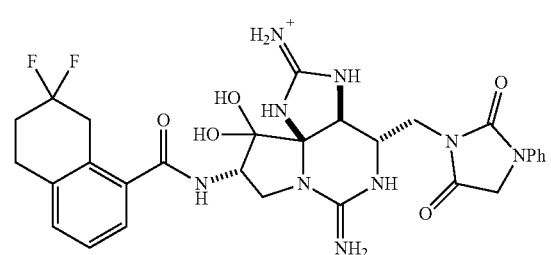
(16)
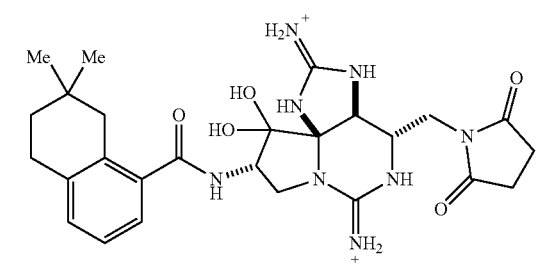
(17)
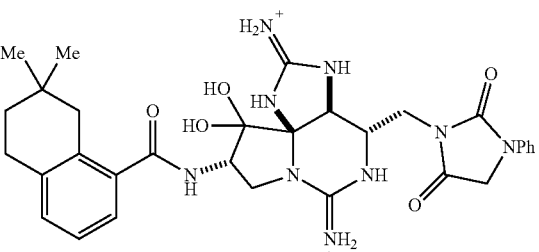
(18)
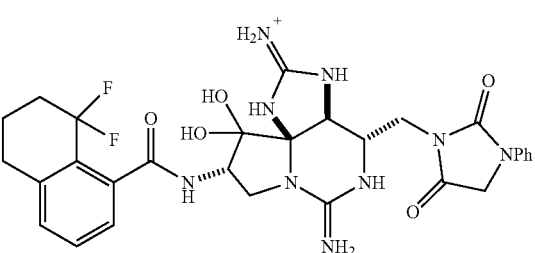
(19)
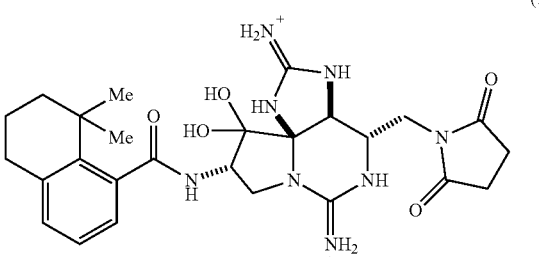
(20)
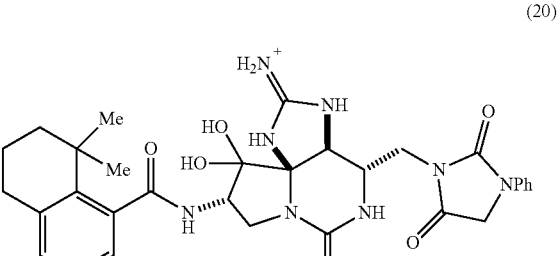
(21)
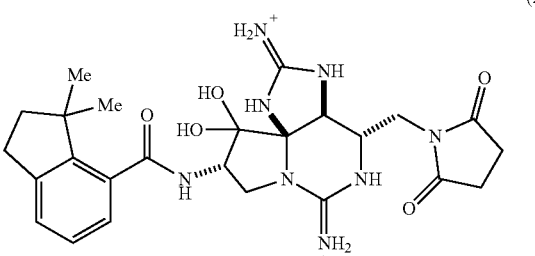

(22)
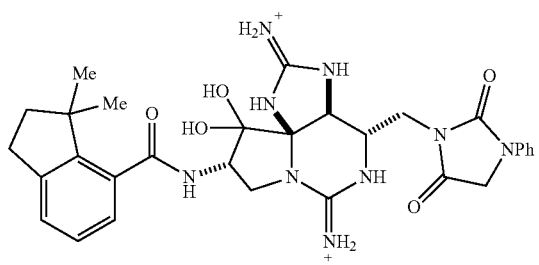
(23)
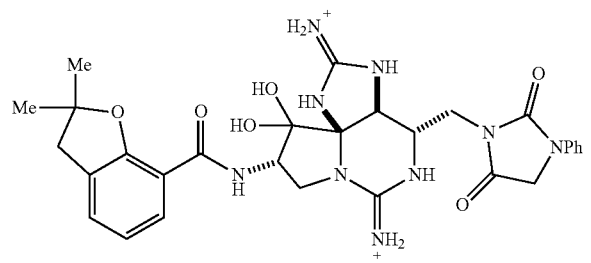
(24)
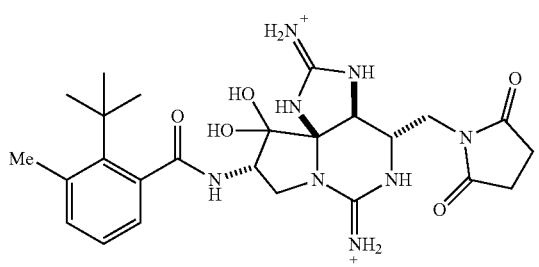
(25)
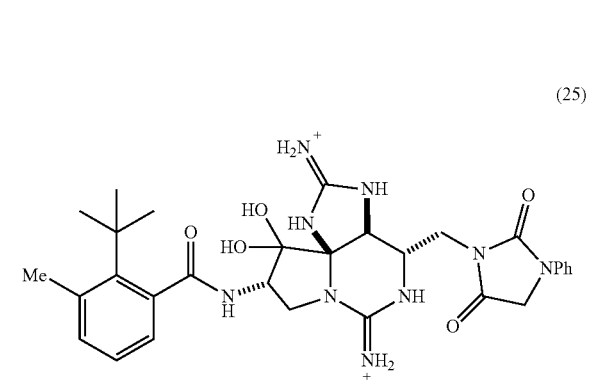
(26)
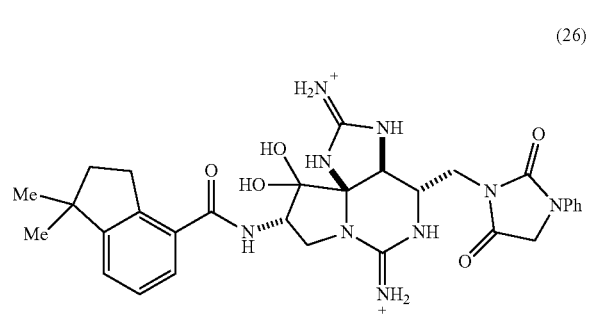
(27)
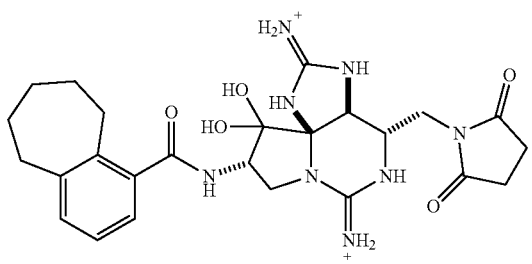
(28)
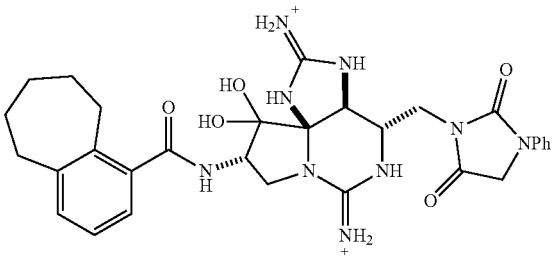
(29)
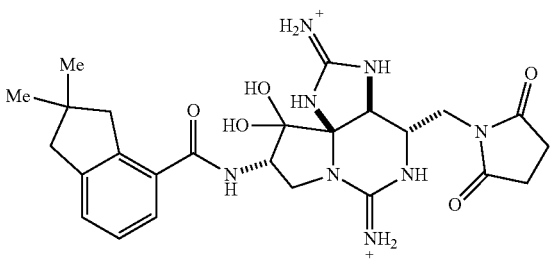
(30)
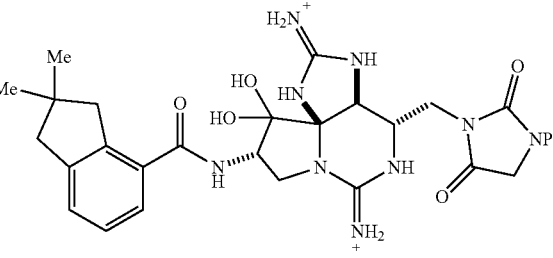
(31)
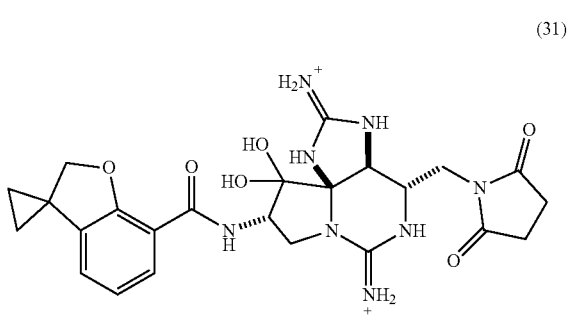

(32)
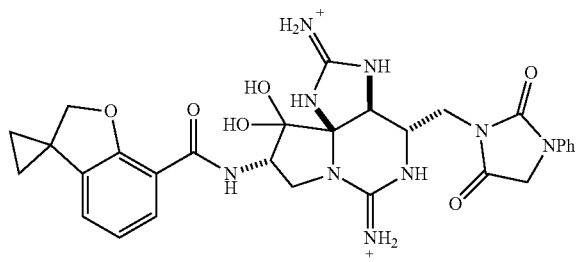
(37)
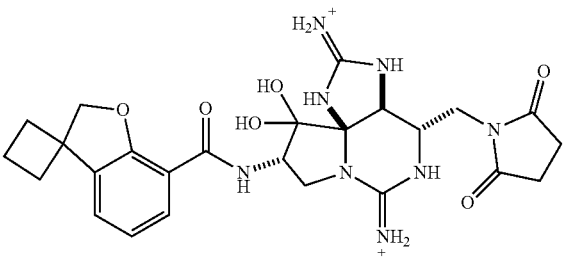
(33)
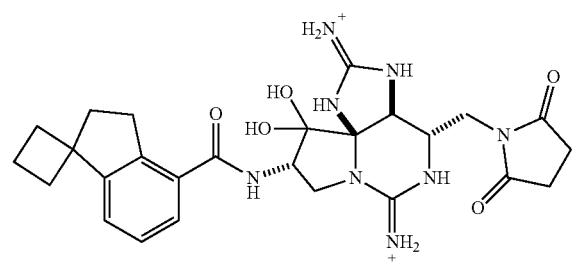
(38)
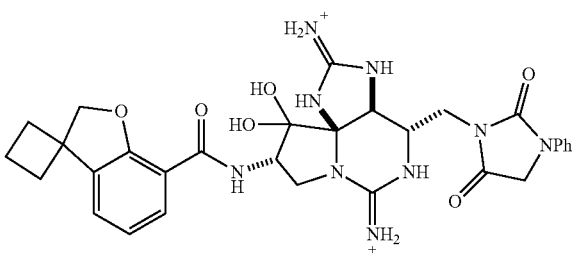
(34)
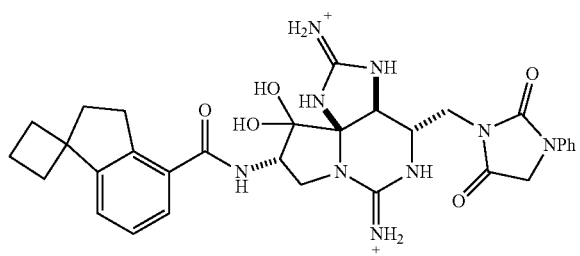
(39)
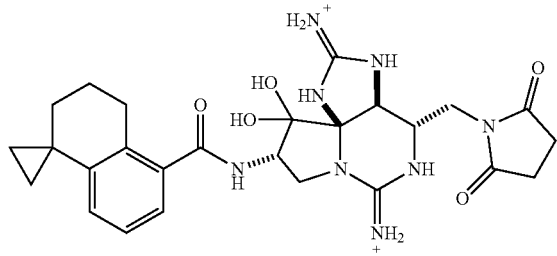
(35)
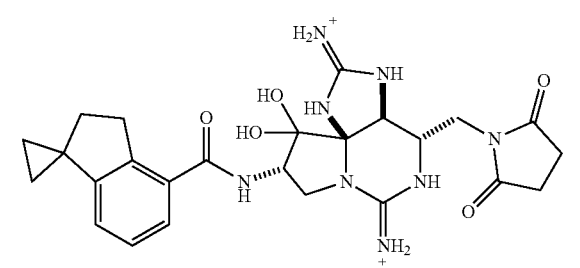
(40)
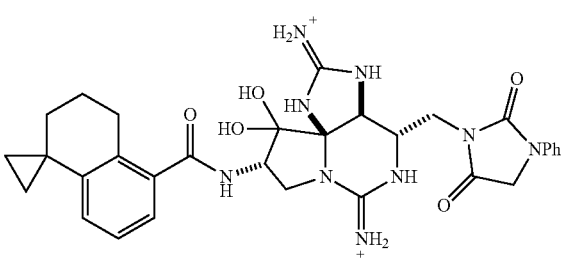
(36)
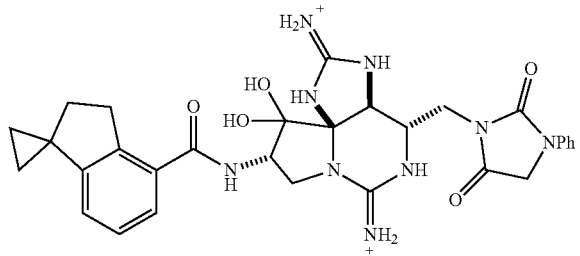
(41)
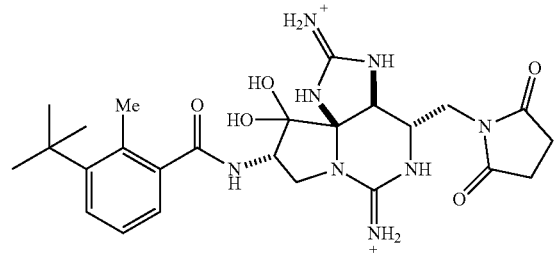

(42)
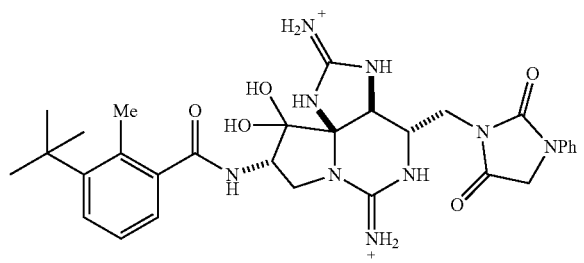
(43)
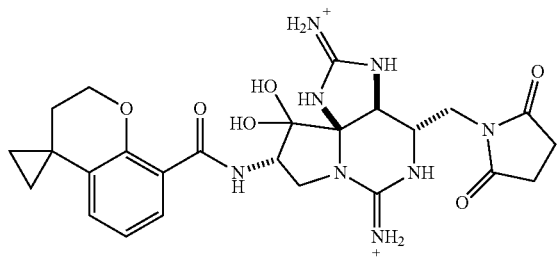
(44)
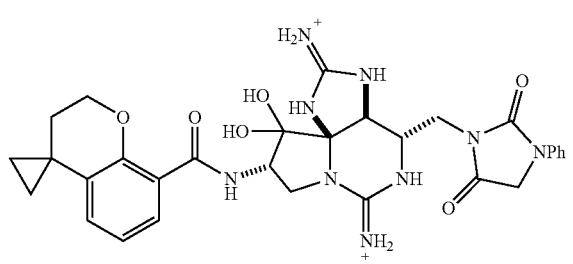
(45)
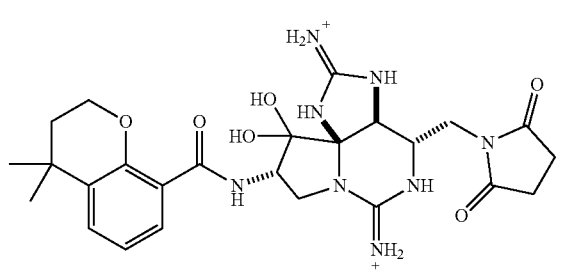
(46)
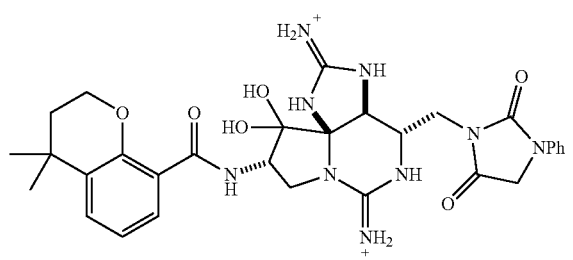
(47)
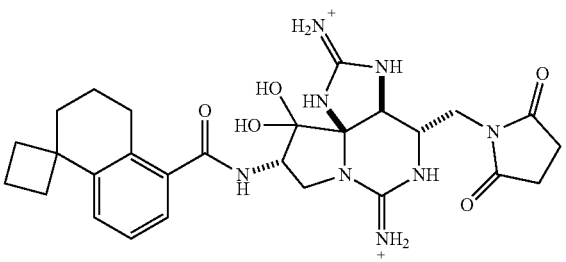
(48)
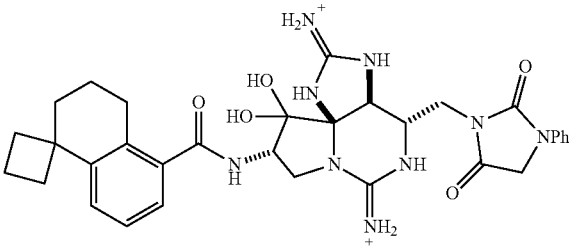
(49)
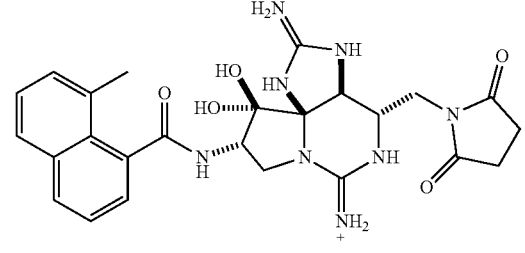
(50)
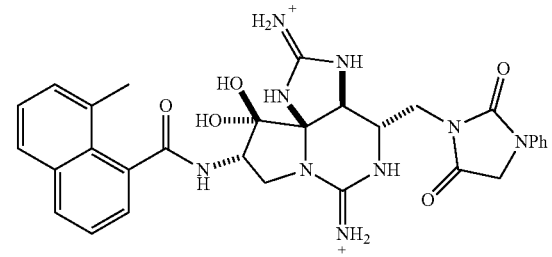
(51)
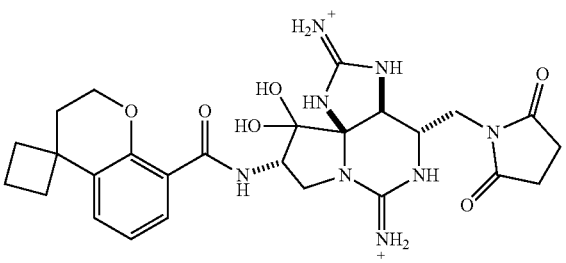

(52)
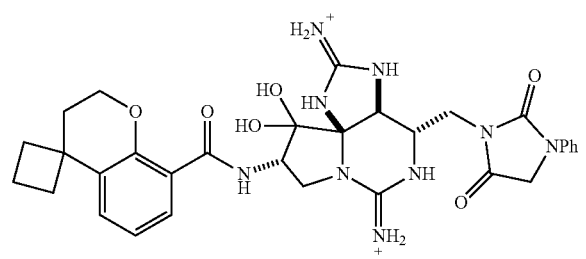
(53)
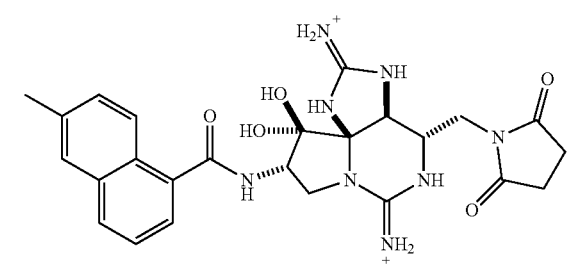
(54)
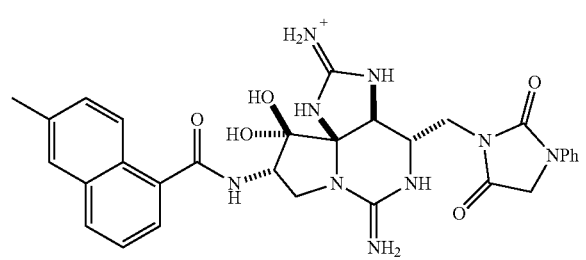
(55)
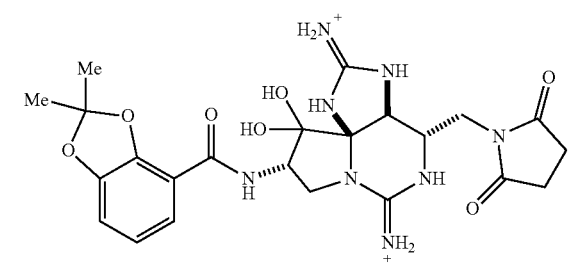
(56)
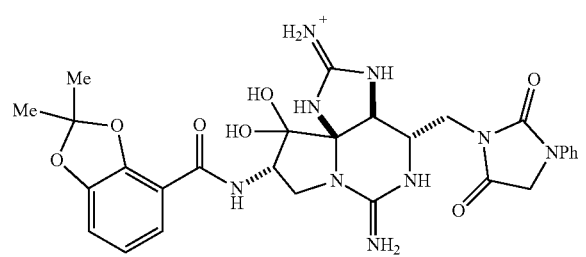
(57)
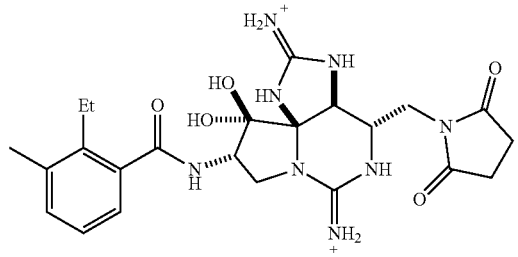
(58)
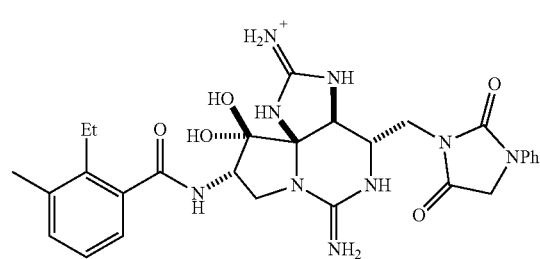
(59)
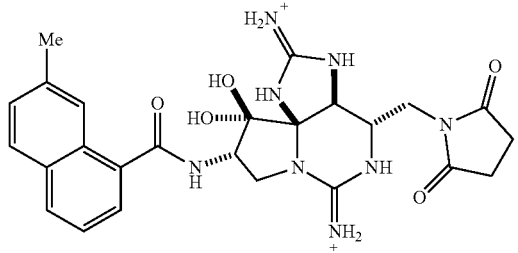
(60)
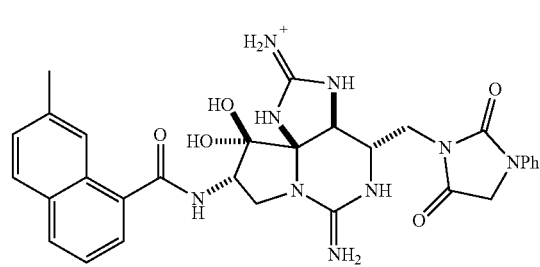
(61)
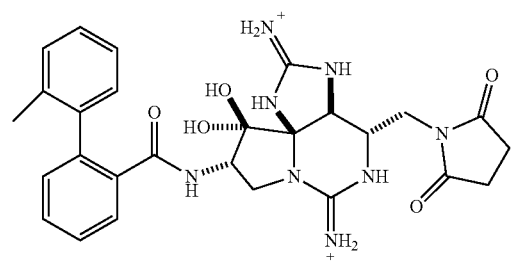

(62)
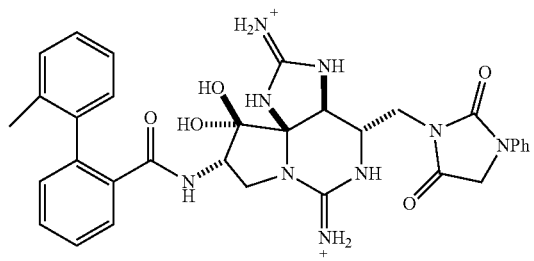
(63)
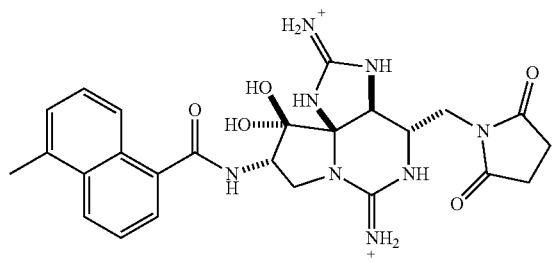
(64)
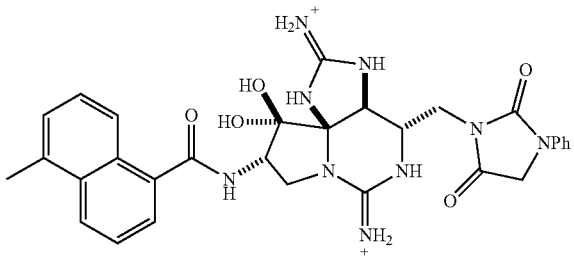
(65)
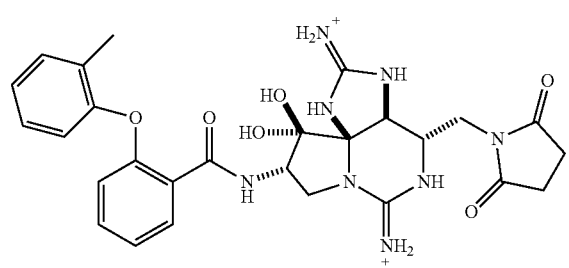
(66)
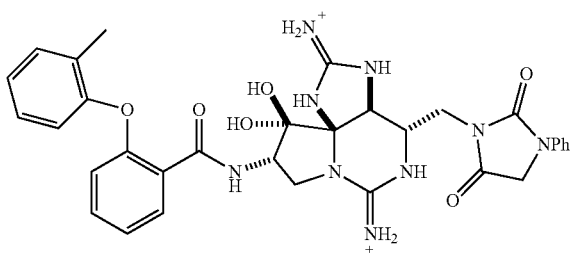
(67)
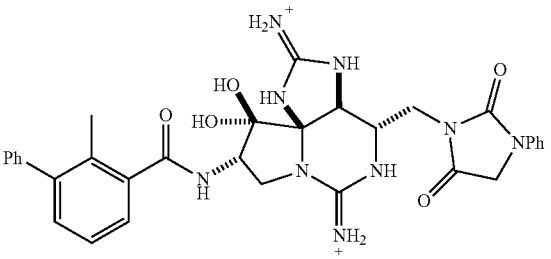
(68)
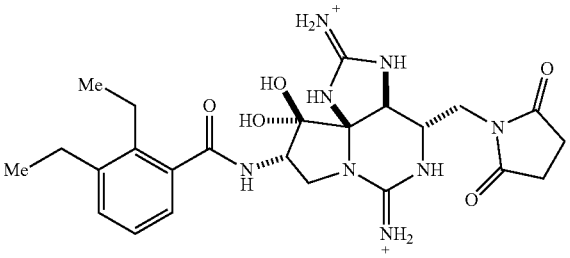
(69)
(70)
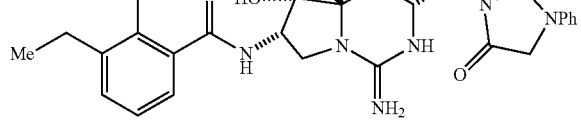
(71)
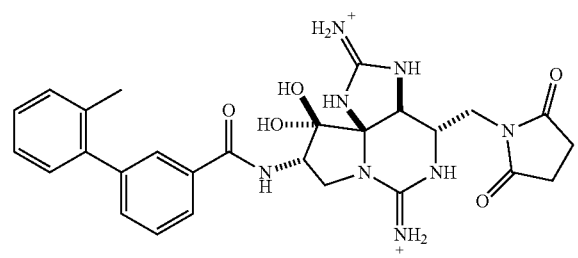

-continued
(72)
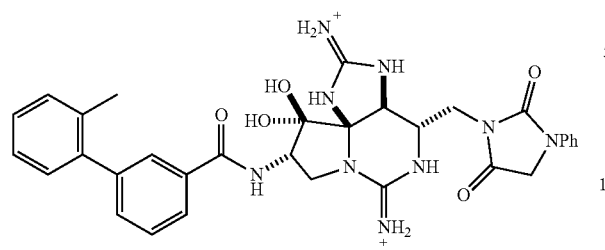
(73)
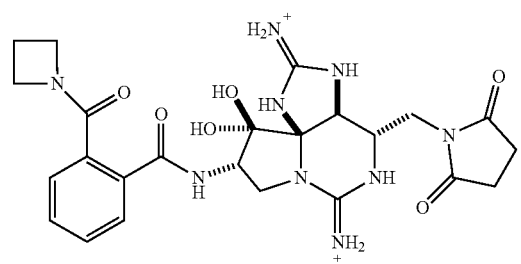
(74)
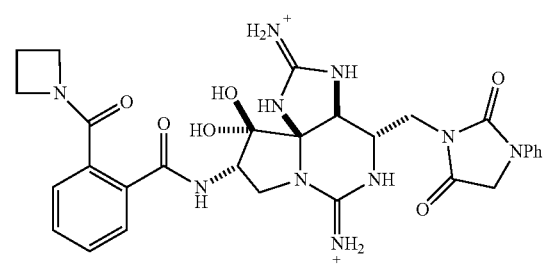
(75)
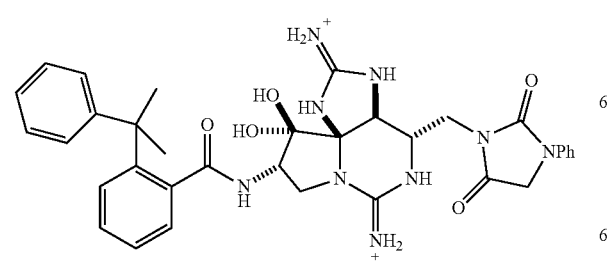
(76)
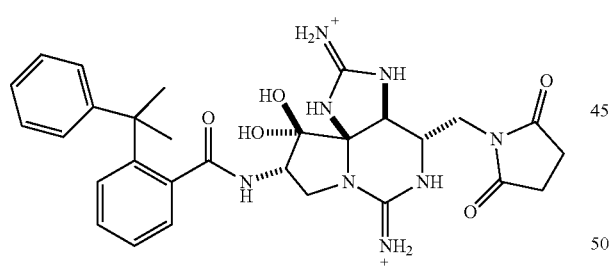
-continued
(77)
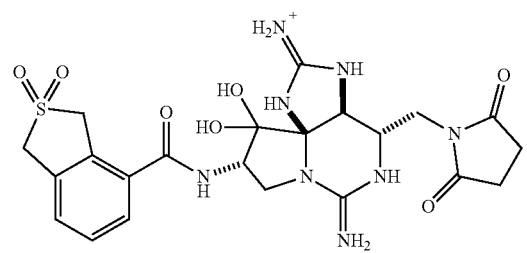
(78)
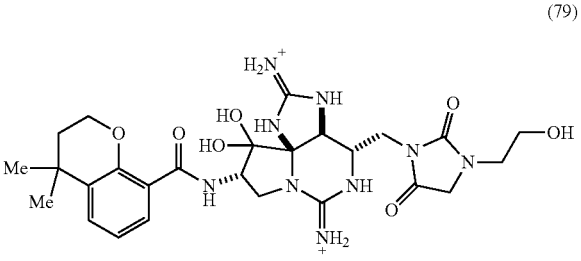
(79)
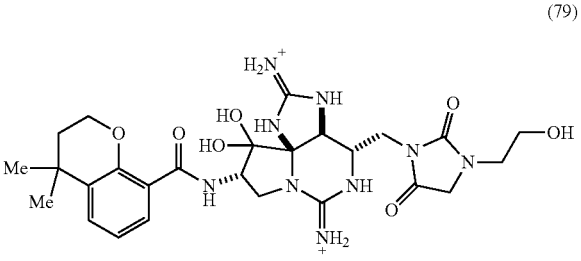
(80)
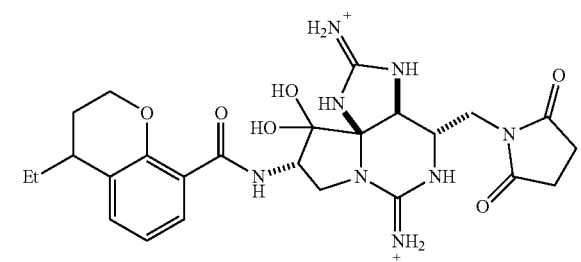
(81)
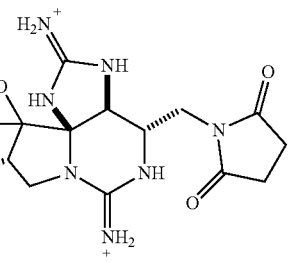

(82) 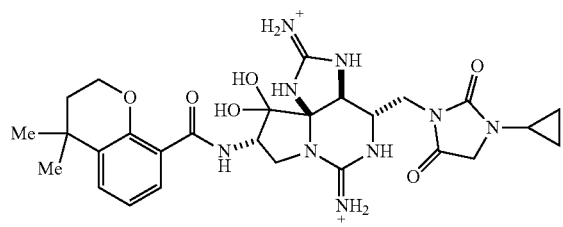
(83) 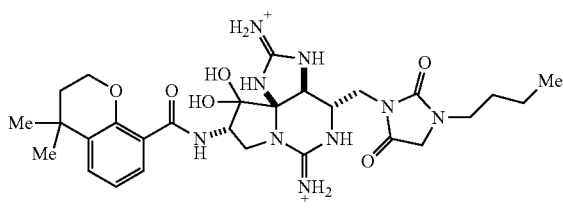
(84) 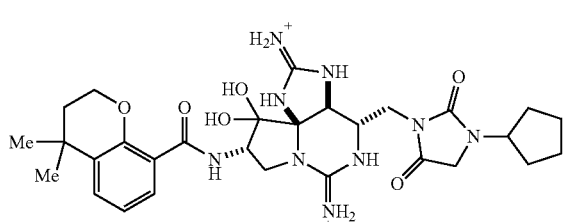
(85) 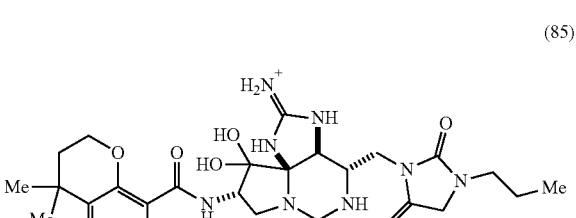
(86) 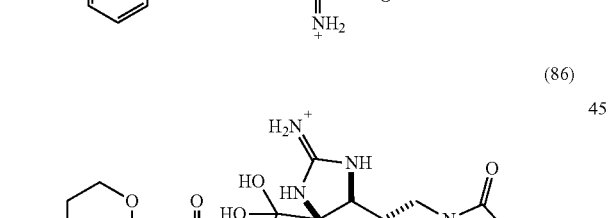
(87) 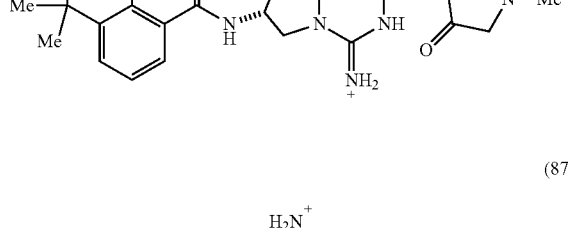
(88) 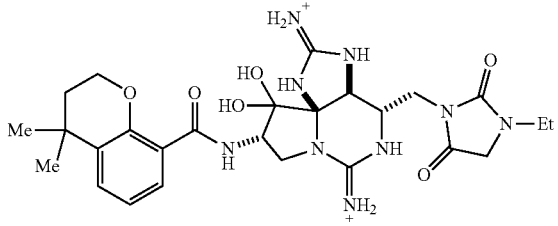
(89) 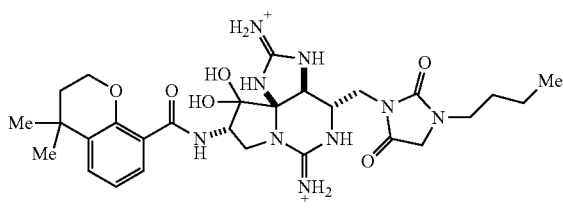
(90) 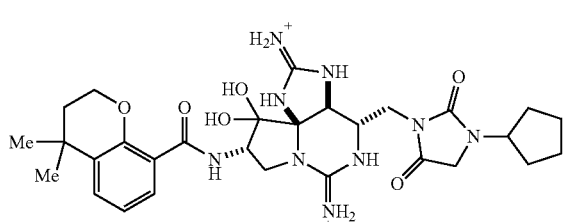
(91) 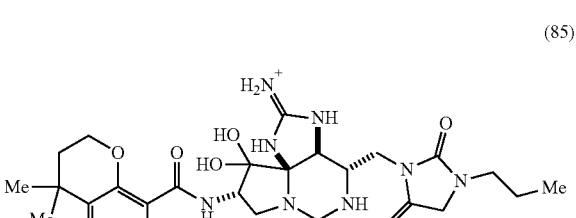
(92) 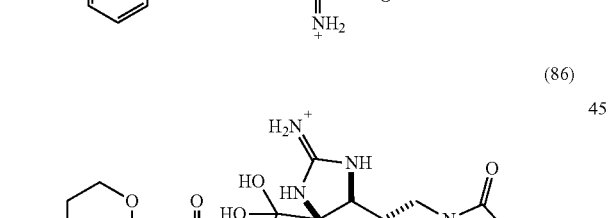
(93) 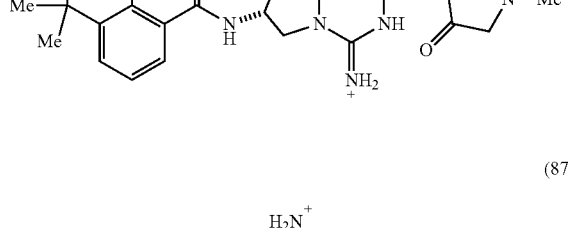

-continued (94)

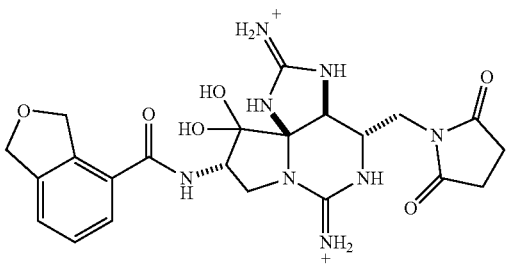

(95)

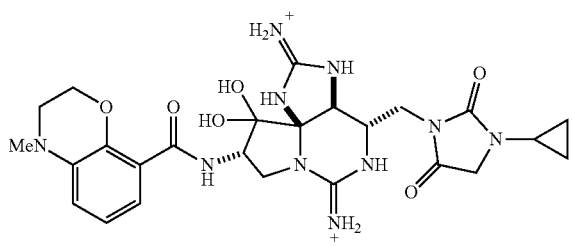

or a pharmaceutically acceptable salt, hydrate, solvate, stereoisomer, tautomer, or mixture thereof.

In some or any embodiments is a compound of Formula Xb

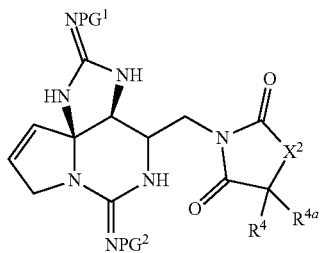
Xb or a salt thereof, where
PG$^1$ is a nitrogen-protecting group;
PG$^2$ is a nitrogen-protecting group;
X$^2$ is —C(R$^4$)(R$^{4a}$)— or —N(R$^8$)—; and
each R$^4$ and R$^{4a}$ is independently hydrogen or C$_{1-6}$alkyl. In some or any embodiments is a compound of Formula Xb1:

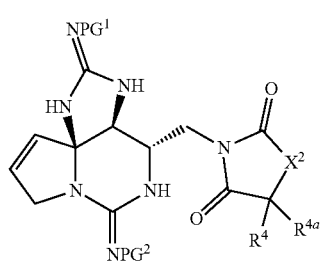
Xb1 or a salt thereof; where PG$^1$, PG$^2$, X$^1$, and X$^2$ are as defined for a compound of formula Xb, above or in any embodiments described herein.

In some or any embodiments is a compound of Formula Xc

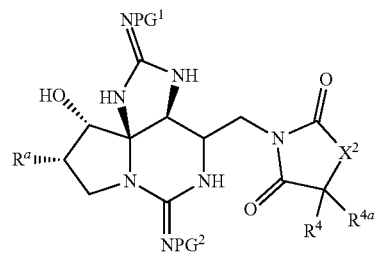
Xc or a salt thereof, where
R$^a$ is —NHPG$^3$ or —NH$_2$;
PG$^1$ is a nitrogen-protecting group;
PG$^2$ is a nitrogen-protecting group;
PG$^3$ is a nitrogen-protecting group;
X$^2$ is —C(R$^4$)(R$^{4a}$)— or —N(R$^8$)—; and
each R$^4$ and R$^{4a}$ is independently hydrogen or C$_{1-6}$alkyl. In some or any embodiments is a compound of Formula Xc4:

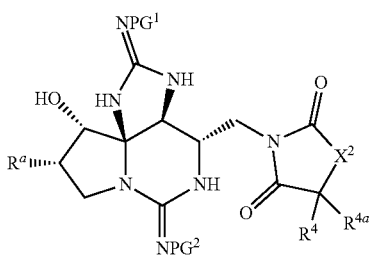
Xc4 or a salt thereof; where R$^a$, PG$^1$, PG$^2$, X$^1$, and X$^2$ are as defined for a compound of formula Xc, above or in any embodiments described herein.

In some or any embodiments is a compound of Formula Xd

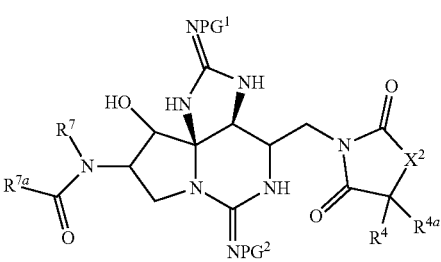
Xd or a salt thereof, where
PG$^1$ is a nitrogen-protecting group;
PG$^2$ is a nitrogen-protecting group;
X$^2$ is —C(R$^4$)(R$^{4a}$)— or —N(R$^8$)—;
each R$^4$ and R$^{4a}$ is independently hydrogen or C$_{1-6}$alkyl;
R$^7$ is hydrogen or C$_{1-6}$alkyl;
R$^{7a}$ is aryl optionally substituted with 1, 2, 3, or 4 R$^{7b}$;
heterocyclic optionally substituted with 1, 2, 3, or 4 R$^{7b}$;
or biphenyl optionally substituted with 1, 2, 3, or 4 R$^{7b}$;

each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and $R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano.

In some or any embodiments is a compound of Formula Xd1

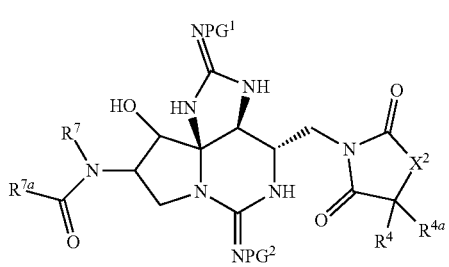

or a salt thereof; where $R^4$, $R^{4a}$, $R^7$, $R^{7a}$, $PG^1$, $PG^2$, and $X^2$ are as defined for a compound of formula Xd, above or in any embodiments described herein.

In some or any embodiments, the compound of Formula Xb, Xb1, Xc, Xc2, Xc3, Xc4, Xd, Xd1, Xe, or Xe1 is that where $PG^1$ is a nitrogen-protecting group selected from Tces, Mbs and tosyl; $PG^2$ is a nitrogen-protecting group selected from —C(O)CCl$_3$ and —C(O)OCH$_2$CCl$_3$; and all other groups are as defined in any of the embodiments. In some or any embodiments, the compound of Formula Xb, Xb1, Xc, Xc2, Xc3, Xc4, Xd, Xd1, Xe, or Xe1 is that where $PG^1$ is Tces, $PG^2$ is —C(O)CCl$_3$, and all other groups are as defined in any of the embodiments.

In some or any embodiments, provided herein are:
(a) compounds as described herein, e.g., of Formula (I)-(Id) and 1-95, and pharmaceutically acceptable salts and compositions thereof;
(b) compounds as described herein, e.g., of Formula (I)-(Id) and 1-95, and pharmaceutically acceptable salts and compositions thereof for use in the treatment of pain and/or conditions modulated by voltage-gated sodium channels;
(c) processes for the preparation of compounds as described herein, e.g., of Formula (I)-(Id) and 1-95, as described in more detail elsewhere herein;
(d) pharmaceutical formulations comprising a compound as described herein, e.g., of Formula (I)-(Id) and 1-95, or a pharmaceutically acceptable salt thereof together with a pharmaceutically acceptable carrier or diluent;
(e) a method for the treatment of a condition associated with voltage-gated sodium channel function in a subject that includes the administration of a therapeutically or prophylactically effective amount of a compound as described herein, e.g., of Formula (I)-(Id) and 1-95, its pharmaceutically acceptable salt or composition;
(f) a method for the treatment of pain in a subject that includes the administration of a therapeutically or prophylactically effective amount of a compound as described herein, e.g., of Formula (I)-(Id) and 1-95, its pharmaceutically acceptable salt or composition;
(g) pharmaceutical formulations comprising a compound as described herein, e.g., of Formula (I)-(Id) and 1-95, or a pharmaceutically acceptable salt thereof together with one or more other effective agents for treating pain and/or conditions modulated by voltage-gated sodium channels, optionally in a pharmaceutically acceptable carrier or diluent;
(h) a method for the treatment of pain in a subject that includes the administration of a therapeutically or prophylactically effective amount of a compound as described herein, e.g., of Formula (I)-(Id) and 1-95, its pharmaceutically acceptable salt or composition in combination and/or alternation with one or more agent for the treatment of pain and/or conditions modulated by voltage-gated sodium channels; and
(i) a method for the treatment of a condition associated with voltage-gated sodium channel function in a subject that includes the administration of a therapeutically or prophylactically effective amount of a compound as described herein, e.g., of Formula (I)-(Id) and 1-95, its pharmaceutically acceptable salt or composition in combination and/or alternation with one or more agent for the treatment of pain.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in some or any embodiments, by resolution of the racemic form by recrystallization techniques, by synthesis from optically-active starting materials, by chiral synthesis, or by chromatographic separation using a chiral stationary phase). In addition, the compounds described herein may epimerize at the C11 position under certain conditions. Such epimers are within the embodiments provided herein.

In some or any embodiments, methods to obtain optically active materials are known in the art, and include at least the following.
i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;
ii) simultaneous crystallization—a technique whereby the individual stereoisomers are separately crystallized from a solution of the racemate, possible only if the latter is a conglomerate in the solid state;
iii) enzymatic resolutions—a technique whereby partial or complete separation of a racemate by virtue of differing rates of reaction for the stereoisomers with an enzyme;
iv) enzymatic asymmetric synthesis—a synthetic technique whereby at least one step of the synthesis uses an enzymatic reaction to obtain an stereoisomerically pure or enriched synthetic precursor of the desired stereoisomer;
v) chemical asymmetric synthesis—a synthetic technique whereby the desired stereoisomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

In some or any embodiments, provided is a composition of a 11,13-modified saxitoxin that comprises a substantially pure designated stereoisomer of the 11,13-modified saxitoxin. In some or any embodiments, in the methods and compounds of this invention, the compounds are substantially free of other stereoisomer. In some or any embodiments, a composition includes a compound that is at least 85%, 90%, 95%, 98%, 99% or 100% by weight, of the 11,13-modified saxitoxin, the remainder comprising other chemical species or stereoisomers.

Isotopically Enriched Compounds

Also provided herein are isotopically enriched compounds, including but not limited to isotopically enriched 11,13-modified saxitoxins.

Isotopic enrichment (in some or any embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in some or any embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In some or any embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art.

Additional steps and reagents not provided in the Exemplary Preparation Scheme would be known to those of skill in the art. For example, the compound of formula A (depicted below) where $PG^1$ is a nitrogen-protecting group, e.g. Tces, and $PG^2$ is a nitrogen-protecting group, e.g. Troc, can be prepared using procedures known to one of ordinary skill in the art (e.g. see US2010/0284913. It would be appreciated by one of ordinary skill in the art that an intermediate of formula A-1:

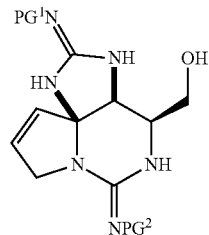

A-1 could be prepared using the procedures known by one of ordinary skill in the art or as disclosed in US2010/0284913 (which is herein incorporated by reference in its entirety, particularly the synthetic methods disclosed therein) but replacing L-serine with D-serine. Exemplary methods of preparation are described in detail in the Examples herein.

General Scheme A

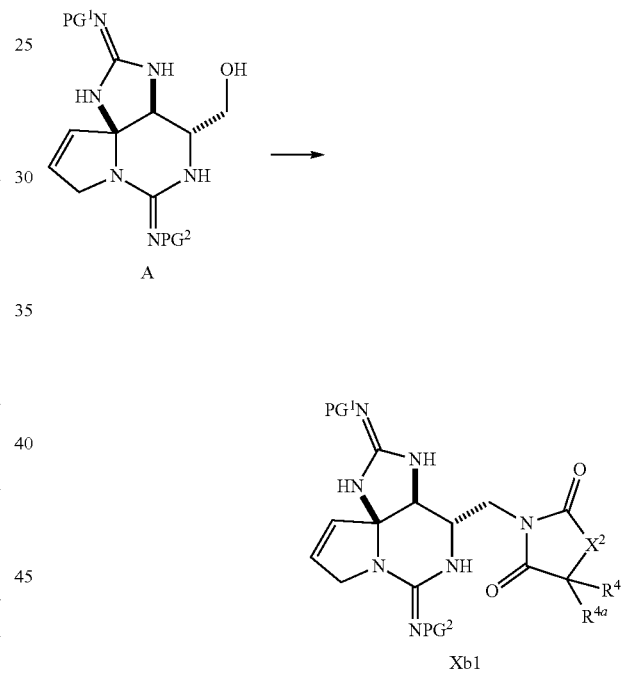

The compound of formula A where $PG^1$ is a nitrogen-protecting group, e.g. Tces, and $PG^2$ is a nitrogen-protecting group, e.g. Troc, can be prepared using procedures known to one of ordinary skill in the art (e.g. see US2010/0284913. The compound of formula A can be treated with succinimide and triphenylphosphine in the presence of an azodicarboxylate such as diisopropyl azodicarboxylate in a solvent such as THF to form the compound of formula Xb1 (where $X^2$ is —$CH_2$— and $R^4$, and $R^{4a}$ are as defined for a Compound of Formula I or as defined in any embodiments described herein) which can be optionally purified (for example by chromatography) before proceeding to the next step.

Alternatively, the compound of formula A can be used to prepare a compound of formula Xb1 where $X^2$ is —$NR^8$—; and all other groups are as defined herein. The compound of formula A can be treated with triphenylphosphine in the presence of an azodicarboxylate such as diisopropyl azodicarboxylate in a solvent such as THF followed by addition of

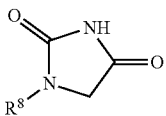

to form the compound of formula Xb1 (where $X^2$ is $-NR^8-$ and $R^4$, and $R^{4a}$ are as defined for a Compound of Formula I or as defined in any embodiments described herein) which can be optionally purified (for example by chromatography) before proceeding to the next step.

General Scheme B

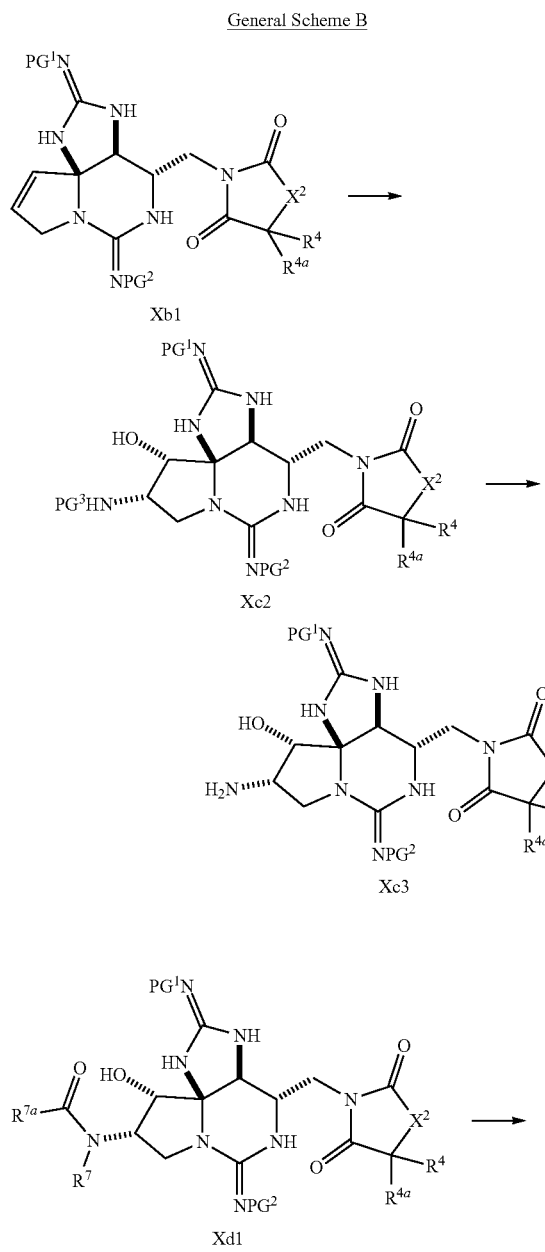

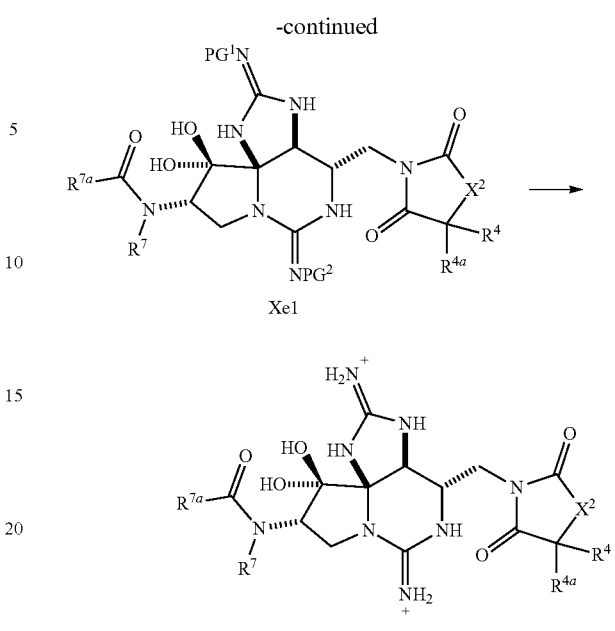

A Compound of Formula I where $R^4$, $R^{4a}$, $R^7$, $R^{7a}$, and $X^2$, and all other groups are as defined in the Summary of the Invention or in any embodiments can be prepared according to General Scheme B. In some or any embodiments, $R^7$ is hydrogen. For example, the compound of formula Xb1 where $PG^1$ is a nitrogen-protecting group, e.g. Tces, and $PG^2$ is a nitrogen-protecting group, e.g. Troc, can be prepared as described above in General Scheme A or in other embodiments herein. Xb1 can be treated with a compound of formula $H_2NPG^3$ where $PG^3$ is as defined in any of the embodiments herein (e.g. $PG^3$ is Boc) in the presence of $OsO_4$ in a solvent such as $CH_3CN$, where the reaction is optionally quenched, for example with $NaHCO_3$ and where the product is optionally extracted and/or purified by chromatography. The $PG^3$ protecting group is then removed using conditions known to one of ordinary skill in the art, e.g. by treating with an acid such as TFA when $PG^3$ is Boc to yield the compound of formula Xc3 or a salt thereof. The product is used in the next step without further purification or is optionally extracted and/or purified by chromatography. Xc3 is then treated with a base such as triethylamine in a solvent such as $CH_2Cl_2$ with a compound of formula of formula $R^{7a}-C(O)OH$ in the presence of a coupling agent such as HBTU and in the presence of a base such as diisopropylethylamine (DIEA) or treated with a compound of formula of formula $R^{7a}-C(O)X$ (where X is a leaving group such as halo) in the presence of a base such as diisopropylethylamine (DIEA) where the product Xd1 is optionally extracted and/or purified by chromatography. The compound of formula Xe1 can be prepared by treating a compound of formula Xd1 with Dess-Martin periodinane in a solvent such as $CH_2Cl_2$ and where the product is optionally purified before using in the next step. The compound of Formula I can be prepared by treating the compound of formula Xe1 with a catalyst such as $PdCl_2$ in the presence of an acid such as trifluoroacetic acid in one more solvents such as methanol and/or water and followed by treating with $H_2$, and where the product is removed by filtration and optionally purified by chromatography.

In another embodiment, provided is a method of preparing a compound of Formula I comprising
a) deprotecting a compound of Formula Xe

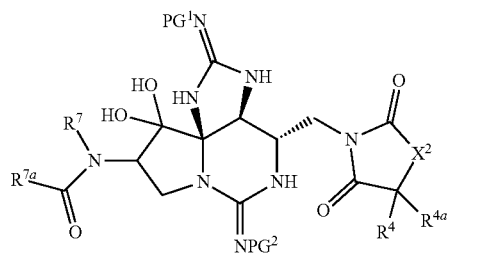

Xe where PG¹ is a nitrogen-protecting group selected from Tces, Mbs, and tosyl; PG² is a nitrogen-protecting group selected from —C(O)CCl₃ and —C(O)OCH₂CCl₃; and $R^4$, $R^{4a}$, $R^7$, $R^{7a}$, and $X^2$ are as defined in any of the embodiments described herein to yield a compounds of Formula I, or according to any of the embodiments described herein; and b) optionally isolating the compound of Formula I.
In some or any embodiments the compound of formula Xe is according to formula Xe I.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of Formula (I)-(Id) and 1-95, if appropriate in a salt form, either used alone or in the form of a combination with one or more compatible and pharmaceutically acceptable carriers, such as diluents or adjuvants, or with another agent for the treatment of pain and/or conditions modulated by voltage-gated sodium channels.

In some or any embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In some or any embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In some or any embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in some or any embodiments, wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, in some or any embodiments, ethyl oleate. These compositions can also contain adjuvants, in particular wetting, isotonizing, emulsifying, dispersing and stabilizing agents. Sterilization can be carried out in several ways, in some or any embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in some or any embodiments, dextran, mannitol or lactose.

In some or any embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in some or any embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in some or any embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In some or any embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in some or any embodiments, in purified form, together with a suitable amount of carrier so as to provide the form for proper administration to the subject. The formulation should suit the mode of administration. In a some or any embodiment, the pharmaceutical compositions or single unit dosage forms are sterile and in suitable form for administration to a subject, in some or any embodiments, an animal subject, such as a mammalian subject, in some or any embodiments, a human subject.

A pharmaceutical composition is formulated to be compatible with its intended route of administration. In some or any embodiments, routes of administration include, but are not limited to, parenteral, e.g., intravenous, intradermal, subcutaneous, intramuscular, subcutaneous, oral, buccal, sublingual, inhalation, intranasal, transdermal, topical (including administration to the eye, and in some embodiments to the cornea), transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal, or topical (including administration to the eye, and in some embodiments to the cornea) administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In some or any embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or nonaqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In some or any embodiments, a dosage form used in the initial treatment of pain may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in some or any embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In some or any embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In some or any embodiments, excipients suitable for use in oral liquid or aerosol dosage forms include, but are not limited to, water, glycols, oils, alcohols, flavoring agents, preservatives, and coloring agents. In some or any embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In some or any embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In some or any embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In some or any embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In some or any embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in some or any embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In some or any embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in some or any embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In some or any embodiments, the drug may be administered using intravenous infusion, an implantable osmotic pump, a transdermal patch, liposomes, or other modes of administration. In some or any embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In some or any embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. In some or any embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In some or any embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In some or any embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In some or any embodiments, doses are from about 1 to about 1000 mg per day for an adult, or from about 5 to about 250 mg per day or from about 10 to 50 mg per day for an adult. In some or any embodiments, doses are from about 5 to about 400 mg per day or 25 to 200 mg per day per adult. In some or any embodiments, dose rates of from about 50 to about 500 mg per day are also contemplated.

In further aspects, provided are methods of treating a condition associated with voltage-gated sodium channel function and/or pain in a subject by administering, to a subject in need thereof, a therapeutically or prophylactically effective amount of a compound provided herein, or a pharmaceutically acceptable salt thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In some or any embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in some or any embodiments, the dosage administered to a subject is 0.140 mg/kg to 3 mg/kg of the subject's body weight, based on weight of the active compound. In some or any embodiments, the dosage administered to a subject is between 0.20 mg/kg and 2.00 mg/kg, or between 0.30 mg/kg and 1.50 mg/kg of the subject's body weight.

In some or any embodiments, the recommended daily dose range of a composition provided herein for the conditions described herein lie within the range of from about 0.1 mg to about 1000 mg per day, given as a single once-a-day dose or as divided doses throughout a day. In some or any embodiments, the daily dose is administered twice daily in equally divided doses. In some or any embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In some or any embodiments, the dosage administered to the subject may be increased to improve the prophylactic or therapeutic effect of the composition or it may be decreased to reduce one or more side effects that a particular subject is experiencing.

In some or any embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In some or any embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In some or any embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In some or any embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In some or any embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some or any embodiments, loading doses can be administered to achieve steady-state blood or serum concentrations of about 1200 to about 8000 ng/mL, or about 2000 to about 4000 ng/mL for one to five days. In some or any embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In some or any embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In some or any embodiments, provided herein are unit dosages comprising a compound, or a pharmaceutically acceptable salt thereof, in a form suitable for administration. Such forms are described in detail herein. In some or any embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In some or any embodiments, dosages of the second agents to be used in a combination therapy are provided herein. In some or any embodiments, dosages lower than those which have been or are currently being used to treat pain are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J.; which are incorporated herein by reference in their entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In some or any embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In some or any embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In some or any embodiments, a compound provided herein and a second agent are administered to a patient, in some or any embodiments, a mammal, such as a human, in a sequence and within a time interval such that the compound provided herein can act together with the other agent to provide an increased benefit than if they were administered otherwise. In some or any embodiments, the second active agent can be administered at the same time or sequentially in any order at different points in time; however, if not administered at the same time, they should be administered sufficiently close in time so as to provide the desired therapeutic or prophylactic effect. In some or any embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In some or any embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In some or any embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In some or any embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In some or any embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In some or any embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of pain and/or a condition associated with voltage-gated sodium channel function or a pain-related disorder. The kits can include a compound or composition provided herein, a second agent or composition, and instructions providing information to a health care provider regarding usage for treating the pain or a pain-related disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some or any embodiments, a compound or composition can be included as a sterile aqueous pharmaceutical composition or dry powder (e.g., lyophilized) composition.

In some or any embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a condition associated with voltage-gated sodium channel function and/or pain in a subject, which comprises contacting the subject with a therapeutically or prophylactically effective amount of a 11,13-modified saxitoxin disclosed herein, e.g., a 11,13-modified saxitoxin of Formula (I)-(Id) and 1-95, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In some or any embodiments, provided herein are methods for treating pain and/or a condition associated with voltage-gated sodium channel function in a subject. In some or any embodiments, the methods encompass the step of administering to the subject in need thereof an amount of a compound effective for the treatment pain and/or a condition associated with voltage-gated sodium channel function in combination with a second agent effective for the treatment or prevention of pain and/or a condition associated with voltage-gated sodium channel function. The compound can be any compound as described herein, and the second agent can be any second agent described in the art or herein. In some or any embodiments, the compound is in the form of a pharmaceutical composition or dosage form, as described elsewhere herein.

In some or any embodiments, provided herein are methods for treating a condition associated with voltage-gated sodium channel function in a subject. In some or any embodiments, the methods encompass the step of administering to the subject in need thereof a therapeutically or prophylactically effective amount of a compound effective for the treatment of a condition associated with voltage-gated sodium channel function in combination with a second agent effective for the treatment of a condition associated with voltage-gated sodium channel function. The compound can be any compound as described herein, and the second agent can be any second agent described in the art or herein. In some or any embodiments, the compound is in the form of a pharmaceutical composition or dosage form, as described elsewhere herein.

In some or any embodiments, the pain to be reduced, ameliorated, treated, or prevented is associated with a condition or is a condition selected from acute pain, anal fissures, back pain, chronic pain, dental pain, joint pain, neck pain, neuropathic pain, obstetric pain, post-herpetic neuralgia, shingles, tension headaches, trigeminal blepharospasm, pain associated with cardiac arrhythmia, focal dystonia, hyperhidrosis, muscle spasms, urinary bladder relaxation, visceral pain, sympathetically maintained pain, myositis pain, musculoskeletal pain, lower back pain, pain from sprains and strains, pain associated with functional bowel disorders, non-cardiac chest pain, pain associated with irritable bowel syndrome, pain associated with myocardial ischemia, toothache pain, pain from dysmenorrhea, erythromelalgia, diabetic peripheral neuropathy, paroxysmal extreme pain disorder, complex regional pain syndrome, trigeminal neuralgia, multiple sclerosis, osteoarthritis, postherpetic neuralgia, cancer, cluster headache, migraine, sciatica, endometriosis, fibromyalgia, dry eye syndrome, (acute) corneal injuries or abrasions, corneal infections, pain associated with Parkinson's disease, pain associated with ALS, and surgery (in some embodiments, post-surgery; in some embodiments, ocular surgery). In some or any embodiments, the pain to be reduced, ameliorated, treated, or prevented is pain in an acute care setting, including post-surgery. In some or any embodiments, the pain to be reduced, ameliorated, treated, or prevented is pain in an acute care setting, including post-surgery and the compound is administered intravenously. In some or any embodiments, the pain to be reduced, ameliorated, treated, or prevented is ocular pain. In some or any embodiments, the pain to be reduced, ameliorated, treated, or prevented is ocular pain and the compound is administered topically. In some or any embodiments, the pain to be reduced, ameliorated, treated, or prevented is subacute or chronic pain. In some or any embodiments, the pain to be reduced, ameliorated, treated, or prevented is subacute or chronic pain and the compound is administered subcutaneously.

In some or any embodiments, the condition associated with voltage-gated sodium channel function is selected from itch, cough, epilepsy, Parkinson's disease, a mood disorder, psychosis, amyotrophic lateral sclerosis (ALS), cardiac arrhythmia, glaucoma, ischemia, a spasticity disorder, and obsessive compulsive disorder. In some or any embodiments, the condition associated with voltage-gated sodium channel function is selected from pain, itch, cough, glaucoma, and ischemia. In some or any embodiments, the condition associated with voltage-gated sodium channel function is selected from pain, itch, and cough. In some or any embodiments, the condition associated with voltage-gated sodium channel function is pain.

In some or any embodiments, the compounds described herein are used for the reduction of the severity or duration of pain. In some or any embodiments, the compounds described herein are used for the reduction of the severity or duration of pain associated with voltage-gated sodium channel function.

In some or any embodiments, the compounds described herein are used for prevention of pain or of a condition associated with voltage-gated sodium channel function.

In some or any embodiments, the compounds described herein are used for treatment of pain or of a condition associated with voltage-gated sodium channel function.

Assay Methods

Compounds can be assayed for efficacy in treating pain and/or a condition associated with voltage-gated sodium channel function according to any assay known to those of skill in the art. Exemplary assay methods are provided elsewhere herein.

Second Therapeutic Agents

In some or any embodiments, the compounds and compositions provided herein are useful in methods of treatment of pain and/or a condition associated with voltage-gated sodium channel function, that comprise further administration of a second agent effective for the treatment of pain and/or a pain-related disorder and/or a condition associated with voltage-gated sodium channel function. The second agent can be any agent known to those of skill in the art to be effective for the treatment of pain and/or a pain-related disorder and/or a condition associated with voltage-gated sodium channel function, including those currently approved by the United States Food and Drug Administration, or other similar body of a country foreign to the United States. In some or any embodiments, the second agent is a local anesthetic (in some or any embodiments, a steroid), an opioid, a vasoconstrictor, a glucocorticoid, adrenergic drugs (in some or any embodiments, alpha agonists or mixed central-peripheral alpha-2-agonists), vanilloids, an anti-inflammatory agent (e.g. NSAID, or an anti-inflammatory agent associated with ocular conditions, including cyclosporine and lifitegrast) or a chemical permeation enhancer. In some or any embodiments, chemical permeation enhancers include anionic surfactants, cationic surfactants, nonionic surfactants. In some or any embodiments, the second agent is bupivacaine, levobupivicaine, tetracaine, ropivacaine, epinephrine, phenylephrine, clonidine, sodium lauryl sulfate, sodium octyl sulfate, dodecyltrimethylammonium bromide, octyltrimethylammonium bromide, polyoxyethylene (20) sorbitan monolaurate, and/or polyoxyethylene (20) sorbitan monooleate.

In some or any embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of pain and/or a pain-related disorder and/or a condition associated with voltage-gated sodium channel function. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the pain or a pain-related disorder to be alleviated. It is to be further understood that for any particular subject, specific dosage regimens and schedules should be adjusted over time according to the individual need and the professional judgment of the person administering or supervising the administration of the compositions.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); Ph (phenyl); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); Tces (2,2,2-trichloroethoxysulfonyl); —Si(tert-Bu)(Ph)$_2$ and —Si$^t$BuPh$_2$ (tert-butyl-diphenylsilyl); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 11,13-Modified Saxitoxin Compounds

Scheme 1

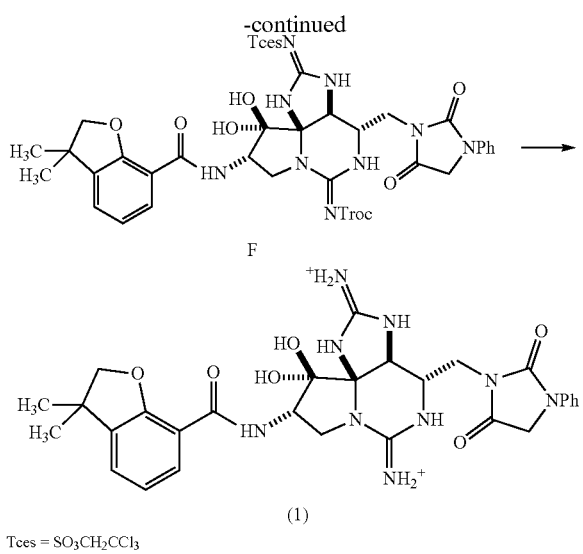

Tces = SO₃CH₂CCl₃

Preparation of Compound (1)

Compound A can be prepared using published procedures by one of ordinary skill in the art (see *J. Am. Chem. Soc.* 2016, 138 (18) pp 5594-6001).

To a solution of triphenylphosphine (118 mg, 0.45 mmol, 2.5 equiv) in 3.0 mL of THF cooled to 0° C. was added diisopropyl azodicarboxylate (89 μL, 0.45 mmol, 2.5 equiv) dropwise over 5 minutes. The mixture was stirred at this temperature for an additional 15 min, during which time a white precipitate formed. In a separate flask, alcohol A (110 mg, 0.18 mmol, 1.0 equiv) was dissolved in 7.0 mL of THF and cooled to 0° C. To the solution of A was added the suspension of PPh₃/DIAD dropwise over ~5 minutes. After an additional 15 minutes, 1-phenylhydantoin (111 mg, 0.63 mmol, 3.5 equiv) was added in a single portion and the reaction was warmed to room temperature. After 14 hours the reaction was concentrated under reduced pressure. Purification of the residue by chromatography on silica gel (gradient elution: CH₂Cl₂→4:1 CH₂Cl₂/acetone) afforded the hydantoin B as a white solid (130 mg, 0.17 mmol, 94%).

To solution of tert-butyl 4-chlorobenzoyloxycarbamate (156 mg, 575 μmol, 3.4 equiv) in 2.8 mL of CH₃CN was added OsO₄ (53.1 μL of a 4% aqueous solution, 7.8 μmol, 0.05 equiv). After 25 minutes a solution of B (130 mg, 169 μmol, 1.0 equiv) in 2.0 mL of CH₃CN was added followed immediately by the addition of 0.48 mL of H₂O. The resulting mixture was stirred at room temperature for 3 days, and quenched by the addition of 0.7 mL of saturated aqueous Na₂S₂O₃. The mixture was stirred for an additional 5 minutes then diluted with H₂O (18 mL) and extracted with 3×40 mL of EtOAc. The combined organic layers were washed with 2×14 mL of saturated aqueous NaHCO₃, dried with MgSO₄ and concentrated in vacuo. Purification of the residue by chromatography on silica gel (gradient elution: CH₂Cl₂→5:1 CH₂Cl₂/acetone) afforded the carbamate C as a white solid (83 mg, 89 μmol, 53%).

To solution of C (83 mg, 89 μmol) in 3.5 mL of dichloromethane was added trifluoroacetic acid (0.7 mL). The resulting solution was stirred at room temperature for 4 hrs and concentrated in vacuo to afford the trifluoroacetate salt D that was used in the following step without purification.

To a solution of D (80 mg, 0.087 mmol, 1.0 equiv) in 0.75 mL of dry DMF under anhydrous condition was added ⁱPr₂NEt (61 μL, 0.35 mmol, 4.0 equiv). The resulting solution was stirred at room temperature for 15 minutes followed by addition of HBTU (43 mg, 0.11 mmol, 1.3 equiv) and the 3,3-dimethyl-2,3-dihydro-1-benzofuran-7-carboxylic acid (22 mg, 0.11 mmol, 1.3 equiv). The resulting solution was stirred under N₂ atmosphere for 48 hours. Following this time, the reaction mixture was diluted with EtOAc (20 mL) and transferred to a separatory funnel. The organic solution was washed with aqueous sat. NH₄Cl (3×6 mL) and brine (2×6 mL). The organic layer was dried over MgSO₄, filtered and concentrated. Purification by chromatography on silica gel (gradient elution: hexanes→1:2 hexanes/EtOAc) afforded the desired product E as a white solid (53 mg, 0.054 mmol, 62%).

To a solution of amide E (53 mg, 0.054 mmol, 1.0 equiv) in 3.6 mL of CH₂Cl₂ was added Dess-Martin periodinane (53 mg, 0.13 mmol, 2.3 equiv). The reaction was stirred for 25 min. The mixture is then quenched by addition of aqueous 2M solution of ascorbic acid (1.0 mL) and the biphasic solution is stirred for 10 min. The reaction mixture was concentrated under reduced pressure. The residue dissolved in 5 mL aqueous 10 mM trifluoroacetic acid solution and acetonitrile (3:1). Purified by reversed-phase HPLC (Bonna-Agela Durashell C18, 10 μM, 21.2×250 mm column, eluting with gradient flow from 50-65% MeCN/H₂O with 10 mM TFA over 30 minutes. At a flow rate of 20 mL/min, compound F had a retention time of 13.5-16 min and isolated as a white solid (40 mg, 0.04 mmol, 74%).

Trifluoroacetic acid (400 μL) and PdCl₂ (15 mg) were added to a solution of intermediate F in 3:1 MeOH/H₂O (6.0 mL). H₂ gas was bubbled through the reaction mixture for 30 minutes, after which time bubbling was ceased and the reaction was stirred under an atmosphere of H₂ for 5 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 μM, 50×250 mm column, eluting with gradient flow from 25-30% MeCN/H₂O with 10 mM TFA over 45 minutes (214 nm UV detection). At a flow rate of 40 mL/min, (1) had a retention time of 35.0-44.5 min and was isolated as a white solid (9.5 mg, 0.018 mmol, 45%). (1): ¹H NMR (D₂O, 400 MHz) δ 7.93-7.90 (m, 1H), 7.74-7.70 (m, 2H), 7.67-7.62 (m, 3H), 7.48-7.43 (m, 1H), 7.28 (t, J=7.2 Hz, 1H), 5.08 (appar. t, J=8.4 Hz, 1H), 5.05 (s, 1H), 4.73 (s, 2H), 4.64 (dd, J=14, 8.4 Hz, 2H), 4.40 (appar. t, J=9.6 Hz, 1H), 4.20 (dd, J=14, 11 Hz, 1H), 4.07 (dd, J=12, 3.6 Hz, 1H), 3.85 (dd, J=14, 3.6 Hz, 1H), 3.60 (dd, J=10, 8.4 Hz, 1H), 1.53 (s, 3H), 1.51 (s, 3H) ppm.

Scheme 2

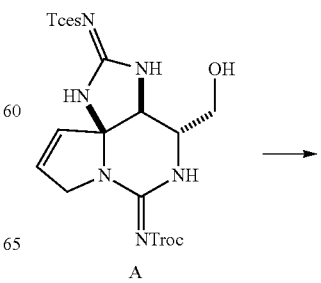

A

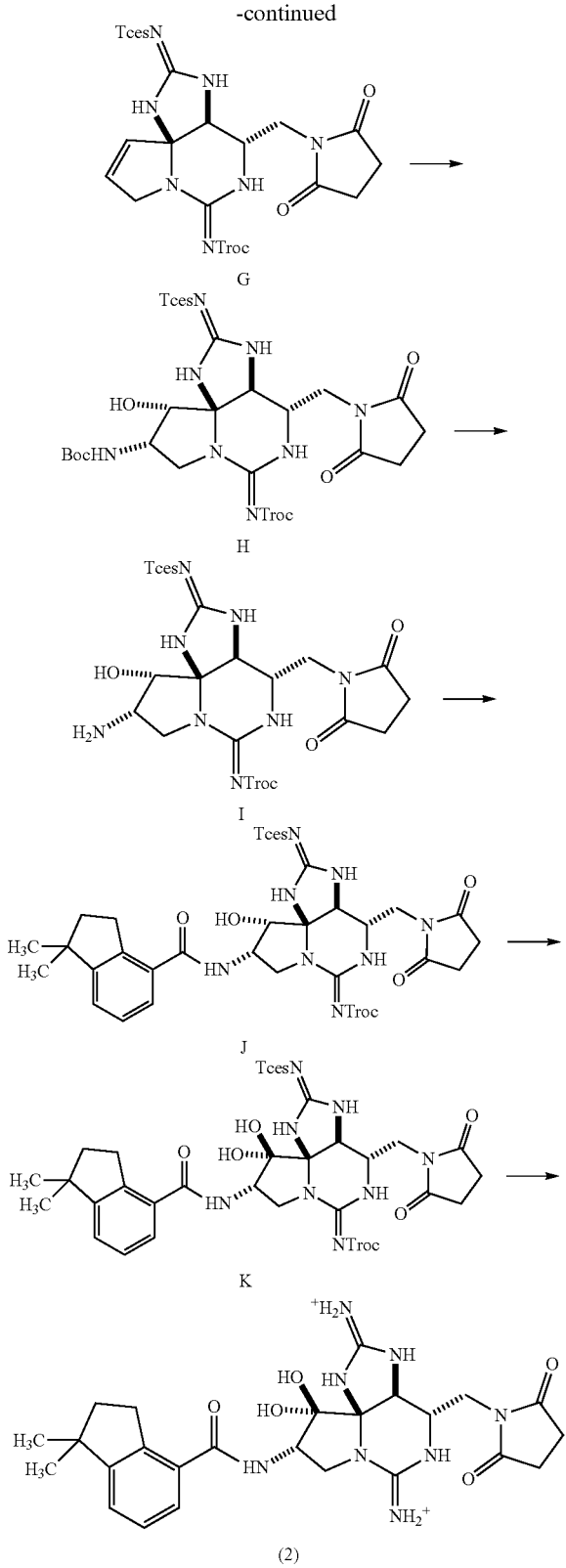

Preparation of Compound (2)

To a solution of triphenylphosphine (376 mg, 1.43 mmol, 2.5 equiv) in THF (9.2 mL) cooled to 0° C. was added diisopropyl azodicarboxylate (283 μL, 1.44 mmol, 2.5 equiv) dropwise over 5 minutes. The mixture was stirred at this temperature for an additional 15 min, during which time a white precipitate formed. In a separate flask, alcohol A (350 mg, 0.575 mmol, 1.0 equiv) was dissolved in 21.5 mL of THF and cooled to 0° C. To the solution of A was added the white suspension of $PPh_3$/DIAD dropwise over ~5 minutes. After an additional 15 minutes, succinimide (197 mg, 2.0 mmol, 3.5 equiv) was added in a single portion and the reaction was warmed to room temperature. After 4 hours the reaction was concentrated under reduced pressure. Purification of the residue by chromatography on silica gel (gradient elution: hexanes→3:1 EtOAc/hexanes) afforded the succinimide G as a white solid (205 mg, 0.297 mmol, 52%).

To solution of tert-butyl 4-chlorobenzoyloxycarbamate (353 mg, 1.30 mmol, 3.4 equiv) in $CH_3CN$ (7.8 mL) was added $OsO_4$ (123 μL of a 4% aqueous solution, 19 μmol, 0.05 equiv). After 25 minutes a solution of G (262 mg, 379 μmol, 1.0 equiv) in 3.0 mL of $CH_3CN$ was added followed immediately by the addition of 1.08 mL of $H_2O$. The resulting mixture was stirred at room temperature for 3 days, and quenched by the addition of 1.8 mL of saturated aqueous $Na_2S2O_3$. The mixture was stirred for an additional 5 minutes then diluted with $H_2O$ (35 mL) and extracted with 3×70 mL of EtOAc. The combined organic layers were washed with 2×28 mL of saturated aqueous $NaHCO_3$, dried with $MgSO_4$ and concentrated in vacuo. Purification of the residue by chromatography on silica gel (gradient elution: hexanes→1:3 hexanes/EtOAc) afforded the carbamate H as a white solid (141 mg, 171 μmol, 45%).

To solution of H (141 mg, 171 μmol) in 6.2 mL of dichloromethane was added trifluoroacetic acid (1.3 mL). The resulting solution was stirred at room temperature for 4 hrs and concentrated in vacuo to afford the trifluoroacetate salt I that was used in the following step without purification.

To a solution of I (95 mg, 0.11 mmol, 1.0 equiv) in 0.75 mL of dry DMF under anhydrous condition was added $^iPr_2NEt$ (79 μL, 0.45 mmol, 4.0 equiv). The resulting solution was stirred at room temperature for 15 minutes followed by addition of HBTU (56 mg, 0.15 mmol, 1.3 equiv) and the desired aryl carboxylic acid (28 mg, 0.15 mmol, 1.3 equiv). The resulting solution was stirred under $N_2$ atmosphere for 48 hours. Following this time, the reaction mixture was diluted with EtOAc (20 mL) and transferred to a separatory funnel. The organic solution was washed with aqueous sat. $NH_4Cl$ (3×10 mL) and brine (2×10 mL). The organic layer was dried over $MgSO_4$, filtered and concentrated. Purification by chromatography on silica gel (gradient elution: $CH_2Cl_2$→5:1 $CH_2Cl_2$/Acetone) afforded the desired product J as a white solid (52 mg, 0.058 mmol, 52%).

To a solution of amide J (52 mg, 0.058 mmol, 1.0 equiv) in 3.8 mL of $CH_2Cl_2$ was added Dess-Martin periodinane (57 mg, 0.13 mmol, 2.3 equiv). The reaction was stirred for 25 min. The mixture is then quenched by addition of aqueous 2M solution of ascorbic acid (1.0 mL) and the biphasic solution is stirred for 10 min. The residue dissolved in 5 mL aqueous 10 mM trifluoroacetic acid solution and acetonitrile (3:1). Purified by reversed-phase HPLC (Bonna-Agela Durashell C18, 10 μM, 21.2×250 mm column, eluting with gradient flow from 30-60% $MeCN/H_2O$ with 10 mM TFA over 30 minutes. At a flow rate of 20 mL/min, compound K had a retention time of 26-27.5 min and isolated as a white solid (30 mg, 0.04 mmol, 56%).

Trifluoroacetic acid (300 μL) and $PdCl_2$ (12 mg) were added to a solution of intermediate K in 3:1 $MeOH/H_2O$ (4.0 mL). $H_2$ gas was bubbled through the reaction mixture for 30 minutes, after which time bubbling was ceased and the reaction was stirred under an atmosphere of H₂ for 5 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 μM, 50×250 mm column, eluting with gradient flow from 20-30% MeCN/with 10 mM TFA over 45 minutes (214 nm UV detection). At a flow rate of 40 mL/min, (2) had a retention time of 34-37.2 min and was isolated as a white solid (13 mg, 0.022 mmol, 53%). ¹H NMR (D₂O, 400 MHz) δ 7.66-7.63 (m, 1H), 7.60-7.58 (m, 1H), 7.50 (t, J=7.6 Hz, 1H), 5.08 (appar. t, J=9.2 Hz, 1H), 5.00 (s, 1H), 4.34 (appar. t, J=9.6 Hz, 1H), 4.11 (dd, J=14, 12 Hz, 1H), 3.95 (dd, J=12, 3.6 Hz, 1H), 3.69 (dd, J=14, 3.6 Hz, 1H), 3.60 (appar. t, J=9.6 Hz, 1H), 3.26-3.19 (m, 2H), 2.95 (s, 4H), 2.13-2.07 (m, 2H), 1.41 (s, 3H), 1.40 (s, 3H) ppm.

Scheme 3

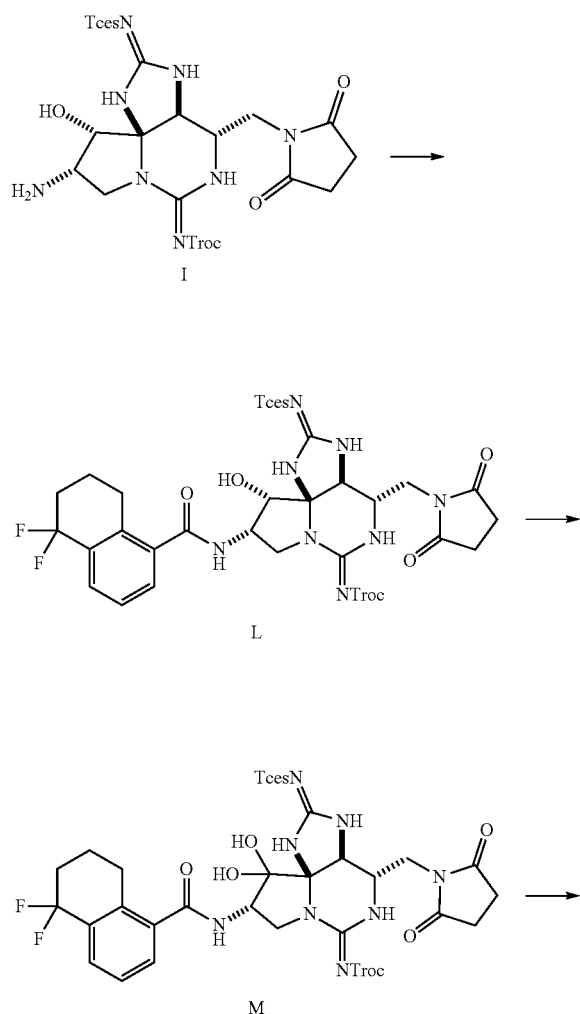

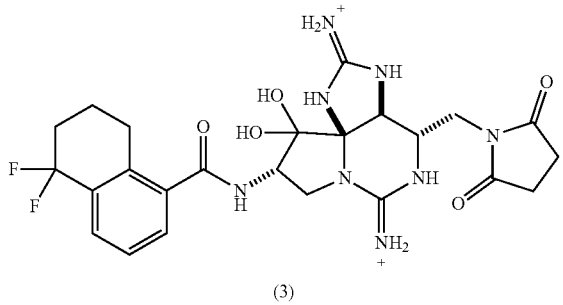

Preparation of (3)

To a solution of I (50 mg, 0.07 mmol, 1.0 equiv) in 0.80 mL of dry DMF under anhydrous condition was added Et₃N (40 μL, 0.28 mmol, 4.0 equiv). The resulting solution was stirred at room temperature for 15 minutes followed by addition of HBTU (35 mg, 0.9 mmol, 1.3 equiv) and carboxylic acid Intermediate 1 (18 mg, 0.085 mmol, 1.2 equiv). The resulting solution was stirred under N₂ atmosphere for 48 hours. Following this time, the reaction mixture was diluted with EtOAc (20 mL) and transferred to a separatory funnel. The organic solution was washed with aqueous sat. NH₄Cl (3×10 mL) and brine (2×10 mL). The organic layer was dried over MgSO₄, filtered and concentrated. Purification by chromatography on silica gel (gradient elution: hexanes→1:3 hexanes/ethyl acetate) afforded the desired product L as a white solid (30 mg, 0.033 mmol, 47%).

To a solution of amide L (50 mg, 0.055 mmol, 1.0 equiv) in 2.5 mL of CH₂Cl₂ was added Dess-Martin periodinane (51 mg, 0.12 mmol, 2.2 equiv). The reaction was stirred for 25 min. The mixture is then quenched by addition of aqueous 2M solution of ascorbic acid (1.0 mL) and the biphasic solution is stirred for 10 min. The residue dissolved in 5 mL aqueous 10 mM trifluoroacetic acid solution and acetonitrile (3:1). Purified by reversed-phase HPLC (Bonna-Agela Durashell C18, 10 μM, 21.2×250 mm column, eluting with gradient flow from 43-47% MeCN/H₂O with 10 mM TFA over 30 minutes. At a flow rate of 20 mL/min, compound M had a retention time of 24-27 min and isolated as a white solid (16 mg, 0.04 mmol, 74%).

Trifluoroacetic acid (150 μL) and PdCl₂ (6 mg) were added to a solution of intermediate M in 3:1 MeOH/H₂O (4.0 mL). H₂ gas was bubbled through the reaction mixture for 30 minutes, after which time bubbling was ceased and the reaction was stirred under an atmosphere of H₂ for 5 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 μM, 21.2×250 mm column, eluting with gradient flow from 10-25% MeCN/H₂O with 10 mM TFA over 30 minutes (214 nm UV detection). At a flow rate of 20 mL/min, (3) had a retention time of 21-22.5 min and was isolated as a white solid (6 mg, 0.018 mmol, 45%)

(3): ¹H NMR (D₂O, 400 MHz) δ 7.99 (d, J=7.6 Hz, 1H), 7.73 (d, J 7.2 Hz, 1H), 7.61 (appar. t, J=8.0 Hz, 1H), 5.06 (appar. t, J=8.8 Hz, 1H), 4.97 (s, 1H), 4.33 (appar. t, J=10

Hz, 1H), 4.06 (dd, J=14, 12 Hz, 1H), 3.92 (dd, J=12, 3.2 Hz, 1H), 3.66 (dd, J=14, 3.6 Hz, 1H), 3.56 (appar. t, J=9.6 Hz, 1H), 3.05-2.98 (m, 2H), 2.92 (s, 4H), 2.52-2.41 (m, 2H), 2.13-2.08 (m, 2H) ppm.

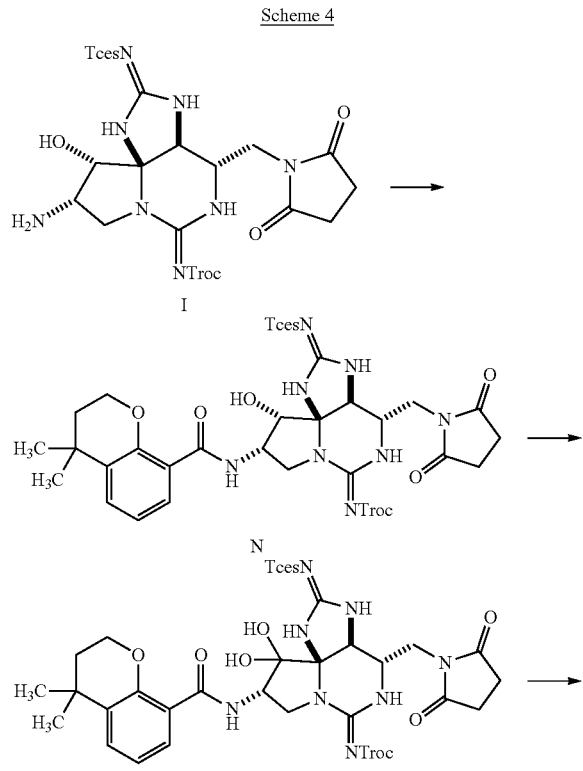

Preparation of (45)

To a solution of I (90 mg, 0.11 mmol, 1.0 equiv) in 0.90 mL of dry DMF under anhydrous condition was added $^i$Pr$_2$NEt (75 µL, 0.44 mmol, 4.0 equiv). The resulting solution was stirred at room temperature for 15 minutes followed by addition of HBTU (53 mg, 0.14 mmol, 1.3 equiv) and carboxylic acid Intermediate 10 (29 mg, 0.14 mmol, 1.3 equiv). The resulting solution was stirred under N$_2$ atmosphere for 48 hours. Following this time, the reaction mixture was diluted with EtOAc (20 mL) and transferred to a separatory funnel. The organic solution was washed with aqueous sat. NH$_4$Cl (3×10 mL) and brine (2×10 mL). The organic layer was dried over MgSO$_4$, filtered and concentrated. Purification by chromatography on silica gel (gradient elution: hexanes→1:3 hexanes/ethyl acetate) afforded the desired product N as a white solid (48 mg, 0.053 mmol, 48%).

To a solution of amide N (48 mg, 0.053 mmol, 1.0 equiv) in 2.5 mL of CH$_2$Cl$_2$ was added Dess-Martin periodinane (52 mg, 0.12 mmol, 2.3 equiv). The reaction was stirred for 25 min. The mixture is then quenched by addition of aqueous 2M solution of ascorbic acid (1.0 mL) and the biphasic solution is stirred for 10 min. The residue dissolved in 5 mL aqueous 10 mM trifluoroacetic acid solution and acetonitrile (3:1). Purified by reversed-phase HPLC (Bonna-Agela Durashell C18, 10 µM, 21.2×250 mm column, eluting with gradient flow from 30-60% MeCN/H$_2$O with 10 mM TFA over 30 minutes. At a flow rate of 20 mL/min, compound O had a retention time of 24-25.2 min and isolated as a white solid (16 mg, 0.017 mmol, 53%).

Trifluoroacetic acid (160 µL) and PdCl$_2$ (7 mg) were added to a solution of intermediate O in 3:1 MeOH/H$_2$O (4.0 mL). H$_2$ gas was bubbled through the reaction mixture for 30 minutes, after which time bubbling was ceased and the reaction was stirred under an atmosphere of H$_2$ for 5 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 µM, 21.2×250 mm column, eluting with gradient flow from 10-25% MeCN/H$_2$O with 10 mM TFA over 30 minutes (214 nm UV detection). At a flow rate of 20 mL/min, (45) had a retention time of 26.7-29 min and was isolated as a white solid (3 mg, 0.0056 mmol, 33%)

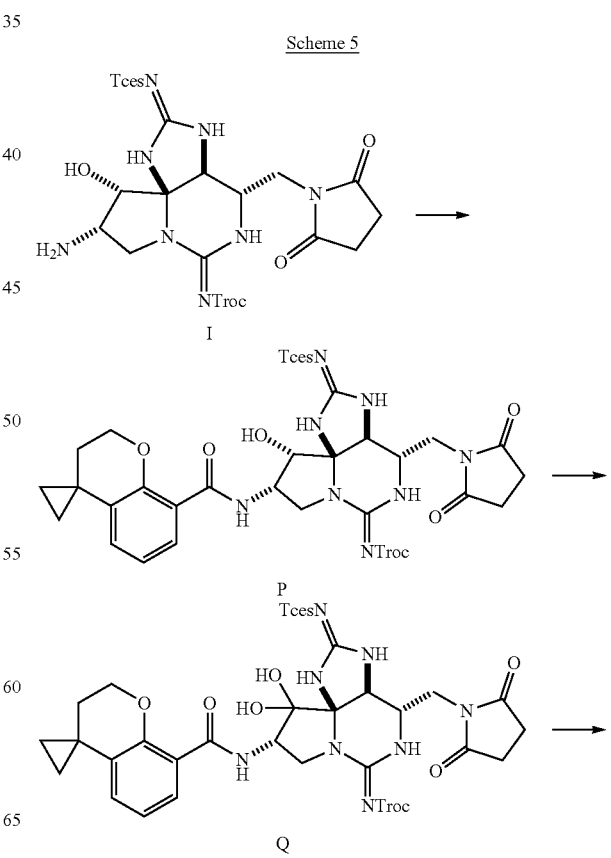

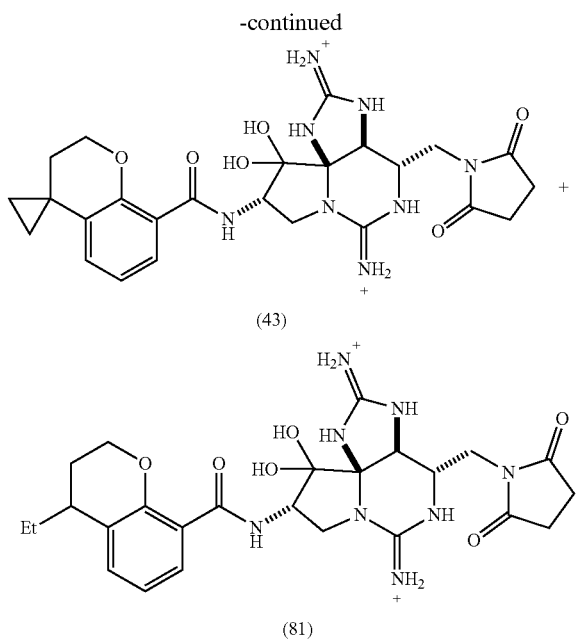

(43)

(81)

Preparation of (43) and (81)

To a solution of I (110 mg, 0.13 mmol, 1.0 equiv) in 1.0 mL of dry DMF under anhydrous condition was added $^i$Pr$_2$NEt (90 µL, 0.52 mmol, 4.0 equiv). The resulting solution was stirred at room temperature for 15 minutes followed by addition of HBTU (64 mg, 0.17 mmol, 1.3 equiv) and carboxylic acid Intermediate 19 (29 mg, 0.14 mmol, 1.3 equiv). The resulting solution was stirred under N$_2$ atmosphere for 48 hours. Following this time, the reaction mixture was diluted with EtOAc (20 mL) and transferred to a separatory funnel. The organic solution was washed with aqueous sat. NH$_4$Cl (3×10 mL) and brine (2×10 mL). The organic layer was dried over MgSO$_4$, filtered and concentrated. Purification by chromatography on silica gel (gradient elution: hexanes→1:2.5 hexanes/ethyl acetate) afforded the desired product P as a white solid (77 mg, 0.085 mmol, 65%).

To a solution of amide P (73 mg, 0.080 mmol, 1.0 equiv) in 5.5 mL of CH$_2$Cl$_2$ was added Dess-Martin periodinane (79 mg, 0.18 mmol, 2.3 equiv). The reaction was stirred for 25 min. The mixture is then quenched by addition of aqueous 2M solution of ascorbic acid (1.0 mL) and the biphasic solution is stirred for 10 min. The residue dissolved in 5 mL aqueous 10 mM trifluoroacetic acid solution and acetonitrile (3:1). Purified by reversed-phase HPLC (Bonna-Agela Durashell C18, 10 µM, 21.2×250 mm column, eluting with gradient flow from 35-65% MeCN/H$_2$O with 10 mM TFA over 30 minutes. At a flow rate of 20 mL/min, compound Q had a retention time of 18-20.1 min and isolated as a white solid (35 mg, 0.038 mmol, 47%).

Trifluoroacetic acid (350 µL) and PdCl$_2$ (16 mg) were added to a solution of intermediate Q (35 mg) in 3:1 MeOH/H$_2$O (6.0 mL). H$_2$ gas was bubbled through the reaction mixture for 30 minutes, after which time bubbling was ceased and the reaction was stirred under an atmosphere of H$_2$ for 5 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 µM, 21.2×250 mm column, eluting with gradient flow from 12-27% MeCN/H$_2$O with 10 mM TFA over 30 minutes (214 nm UV detection). At a flow rate of 20 mL/min, (81) had a retention time of 22-25.5 min and was isolated as a white solid (8 mg, 0.015 mmol, 39%). (81): $^1$H NMR (D$_2$O, 400 MHz) δ p 8.01-7.97 (m, 1H), 7.71-7.67 (m, 1H), 7.28 (t, J=7.6 Hz, 1H), 5.09 (appar. t, J=8.4 Hz, 1H), 5.06 (s, 1H), 4.61-4.56 (m, 2H), 4.45 (appar. t, J=10 Hz, 1H), 4.17 (dd, J=14, 12 Hz, 1H), 4.03 (dd, J=12, 3.4 Hz, 1H), 3.77 (dd, J=14, 3.5 Hz, 1H), 3.62 (dd, J=10, 8.7 Hz, 1H), 3.09-2.99 (m, 5H), 2.34-2.24 (m, 1H), 2.19-2.10 (m, 1H), 2.09-1.99 (m, 1H), 1.86-1.77 (m, 1H), 1.22-1.15 (m, 3H) ppm.

Palladium on carbon (5 mg) was added to a solution of intermediate Q (14 mg) in 3:1 MeOH/H$_2$O (6.0 mL). H$_2$ gas was bubbled through the reaction mixture for 1 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 µM, 21.2×250 mm column, eluting with gradient flow from 15-21% MeCN/H$_2$O with 10 mM TFA over 30 minutes (214 nm UV detection). At a flow rate of 20 mL/min, (43) had a retention time of 19-22.7 min and was isolated as a white solid (4 mg, 0.007 mmol, 49%). (43): $^1$H NMR (D$_2$O, 400 MHz) δ 7.91-7.88 (m, 1H), 7.22-7.20 (m, 2H), 5.07 (appar. t, J=9.2 Hz, 1H), 5.04 (s, 1H), 4.66 (appar. t, J=5.2 Hz, 2H), 4.42 (appar. t, J=9.6 Hz, 1H), 4.15 (dd, J=14, 12 Hz, 1H), 4.00 (dd, J=12, 3.2 Hz, 1H), 3.74 (dd, J=14, 4.0 Hz, 1H), 3.61 (dd, J=10, 8.4 Hz, 1H), 3.00 (s, 4H), 2.14-2.09 (m, 2H), 1.31-1.27 (m, 2H), 1.17-1.13 (m, 2H) ppm.

Scheme 6

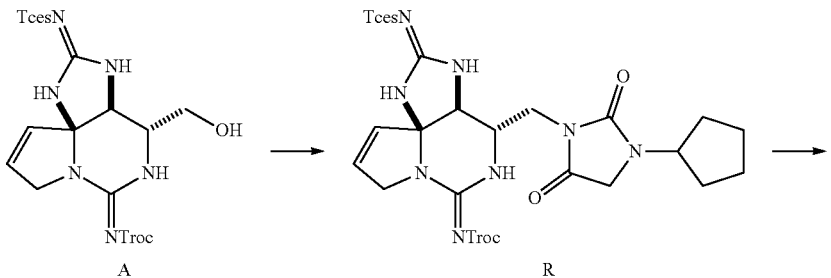

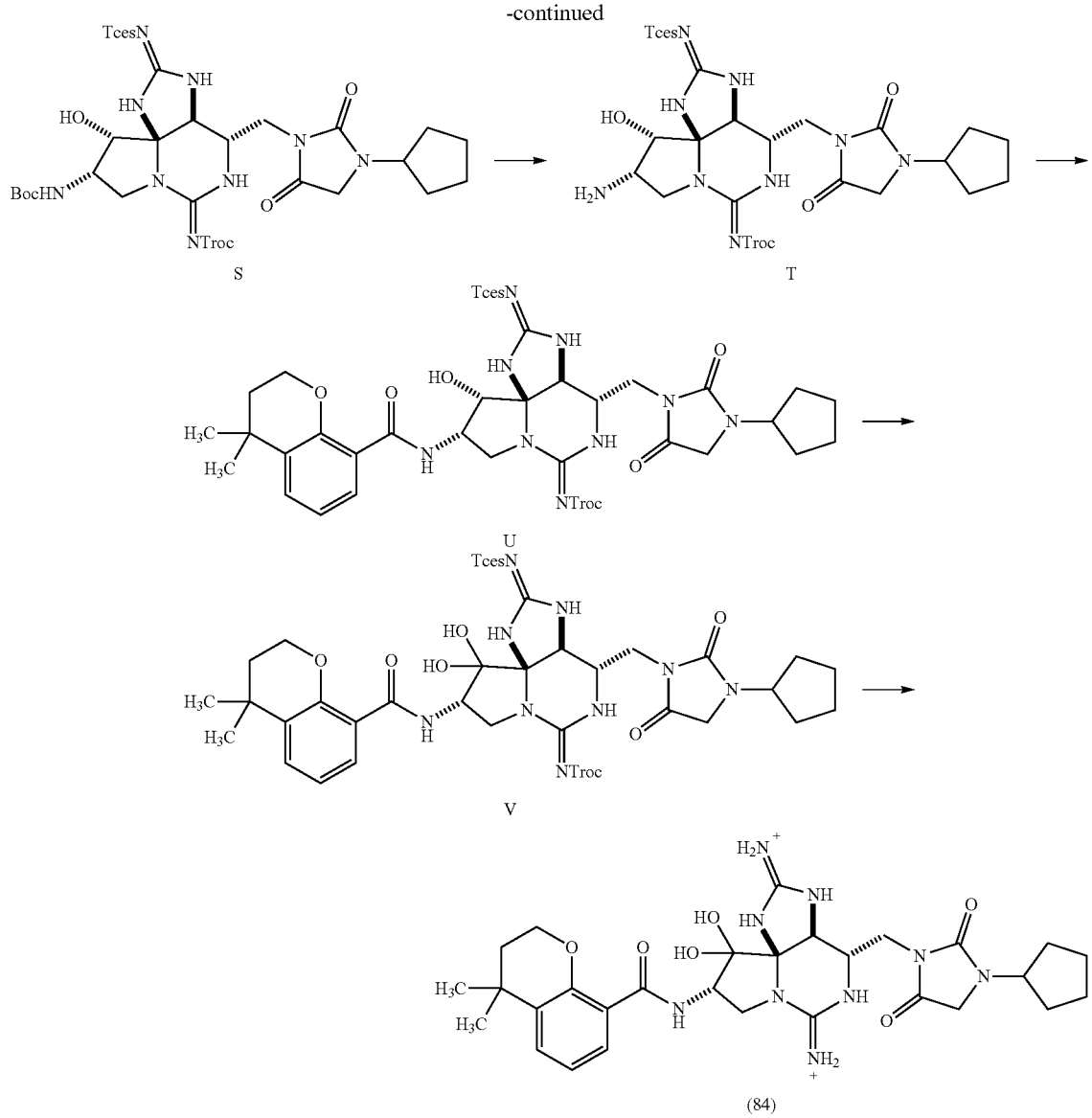

Preparation of (84)

To a solution of triphenylphosphine (433 mg, 1.64 mmol, 2.5 equiv) in 13.0 mL of THF cooled to 0° C. was added diisopropyl azodicarboxylate (324 µL, 1.64 mmol, 2.5 equiv) dropwise over 5 minutes. The mixture was stirred at this temperature for an additional 15 min, during which time a white precipitate formed. In a separate flask, alcohol A (400 mg, 0.66 mmol, 1.0 equiv) was dissolved in 25.0 mL of THF and cooled to 0° C. To the solution of A was added the suspension of $PPh_3$/DIAD dropwise over ~5 minutes. After an additional 15 minutes, 1-cyclopentylhydantoin (250 mg, 1.48 mmol, 2.25 equiv) was added in a single portion and the reaction was warmed to room temperature. After 14 hours the reaction was concentrated under reduced pressure. Purification of the residue by chromatography on silica gel (gradient elution: $CH_2Cl_2 \rightarrow 4:1$ $CH_2Cl_2$/acetone) afforded the hydantoin R as a white solid (320 mg, 0.42 mmol, 64%).

To solution of tert-butyl 4-chlorobenzoyloxycarbamate (343 mg, 1.26 mmol, 3.0 equiv) in 5.0 mL of $CH_3CN$ was added $OsO_4$ (173 µL of a 4% aqueous solution, 0.027 mmol, 0.065 equiv). After 25 minutes a solution of R (320 mg, 0.42 mmol, 1.0 equiv) in 3.0 mL of $CH_3CN$ was added followed immediately by the addition of 0.80 mL of $H_2O$. The resulting mixture was stirred at room temperature for 3 days, and quenched by the addition of 2.0 mL of saturated aqueous $Na_2S_2O_3$. The mixture was stirred for an additional 5 minutes then diluted with $H_2O$ (40 mL) and extracted with 3×110 mL of EtOAc. The combined organic layers were washed with 2×32 mL of saturated aqueous $NaHCO_3$, dried with $MgSO_4$ and concentrated in vacuo. Purification of the residue by chromatography on silica gel (gradient elution: $CH_2Cl_2 \rightarrow 5:1$ $CH_2Cl_2$/acetone) afforded the carbamate S as a white solid (110 mg, 0.12 mmol, 30%).

To solution of S (110 mg, 0.12 mmol) in 5.0 mL of dichloromethane was added trifluoroacetic acid (1.0 mL). The resulting solution was stirred at room temperature for 4 hrs and concentrated in vacuo to afford the trifluoroacetate salt T that was used in the following step without purification.

To a solution of T (110 mg, 0.121 mmol, 1.0 equiv) in 1.0 mL of dry DMF under anhydrous condition was added $^i$Pr$_2$NEt (85 µL, 0.48 mmol, 4.0 equiv). The resulting solution was stirred at room temperature for 15 minutes followed by addition of HBTU (60 mg, 0.16 mmol, 1.3 equiv) and Intermediate 10 (30 mg, 0.15 mmol, 1.2 equiv). The resulting solution was stirred under N$_2$ atmosphere for 48 hours. Following this time, the reaction mixture was diluted with EtOAc (10 mL) and transferred to a separatory funnel. The organic solution was washed with aqueous sat. NH$_4$Cl (3×6 mL) and brine (2×6 mL). The organic layer was dried over MgSO$_4$, filtered and concentrated. Purification by chromatography on silica gel (gradient elution: hexanes→1:2 hexanes/EtOAc) afforded the desired product U as a white solid (51 mg, 0.065 mmol, 54%).

To a solution of amide U (51 mg, 0.065 mmol, 1.0 equiv) in 3.4 mL of CH$_2$Cl$_2$ was added Dess-Martin periodinane (50 mg, 0.15 mmol, 2.3 equiv). The reaction was stirred for 25 min. The mixture is then quenched by addition of aqueous 2M solution of ascorbic acid (1.0 mL) and the biphasic solution is stirred for 10 min. The residue dissolved in 5 mL aqueous 10 mM trifluoroacetic acid solution and acetonitrile (3:1). Purified by reversed-phase HPLC (Bonna-Agela Durashell C18, 10 µM, 21.2×250 mm column, eluting with gradient flow from 35-62% MeCN/H$_2$O with 10 mM TFA over 30 minutes. At a flow rate of 20 mL/min, compound V had a retention time of 26-27.5 min and isolated as a white solid (30 mg, 0.03 mmol, 46%).

Trifluoroacetic acid (300 µL) and PdCl$_2$ (12 mg) were added to a solution of intermediate V in 3:1 MeOH/H$_2$O (4.0 mL). H$_2$ gas was bubbled through the reaction mixture for 30 minutes, after which time bubbling was ceased and the reaction was stirred under an atmosphere of H$_2$ for 5 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 12 h the reaction mixture was concentrated under reduced pressure, dissolved in 5 mL aqueous 10 mM trifluoroacetic acid solution and acetonitrile (3:1) and purified by reversed-phase HPLC (Bonna-Agela Durashell C18, 10 µM, 21.2×250 mm column, eluting with gradient flow from 17-31% MeCN/H$_2$O with 10 mM TFA over 30 minutes (214 nm UV detection). At a flow rate of 20 mL/min, (84) had a retention time of 23-27.5 min and was isolated as a white solid (7 mg, 0.011 mmol, 38%)

Intermediates Useful in the Preparation of Compounds of Formula I

The following schemes provide methods of preparing intermediates useful in the preparation of Compounds of Formula I. Certain intermediates, such as 1-cyclopentyl-hydantoin, 1-phenyl-hydantoin, 1-cyclopropyl-hydantoin, succinimide, 1-methyl-hydantoin, 1-n-butyl-hydantoin, and 1-n-propyl-hydantoin, are commercially available. In addition, the person of ordinary skill in the art would understand how to use the procedures disclosed here and in the art to prepare additional intermediates useful in the synthesis of compounds according to Formula (I).

Scheme 7

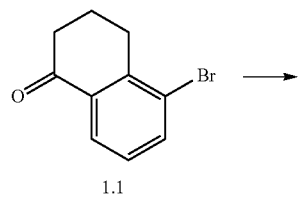

1.1

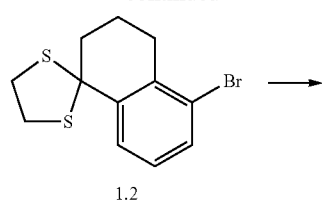

1.2

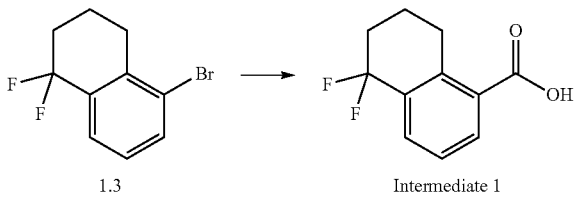

1.3  Intermediate 1

Preparation of Intermediate 1

To a solution of ketone 1.1 (2.0 g, 8.9 mmol, 1.0 equiv) in 20 mL CH$_2$Cl$_2$ was added 1,2-ethanedithiol. The solution was cooled to −15° C. and BF$_3$.OEt$_2$ (6.25 mL, 50 mmol, 5.6 equiv) was added dropwise. After 2 h the reaction was warmed to room temperature and stirred for an additional 2 h. The mixture was poured into 100 mL of saturated aqueous NaHCO$_3$ and extracted with 3×30 mL of CH$_2$Cl$_2$. The combined organic extracts were dried over MgSO$_4$, filtered and concentrated in vacuo. Purification by chromatography on silica gel (gradient elution: hexanes→10:1 hexanes/ethyl acetate) afforded the desired product 1.2 as a white solid (2.08 g).

N-iodosuccinimide (3.1 g, 14 mmol, 2.0 equiv) was suspended in 28 mL of CH$_2$Cl$_2$ and cooled to −78° C. HF-pyridine (2.56 mL, 28 mmol, 4.0 equiv) was added, followed by a solution of 1.2 in 17.3 mL of CH$_2$Cl$_2$. The reaction was stirred for 1 h at −78° C., warmed to 0° C. and stirred for an additional 30 min. At this time, the mixture was quenched by the addition of 40 mL of saturated aqueous NaHCO$_3$ and poured into an additional 50 mL of saturated NaHCO$_3$. Saturated sodium thiosulfate (50 mL) was added and the mixture was extracted with 3×40 mL of CH$_2$Cl$_2$. The combined organic extracts were washed with brine (30 mL), dried over MgSO$_4$, filtered and concentrated in vacuo. Purification by chromatography on silica gel (hexanes) afforded the desired product 1.3 (200 mg).

A solution of 1.3 (135 mg, 0.55 mmol, 1.0 equiv) in 2.7 mL of THF was cooled to −78° C. and n-butyllithium (0.34 mL of a 1.6M sol'n, 0.55 mmol, 1.0 equiv) was added dropwise. After 15 min, gaseous CO$_2$ was bubbled through the reaction mixture for 15 minutes. Bubbling was ceased and the reaction was maintained at −78° C. for an additional 2 h. The reaction was diluted with Et$_2$O, slowly allowed to warm, and quenched with 5 mL of 1.0 M aqueous HCl. The organic layer was separated, dried over MgSO$_3$, filtered and concentrated in vacuo. Purification by chromatography on silica gel (gradient elution: CH$_2$Cl$_2$→8:1 CH$_2$Cl$_2$/acetone) afforded the desired product Intermediate 1 as a white solid (45 mg).

Scheme 8

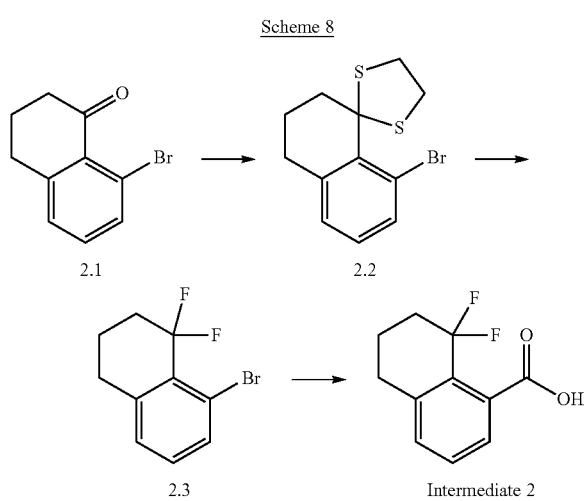

Preparation of Intermediate 2

Intermediate 2 was prepared by procedures analogous to those described Preparation of Intermediate 1.

Scheme 9

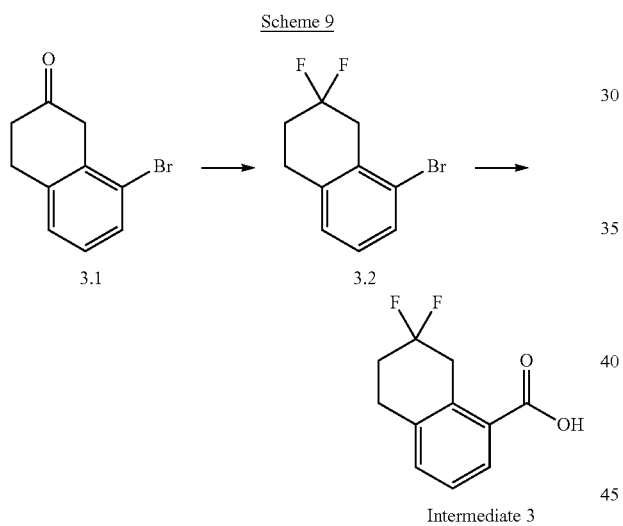

Preparation of Intermediate 3

Compound 3.1 (357 mg, 1.59 mmol, 1.0 equiv) was dissolved in 1.0 mL of CH$_2$Cl$_2$. EtOH (9 µL) and bis(2-methoxyethyl)aminosulfur trifluoride (1.47 mL of a 2.7M sol'n, 4.0 mmol, 2.5 equiv) was added. After 20 h the reaction was quenched by addition of saturated aqueous NaHCO$_3$ (2.0 mL) and extracted with CH$_2$Cl$_2$. The organic extracts were dried over MgSO$_4$, filtered and concentrated in vacuo. Purification by chromatography on silica gel (gradient elution: hexanes→9:1 hexanes/ethyl acetate) afforded the desired product 3.2 (230 mg).

A solution of 3.2 (230 mg, 0.93 mmol, 1.0 equiv) in 4.5 mL of THF was cooled to −78° C. and n-butyllithium (0.59 mL of a 1.6M sol'n, 0.93 mmol, 1.0 equiv) was added dropwise. After 15 min, gaseous CO$_2$ was bubbled through the reaction mixture for 15 minutes. Bubbling was ceased and the reaction was maintained at −78° C. for an additional 1 h. The reaction allowed to warm to room temperature, quenched with 8 mL of 1.0 M aqueous HCl and extracted with 2×10 mL of Et$_2$O. The combined organic extracts were dried over MgSO$_3$, filtered and concentrated in vacuo. Purification by chromatography on silica gel (gradient elution: CH$_2$Cl$_2$→8:1 CH$_2$Cl$_2$/acetone) afforded the desired product Intermediate 3 as a white solid (100 mg).

Scheme 10

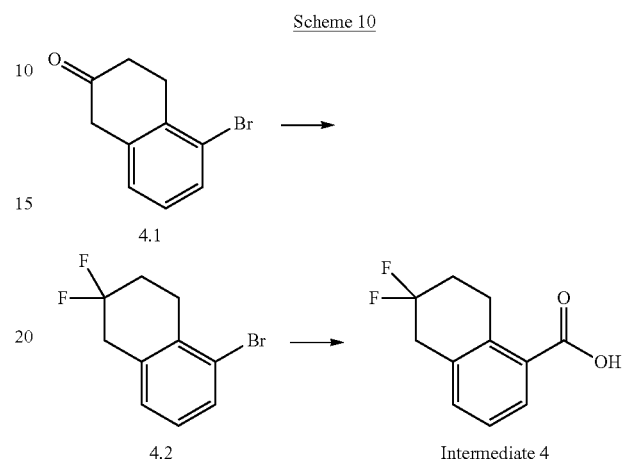

Preparation of Intermediate 4

Intermediate 4 was prepared by procedures analogous to those described Preparation of Intermediate 3.

Scheme 11

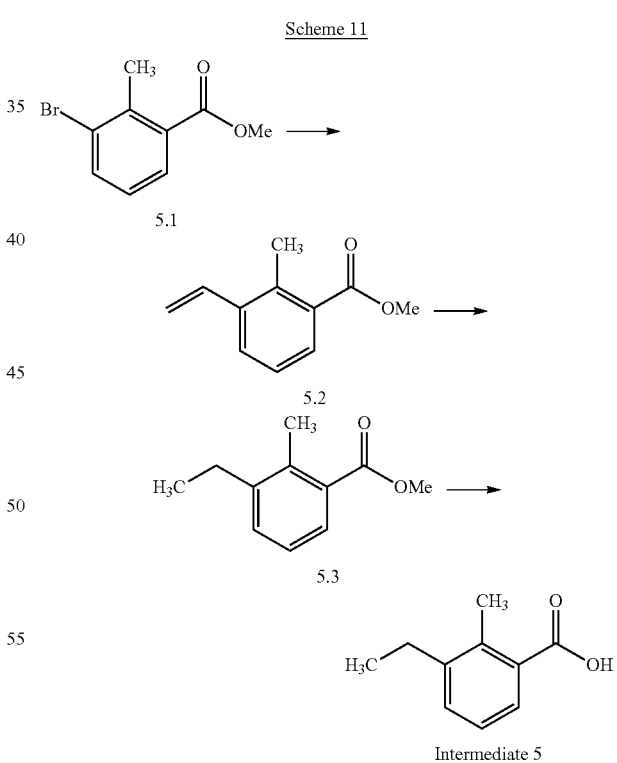

Preparation of Intermediate 5

In a sealed tube, a solution of compound 5.1 (1.0 g, 0.43 mmol), potassium vinyltrifluoroborate (0.646 g, 0.48 mmol) and Cs$_2$CO$_3$ (2.85 g, 0.87 mmol) in THF/H$_2$O (10 mL, 9:1) was degassed by using argon for 10 minutes. Then PdCl$_2$ (dppf). DCM (16 mg, 0.02 mmol) was added into the solution under argon atmosphere and further degassed with argon for 5 minutes. The vial was closed and heated at 85° C. for 16 h. After completion of the reaction, the reaction mixture was cooled to rt, diluted with water (20 mL) and extracted with EtOAc (2×10 mL). The combined organic layer was dried over anhydrous $Na_2SO_4$ and concentrated under reduced pressure to give the crude material. The crude compound was purified by silica gel column chromatography (2% EtOAc in hexanes) to afford the compound 5.2 as a colourless oil. $^1$H NMR (400 MHz, $CDCl_3$): δ 7.68 (d, J=7.5 Hz, 1H), 7.56 (d, J=7.5 Hz, 1H), 7.21 (t, J=7.8 Hz, 1H), 7.04-6.97 (m, 1H), 5.58 (d, J=17.4 Hz, 1H), 5.35 (d, J=10.2 Hz, 1H), 3.89 (s, 3H), 2.51 (s, 3H).

To a stirred solution of compound 5.2 (0.51 g, 0.29 mmol) in methanol (8 mL) was added 10% Pd/C (50 mg) under nitrogen. The reaction was stirred at rt under an $H_2$ balloon pressure for 1 h. After completion of the reaction, the reaction mixture was filtered through a pad of celite and washed with methanol. The combined filtrates were evaporated under reduced pressure to afford the compound 5.3 as a colourless liquid which was used for the next step.

To a stirred solution of compound 5.3 (0.38 g, 0.2 mmol) in methanol (5 mL) was added a solution of NaOH (0.17 g, 0.42 mmol, 2 mL) at 0° C. The resulting solution was stirred at rt for 30 h. Then the reaction mixture was concentrated under reduced pressure, the residue was dissolved in 10 mL of water and acidified with 1N HCl to pH 1-2. The aqueous layer was extracted with EtOAc (50 mL). The organic layer was dried over anhydrous $Na_2SO_4$ and concentrated under reduced pressure to afford pure Intermediate 5 as a white solid.

Preparation of Intermediate 6

In a sealed tube a solution of compound 6.1 (1.0 g, 0.43 mmol), potassium vinyltrifluoroborate (0.646 g, 0.48 mmol) and $Cs_2CO_3$ (2.85 g, 0.87 mmol) in $THF/H_2O$ (10 mL, 9:1) was degassed by using argon for 10 minutes. Then $PdCl_2$ (dppf). DCM (16 mg, 0.02 mmol) was added in the solution under argon atmosphere and further degassed with argon for 5 minutes. The vial was closed and heated at 85° C. for 16 h. After completion of the reaction, the mixture was cooled to rt and diluted with water (20 mL) and extracted with EtOAc (2×10 mL). The combined organic layer was dried over anhydrous $Na_2SO_4$ and concentrated under reduced pressure to give the crude material. The crude compound was purified by silica gel chromatography (2% EtOAc in hexanes) to afford the compound 6.2 as a colourless oil.

$^1$H NMR (400 MHz, $CDCl_3$): δ 7.56 (d, J=7.4 Hz, 1H), 7.31 (d, J=7.1 Hz, 1H), 7.20 (t, J=7.5 Hz, 1H), 7.01-6.94 (m, 1H), 5.45 (d, J=11.4 Hz, 1H), 5.18 (d, J=17.84 Hz, 1H), 3.83 (s, 3H), 2.34 (s, 3H).

To a stirred solution of compound 6.2 (0.70 g, 0.39 mmol) in methanol was added 10% Pd/C (70 mg) under nitrogen. The reaction was stirred at rt under an $H_2$ balloon pressure for 1 h. After completion of the reaction, the reaction mixture was filtered through a pad of celite and washed with methanol. The combined filtrate was evaporated under reduced pressure to afford the compound 6.3 as a colourless liquid which was used for the next step.

To a stirred solution of compound 6.3 (0.57 g, 0.32 mmol) in methanol (5 mL) was added a solution of NaOH (0.26 g, 0.64 mmol, 3 mL) at 0° C. The resulted solution was stirred at rt for 30 h. Then the reaction mixture was concentrated under reduced pressure, the residue was dissolved in 10 mL of water and acidified with 1N HCl to pH 1-2. The aqueous layer was extracted with EtOAc (50 mL). The organic layer was dried over anhydrous $Na_2SO_4$ and concentrated under reduced pressure to afford the Intermediate 6 as a white solid.

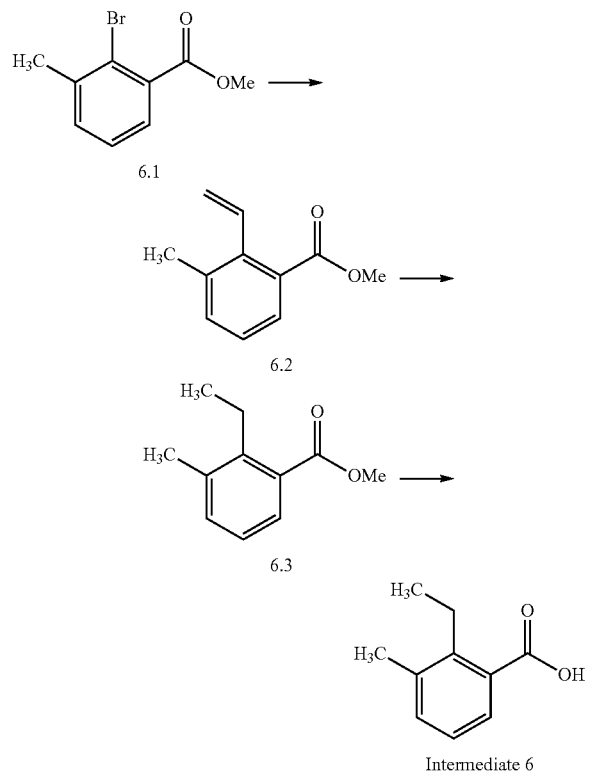

Scheme 12

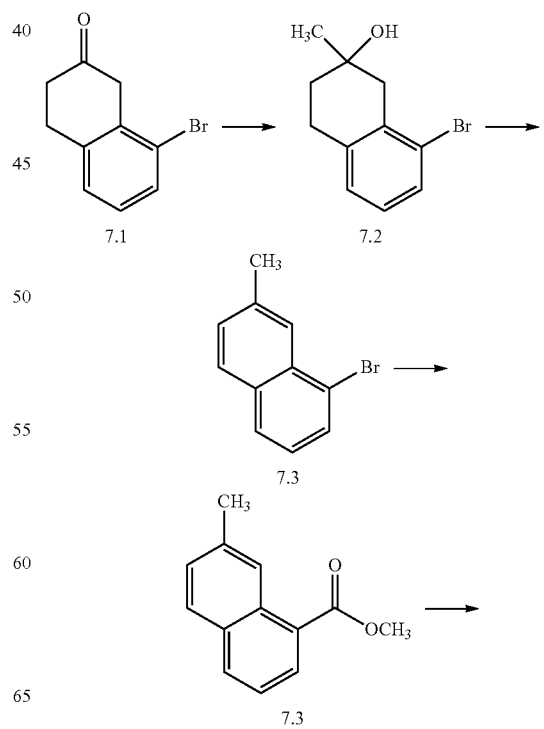

Scheme 13

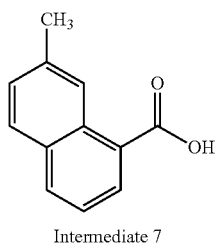

Intermediate 7

Scheme 14

8.1 → 8.2

8.3 → Intermediate 8

Preparation of Intermediate 7

To a solution of compound 7.1 (3.60 g, 15.9 mmol) in diethyl ether (30 mL) was added 1.0 M solution of MeMgBr (23.8 mL, 23.8 mmol) at 0° C. Then the reaction mixture was slowly allowed to warm to room temperature and stirred for 3 h. After completion of the reaction, the reaction mixture was diluted with ice-water and extracted with EtOAc (150 mL). The organic layer was washed with saturated brine solution (40 mL), dried over $Na_2SO_4$ and concentrated. The crude compound was purified by silica gel column chromatography (0-40% EtOAc in hexanes) to give the desired compound 7.2 as a colourless liquid. $^1$H-NMR (400 MHz, $CDCl_3$): δ 7.39 (d, J=7.6 Hz, 1H), 7.11 (d, J=7.2 Hz, 1H), 7.03 (t, J=8.0 Hz, 1H), 4.4 (s, 1H), 2.95 (t, J=6.4 Hz, 1H), 2.72-2.55 (m, 3H), 1.72-1.58 (m, 2H), 1.24 (s, 3H).

To a solution of compound 7.2 (2.40 g, 9.95 mmol) in TFA (6.9 mL) was added triphenylmethanol (2.2 g, 9.95 mmol) at room temperature and the reaction mixture was stirred at RT for 2 days. After completion, the reaction mixture was diluted with saturated $NaHCO_3$ solution and extracted with hexane (100 mL). The organic layer was dried over $Na_2SO_4$ and concentrated. The crude compound was purified by silica gel column chromatography (0-5% EtOAc in hexanes) to give the desired compound 7.3 as a colourless liquid. $^1$H-NMR (400 MHz, $CDCl_3$): δ 7.94-7.90 (m, 3H), 7.83 (d, J=7.2 Hz, 1H), 7.46 (d, J=8.4 Hz, 1H), 7.36 (t, J=8.0 Hz, 1H), 2.53 (s, 3H).

To a solution of compound 7.3 (0.20 g, 0.9 mmol) in methanol (10 mL) was added $Et_3N$ (0.25 mL, 1.82 mmol) and the reaction was degassed with argon for 10 minutes. Then $PdCl_2$(dppf)·DCM (0.074 g, 0.09 mmol) was added and the reaction was stirred at 90° C. for 8 h in a sealed vessel in the presence of CO gas. After completion, the reaction mixture was concentrated under reduced pressure. The crude compound was purified by silica gel column chromatography (0-30% EtOAc in hexanes) to give the desired compound 7.4 as a colourless liquid. $^1$H-NMR (400 MHz, $CDCl_3$): δ 8.69 (s, 1H), 8.14 (d, J=7.2 Hz, 1H), 7.97 (d, J=8.0 Hz, 1H), 7.78 (d, J=8.4 Hz, 1H), 7.44-7.36 (m, 2H), 4.05 (s, 3H), 2.56 (s, 3H).

To a solution of compound 7.4 (0.16 g, 0.8 mmol) in methanol (5 mL) was added 6N aqueous sodium hydroxide solution (5 mL) at room temperature and the reaction mixture was heated at 55° C. for 1 h. After completion, the solution was cooled to 0° C. and acidified with 1N HCl to pH 2-3. Then the aqueous layer was extracted with EtOAc and the organic layer was dried over $Na_2SO_4$. Then solvents were evaporated to give the solid residue which was washed with diethyl ether and n-pentane to give the desired Intermediate 7 as an off white solid.

Preparation of Intermediate 8

To a solution of compound 8.1 (1.00 g, 4.0 mmol) in DMF (10 mL) was added $K_2CO_3$ (1.38 g, 10.0 mmol) followed by EtI (0.64 mL, 8.0 mmol) at room temperature and the reaction mixture was stirred at RT for 3 h. After completion of the reaction, the reaction mixture was diluted with ice-water and extracted with EtOAc (100 mL). The organic layer was washed with saturated brine solution (40 mL), dried over $Na_2SO_4$ and concentrated. The crude compound was purified by silica gel column chromatography (0-10% EtOAc in hexanes) to give the desired compound 8.2 as a colourless liquid. $^1$H-NMR (400 MHz, $CDCl_3$): δ 7.92 (d, J=8.1 Hz, 1H), 7.87-7.84 (m, 2H), 7.64 (d, J=6.9 Hz, 1H), 7.50 (t, J=8.0 Hz, 1H), 7.35 (t, J=8.0 Hz, 1H), 4.46 (q, J=7.2 Hz, 2H), 1.41 (t, J=6.8 Hz, 3H).

To a solution of compound 8.2 (0.57 g, 2.1 mmol) and trimethylboroxine (0.296 g, 2.3 mmol) in 1,4-dioxane/water (10 mL, 4:1) was added $K_2CO_3$ (0.59 g, 4.3 mmol) and the reaction was degassed with argon for 10 minutes. Then tetrakis(triphenylphosphine)palladium (0.24 g, 0.2 mmol) was added and the reaction was stirred at 90° C. for 16 h in a sealed vessel. After completion, the reaction mixture was diluted with water and extracted with EtOAc (50 mL). The organic layer was washed with saturated brine solution, dried over $Na_2SO_4$ and concentrated under reduced pressure. The crude compound was purified by silica gel column chromatography (0-10% EtOAc in hexanes) to give the desired compound 8.3 as a colourless liquid. $^1$H-NMR (400 MHz, $CDCl_3$): δ 7.92 (d, J=8.0 Hz, 1H), 7.73 (d, J=7.6 Hz, 1H), 7.56 (d, J=6.8 Hz, 1H), 7.46-7.33 (m, 4H), 4.45 (q, J=6.9 Hz, 2H), 2.63 (s, 3H), 1.43 (t, J=7.1 Hz, 3H).

To a solution of compound 8.3 (0.13 g, 0.6 mmol) in ethanol (4 mL) was added 6N aqueous sodium hydroxide solution (4 mL) at room temperature and the reaction mixture was heated at 80° C. for 6 h. After completion, the solution was cooled to 0° C. and acidified with 1N HCl to pH 2-3. Then aqueous layer was extracted with EtOAc and the organic layer was dried over $Na_2SO_4$. Then solvents were evaporated to give the solid residue which was washed with diethyl ether and n-pentane to give the desired Intermediate 8 as an off white solid.

Scheme 15

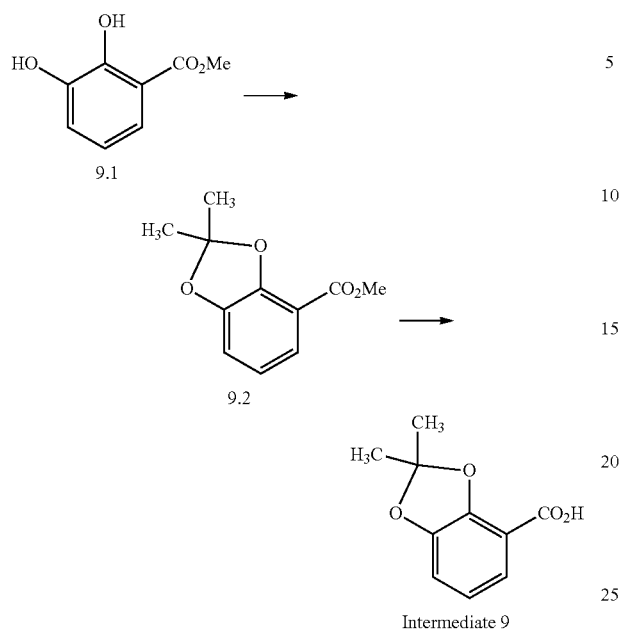

Preparation of Intermediate 9

To a solution of compound 9.1 (1.50 g, 8.9 mmol) in benzene (10 mL) was added acetone (1.31 mL, 17.8 mmol) followed by $PCl_3$ (0.38 mL, 4.4 mmol) at room temperature and the reaction mixture was stirred at 50° C. for 28 h. After completion of reaction, the reaction mixture was diluted with ice-water and extracted with EtOAc (100 mL). The organic layer was washed with saturated brine solution (40 mL), dried over $Na_2SO_4$ and concentrated. The crude compound was purified by silica gel column chromatography (0-10% EtOAc in hexanes) to give the desired compound 9.2 as a white solid. $^1$H-NMR (400 MHz, $CDCl_3$): δ 7.35 (d, J=8.0 Hz, 1H), 6.86 (d, J=7.6 Hz, 1H), 6.79 (t, J=8.0 Hz, 1H), 3.89 (s, 3H), 1.73 (s, 6H).

To a solution of compound 9.2 (0.31 g, 1.49 mmol) in methanol (5 mL) was added 6 N aqueous sodium hydroxide solution (4 mL) at room temperature and the reaction mixture was stirred at rt for 3 h. After completion of reaction, the reaction mixture was cooled to 0° C. and acidified with 1N HCl to pH 2-3. Then the aqueous layer was extracted with EtOAc, the organic layer was dried over $Na_2SO_4$ and concentrated. The solid residue which was washed with diethyl ether and n-pentane to give the desired Intermediate 9 as an off white solid.

Scheme 16

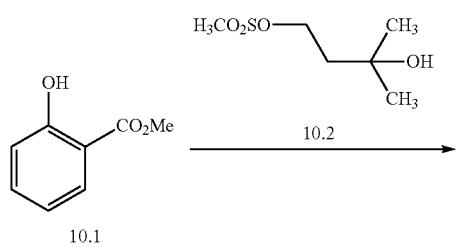

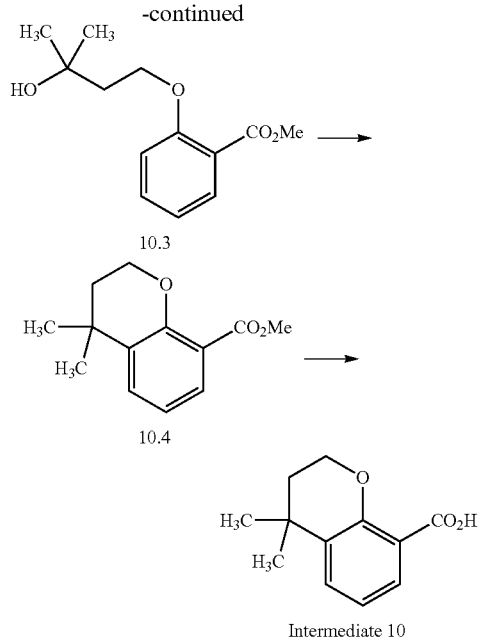

Preparation of Intermediate 10

To a solution of compound 10.1 (3.50 g, 23.0 mmol) in DMF (30 mL) was added $K_2CO_3$ (7.80 g, 57.5 mmol) followed by compound 10.2 (4.60 g, 25.3 mmol) at room temperature and the reaction mixture was stirred at 100° C. for 1 h. After completion, the reaction mixture was diluted with ice-water and extracted with EtOAc (100 mL). The organic layer was washed with saturated brine solution (40 mL), dried over $Na_2SO_4$ and concentrated. The crude compound was purified by silica gel column chromatography (0-30% EtOAc in hexanes) to give the desired compound 10.3 as a colourless liquid. $^1$H-NMR: (400 MHz, DMSO-$d_6$): δ 7.62 (d, J=7.4 Hz, 1H), 7.51 (t, J=7.2 Hz, 1H), 7.15 (d, J=8.3 Hz, 1H), 6.9 (t, J=7.2 Hz, 1H), 4.3 (s, 1H), 4.14 (t, J=6.4 Hz, 2H), 3.76 (s, 3H), 1.84 (t, J=6.4 Hz, 2H), 1.15 (s, 6H).

Note: Compound 10.2 was synthesized according to the reported procedure in *Bioorg. Med. Chem.* 2011, 19 (17), 5207-5224

To a solution of compound 10.3 (4.00 g, 16.8 mmol) in $CHCl_3$ (50 mL) was added $AlCl_3$ (6.70 g, 50.4 mmol) at room temperature and the reaction mixture was stirred at 60° C. for 2 h. After completion, the reaction mixture was diluted with ice-water and extracted with DCM (100 mL). The organic layer was washed with saturated brine solution (40 mL), dried over $Na_2SO_4$ and concentrated. The crude compound was purified by silica gel column chromatography (0-10% EtOAc in hexanes) to give the desired compound 2 as a light yellow liquid. $^1$H-NMR: (400 MHz, DMSO-$d_6$): δ 7.52 (d, J=7.3 Hz, 1H), 7.38 (d, J=6.5 Hz, 1H), 6.91 (t, J=7.9 Hz, 1H), 4.18 (t, J=5.28 Hz, 2H), 3.75 (s, 3H), 1.79 (t, J=5.28 Hz, 2H), 1.29 (s, 6H).

To a solution of compound 10.4 (0.55 g, 2.5 mmol) in methanol (7 mL) was added 6N aqueous sodium hydroxide solution (5 mL) at room temperature and the reaction mixture was heated at 55° C. for 1 h. After completion, the solution was cooled to 0° C. and acidified with 1N HCl to pH 2-3. Then the aqueous layer was extracted with EtOAc and the organic layer was dried over $Na_2SO_4$. Then solvents were evaporated to give the solid residue which was washed with diethyl ether and n-pentane to give the desired Intermediate 10 as an off white solid.

Scheme 17

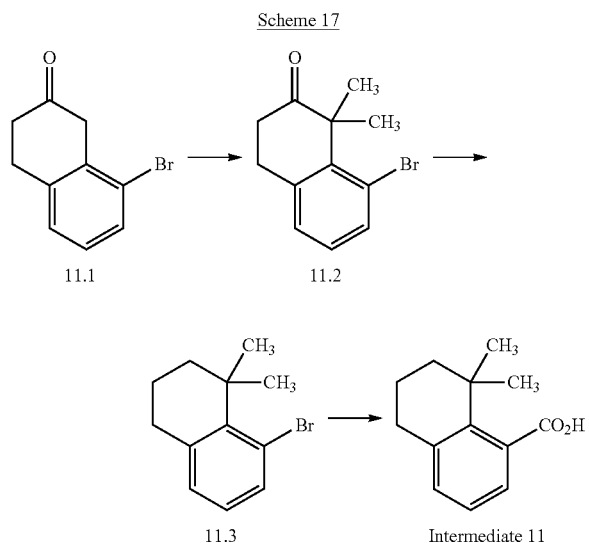

Preparation of Intermediate 11

To a suspension of NaH (1.5 g, 39.062 mmol, 60% suspension) in THF (20 mL), a solution of compound 11.1 (3.5 g, 15.63 mmol) in THF (20 mL) was added slowly over a period of 10 min at 0° C. After stirring at room temperature for 10 min MeI (2.9 mL, 46.87 mmol) was added and stirring was continued for 2 h. Then the reaction mixture was quenched with ice-water and extracted with EtOAc (100 mL). The organic layer was dried over $Na_2SO_4$, filtered, and concentrated. The residue was purified by silica gel column chromatography (0-20% EtOAc in hexanes) to give the compound 11.2 as a colorless liquid.

$^1$H-NMR: (400 MHz, DMSO-$d_6$): δ 7.55 (d, J=7.9 Hz, 1H), 7.24 (d, J=7.3 Hz, 1H), 7.11 (t, J=7.6 Hz, 1H), 3.04 (t, J=6.8 Hz, 2H), 2.70 (t, J=7.2 Hz, 2H), 1.60 (s, 6H).

A mixture of compound 11.2 (3.5 g, 13.89 mmol), potassium hydroxide (7.4 g, 138.89 mmol), and hydrazine (10 mL, 138.89 mmol) in 30 mL ethylene glycol in seal tube was stirred at 200° C. After 2 h, the mixture was allowed to cool to room temperature and diluted with water and extracted with EtOAc (150 mL). Organic phase was dried over $Na_2SO_4$, filtered, and concentrated to give the desired compound 11.3 as a colorless liquid.

$^1$H-NMR: (400 MHz, DMSO-$d_6$): δ 7.40 (d, J=7.5 Hz, 1H), 7.08 (d, J=7.5 Hz, 1H), 6.97 (t, J=7.7 Hz, 1H), 2.78 (m, 2H), 2.70 (t, J=7.2 Hz, 2H), 1.66 (s, 3H). 1.49 (s, 6H).

To a solution of compound 11.3 (1.1 g, 4.6 mmol) in diethyl ether (15 mL) was drop wise added 1.6 M n-BuLi solution in hexane (49 mL, 9.2 mmol) at −78° C. and the mixture was stirred at same temperature for 2 min. The mixture was allowed to warm to room temperature and stirred for 1 h, carbon dioxide gas was purged in to the reaction mixture for 10 min. After completion, the reaction mixture was quenched with 1 N HCl and extracted with diethyl ether. The organic layer was washed with brine, dried over $Na_2SO_4$ and concentrated to get the Intermediate 11 as a white solid.

Scheme 18

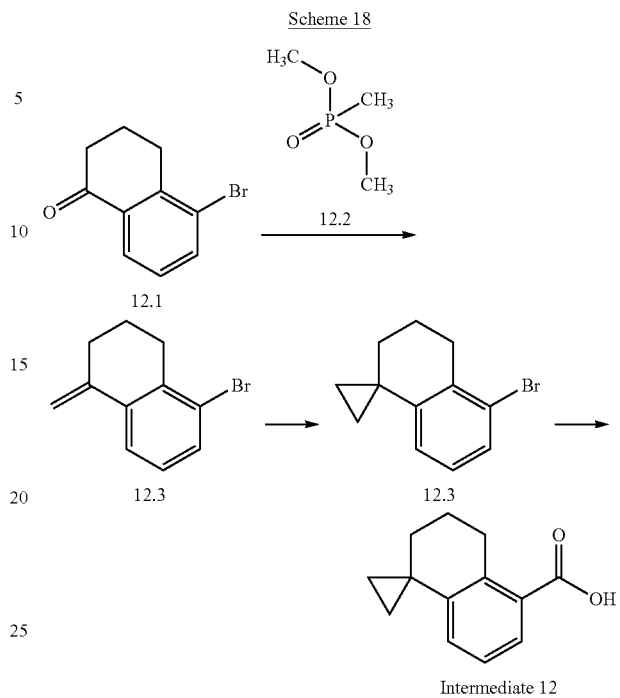

Preparation of Intermediate 12

To a solution of compound 12.2 (8.3 g, 66.9 mmol) in dry THF (55 mL) under $N_2$ was added n-BuLi in hexane (1.6 M, 27.9 mL, 44.6 mmol) drop wise over 1 h at −78° C. The mixture was stirred for 30 minutes at −78° C. and then a solution of compound 12.1 (5.0 g, 22.3 mmol) in dry THF (15 mL) was added drop wise over 30 minutes at −78° C. The reaction mixture was stirred for additional 2 h at −78° C. and quenched with aqueous $NH_4Cl$ solution (50 mL). The solution was extracted with EtOAc (100 mL) and the organic layer was washed with brine, dried and concentrated under reduced pressure. The residue was dissolved in DMF (50 mL) and water (3.6 ml) and anhydrous potassium carbonate (29.0 g, 223.6 mmol) was added. The mixture was heated at 120° C. for 2 h and after completed cooled to room temperature. The solution was diluted with water (80 mL) and extracted with EtOAc (2×150 mL). The combined organic layer was washed with 10% citric acid solution and with brine, dried and evaporated. The crude product was purified by silica gel column chromatography (0-10% EtOAc in hexanes) to give the compound 12.3 as a colorless liquid.

$^1$H-NMR: (400 MHz, DMSO-$d_6$): δ 7.57 (d, J=7.8 Hz, 1H), 7.45 (d, J=7.8 Hz, 1H), 7.01 (t, J=7.8 Hz, 1H), 5.45 (s, 1H), 4.99 (s, 1H), 2.84 (t, J=6.4 Hz, 2H), 2.48 (t, J=12.1 Hz, 2H), 1.94-1.88 (m, 2H).

$CH_2I_2$ (6.7 g, 25.2 mmol) was added drop wise to a stirred solution of $ZnEt_2$ (1 M in toluene, 12.6 mL, 12.6 mmol) in dichloromethane (15 mL) at −78° C. under nitrogen and the mixture was stirred at 0° C. for 15 min resulting in the formation of a white precipitate. TFA (0.96 mL, 12.6 mmol) was added to the mixture and the resulting homogeneous colorless solution was stirred at 0° C. for 15 min. Then a solution of compound 12.3 (1.5 g, 6.3 mmol) in dichloromethane (10 mL) was added and stirred at room temperature for 16 h. After completion water (70 mL) was added and extracted with dichloromethane. The organic layer was washed with brine and dried over $Na_2SO_4$ and concentrated under vacuum. The residue was purified by silica gel column chromatography (0-5% EtOAc in hexanes) to give the compound 12.4 as a colorless liquid. ¹H-NMR: (400 MHz, DMSO-d₆): δ 7.34 (d, J=7.4 Hz, 1H), 6.9 (t, J=7.8 Hz, 1H), 6.73 (d, J=7.7 Hz, 1H), 2.77 (t, J=6.4 Hz, 2H), 1.85-1.81 (m, 2H), 1.59-1.56 (m, 2H), 0.96-0.94 (m, 2H), 0.82-0.80 (m, 2H).

To a solution of compound 12.4 (0.55 g, 2.3 mmol) in diethyl ether (10 mL) was drop wise added a solution of n-BuLi (3.6 mL, 5.8 mmol, 1.6 M in hexane) at −78° C. and the mixture was slowly warmed to room temperature and stirred for 1 h. Then carbon dioxide gas was purged in to the reaction mixture over 15 min. After completion the reaction mixture was quenched with 1 N HCl and extracted with diethyl ether (2×10 mL). The organic layer was washed with brine and dried over Na₂SO₄ and concentrated to get the Intermediate 12 as a white solid.

Scheme 19

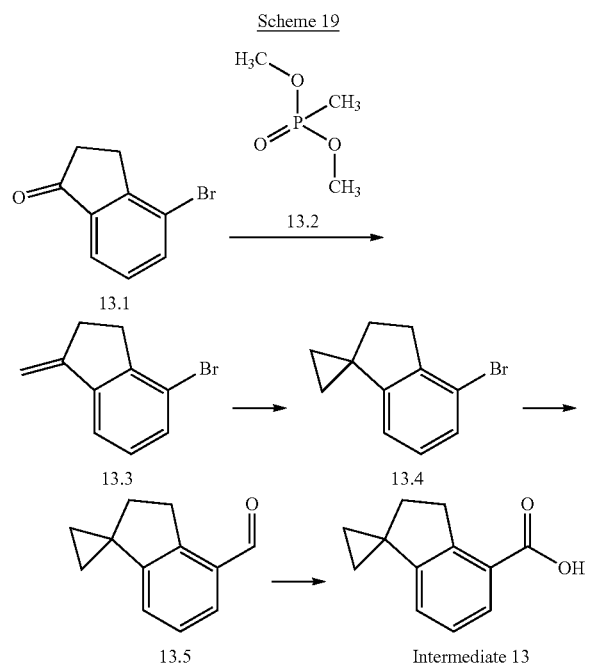

Preparation of Intermediate 13

To a solution of compound 13.2 (33.0 g, 270.0 mmol) in dry THF (100 mL) was slowly added n-BuLi in hexane (1.6M, 112 mL, 180 mmol) under at −78° C. After 30 minutes a solution of compound 13.1 (20.0 g, 90.0 mmol) in dry THF (100 mL) was added drop wise over 30 minutes at −78° C. The reaction mixture was stirred for 2 h at −78° C. and after completion the reaction mixture was quenched with NH₄Cl solution. The solution was extracted with EtOAc (200 mL) and the organic layer was washed with brine, dried over Na2SO4 and concentrated. The residue was re-dissolved in DMF (250 mL) and potassium carbonate (117.0 g, 900 mmol) in water (10 mL) was added. The mixture was heated at 120° C. for 2 h. After the mixture was cooled to the room temperature, water (300 mL) was added and the mixture was extracted with EtOAc (2×150 mL). The combined organic layer was washed with 10% citric acid solution, dried over Na2SO4 and evaporated under reduced pressure. The crude product was purified by silica gel column chromatography (0-3% EtOAc in hexanes) to give compound 13.3 as a colorless liquid. ¹H-NMR: (400 MHz, DMSO-d₆): δ 7.41 (d, J=7.6 Hz, 1H), 7.37 (d, J=7.8 Hz, 1H), 7.07 (t, J=7.7 Hz, 1H), 5.45-5.44 (m, 1H), 5.06-5.00 (m, 1H), 2.99-2.95 (m, 2H), 2.83-2.81 (m, 2H).

CH₂I₂ (30.0 g, 115.3 mmol) was added drop wise to a stirred solution of ZnEt₂ (57.6 mL, 57.6 mmol, 1 M in toluene) in dichloromethane (40 mL) at −78° C. under nitrogen and the mixture was stirred at 0° C. for 15 min resulting the formation of a white precipitate. Then TFA (4.4 mL, 57.6 mmol) was added to the mixture and the homogeneous colorless solution was stirred at 0° C. for 15 min. Then a solution of compound 13.3 (6.0 g, 28.8 mmol) in dichloromethane (70 mL) was added and stirred at room temperature for 16 h. Then water (150 mL) was added and extracted with dichloromethane. The organic layer was washed with brine, dried over Na₂SO₄ and concentrated under vacuum. The residue was purified by silica gel column chromatography (0-5% EtOAc in hexanes) to give compound 13.4 as a colorless liquid. ¹H-NMR: (400 MHz, DMSO-d₆): δ 7.28 (d, J=7.8 Hz, 1H), 7.05 (t, J=15 Hz, 1H), 6.72 (d, J=7.5 Hz, 1H), 2.95 (t, J=7.6 Hz, 2H), 2.10 (t, J=7.64 Hz, 2H), 0.90-0.88 (m, 2H), 0.81-0.79 (m, 2H).

To a solution of compound 13.4 (2.0 g, 9.0 mmol) in THF (20 mL) was slowly added 1.6 M n-BuLi in hexane (11.2 mL, 18 mmol) at −78° C. and the mixture was stirred at same temperature for 30 min. The reaction mixture was quenched with DMF and diluted with water. The resulting solution was extracted with EtOAc (2×30 mL). The organic layer was washed with brine, dried over Na₂SO₄ and concentrated to get the compound 13.5 (3.0 g, crude). The crude compound was used to next step without further any purification.

To a solution of compound 13.5 (2.0 g, 11.6 mmol) in 1,4-dioxane:water (4:1, 30 mL) were added sulfamic acid (15.0 g, 69.7 mmol) and sodium chlorite (3.6 g, 17.4 mmol). The suspension was stirred at room temperature for 30 min. After completion, the reaction mixture was quenched with water (20 mL) and extracted with EtOAc (2×20 mL). The organic layer was washed with brine and concentrated under reduced pressure. The residue was purified by silica gel column chromatography (0-15% EtOAc in hexanes) to give compound the target Intermediate 13.

Scheme 20

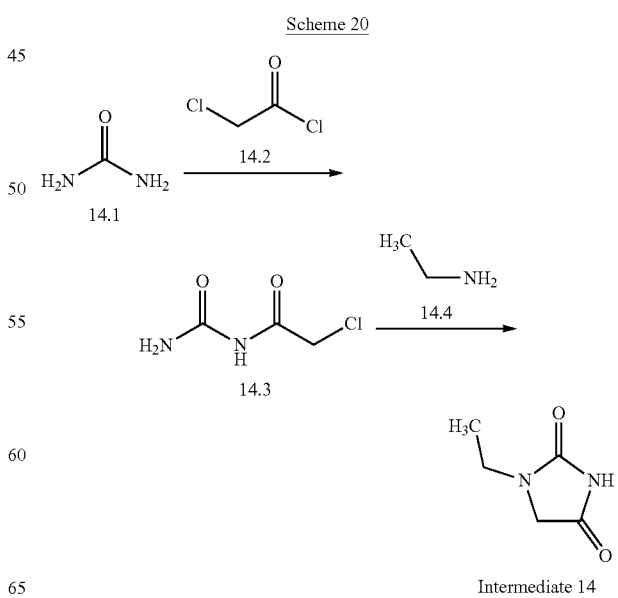

Preparation of Intermediate 14

To a solution of urea 14.1 (50.0 g, 833.0 mmol) in anhydrous toluene (500 mL) was added chloroacetyl chloride 14.2 (55.0 mL, 999.0 mmol) and the reaction mixture was heated to reflux for 2 hours. The reaction mixture was cooled to room temperature and toluene was removed by filtration. The resulting solid was further washed with toluene (100 mL) and mixed with water (100 mL). The solid was filtered and washed with cold water (500 mL) and dried to give compound 14.3 as a white solid. $^1$H-NMR: (400 MHz, DMSO-$d_6$): δ 10.4 (s, 1H), 7.4-7.3 (m, 2H), 4.27 (s, 2H).

A solution of compound 14.3 (2.0 g, 14.7 mmol) and compound 14.4 (22 mL, 2M in THF, 44.1 mmol) in THF was stirred at RT for 3 h. After that, the reaction mixture was concentrated under reduced pressure. The residue was re-dissolved in DMF and stirred at 140° C. for 16 h. After completion, DMF was removed under reduced pressure and the residue was purified by column chromatography using silica gel (30-40% EtOAc in hexanes) to give Intermediate 14 as a white solid.

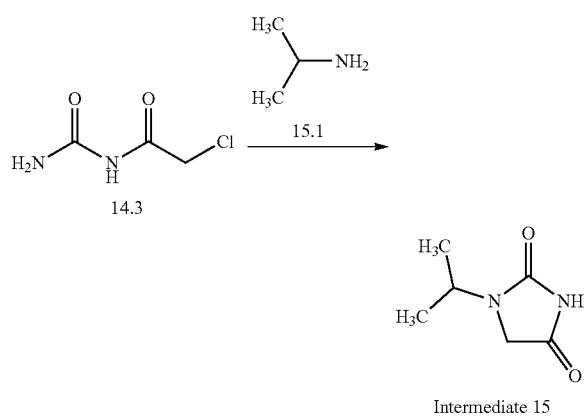

Intermediate 15

Preparation of Intermediate 15

A mixture of compound 14.3 (1.0 g, 7.3 mmol) and compound 15.1 (1.2 mL, 14.6 mmol) in DMF was stirred at 140° C. for 16 h. After completion, DMF was removed under reduced pressure and the residue was purified by silica gel column chromatography (30-40% EtOAc in hexanes) to give intermediate 15 as a white solid.

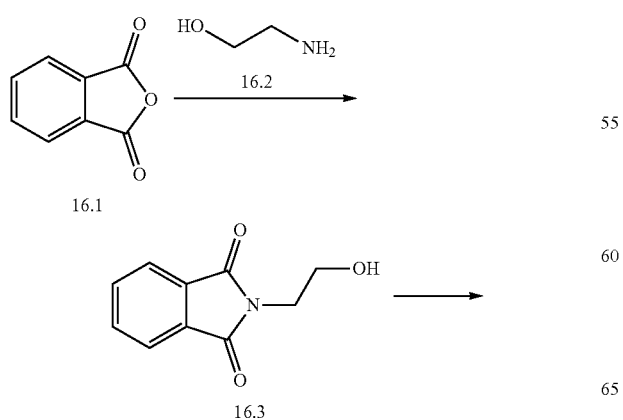

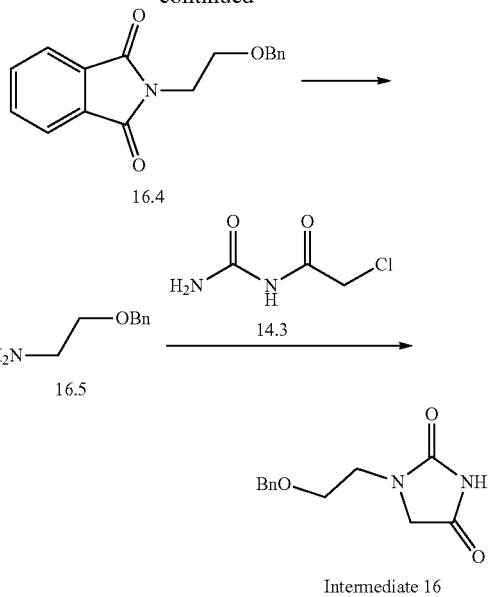

Intermediate 16

Preparation of Intermediate 16

Compound 16.5 was synthesized according to the literature reported procedure (Bioorganic and Medicinal Chemistry Letters, 2015, 25 (14), 2782-2787).

A mixture of compound 16.5 (2.5 g, 16.5 mmol), compound 14.3 (2.7 g, 19.8 mmol) in DMF was stirred at 140° C. for 16 h. After completion, DMF was removed under vacuum and the residue was purified by column chromatography using silica gel (40-50% EtOAc in hexanes) to give Intermediate 16 as a white solid.

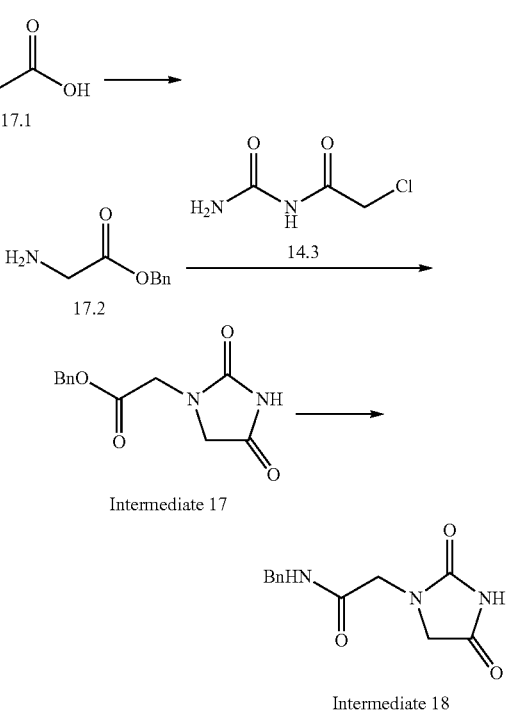

Intermediate 17

Intermediate 18

Preparation of Intermediates 17 and 18

Glycine 17.1 (5.0 g, 66.6 mmol) and p-TSA (15.0 g, 79.9 mmol) were added to a solution of benzyl alcohol (25 ml) in toluene (100 ml). The mixture was refluxed equipped with a Dean-Stark apparatus for 3 h and then cooled to room temperature. Then diethyl ether (100 ml) was added and the mixture was cooled in an ice-bath. The white precipitate was filtered and washed with diethyl ether and dried to give compound 17.2 as a white solid.

Note: This synthesis was also reported in the literature (Bioorganic and Medicinal Chemistry, 2005, 13 (2), 519-532)

A mixture of compound 17.2 (19.0 g, 56.3 mmol), compound 14.3 (11.5 g, 84.5 mmol) and Et3N (24 mL, 169.0 mmol) in DMF was stirred at 140° C. for 16 h. After completion, DMF was removed under vacuum and the residue was purified by column chromatography using silica gel (40-50% EtOAc in hexanes) to give Intermediate 17 as a Light Brown solid. ESI-MS: m/z=247 [M-1]

A mixture of Intermediate 17 (1.5 g, 6.0 mmol), benzyl amine (0.84 g, 7.8 mmol) and CP₂ZrCl₂ (0.17 g, 0.6 mmol) in toluene (15 mL) was stirred at 120° C. for 16 h. The reaction mixture was cooled to RT, filtered through a celite bed and washed with EtOAc. The filtrate was concentrated under reduced pressure. The crude material was purified by silica gel column chromatography (40-50% EtOAc in hexanes) to give Intermediate 18 as a white solid.

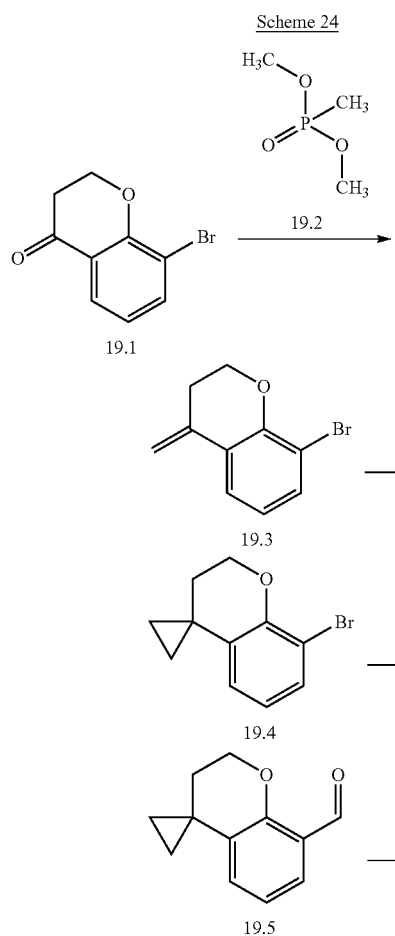

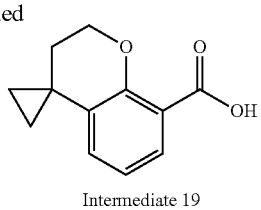

Intermediate 19

Preparation of Intermediate 19

Intermediate 19 was prepared by procedures analogous to those described Preparation of Intermediate 13.

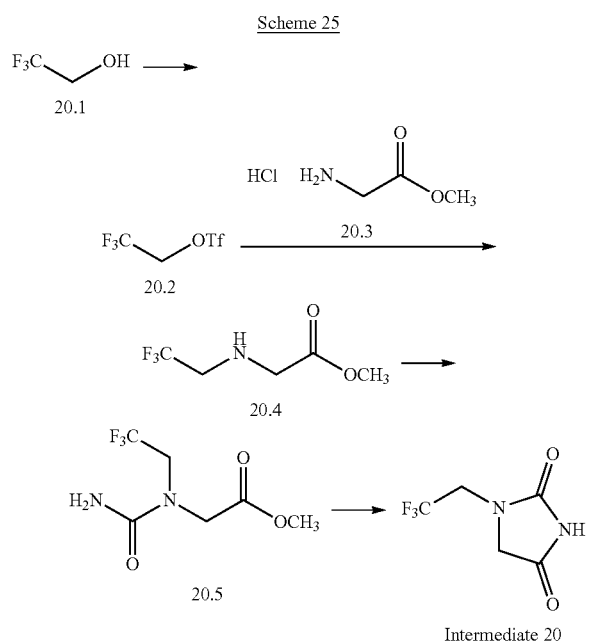

Preparation of Intermediate 20

Compound 20.2 was synthesized according to the reported procedure (US2014/249162).

To a solution of compound 20.3 (0.5 g, 4 mmol) in DMF/water (8 mL, 1:1) was added DIPEA (2.2 mL, 12 mmol) followed by compound 20.2 (0.92 g, 4 mmol) at 0° C. After stirring at rt for 16 h, the reaction mixture was concentrated under reduced pressure and the residue was purified by silica gel column chromatography (20% EtOAc/hexanes) to afford the compound 20.4 as a colorless liquid. Yield: 0.75 g (39%).

$^1$H NMR (400 MHz, CDCl₃) δ 3.74 (s, 3H), 3.53 (s, 2H), 3.27-3.20 (m, 2H), 1.84 (s, 1H).

To a suspension of compound 20.4 (0.75 g, 4.3 mmol) in AcOH (8 mL) was added potassium isocyanate (0.71 g, 8.7 mmol). After stirring at room temperature for 2.5 h and the solution was refluxed for 6 h. After completion, then reaction mixture was quenched by addition of water. The aqueous phase was neutralized with a saturated aqueous solution of NaHCO₃ and the product was extracted into ethyl acetate. The combined organic layer was washed with brine, dried over sodium sulfate and concentrated under reduced pressure to give compound 20.5 as a colorless semisolid. Yield: (1.0 g, crude).

To a stirred solution of compound 20.5 (1.0 g, crude) in MeOH (10 mL) was added NaOMe solution (5 mL, 25% in MeOH) and stirred at RT for 3 h. After completion, the reaction mixture was diluted with sat NH₄Cl solution and extracted with DCM. The organic layer was dried over Na₂SO₄ and concentrated. The residue was washed with ether, filtered and dried to give Intermediate 20 as a white solid. Yield: 0.1 g (12%, overall 2 steps).

Characterization Data for Additional Compounds

The following compounds were prepared using procedures as described above, replacing as appropriate the starting materials. For example, Intermediate A is treated with succinimide or the appropriate intermediate of formula

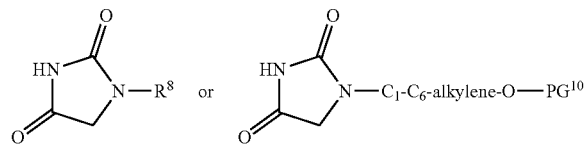

(where $PG^{10}$ is an oxygen-protecting group, e.g. benzyl, or one known to one of ordinary skill in the art), using procedures described in Schemes 1, 2, and/or 3 to prepare Compounds of Formula I, including the following. Additional methods are known to one of ordinary skill in the art.

(4): $^1$H NMR (D₂O, 400 MHz) δ 7.57 (appar. t, J=8.4 Hz, 2H), 7.50 (d, J=7.6 Hz, 1H), 5.08 (appar. t, J=9.2 Hz, 1H), 5.00 (s, 1H), 4.36 (appar. t, J=9.2 Hz, 1H), 4.09 (dd, J=14, 12 Hz, 1H), 3.95 (dd, J=12, 3.6 Hz, 1H), 3.68 (dd, J=14, 4.0 Hz, 1H), 3.63-3.46 (m, 3H), 3.27-3.20 (m, 2H), 2.95 (s, 4H), 2.50-2.37 (m, 2H) ppm.

(5): $^1$H NMR (D₂O, 400 MHz) δ 7.62 (appar. t, J=8.4 Hz, 1H), 7.53 (d, J=8.0 Hz, 1H), 7.48 (d, J=6.8 Hz, 1H), 5.01 (appar. t, J=8.8 Hz, 1H), 4.95 (s, 1H), 4.33 (appar. t, J=9.6 Hz, 1H), 4.04 (dd, J=14, 11 Hz, 1H), 3.91 (dd, J=12, 3.6 Hz, 1H), 3.64 (dd, J=14, 3.2 Hz, 1H), 3.51 (appar. t, J=10 Hz, 1H), 3.07-3.00 (m, 2H), 2.91 (s, 4H), 2.48-2.36 (m, 2H), 2.13-2.07 (m, 2H) ppm.

(6): $^1$H NMR (D₂O, 400 MHz) δ 7.54-7.43 (m, 3H), 5.07 (appar. t, J=9.2 Hz, 1H), 4.98 (s, 1H), 4.34 (appar. t, J=9.6 Hz, 1H), 4.08 (dd, J=14, 12 Hz, 1H), 3.94 (dd, J=12, 3.2 Hz, 1H), 3.67 (dd, J=14, 3.6 Hz, 1H), 3.60-3.44 (m, 3H), 3.27-3.16 (m, 2H), 2.93 (s, 4H), 2.47-2.33 (m, 2H) ppm.

(7): $^1$H NMR (D₂O, 400 MHz) δ 7.89 (t, J=8.0 Hz, 1H), 7.64 (d, J=7.2 Hz, 1H), 7.27 (t, J=8.0 Hz, 1H), 5.07 (appar. t, J=8.8 Hz, 1H), 5.00 (s, 1H), 4.66-4.59 (m, 2H), 4.38 (appar. t, J=9.6 Hz, 1H), 4.11 (dd, J=14, 12 Hz, 1H), 3.96 (dd, J=12, 3.6 Hz, 1H), 3.71 (dd, J=14, 3.2 Hz, 1H), 3.56 (appar. t, J=8.8 Hz, 1H), 2.95 (s, 4H), 1.52 (s, 3H), 1.50 (s, 3H) ppm.

(8): $^1$H NMR (D₂O, 400 MHz) δ 7.71 (d, J=8.0 Hz, 1H), 7.42-7.33 (m, 2H), 5.02 (appar. t, J=8.8 Hz, 1H), 4.96 (s, 1H), 4.31 (appar. t, J=10 Hz, 1H), 4.05 (dd, J=14, 12 Hz, 1H), 3.90 (dd, J=12, 3.6 Hz, 1H), 3.64 (dd, J=14, 3.6 Hz, 1H), 3.54 (dd, J=10, 9.2 Hz, 1H), 2.93-2.84 (m, 6H), 1.92-1.83 (m, 2H), 1.81-1.75 (m, 2H), 1.39 (s, 6H) ppm.

(9): $^1$H NMR (D₂O, 400 MHz) δ 7.82 (d, 7.2 Hz, 1H), 7.58 (d, J=7.2 Hz, 1H), 7.15 (t, J=7.6 Hz, 1H), 4.98-4.93 (m, 2H), 4.35 (dd, J=10, 9.2 Hz, 1H), 4.11 (dd, J=14, 12 Hz, 1H), 3.94 (dd, J=12, 3.6 Hz, 1H), 3.67 (dd, J=14, 3.6 Hz, 1H), 3.52 (dd, 10, 8.0 Hz, 1H), 3.25 (s, 2H), 2.92 (s, 4H), 1.64 (s, 3H), 1.63 (s, 3H) ppm.

(2): $^1$H NMR (D₂O, 400 MHz) δ 7.66-7.63 (m, 1H), 7.60-7.58 (m, 1H), 7.50 (t, J=7.6 Hz, 1H), 5.08 (appar. t, J=9.2 Hz, 1H), 5.00 (s, 1H), 4.34 (appar. t, J=9.6 Hz, 1H), 4.11 (dd, J=14, 12 Hz, 1H), 3.95 (dd, J=12, 3.6 Hz, 1H), 3.69 (dd, J=14, 3.6 Hz, 1H), 3.60 (appar. t, J=9.6 Hz, 1H), 3.26-3.19 (m, 2H), 2.95 (s, 4H), 2.13-2.07 (m, 2H), 1.41 (s, 3H), 1.40 (s, 3H) ppm.

(11): $^1$H NMR (D₂O, 400 MHz) δ 7.78-7.70 (m, 3H), 7.66 (appar. t, J=Hz, 2H), 7.49-7.41 (m, 3H), 5.08 (appar. t, J=9.2 Hz, 1H), 5.05 (s, 1H), 4.72 (s, 2H), 4.39 (appar. t, J=9.6 Hz, 1H), 4.18 (dd, J=14, 12 Hz, 1H), 4.06 (dd, J=12, 3.2 Hz, 1H), 3.82 (dd, J=14, 3.2 Hz, 1H), 3.61 (dd, J=10, 8.8 Hz, 1H), 2.98-2.90 (m, 2H), 1.99-1.91 (m, 2H), 1.87-1.83 (m, 2H), 1.46 (s, 6H) ppm.

(27): $^1$H NMR (D₂O, 400 MHz) δ 7.46-7.42 (m, 1H), 7.39-7.31 (m, 2H), 5.04 (appar. t, J=9.2 Hz, 1H), 4.97 (s, 1H), 4.35 (appar. t, J=10 Hz, 1H), 4.07 (dd, J=14, 12 Hz, 1H), 3.93 (dd, J=12, 3.2 Hz, 1H), 3.66 (dd, J=14, 3.2 Hz, 1H), 3.56 (appar. t, J=9.2 Hz, 1H), 3.03-2.90 (m, 8H), 2.00-1.91 (m, 2H), 1.79-1.71 (m, 4H) ppm.

(41): $^1$H NMR (D₂O, 400 MHz) δ 7.79 (appar. t, J=5.0 Hz, 1H), 7.48-7.44 (m, 2H), 5.11 (appar. t, J=8.8 Hz, 1H), 5.03 (s, 1H), 4.41 (appar. t, J=10 Hz, 1H), 4.12 (dd, J=14, 12 Hz, 1H), 3.98 (dd, J=12, 3.2 Hz, 1 Hz), 3.71 (dd, J=14, 4.0 Hz, 1H), 3.62 (appar. t, J=9.6 Hz, 1H), 2.99 (s, 4H), 2.73 (s, 3H), 1.63 (s, 9H) ppm.

(45): $^1$H NMR (D₂O, 400 MHz) δ 7.99-7.95 (m, 1H), 7.88-7.83 (m, 1H), 7.30 (t, J=7.6 Hz, 1H), 5.07 (appar. t, J=8.4 Hz, 1H), 5.05 (s, 1H), 4.61-4.57 (m, 2H), 4.44 (appar. t, J=10 Hz, 1H), 4.16 (dd, J=14, 12 Hz, 1H), 4.01 (dd, J=12, 3.2 Hz, 1H), 3.76 (dd, J=14, 3.6 Hz, 1H), 3.61 (dd, J=10, 8.4 Hz, 1H), 3.01 (m, 4H), 2.14-2.10 (m, 2H), 1.56 (s, 3H), 1.55 (s, 3H) ppm.

(55): $^1$H NMR (D₂O, 400 MHz) δ 7.56-7.53 (m, 1H), 7.26-7.16 (m, 2H), 5.07 (appar. t, J=8.4 Hz), 5.02 (s, 1H), 4.41 (dd, J=10, 9.2 Hz, 1H), 4.14 (dd, J=14, 12 Hz, 1H), 3.99 (dd, J=12, 3.2 Hz, 1H), 3.73 (dd, 1H, J=14, 3.6 Hz, 1H), 3.61 (dd, J=10, 8.4 Hz, 1H), 2.99 (s, 4H), 1.95 (s, 3H), 1.94 (s, 3H) ppm.

(67): $^1$H NMR (D₂O, 400 MHz) δ 7.73-7.53 (m, 8H), 5.13, (appar. t, J=9.2 Hz, 1H), 5.03 (s, 1H), 4.41 (appar. t, J=9.6 Hz, 1H), 4.13 (dd, J=14, 12 Hz, 1H), 4.00-3.94 (m, 1H), 3.74-3.68 (m, 1H), 3.63 (appar. t, J=10 Hz, 1H), 2.98 (s, 4H), 2.44 (s, 3H) ppm.

(53): $^1$H NMR (D₂O, 400 MHz) δ 8.29 (d, J=8.8 Hz, 1H), 8.21 (d, J=8.4 Hz, 1H), 8.01 (d, J=8.4 Hz, 1H), 7.93-7.87 (m, 1H), 7.77-7.68 (m, 2H), 5.25 (appar. t, J=9.2 Hz, 1H), 5.06 (s, 1H), 4.47 (appar. t, J=9.6 Hz, 1H), 4.14 (dd, J=14, 12 Hz, 1H), 4.03-3.97 (m, 1H), 3.75-3.65 (m, 2H), 2.98 (s, 4H), 2.71 (s, 3H) ppm.

(79): $^1$H NMR (D₂O, 400 MHz) δ 7.85 (dd, J=7.8, 1.7 Hz, 1H), 7.78 (dd, J=7.8, 1.7 Hz, 1H), 7.21 (t, J=7.8 Hz, 1H), 5.02 (appar. t, J=8.8 Hz, 1H), 4.98 (s, 1H), 4.53-4.48 (m, 2H), 4.35 (appar. t, J=10 Hz, 1H), 4.29 (s, 2H), 4.07 (dd, J=14, 12 Hz, 1H), 3.98 (dd, J=12, 3.2 Hz, 1H), 3.86 (appar. t, J=5.3 Hz, 2H), 3.73 (dd, J=14, 3.2 Hz, 1H), 3.65 (appar. t, J=5.5 Hz, 2H), 3.56 (dd, J=10, 8.3 Hz, 1H), 2.05-2.01 (m, 2H), 1.47 (s, 3H), 1.47 (s, 3H) ppm.

(80): $^1$H NMR (D₂O, 400 MHz) δ 7.54-7.50 (m, 1H), 7.46-7.38 (m, 2H), 5.09 (appar. t, J=8.8 Hz, 1H), 5.00 (s, 1H), 4.37 (appar. t, J=10 Hz, 1H), 4.10 (dd, J=14, 12 Hz, 1H), 3.95 (dd, J=12, 3.2 Hz, 1H), 3.68 (dd, J=14, 3.6 Hz, 1H), 3.60 (appar. t, J=10 Hz, 1H), 2.95 (s, 4H), 2.84 (q, J=7.6 Hz, 2H), 2.47 (s, 3H), 1.33 (t, J=7.6 Hz, 3H) ppm.

(82): $^1$H NMR (D₂O, 400 MHz) δ 7.94 (dd, J=7.8, 1.7 Hz, 1H), 7.84 (dd, J=7.8, 1.7 Hz, 1H), 7.28 (t, J=7.8 Hz, 1H), 5.06 (appar. t, J=8.8 Hz, 1H), 5.02 (d, J=0.8 Hz, 1H), 4.59-4.55 (m, 2H), 4.41 (dd, J=10, 9.3 Hz, 1H), 4.24 (s, 2H), 4.09 (dd, J=14, 12 Hz, 1H), 4.00 (dd, J=12, 2.6 Hz, 1H), 3.74

(dd, J=14, 3.5 Hz, 1H), 3.60 (J=10, 8.3 Hz, 1H), 2.87-i2.81 (m, 1H), 2.12-2.07 (m, 2H), 1.54 (s, 3H), 1.53 (s, 3H), 1.04-0.89 (m, 4H) ppm.

(83): $^1$H NMR (D$_2$O, 400 MHz) δ 8.01-7.96 (m, 1H), 7.89-7.85 (m, 1H), 7.31 (t, J=7.8 Hz, 1H), 5.07 (appar. t, J=8.9 Hz, 1H), 5.05 (s, 1H), 4.64-4.58 (m, 2H), 4.44 (appar. t, J=10 Hz, 1H), 4.30 (s, 2H), 4.14 (dd, J=14, 12 Hz, 1H), 4.03 (dd, J=12, 3.9 Hz, 1H), 3.78 (dd, J=14, 3.4 Hz, 1H), 3.65-3.55 (m, 2H), 2.17-2.11 (m, 2H), 1.81-1.72 (m, 2H), 1.58 (s, 3H), 1.57 (s, 3H), 1.55-1.46 (m, 2H), 1.12 (t, J=7.3 Hz, 3H) ppm.

(84): $^1$H NMR (D$_2$O, 400 MHz) δ 7.93 (dd, J=7.8, 1.7 Hz, 1H), 7.83 (dd, J=7.8, 1.7 Hz, 1H), 7.27 (t, J=7.8 Hz, 1H), 5.05 (appar. t, J=9.0 Hz, 1H), 5.02 (s, 1H), 4.59-4.55 (m, 2H), 4.55-4.46 (m, 1H), 4.40 (dd, J=10, 9.5 Hz, 1H), 4.26 (s, 2H), 4.10 (dd, J=14, 12 Hz, 1H), 4.00 (dd, J=11, 3.2 Hz), 3.74 (dd, J=14, 3.3 Hz), 3.59 (dd, J=10, 8.2 Hz, 1H), 2.12-2.02 (m, 4H), 1.91-1.71 (m, 6H), 1.53 (s, 3H), 1.52 (s, 3H) ppm.

(85): $^1$H NMR (D$_2$O, 400 MHz) δ p 7.94 (dd, J=7.6, 1.6 Hz, 1H), 7.83 (dd, J=7.6, 1.6 Hz, 1H), 7.27 (t, J=7.6 Hz, 1H), 5.05 (appar. t, J=10 Hz, 1H), 5.02 (s, 1H), 4.58-4.54 (m, 2H), 4.40 (appar. t, J=10 Hz, 1H), 4.27 (s, 2H), 4.11 (dd, J=14, 12 Hz, 1H), 4.00 (dd, J=11, 3.2 Hz, 1H), 3.75 (dd, J=14, 3.5 Hz, 1H), 3.59 (dd, J=10, 8.1 Hz, 1H), 3.54-3.48 (m, 2H), 2.12-2.06 (m, 2H), 1.79-1.71 (m, 2H), 1.53 (s, 3H), 1.53 (s, 3H), 1.05 (t, J=7.3 Hz, 3H) ppm.

(86): H NMR (D$_2$O, 400 MHz) δ 7.94 (dd, J=7.8, 1.7 Hz, 1H), 7.84 (dd, J=7.8, 1.7 Hz, 1H), 7.27 (t, J=7.8 Hz, 1H), 5.06 (appar. t, J=8.9 Hz, 1H), 5.02 (s, 1H), 4.59-4.55 (m, 2H), 4.41 (appar. t, J=10 Hz, 1H), 4.26 (s, 2H), 4.10 (dd, J=14, 12 Hz, 1H), 4.00 (dd, J=11, 3.0 Hz, 1H), 3.76 (dd, J=14, 3.2 Hz, 1H), 3.60 (dd, J=10, 8.3 Hz, 1H), 3.14 (s, 3H), 2.12-2.08 (m, 2H), 1.54 (s, 3H), 1.53 (s, 3H) ppm.

(87): $^1$H NMR (D$_2$O, 400 MHz) δ 7.81 (dd, J=7.9, 1.7 Hz, 1H), 7.69 (dd, J=1.7, 7.6 Hz, 1H), 7.41 (t, J=7.7 Hz, 1H), 5.16 (appar. t, J=9.0 Hz, 1H), 5.04 (s, 1H), 4.45 (appar. t, J=9.5 Hz, 1H), 4.28 (s, 2H), 4.11 (dd, J=14, 12 Hz, 1H), 4.05-4.00 (m, 4H), 3.77 (dd, J=14, 3.2 Hz, 1H), 3.66 (dd, J=10, 8.9 Hz, 1H), 3.16 (s, 3H), 1.60 (s, 9H) ppm.

(88): $^1$H NMR (D$_2$O, 400 MHz) δ 7.88 (dd, J=7.8, 1.7 Hz, 1H), 7.84 (dd, J=7.8, 1.7 Hz, 1H), 7.27 (t, J=7.8 Hz, 1H), 5.06 (appar. t, J=8.6 Hz, 1H), 5.03 (s, 1H), 4.59-4.55 (m, 2H), 4.41 (appar. t, J=10 Hz, 1H), 4.28 (s, 2H), 4.10 (dd, J=14, 12 Hz, 1H), 4.01 (dd, J=12, 3.0 Hz, 1H), 3.75 (dd, J=14, 3.3 Hz, 1H), 3.63-3.57 (m, 2H), 2.12-2.07 (m, 2H), 1.54 (s, 3H), 1.53 (s, 3H), 1.33 (t, J=7.2 Hz, 3H) ppm.

(89): $^1$H NMR (D$_2$O, 400 MHz) δ p 7.95 (dd, J=7.8, 1.7 Hz, 1H), 7.84 (dd, J=7.8, 1.7 Hz, 1H), 7.28 (appar. t, J=7.8 Hz, 1H), 5.06 (appar. t, J=8.8 Hz, 1H), 5.03 (d, J=0.8 Hz, 1H), 4.60-4.55 (m, 2H), 4.44-4.36 (m, 2H), 4.25 (s, 2H), 4.11 (dd, J=14, 12 Hz, 1H), 4.01 (dd, J=11, 3.3 Hz, 1H), 3.75 (dd, J=14, 3.3 Hz, 1H), 3.60 (dd, J=10, 8.3 Hz, 1H), 2.12-2.08 (m, 2H), 1.55 (s, 3H), 1.54 (s, 3H), 1.38 (d, J=1.6 Hz, 3H), 1.37 (d, J=1.6 Hz, 3H) ppm.

(90): $^1$H NMR (D$_2$O, 400 MHz) δ 7.94 (dd, J=7.8, 1.7 Hz, 1H), 7.84 (dd, J=7.8, 1.7 Hz, 1H), 7.27 (t, J=7.8 Hz, 1H), 5.06 (appar. t, J=8.7 Hz, 1H), 5.03 (s, 1H), 4.60-4.55 (m, 2H), 4.41 (appar. t, J=10 Hz, 1H), 4.26 (s, 2H), 4.11 (dd, J=14, 12 Hz, 1H), 4.02 (dd, J=3.2, 12 Hz), 3.76 (dd, J=14, 3.3 Hz, 1H), 3.60 (dd, J=10, 8.5 Hz, 1H), 2.12-2.07 (m, 2H), 1.54 (s, 3H), 1.53 (s, 3H) ppm.

(91): $^1$H NMR (D$_2$O, 400 MHz) δ p 7.84 (dd, J=7.8, 1.7 Hz, 1H), 7.78 (dd, J=7.8, 1.7 Hz, 1H), 7.21 (t, J=7.8 Hz, 1H), 5.02 (appar. t, J=8.8 Hz, 1H), 4.99 (s, 1H), 4.53-4.48 (m, 2H), 4.40-4.32 (m, 3H), 4.31-4.22 (m, 2H), 4.10 (dd, J=14, 12 Hz, 1H), 3.98 (dd, J=12, 3.8 Hz, 1H), 3.76 (dd, J=14, 3.5 Hz, 1H), 3.56 (dd, J=10, 8.2 Hz, 1H), 2.06-2.01 (m, 2H), 1.47 (s, 3H), 1.47 (s, 3H) ppm.

Example 2

Na$_V$ Inhibition Assay

Electrophysiology experiments were performed on Human Embryonic Kidney 293 cells (HEK) or Chinese hamster ovary cells (CHO) transfected with the full-length cDNA coding for the appropriate human Na$_V$ sodium channel α-subunit, including Na$_V$ 1.7, Na$_V$ 1.4, and Na$_V$ 1.6.

Sodium currents were measured using the patch-clamp technique in the whole-cell configuration with a HEKA EPC 9 amplifier (HEKA Elektronik Dr. Schulze GmbH, Germany) or can be measured with an IonFlux 16 automated patch clamp system (Fluxion Biosciences, South San Francisco, USA) as previously described by Moran. See, Moran O, Picollo A, Conti F (2003) Tonic and phasic guanidinium toxin-block of skeletal muscle Na channels expressed in Mammalian cells, Biophys J 84(5):2999-3006. For manual patch-clamp experiments, borosilicate glass micropipettes (Sutter Instruments, Novato, Calif.) were pulled to a tip diameter yielding a resistance of 1.0-2.0 MQ in the working solutions. The composition of intracellular solution was (in mM): CsF 110, EDTA 20, HEPES 10, NaCl 10, and the pH was adjusted to 7.2 with CsOH. The composition of extracellular solution was (in mM): NaCl 135, KCl 4.5, CaCl$_2$ 2, MgCl$_2$ 1, HEPES 10, and the pH was adjusted to 7.4 with NaOH. Peak currents were generally between 0.5-20 nA.

Lyophilized stock of each of the toxin derivatives were stored at −20° C. and dissolved in the external solution prior to recording. (+)-Saxitoxin and (+)-gonyautoxin-III were synthesized according to routes previously published. (Fleming J J, McReynolds M D, Du Bois J. (+)-saxitoxin: a first and second generation stereoselective synthesis. J Am Chem Soc. 2007; 129(32):9964-9975; Mulcahy J V, Du Bois J. A stereoselective synthesis of (+)-gonyautoxin 3. J Am Chem Soc. 2008; 130:12630-12631). Current measurements were recorded under continuous perfusion, controlled manually by syringe addition.

The output of the EPC 9 patch-clamp amplifier was filtered with a built-in low-pass, four-pole Bessel filter having a cutoff frequency of 10 kHz and sampled at 20 kHz. For both manual and automated recordings, the membrane was kept at a holding potential of between −120 and −90 mV. Pulse stimulation and data acquisition were controlled with the Pulse software (HEKA Elektronik Dr. Schulze GmbH, Germany) or the IonFlux software (Fluxion Biosciences, South San Francisco, USA). All measurements were performed at room temperature (about 20-22° C.). Recordings were made at least 5 min after establishing the whole-cell and voltage-clamp configuration to allow for stabilization of the voltage-dependent properties of the channels. Currents were elicited by 10 ms step depolarizations from a holding potential to a value between −40 and 0 mV. Data were normalized to control currents, plotted against toxin concentration and analyzed in Microsoft Excel software. Data were fit to a four-parameter logistic equation to determine IC$_{50}$ values and expressed as mean.

Tables 1 and 2—Na$_V$ Isoform Potency and Selectivity

For both Tables 1 and 2, all data were measured in HEK cells. Column 1 provides IC$_{50}$ data for Na$_V$ 1.7 as measured using the patch-clamp technique in the whole-cell configuration with a HEKA EPC 9 amplifier. Column 2 provides IC$_{50}$ data for Na$_V$ 1.4 as measured using the patch-clamp technique in the whole-cell configuration with a HEKA EPC 9 amplifier. Column 3 provides selectivity data for column 1 over column 2. Column 4 provides IC$_{50}$ data for Na$_V$ 1.6 as measured using the patch-clamp technique in the whole-cell configuration with a HEKA EPC 9 amplifier. Column 5 provides selectivity data for column 1 over column 4. IC$_{50}$ results are provided in Table 1. ND means not detectable.

TABLE 1

Compounds of the Invention

| Compound | 1 (nM) | 2 (μM) | 3 | 4 (μM) | 5 |
|---|---|---|---|---|---|
| 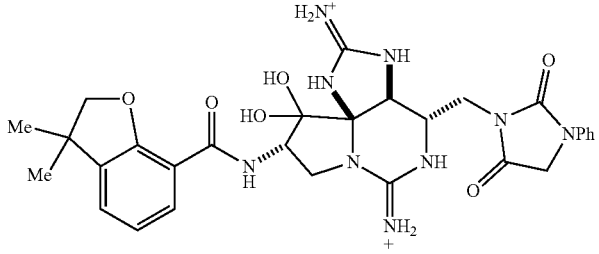 (1) | 74 | 54 | 730 | 40 | 541 |
| 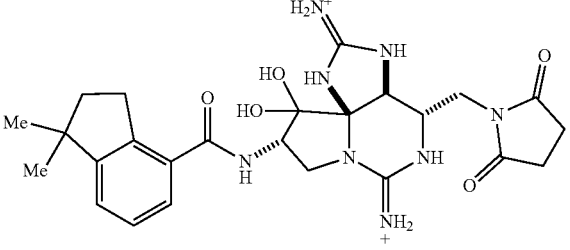 (2) | 44 | 75 | 1705 | 29 | 659 |
| 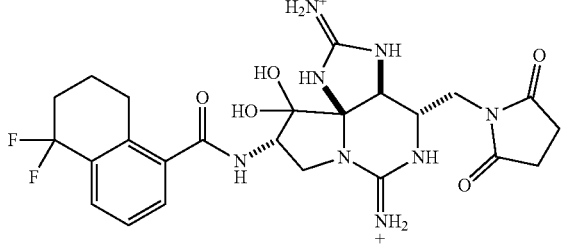 (3) | 130 | >100 | >769 | 40 | 320 |
| 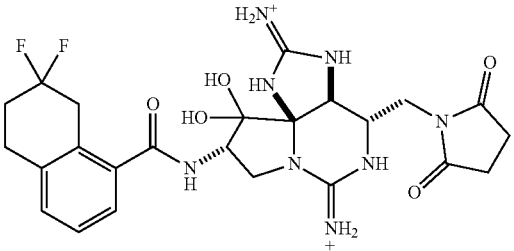 (4) | 250 | NT | — | >30 | >120 |

TABLE 1-continued
Compounds of the Invention
| Compound | 1 (nM) | 2 (µM) | 3 | 4 (µM) | 5 |
|---|---|---|---|---|---|
| 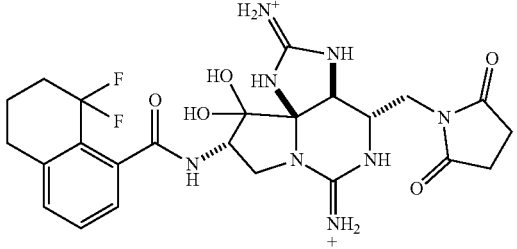 (5) | 110 | >100 | >909 | 23.5 | 213.64 |
| 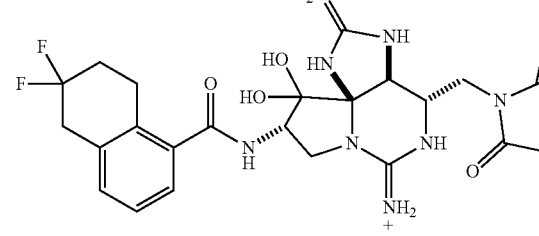 (6) | 100 | 18.50 | 193 | 8.5 | 89 |
| 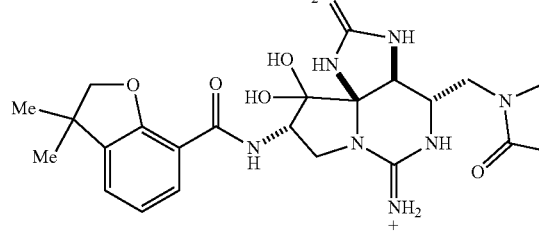 (7) | 80 | >100 | >1250 | 120 | 1463 |
| 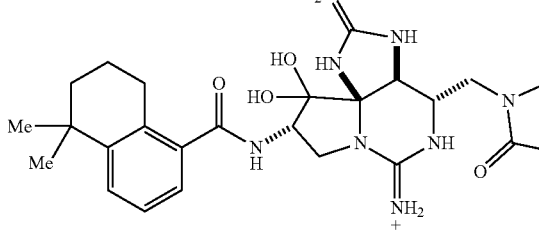 (8) | 40 | 40.00 | 930 | 12.5 | 291 |
| 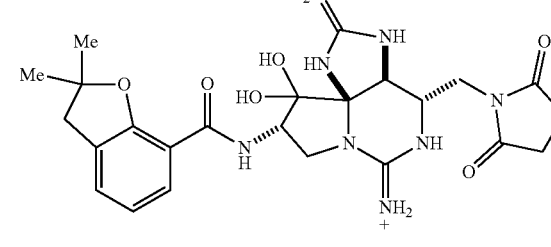 (9) | 790 | >100 | >127 | >100 | >127 |

TABLE 1-continued

Compounds of the Invention

| Compound | 1 (nM) | 2 (μM) | 3 | 4 (μM) | 5 |
|---|---|---|---|---|---|
| (11) | 75 | 29 | 387 | 8.1 | 108 |
| (27) | 82 | 120 | 1463 | 26.5 | 323 |
| (41) | 305 | 91 | 298 | 53 | 174 |
| (43) | 130 | 97 | 746 | 26 | 200 |
| (45) | 69 | 65.5 | 949 | 45 | 652 |

TABLE 1-continued
Compounds of the Invention
| Compound | 1 (nM) | 2 (μM) | 3 | 4 (μM) | 5 |
|---|---|---|---|---|---|
| 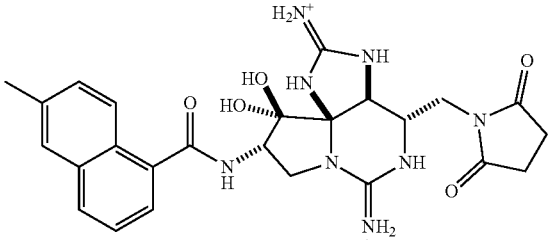 (53) | 155 | 23 | 148 | NT | NT |
| 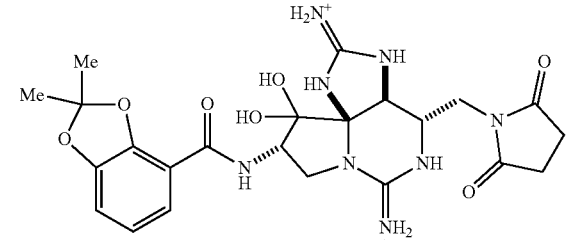 (55) | 3 μM | 26 | 9 | 5 | 1.5 |
| 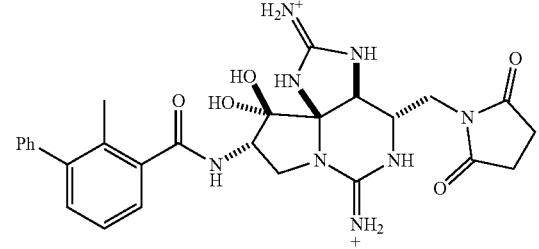 (67) | 250 | 25 | 100 | 1.8 | 7 |
| 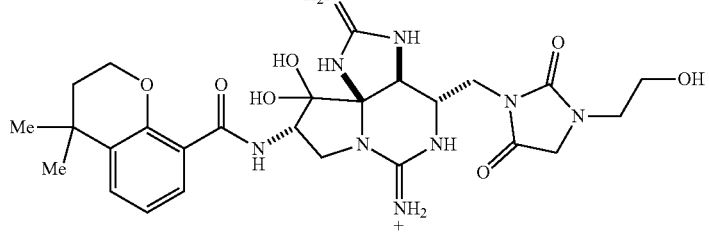 (79) | 69 | 96 | 1391 | 89 | 1290 |
| 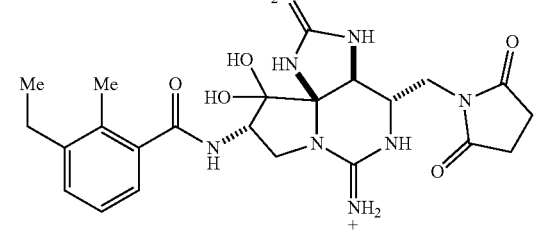 (80) | 40 | 51 | 1275 | 7.1 | 178 |

TABLE 1-continued
Compounds of the Invention
| Compound | 1 (nM) | 2 (μM) | 3 | 4 (μM) | 5 |
|---|---|---|---|---|---|
| 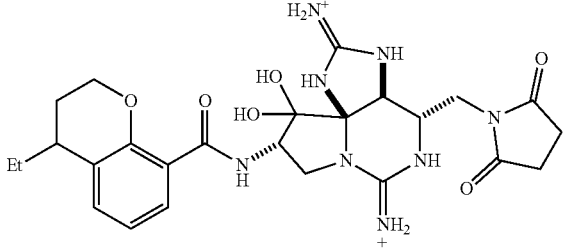 (81) | 99 | 60 | 606 | 9.8 | 99 |
| 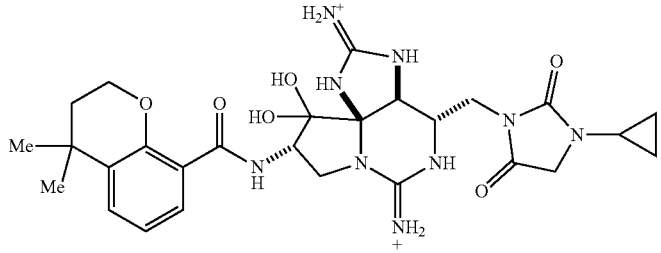 (82) | 83 | 175 | 2108 | 205 | 2470 |
| 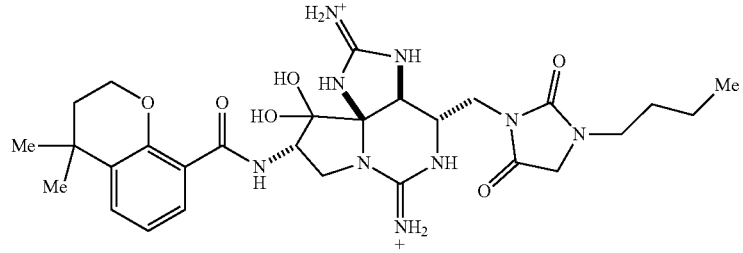 (83) | 150 | 67 | 447 | 60 | 400 |
| 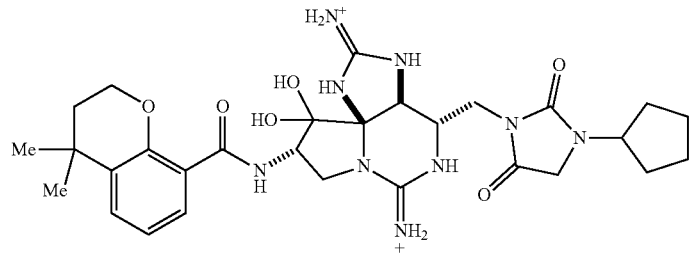 (84) | 130 | 67 | 515 | 36 | 277 |
| 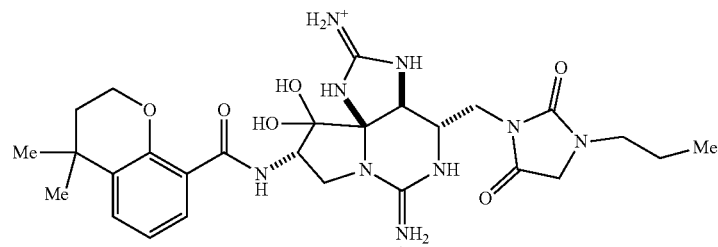 (85) | 92 | 140 | 1522 | 105 | 1141 |

TABLE 1-continued

Compounds of the Invention

| Compound | 1 (nM) | 2 (μM) | 3 | 4 (μM) | 5 |
|---|---|---|---|---|---|
| (86) | 56 | 25 | 446 | 34 | 607 |
| (87) | 335 | 135 | 402 | 50 | 149 |
| (88) | 115 | 155 | 1348 | 89 | 774 |
| (89) | 220 | 85 | 386 | 85 | 386 |
| (90) | 90 | 79 | 878 | 38 | 422 |

TABLE 1-continued
Compounds of the Invention
| Compound | 1 (nM) | 2 (µM) | 3 | 4 (µM) | 5 |
|---|---|---|---|---|---|
| 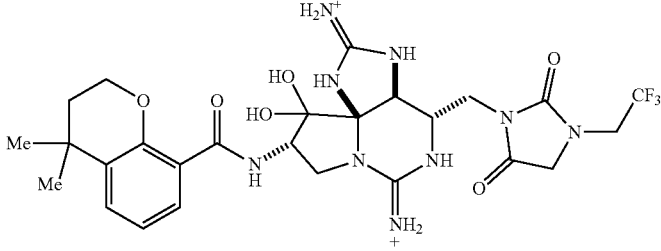 (91) | 270 | 100 | 370 | 105 | 389 |
| 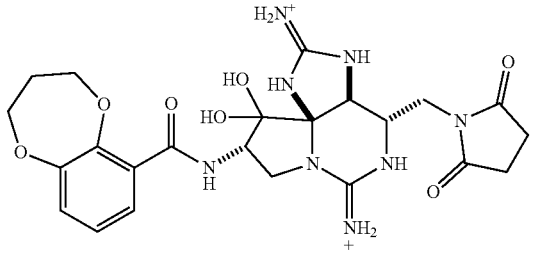 (93) | 500 | NT | — | 19 | 38 |
| 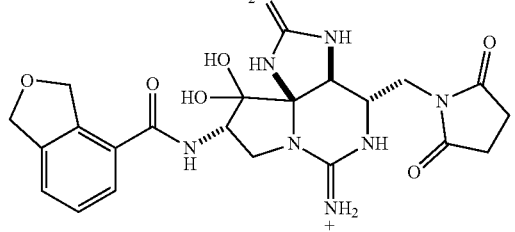 (94) | 2.6 µM | 48 | 18 | NT | — |
Certain compounds disclosed herein have surprisingly improved potency for isoform $Na_V$ 1.7 and/or improved selectivity over the undesired isoforms, as compared to compounds in the art, including certain compounds in PCT/US2016/055050.
TABLE 2
Selected Compounds from PCT/US2016/055050
| Compound | 1 (nM) | 2 (µM) | 3 | 4 (µM) | 5 |
|---|---|---|---|---|---|
| 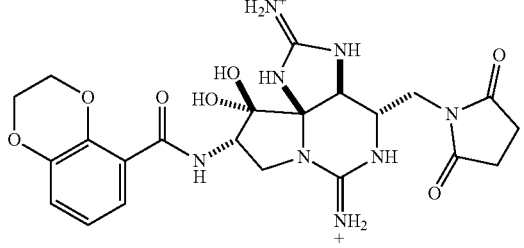 (C50) | 490 | 35 | 71 | NT | — |

TABLE 2-continued
Selected Compounds from PCT/US2016/055050
| Compound | 1 (nM) | 2 (μM) | 3 | 4 (μM) | 5 |
|---|---|---|---|---|---|
| (C52) 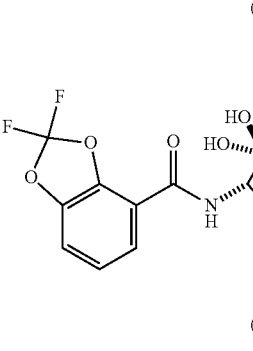 | 630 | 240 | 381 | NT | — |
| (C77) 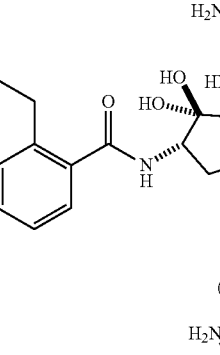 | 800 | 210 | 263 | NT | — |
| (C83) 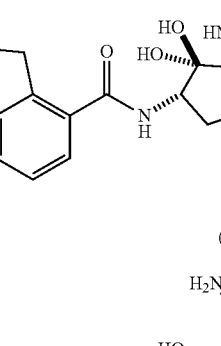 | 52 | 9.1 | 175 | 0.85 | 16 |
| (C85) 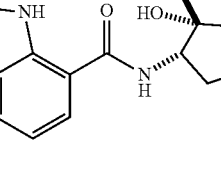 | 86 | 51 | 593 | 3.1 | 36 |
| (C88)  | 12.5 μM | 160 | 13 | NT | — |

TABLE 2-continued

Selected Compounds from PCT/US2016/055050

| Compound | 1 (nM) | 2 (µM) | 3 | 4 (µM) | 5 |
|---|---|---|---|---|---|
| (C92) | 140 | 79 | 564 | 14 | 100 |
| (C93) | 135 | 75 | 556 | 13 | 96 |
| (C120) | 950 | 1000 | 1053 | 500 | 526 |

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A Compound of Formula (I):

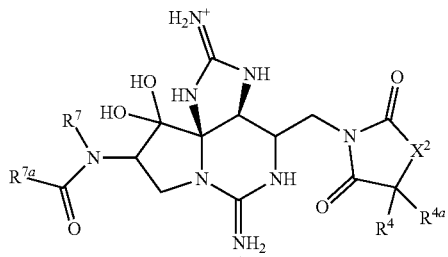

(I)

wherein $X^2$ is —N($R^8$)—;

$R^4$ and $R^{4a}$ are independently hydrogen or $C_{1-6}$alkyl;

$R^7$ is hydrogen or $C_{1-6}$alkyl;

$R^{7a}$ is aryl optionally substituted with 1, 2, 3, or 4 $R^{7b}$; heterocyclic optionally substituted with 1, 2, 3, or 4 $R^{7b}$; or biphenyl optionally substituted with 1, 2, 3, or 4 $R^{7b}$;

each $R^{7b}$, when present, is independently halo, $C_{1-6}$alkyl, halo-$C_{1-6}$alkyl, aryl-$C_{1-6}$alkyl, hydroxy, $C_{1-6}$alkoxy, halo-$C_{1-6}$alkoxy, aryloxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, —C(O)(heterocycloalkyl), or cyano; where the aryl in aryloxy and aryl-$C_{1-6}$alkyl are optionally substituted with 1, 2, or 3 groups independently selected from $C_{1-6}$alkyl, halo, and halo-$C_{1-6}$alkyl; and $R^8$ is $C_3$-$C_8$-cycloalkyl; or as a pharmaceutically acceptable salt or salts thereof; or a hydrate, solvate, stereoisomer, tautomer, or mixture thereof.

2. The Compound of claim 1, where the compound is according to Formula (Ib):

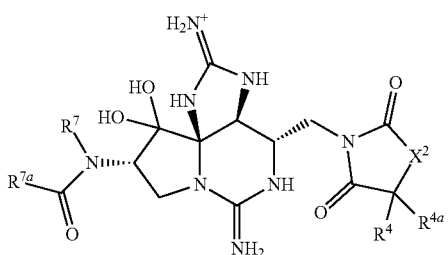

(Ib)

as a pharmaceutically acceptable salt or salts thereof; or a hydrate, solvate, stereoisomer, tautomer, or mixture thereof.

3. The Compound of claim 1, where $R^4$ and $R^{4a}$ are each hydrogen; as a pharmaceutically acceptable salt or salts thereof; or a hydrate, solvate, stereoisomer, tautomer, or mixture thereof.

4. The Compound of claim 1, where $R^7$ is hydrogen; as a pharmaceutically acceptable salt or salts thereof; or a hydrate, solvate, stereoisomer, tautomer, or mixture thereof.

5. The Compound of claim 1, where the aryl in $R^{7a}$ is phenyl, naphthyl, tetrahydronaphthyl, fluorenyl, 6,7,8,9-tetrahydro-5H-benzo[7]annulenyl,

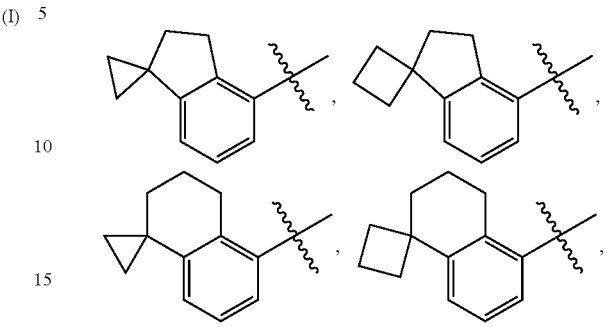

or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; as a pharmaceutically acceptable salt or salts thereof; or a hydrate, solvate, stereoisomer, tautomer, or mixture thereof.

6. The Compound of claim 1, where the heterocyclic in $R^{7a}$ is benzo-1,4-dioxanyl, benzodioxolyl, 2,3-dihydrobenzofuranyl, chromanyl,

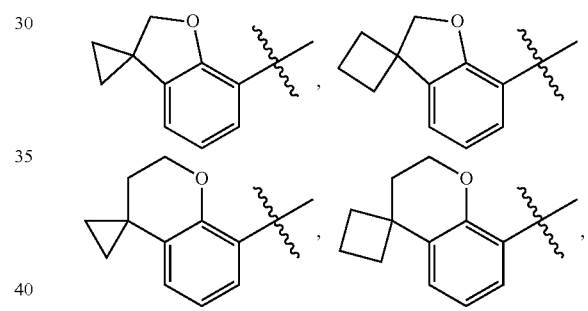

or 2,2-dioxo-1,3-dihydrobenzo[c]thienyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; as a pharmaceutically acceptable salt or salt thereof; or a hydrate, solvate, stereoisomer, tautomer, or mixture thereof.

7. The Compound of claim 1, where $R^{7a}$ is

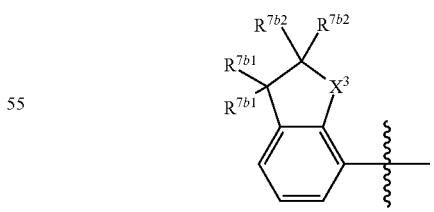

where $X^3$ is —O—, —O—C($R^{7b3}$)($R^{7b3}$)—, —C($R^{7b3}$)($R^{7b3}$)—O—, —C($R^{7b3}$)($R^{7b3}$)—C($R^{7b4}$)($R^{7b4}$)—, or —C($R^{7b3}$)($R^{7b3}$)—C($R^{7b4}$)($R^{7b4}$)—C($R^{7b5}$)($R^{7b5}$)— and each $R^{7b1}$, $R^{7b2}$, $R^{7b3}$, $R^{7b4}$, and $R^{7b5}$ is independently hydrogen, halo, or $C_{1-3}$-alkyl; as a pharmaceutically acceptable salt or salts thereof; or a hydrate, solvate, stereoisomer, tautomer, or mixture thereof.

8. The Compound of claim 7, where a) one $R^{7b1}$ is methyl or ethyl and the other $R^{7b1}$ is hydrogen, or b) the two $R^{7b1}$ are both hydrogen, or c) the two $R^{7b1}$ are both methyl; and each $R^{7b2}$, $R^{7b3}$, $R^{7b4}$, and $R^{7b5}$ are hydrogen; as a pharmaceutically acceptable salt or salts thereof; or a hydrate, solvate, stereoisomer, tautomer, or mixture thereof.

9. The Compound of claim 1, where $R^{7a}$ is

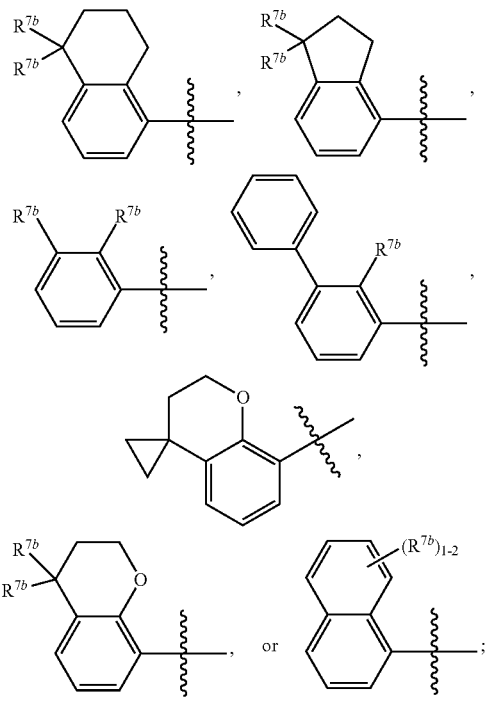

as a pharmaceutically acceptable salt or salts thereof; or a hydrate, solvate, stereoisomer, tautomer, or mixture thereof.

10. The Compound of claim 9, where $R^{7a}$ is

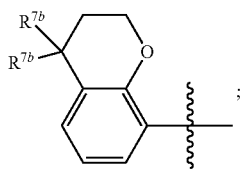

as a pharmaceutically acceptable salt or salts thereof; or a hydrate, solvate, stereoisomer, tautomer, or mixture thereof.

11. The Compound of claim 1, selected from

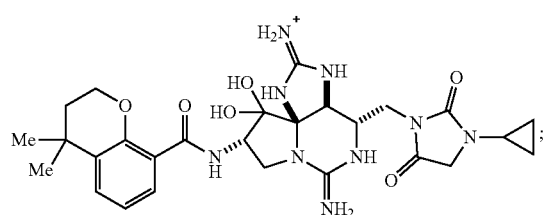

(82)

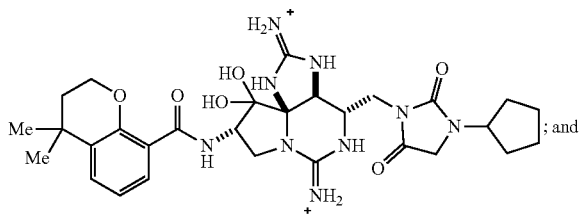

(84)

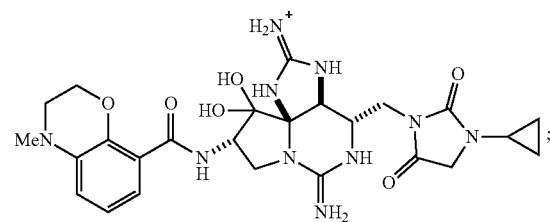

(95)

as a pharmaceutically acceptable salt or salts thereof; or a hydrate, solvate, stereoisomer, tautomer, or mixture thereof.

12. A pharmaceutical composition comprising the compound of claim 1, as a pharmaceutically acceptable salt or salts thereof; or a hydrate, solvate, stereoisomer, tautomer, or mixture thereof; and a pharmaceutically acceptable excipient, carrier or diluent.

13. A method for the treatment of a condition associated with voltage-gated sodium channel function in a mammal, comprising the administration of a therapeutically or prophylactically effective amount of a pharmaceutical composition of claim 12, wherein the condition is pain, cough, itch, or discomfort associated with dry eye syndrome.

14. The method of claim 13, wherein the mammal is a human.

15. The method of claim 14, where the condition is pain.

16. The method of claim 15, where the condition is pain selected from pain associated with erythromelalgia, pain associated with diabetic peripheral neuropathy, paroxysmal extreme pain disorder, complex regional pain syndrome, pain associated with trigeminal neuralgia, pain associated with multiple sclerosis, pain associated with arthritis, pain associated with osteoarthritis, pain associated with postherpetic neuralgia, cancer pain, pain associated with cluster headache, pain associated with migraine, pain associated with sciatica, pain associated with endometriosis, pain associated with fibromyalgia, postsurgical pain, subacute pain, chronic pain, pain associated with dry eye syndrome, pain associated with (acute) corneal injuries or abrasions, acute ocular pain, chronic ocular pain, pain associated with corneal infections, pain associated with Parkinson's disease, pain associated with ALS, and pain associated with ocular surgery.

17. The method of claim 13, where the condition is selected from acute pain, subacute pain, and postsurgical pain.

18. A compound of Formula Xe

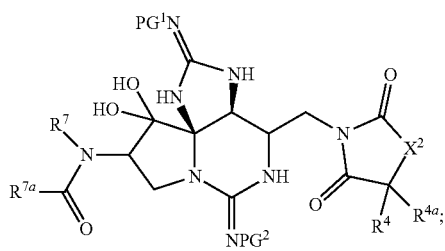

or salt(s) thereof, where

PG$^1$ is a nitrogen-protecting group;
PG$^2$ is a nitrogen-protecting group;
X$^2$ is —N(R$^8$)—;
R$^4$ and R$^{4a}$ are independently hydrogen or C$_{1-6}$alkyl;
R$^7$ is hydrogen or C$_{1-6}$alkyl;
R$^{7a}$ is aryl optionally substituted with 1, 2, 3, or 4 R$^{7b}$; heterocyclic optionally substituted with 1, 2, 3, or 4 R$^{7b}$; or biphenyl optionally substituted with 1, 2, 3, or 4 R$^{7b}$;
each R$^{7b}$, when present, is independently halo, C$_{1-6}$alkyl, halo-C$_{1-6}$alkyl, aryl-C$_{1-6}$alkyl, hydroxy, C$_{1-6}$alkoxy, halo-C$_{1-6}$alkoxy, aryloxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, —C(O)(heterocycloalkyl), or cyano; where the aryl in aryloxy and aryl-C$_{1-6}$alkyl are optionally substituted with 1, 2, or 3 groups independently selected from C$_{1-6}$alkyl, halo, and halo-C$_{1-6}$alkyl; and
R$^8$ is C$_3$-C$_8$-cycloalkyl.

19. A method of preparing a compound of Formula (I) comprising a) deprotecting a compound of Formula Xe

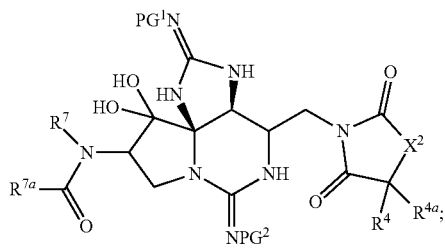

or salt thereof, where

PG$^1$ is a nitrogen-protecting group;
PG$^2$ is a nitrogen-protecting group;
X$^2$ is —N(R$^8$)—;
R$^4$ and R$^{4a}$ are independently hydrogen or C$_{1-6}$alkyl;
R$^7$ is hydrogen or C$_{1-6}$alkyl;
R$^{7a}$ is aryl optionally substituted with 1, 2, 3, or 4 R$^{7b}$; heterocyclic optionally substituted with 1, 2, 3, or 4 R$^{7b}$; or biphenyl optionally substituted with 1, 2, 3, or 4 R$^{7b}$;
each R$^{7b}$, when present, is independently halo, C$_{1-6}$alkyl, halo-C$_{1-6}$alkyl, aryl-C$_{1-6}$alkyl, hydroxy, C$_{1-6}$alkoxy, halo-C$_{1-6}$alkoxy, aryloxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, —C(O)(heterocycloalkyl), or cyano; where the aryl in aryloxy and aryl-C$_{1-6}$alkyl are optionally substituted with 1, 2, or 3 groups independently selected from C$_{1-6}$alkyl, halo, and halo-C$_{1-6}$alkyl; and
R$^8$ is C$_3$-C$_8$-cycloalkyl;
to yield a compound of Formula I; and
b) optionally isolating the compound of Formula I.

20. The compound of claim 9, where each R$^{7b}$ is methyl; as a pharmaceutically acceptable salt or salts thereof; or a hydrate, solvate, stereoisomer, tautomer, or mixture thereof.

21. The compound of claim 1, according to compound 82:

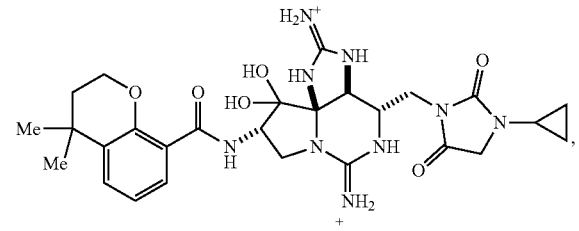

as a pharmaceutically acceptable salt or salts thereof; or
as a pharmaceutically acceptable salt or salts thereof and a stereoisomer thereof.

22. The compound of claim 1, according to compound 84:

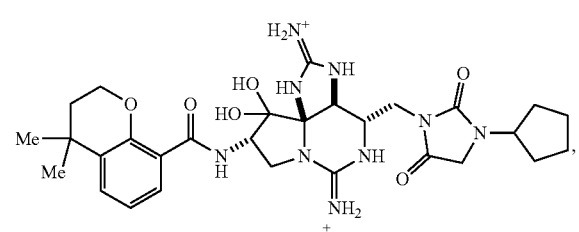

as a pharmaceutically acceptable salt or salts thereof; or
as a pharmaceutically acceptable salt or salts thereof and a stereoisomer thereof.

23. The compound of claim 1, according to compound 95:

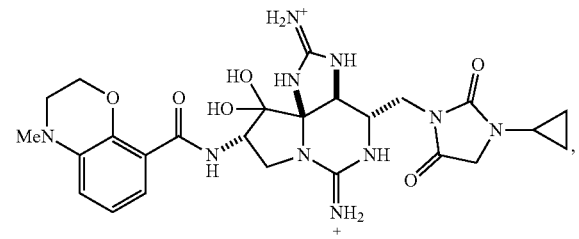

as a pharmaceutically acceptable salt or salts thereof; or
as a pharmaceutically acceptable salt or salts and a stereoisomer thereof.

24. The compound of claim 1, according to compound 82:

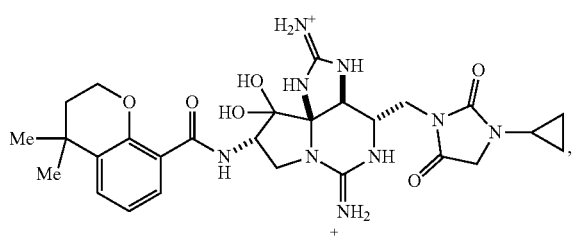

as a pharmaceutically acceptable salt or salts and a stereoisomer thereof.

25. The compound of claim 1, according to compound 84:

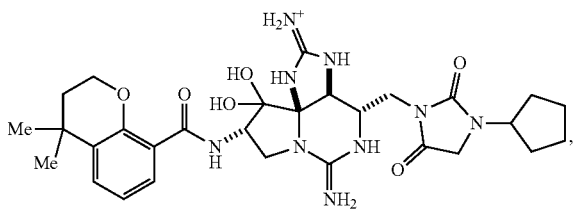

as a pharmaceutically acceptable salt or salts and a stereoisomer thereof.

26. The compound of claim 1, according to compound 95:

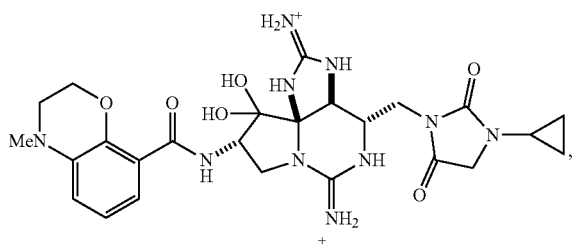

as a pharmaceutically acceptable salt or salts and a stereoisomer thereof.

27. The method of claim 13, wherein the pharmaceutical composition comprises compound 82:

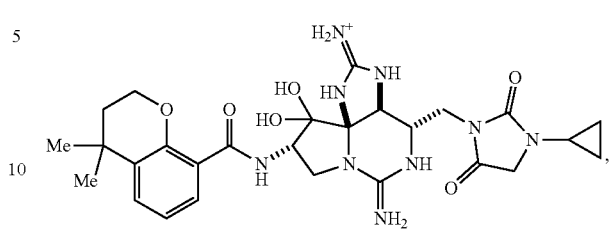

as a pharmaceutically acceptable salt or salts thereof; or as a pharmaceutically acceptable salt or salts and a stereoisomer thereof.

28. The method of claim 13, wherein the pharmaceutical composition comprises compound 84:

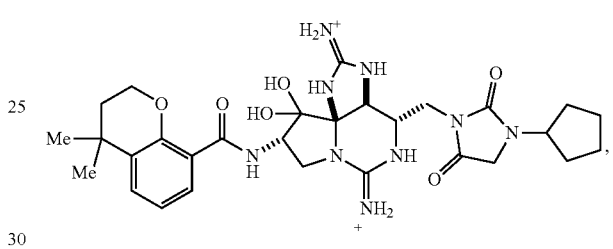

as a pharmaceutically acceptable salt or salts thereof; or as a pharmaceutically acceptable salt or salts and a stereoisomer thereof.

29. The method of claim 13, wherein the pharmaceutical composition comprises compound 95:

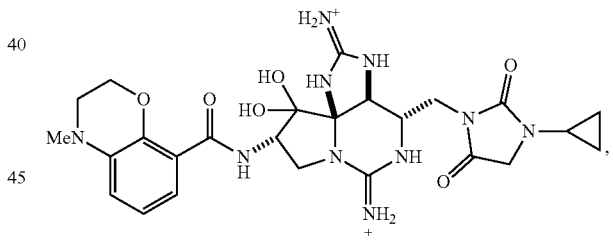

as a pharmaceutically acceptable salt or salts thereof; or as a pharmaceutically acceptable salt or salts and a stereoisomer thereof.

* * * * *

UNITED STATES PATENT AND TRADEMARK OFFICE
CERTIFICATE OF CORRECTION

PATENT NO. : 11,236,097 B2
APPLICATION NO. : 16/499205
DATED : February 1, 2022
INVENTOR(S) : John Mulcahy et al.

It is certified that error appears in the above-identified patent and that said Letters Patent is hereby corrected as shown below:

In the Claims

In Column 181, at Line 37 Claim 1, the word "or" should be deleted.

Signed and Sealed this
Third Day of September, 2024

Katherine Kelly Vidal
Director of the United States Patent and Trademark Office